(12) United States Patent
Blake et al.

(10) Patent No.: US 9,388,171 B2
(45) Date of Patent: Jul. 12, 2016

(54) SERINE/THREONINE KINASE INHIBITORS

(71) Applicants: Array BioPharma Inc., Boulder, CO (US); Genentech, Inc., South San Francisco, CA (US)

(72) Inventors: Jim Blake, Boulder, CO (US); Huifen Chen, South San Francisco, CA (US); Mark Chicarelli, Boulder, CO (US); John Gaudino, Boulder, CO (US); Lewis Gazzard, South San Francisco, CA (US); Sam Kintz, South San Francisco, CA (US); Pete Mohr, Boulder, CO (US); Kirk Robarge, South San Francisco, CA (US); Jacob Schwarz, South San Francisco, CA (US); Aihe Zhou, South San Francisco, CA (US)

(73) Assignees: GENETECH, INC., South San Francisco, CA (US); ARRAY BIOPHARMA INC., Boulder, CO (US)

( * ) Notice: Subject to any disclaimer, the term of this patent is extended or adjusted under 35 U.S.C. 154(b) by 41 days.

(21) Appl. No.: 14/011,501

(22) Filed: Aug. 27, 2013

(65) Prior Publication Data
US 2014/0066453 A1 Mar. 6, 2014

Related U.S. Application Data

(60) Provisional application No. 61/693,671, filed on Aug. 27, 2012.

(51) Int. Cl.
| | |
|---|---|
| C07D 471/04 | (2006.01) |
| C07D 217/22 | (2006.01) |
| C07D 401/12 | (2006.01) |
| C07D 401/14 | (2006.01) |
| C07D 405/12 | (2006.01) |
| C07D 405/14 | (2006.01) |
| A61K 31/4725 | (2006.01) |
| A61K 31/4375 | (2006.01) |
| A61K 31/472 | (2006.01) |
| A61P 35/00 | (2006.01) |

(52) U.S. Cl.
CPC ............ *C07D 405/14* (2013.01); *C07D 217/22* (2013.01); *C07D 401/12* (2013.01); *C07D 401/14* (2013.01); *C07D 405/12* (2013.01); *C07D 471/04* (2013.01)

(58) Field of Classification Search
CPC .. C07D 471/04; C07D 217/22; C07D 401/12; C07D 401/14; C07D 405/12; C07D 405/14; A61K 31/4375; A61K 31/472; A61K 31/4725
USPC ............. 546/143, 146, 123; 514/253.05, 300, 514/310, 307
See application file for complete search history.

(56) References Cited

U.S. PATENT DOCUMENTS

| 8,697,715 B2 | 4/2014 | Blake et al. |
| 2003/0171383 A1 | 9/2003 | Yasuda et al. |
| 2009/0246198 A1 | 10/2009 | Dong et al. |
| 2013/0252934 A1 | 9/2013 | Blake et al. |
| 2013/0338140 A1 | 12/2013 | Blake et al. |

FOREIGN PATENT DOCUMENTS

| WO | WO 95/09847 A1 | 4/1995 |
| WO | WO 95/09851 A1 | 4/1995 |
| WO | WO 98/24780 A2 | 6/1998 |
| WO | WO 01/42241 A1 | 6/2001 |
| WO | WO 01/62233 A2 | 8/2001 |
| WO | WO 02/087513 A2 | 11/2002 |
| WO | WO 03/030909 A1 | 4/2003 |
| WO | WO 03/099808 A1 | 12/2003 |
| WO | WO 2004/007468 A1 | 1/2004 |
| WO | WO 2005/066139 A2 | 7/2005 |
| WO | WO 2005/099711 A1 | 10/2005 |
| WO | WO 2005/123680 A1 | 12/2005 |
| WO | WO 2006/021458 A2 | 3/2006 |
| WO | WO 2006/030032 A1 | 3/2006 |
| WO | WO 2006/070208 A1 | 7/2006 |
| WO | WO 2006/113704 A2 | 10/2006 |
| WO | WO 2007/071348 A1 | 6/2007 |
| WO | WO 2007/097937 A1 | 8/2007 |
| WO | WO 2007/125405 A2 | 11/2007 |

(Continued)

OTHER PUBLICATIONS

Burkhard et al., "Development of Extracellular Signal-Regulated Kinase Inhibitors", *Curr Top Med Chem* 9(8), 678-689 (2009).

(Continued)

*Primary Examiner* — Sreeni Padmanabhan
*Assistant Examiner* — Irina Neagu
(74) *Attorney, Agent, or Firm* — Viksnins Harris & Padys PLLP

(57) ABSTRACT

Compounds having the formula I wherein $R^2$, X and Z as defined herein are inhibitors of ERK kinase. Also disclosed are compositions and methods for treating hyperproliferative disorders.

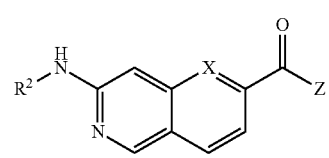

(I)

2 Claims, No Drawings

(56) References Cited

FOREIGN PATENT DOCUMENTS

| | | |
|---|---|---|
| WO | WO 2008/023239 A1 | 2/2008 |
| WO | WO 2008/039882 A1 | 4/2008 |
| WO | WO 2008/079933 A1 | 7/2008 |
| WO | WO 2008/014889 A1 | 12/2008 |
| WO | WO 2009/032861 A1 | 3/2009 |
| WO | WO 2009/061761 A2 | 5/2009 |
| WO | WO 2009/156484 A2 | 12/2009 |
| WO | WO 2009/158571 A1 | 12/2009 |
| WO | WO 2010/077275 A1 | 7/2010 |
| WO | WO 2012/118850 A1 | 9/2012 |
| WO | WO 2013/020062 A1 | 2/2013 |

OTHER PUBLICATIONS

Kohno et al., "Pharmacological inhibitors of the ERK signaling pathway: application as anticancer drugs", *Prog Cell Cycle Res.*, 5, 219-224 (2003).

Patent Cooperation Treaty, International Searching Authority, Search Report and Written Opinion for PCT/US2013/056876, 10 pages, Nov. 4, 2013.

Yap et al., "Small Molecule Inhibitors of the ERK Signalling Pathway: Towards Novel Anti-cancer Therapeutics", *ChemMedChem*, 6(1), 38-48 (2011).

Ashton et al., "Design and synthesis of novel amide AKT1 inhibitors with selectivity over CDK2", *Bioorganic & Medicinal Chemistry Letters*, vol. 21 (18), 5191-5196 (2011).

Ma et al., "The ERK/MAPK pathway, as a target for the treatment of neuropathic pain", *Expert Opin. Ther. Targets*, 9(4), 699-713 (2005).

McIntyre et al., "Pyridazine Based Inhibitors of p38 MAPK", *Bioorganic & Medicinal Chemistry Letters 12*, 689-692 (2002).

Sommer et al., "Resolvins and inflammatory pain", *F1000 Medicine Reports*, 3, 19, 6 pages (2011).

Stanetty et al., "Novel and Efficient Access to Phenylaminopyrimidine Type Protein Kinase C Inhibitors Utilizing a Negishi Cross-Coupling Strategy", *Journal of Organic Chemistry 70*, 5215-5220 (2005).

Traynor et al., *Drugs of Today*, 40(8), 697-710, 698 (2004).

SERINE/THREONINE KINASE INHIBITORS

RELATED APPLICATIONS

This application claims priority to U.S. Provisional Application No. 61/693,671 that was filed on Aug. 27, 2012. The entire content of the provisional application is hereby incorporated herein by reference.

FIELD ON THE INVENTION

The present invention relates to compounds which inhibit serine/threonine kinases and which are useful for treating hyperproliferative and neoplastic diseases by inhibiting signal transduction pathways which commonly are overactive or overexpressed in cancerous tissue. The present compounds are selective inhibitors of ERK (extracellular-signal regulated kinase). The present invention further relates to methods for treating cancer or hyperproliferative diseases with compounds within the scope of the present invention

BACKGROUND OF THE INVENTION

The processes involved in tumor growth, progression, and metastasis are mediated by signaling pathways that are activated in cancer cells. The ERK pathway plays a central role in regulating mammalian cell growth by relaying extracellular signals from ligand-bound cell surface receptor tyrosine kinase (RTK's) such as erbB family, PDGF, FGF, and VEGF receptor tyrosine kinase. Activation of an RTK induces a cascade of phosphorylation events that begins with activation of Ras. Activation of Ras leads to the recruitment and activation of Raf, a serine-threonine kinase. Activated Raf then phosphorylates and activates MEK1/2, which then phosphorylates and activates ERK1/2. When activated, ERK1/2 phosphorylates several downstream targets involved in a multitude of cellular events including cytoskeletal changes and transcriptional activation. The ERK/MAPK pathway is one of the most important for cell proliferation, and it is believed that the ERK/MAPK pathway is frequently activated in many tumors. Ras genes, which are upstream of ERK1/2, are mutated in several cancers including colorectal, melanoma, breast and pancreatic tumors. The high Ras activity is accompanied by elevated ERK activity in many human tumors. In addition, mutations of BRAF, a serine-threonine kinase of the Raf family, are associated with increased kinase activity. Mutations in BRAF have been identified in melanomas (60%), thyroid cancers (greater than 40%) and colorectal cancers. These observations indicate that the ERK1/2 signaling pathway is an attractive pathway for anticancer therapies in a broad spectrum of human tumors. (M. Hohno and J. Pouyssegur, *Prog. in Cell Cycle Res.* 2003 5:219)

Therefore, small-molecular inhibitors of ERK activity (i.e., ERK1 and/or ERK2 activity) would be useful for treating a broad spectrum of cancers, such as, for example, melanoma, pancreatic cancer, thyroid cancer, colorectal cancer, lung cancer, breast cancer, and ovarian cancer. Such a contribution is provided by this invention.

SUMMARY OF THE INVENTION

In one aspect of the present invention there is provided a compound according to formula I, wherein:

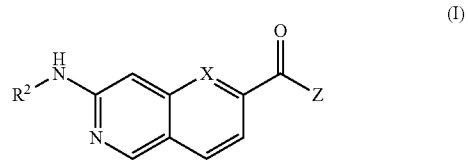

X is CH or N;

Z is (i) $NH(CH_2)_n CHR^1 Ar$ wherein n is 0 or 1, or (ii) 1-alkyl-4-aryl-pyrrolidin-3-ylamine or 4-aryl-pyrrolidin-3-ylamine wherein alkyl is $C_{1-3}$ alkyl optionally substituted by a phenyl ring and aryl substituent on the pyrrolidine is optionally substituted phenyl;

$R^1$ is (a) hydrogen, (b) $C_1$-$C_6$ alkyl optionally substituted with one or more hydroxyl or $C_{1-6}$ alkoxy groups, (c) $C_1$-$C_6$ alkenyl optionally substituted with one or more hydroxyl or $C_{1-6}$ alkoxy groups, (d) $C_1$-$C_6$ alkynyl with one or more hydroxyl or $C_{1-6}$ alkoxy groups, (e) $C_3$-$C_6$ cycloalkyl optionally substituted with one or more groups selected from the group consisting of hydroxyl, $C_{1-6}$ alkoxy, $C_{1-6}$ alkyl and halogen; (f) a 4 to 6 membered heterocycle with one or two heteroatoms selected from N or O, wherein the heterocycle is optionally substituted with one or more groups selected from the group consisting of hydroxyl, $C_{1-6}$ alkoxy, $C_{1-6}$ alkyl and halogen, or (g) a 5 to 6 membered heteroaryl with one or two heteroatoms selected from N or O, wherein the heteroaryl is optionally substituted with one or more groups selected from the group consisting of hydroxyl, $C_{1-6}$ alkoxy, $C_{1-6}$ alkyl and halogen;

Ar is phenyl, pyridinyl or indolyl optionally substituted by 1 to 3 groups independently selected from (a) $C_{1-6}$ alkyl, (b) $C_{1-6}$ haloalkyl, (c) $C_{1-6}$ alkoxy, (d) $C_{3-6}$ cycloalkyl, (e) halogen, (f) $C_{1-6}$ haloalkoxy, (g) $C_{1-6}$ alkylthio, (f) cyano, (g) benzyl, (h) phenoxy wherein said benzyl and phenoxy are optionally substituted with halogen, $C_{1-6}$ alkyl or $C_{1-6}$ alkoxy, (i) 4-methylpiperazin-1-yl, or (j) heteroaryl selected from the group consisting of pyridinyl, pyrazinyl, pyridazinyl, pyrimidinyl and pyrazolyl wherein said heteroaryl is optionally substituted by one or more $C_{1-10}$ alkyl;

$R^2$ is selected from the group consisting of (a) $C_{1-10}$ alkyl, (b) $C_{1-10}$ hydroxyalkyl, (c) $C_{1-6}$ haloalkyl, (d) heterocyclyl wherein said heterocycle is selected from the group consisting of tetrahydropyranyl, tetrahydrofuranyl, oxetanyl, 2-oxabicyclo[2.2.1]heptan-5-yl, piperidinyl, and pyrrolidinyl and wherein said heterocyclyl or heterocyclyl-$C_{1-6}$ alkyl is optionally substituted by 1 to 3 groups independently selected from the group consisting of $C_{1-6}$ alkyl, $C_{1-6}$ haloalkyl, $C_{1-4}$ acyloxy-$C_{1-2}$ alkyl, halogen, hydroxyl, phenyl, $C_{1-3}$ hydroxyalkyl and oxo, (e) heteroaryl wherein said heteroaryl is selected from the group consisting of pyrazolyl and pyridinyl and wherein said heteroaryl is optionally substituted with 1 to 3 $C_{1-3}$ alkyl groups, and (f) $C_{3-7}$ cycloalkyl or $C_{3-7}$ cycloalkyl-$C_{1-6}$ alkyl wherein said cycloalkyl or $C_{3-7}$ cycloalkyl-$C_{1-6}$ alkyl are optionally substituted by hydroxyl or halo; or, a stereoisomer, tautomer or pharmaceutically acceptable salt thereof.

The present invention also relates to a method for treating a hyperproliferative disorder by administering a therapeutically effective quantity of a compound according to formula I to a patient in need thereof. The compound of formula I can be administered alone or co-administered with at least one other anti-hyperproliferative or chemotherapeutic compound.

The present invention also relates to a method for inhibiting ERK protein kinase activity in a cell comprising treating a cell with a compound according to formula I in an amount effective to attenuate or eliminate ERK kinase activity.

The present invention also relates to a pharmaceutical composition comprising a compound according to formula I and at least one pharmaceutically acceptable carrier, diluent or excipient.

DETAILED DESCRIPTION OF THE INVENTION

The phrase "a" or "an" entity as used herein refers to one or more of that entity; for example, a compound refers to one or more compounds or at least one compound. As such, the terms "a" (or "an"), "one or more", and "at least one" can be used interchangeably herein.

The phrase "as defined herein above" refers to the broadest definition for each group as provided in the Summary of the Invention or the broadest claim. In all other embodiments provided below, substituents which can be present in each embodiment and which are not explicitly defined retain the broadest definition provided in the Summary of the Invention.

As used in this specification, whether in a transitional phrase or in the body of the claim, the terms "comprise(s)" and "comprising" are to be interpreted as having an open-ended meaning. That is, the terms are to be interpreted synonymously with the phrases "having at least" or "including at least". When used in the context of a process, the term "comprising" means that the process includes at least the recited steps, but may include additional steps. When used in the context of a compound or composition, the term "comprising" means that the compound or composition includes at least the recited features or components, but may also include additional features or components.

The term "independently" is used herein to indicate that a variable is applied in any one instance without regard to the presence or absence of a variable having that same or a different definition within the same compound. Thus, in a compound in which R" appears twice and is defined as "independently carbon or nitrogen", both R"s can be carbon, both R"s can be nitrogen, or one R" can be carbon and the other nitrogen.

When any variable (e.g., $R^1$, $R^{4a}$, Ar, $X^1$ or Het) occurs more than one time in any moiety or formula depicting and describing compounds employed or claimed in the present invention, its definition on each occurrence is independent of its definition at every other occurrence. Also, combinations of substituents and/or variables are permissible only if such compounds result in stable compounds.

The symbols "*" at the end of a bond or "------" drawn through a bond each refer to the point of attachment of a functional group or other chemical moiety to the rest of the molecule of which it is a part. Thus, for example:
MeC(=O)OR$^4$ wherein

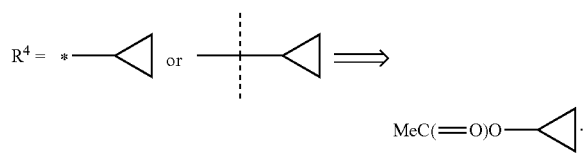

A bond drawn into ring system (as opposed to connected at a distinct vertex) indicates that the bond may be attached to any of the suitable ring atoms.

The term "optional" or "optionally" as used herein means that a subsequently described event or circumstance may, but need not, occur, and that the description includes instances where the event or circumstance occurs and instances in which it does not. For example, "optionally substituted" means that the optionally substituted moiety may incorporate a hydrogen or a substituent.

The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%.

As used herein, the recitation of a numerical range for a variable is intended to convey that the invention may be practiced with the variable equal to any of the values within that range. Thus, for a variable which is inherently discrete, the variable can be equal to any integer value of the numerical range, including the end-points of the range. Similarly, for a variable which is inherently continuous, the variable can be equal to any real value of the numerical range, including the end-points of the range. As an example, a variable which is described as having values between 0 and 2, can be 0, 1 or 2 for variables which are inherently discrete, and can be 0.0, 0.1, 0.01, 0.001, or any other real value for variables which are inherently continuous.

Compounds of formula I exhibit tautomerism. Tautomeric compounds can exist as two or more interconvertable species. Prototropic tautomers result from the migration of a covalently bonded hydrogen atom between two atoms. Tautomers generally exist in equilibrium and attempts to isolate an individual tautomers usually produce a mixture whose chemical and physical properties are consistent with a mixture of compounds. The position of the equilibrium is dependent on chemical features within the molecule. For example, in many aliphatic aldehydes and ketones, such as acetaldehyde, the keto form predominates while; in phenols, the enol form predominates. Common prototropic tautomers include keto/enol (—C(=O)—CH$_2$—↔—C(—OH)=CH—), amide/imidic acid (—C(=O)—NH—↔—C(—OH)=N—) and amidine (—C(=NR)—NH—↔—C(—NHR)=N—) tautomers. The latter two are particularly common in heteroaryl and heterocyclic rings and the present invention encompasses all tautomeric forms of the compounds.

It will be appreciated by the skilled artisan that some of the compounds of formula I may contain one or more chiral centers and therefore exist in two or more stereoisomeric forms. The racemates of these isomers, the individual isomers and mixtures enriched in one enantiomer, as well as diastereomers when there are two chiral centers, and mixtures partially enriched with specific diastereomers are within the scope of the present invention. The present invention includes all the individual stereoisomers (e.g., enantiomers), racemic mixtures or partially resolved mixtures of the compounds of formula I and, where appropriate, the individual tautomeric forms thereof.

The compounds of formula I may contain a basic center and suitable acid addition salts are formed from acids which form non-toxic salts. Examples of salts of inorganic acids include the hydrochloride, hydrobromide, hydroiodide, chloride, bromide, iodide, sulfate, bisulfate, nitrate, phosphate, and hydrogen phosphate. Examples of salts of organic acids include acetate, fumarate, pamoate, aspartate, besylate, carbonate, bicarbonate, camsylate, D and L-lactate, D and L-tartrate, esylate, mesylate, malonate, orotate, gluceptate, methylsulfate, stearate, glucuronate, 2-napsylate, tosylate, hibenzate, nicotinate, isethionate, malate, maleate, citrate, gluconate, succinate, saccharate, benzoate, esylate, and pamoate salts. For a review on suitable salts see Berge et al, *J. Pharm. Sci.*, 1977 66:1-19 and G. S. Paulekuhn et al. *J. Med. Chem.* 2007 50:6665.

The definitions described herein may be appended to form chemically-relevant combinations, such as "heteroalkylaryl," "haloalkylheteroaryl," "arylalkylheterocyclyl," "alkylcarbonyl," "alkoxyalkyl," and the like. When the term "alkyl" is used as a suffix following another term, as in "phenylalkyl," or "hydroxyalkyl," this is intended to refer to an alkyl group, as defined above, being substituted with one to two substituents selected from the other specifically-named group. Thus, for example, "phenylalkyl" refers to an alkyl group having one to two phenyl substituents, and thus includes benzyl and phenylethyl. An "alkylaminoalkyl" is an alkyl group having one to two alkylamino substituents. "Hydroxyalkyl" includes 2-hydroxyethyl, 2-hydroxypropyl, 1-(hydroxymethyl)-2-methylpropyl, 2-hydroxybutyl, 2,3-dihydroxybutyl, 2-(hydroxymethyl), 3-hydroxypropyl, and so forth. Accordingly, as used herein, the term "hydroxyalkyl" is used to define a subset of heteroalkyl groups defined below. The term -(ar)alkyl refers to either an unsubstituted alkyl or an aralkyl group. The term (hetero)aryl or (het)aryl refers to a moiety that is either an aryl or a heteroaryl group.

The term "alkyl" as used herein alone or in combination with other groups, denotes an unbranched or branched chain, saturated, monovalent hydrocarbon residue containing 1 to 10 carbon atoms. The term "lower alkyl" denotes a straight or branched chain hydrocarbon residue containing 1 to 6 carbon atoms. "$C_{1-6}$ alkyl" as used herein refers to an alkyl composed of 1 to 6 carbons. Examples of alkyl groups include, but are not limited to, methyl, ethyl, propyl, i-propyl, n-butyl, i-butyl, t-butyl, neopentyl, hexyl, and octyl.

The term "alkenyl" as used herein denotes an unsubstituted hydrocarbon chain radical having from 2 to 10 carbon atoms having one or two olefinic double bonds. "$C_{2-10}$ alkenyl" as used herein refers to an alkenyl composed of 2 to 10 carbons. Examples are vinyl, 1-propenyl, 2-propenyl(allyl) or 2-butenyl(crotyl).

The term "alkynyl" as used herein denotes an unbranched or branched hydrocarbon chain radical having from 2 to 10 carbon atoms, and having one or where possible two triple bonds. "$C_{2-10}$ alkenyl" as used herein refers to an alkenyl composed of 2 to 10 carbons Examples are ethynyl, 1-propynyl, 2-propynyl, 1-butynyl, 2-butynyl or 3-butynyl.

The term "cycloalkyl" denotes a monovalent saturated monocyclic or bicyclic hydrocarbon group of 3 to 10 ring carbon atoms Fused cycloalkyl groups can have one (i.e., spirocyclic), two (i.e., bicyclic) or more (i.e., polycyclic) carbon atoms in common. Particular cycloalkyl groups are monocyclic. "$C_{3-7}$ cycloalkyl" as used herein refers to a cycloalkyl composed of 3 to 7 carbons in the carbocyclic ring. Examples for monocyclic cycloalkyl are cyclopropyl, cyclobutanyl, cyclopentyl, cyclohexyl or cycloheptyl. Examples for bicyclic cycloalkyl are bicyclo[2.2.1]heptanyl, or bicyclo[2.2.2]octanyl.

The term "cycloalkylalkyl" as used herein refers to the radical R'R"—, wherein R' is a cycloalkyl radical, and R" is an alkylene radical as defined herein with the understanding that the attachment point of the cycloalkylalkyl moiety will be on the alkylene radical. Examples of cycloalkylalkyl radicals include, but are not limited to, cyclopropylmethyl, cyclohexylmethyl, cyclopentylethyl. $C_{3-7}$ cycloalkyl-$C_{1-3}$ alkyl refers to the radical R'R" where R' is $C_{3-7}$ cycloalkyl and R" is $C_{1-3}$ alkylene as defined herein.

The term "alkylene" as used herein denotes a divalent saturated linear hydrocarbon radical of 1 to 10 carbon atoms (e.g., $(CH_2)_n$) or a branched saturated divalent hydrocarbon radical of 2 to 10 carbon atoms (e.g., —CHMe- or —CH$_2$CH (i-Pr)CH$_2$—), unless otherwise indicated. "$C_{0-4}$ alkylene" refers to a linear or branched saturated divalent hydrocarbon radical comprising 1-4 carbon atoms or, in the case of $C_0$, the alkylene radical is omitted. "$(CH_2)_{0-4}$" refers to a linear saturated divalent hydrocarbon radical comprising 0-4 carbon atoms or, in the case of $C_0$, the alkylene radical is omitted. Except in the case of methylene, the open valences of an alkylene group are not attached to the same atom. Examples of alkylene radicals include, but are not limited to, methylene, ethylene, propylene, 2-methyl-propylene, 1,1-dimethyl-ethylene, butylene, 2-ethylbutylene.

The term "alkoxy" as used herein means an —O-alkyl group, wherein alkyl is as defined above, such as methoxy, ethoxy, n-propyloxy, i-propyloxy, n-butyloxy, i-butyloxy, t-butyloxy, pentyloxy, hexyloxy, including their isomers. "Lower alkoxy" as used herein denotes an alkoxy group with a "lower alkyl" group as previously defined. "$C_{1-10}$ alkoxy" as used herein refers to an —O-alkyl wherein alkyl is $C_{1-10}$.

The term "haloalkyl" as used herein denotes an alkyl group as defined above wherein at least one hydrogen atom is substituted by a halogen. Examples are 1-fluoromethyl, 1-chloromethyl, 1-bromomethyl, 1-iodomethyl, difluoromethyl, trifluoromethyl, trichloromethyl, 1-fluoroethyl, 1-chloroethyl, 2-fluoroethyl, 2-chloroethyl, 2-bromoethyl, 2,2-dichloroethyl, 3-bromopropyl or 2,2,2-trifluoroethyl.

The term "haloalkoxy" as used herein refers to a group —OR where R is haloalkyl as defined herein. The term "haloalkylthio" as used herein refers to a group —SR where R is haloalkyl as defined herein.

The term "halogen" or "halo" as used herein means fluorine, chlorine, bromine, or iodine. The term "halo", "halogen", and "halide" are used interchangeably herein and denote fluoro, chloro, bromo, or iodo.

The term "alkylthio" or "alkylsulfanyl" means an —S-alkyl group, wherein alkyl is as defined above, such as methylthio, ethylthio, n-propylthio, i-propylthio, n-butylthio, hexylthio, including their isomers. "Lower alkylthio" as used herein denotes an alkylthio group with a "lower alkyl" group as previously defined. "$C_{1-10}$ alkylthio" as used herein refers to an S-alkyl wherein alkyl is $C_{1-10}$.

The term "acyloxy" as used herein denotes the radical —OC(O)R, wherein R is a lower alkyl radical as defined herein. Examples of acyloxy radicals include, but are not limited to, acetoxy, propionyloxy. Acyloxy-$C_{1-2}$ alkyl as used herein refers to the radical R'R"—, wherein R' is an acyloxy radical, and R" is an methylene or ethylene radical as defined herein with the understanding that the attachment point of the acyloxy-$C_{1-2}$ alkyl moiety will be on the alkyl radical.

The terms "hydroxyalkyl" and "alkoxyalkyl" as used herein denotes alkyl radical as herein defined wherein one to three hydrogen atoms on different carbon atoms is/are replaced by hydroxyl or alkoxy groups respectively. A $C_{1-3}$ alkoxy-$C_{1-6}$ alkyl moiety refers to a $C_{1-6}$ alkyl substituent in which 1 to 3 hydrogen atoms are replaced by a $C_{3-3}$ alkoxy and the point of attachment of the alkoxy is the oxygen atom.

The terms "heterocycle" and "heterocyclic" include four to seven membered saturated or partially unsaturated rings containing one, two or three heteroatoms selected from the group consisting of O, N, S, S(=O) and S(=O)$_2$. These terms include bicyclic rings such as 2-oxabicyclo[2.2.1]heptane. In certain instances, these terms may be specifically further limited, such as, "five to six membered heterocyclic" only including five and six membered rings.

The term "heterocycloalkyl" (or "heterocyclylalkyl") denotes the radical of the formula R'R", wherein R' is a heterocyclic radical as defined herein, and R" is an alkylene radical as defined herein, and the attachment point of the heterocycloalkyl radical will be on the alkylene radical. Examples of heterocycloalkyl radicals include, but are not limited to, 1-piperazinylmethyl, 2-morpholinomethyl, and the like.

The term "aryl" as used herein denotes a monovalent aromatic carbocyclic radical containing 6 to 15 carbon atoms consisting of one individual ring, or one or more fused rings in which at least one ring is aromatic in nature. An aryl group can optionally be substituted with one or more, preferably one to three substituents. Alternatively two adjacent atoms of the aryl ring may be substituted with a methylenedioxy or ethylenedioxy group. Examples of aryl radicals include phenyl, naphthyl, indanyl, 3,4-methylenedioxyphenyl, 1,2,3,4-tetrahydroquinolin-7-yl, 1,2,3,4-tetrahydroisoquinoline-7-yl, and the like.

The term "aryloxy" as used herein denotes an O-aryl group, wherein aryl is as defined above. An aryloxy group can be unsubstituted or substituted with one or three suitable substituents. The term "phenoxy" refers to an aryloxy group wherein the aryl moiety is a phenyl ring.

The term "heteroaryl" includes five to six membered aromatic rings containing one, two, three or four heteroatoms selected from the group consisting of O, N and S. In certain instances, these terms may be specifically further limited, such as, five to six membered heteroaryl, wherein the heteroaryl contains one or two nitrogen heteroatoms. As well known to those skilled in the art, heteroaryl rings have less aromatic character than their all-carbon counter parts. Thus, for the purposes of the invention, a heteroaryl group need only have some degree of aromatic character.

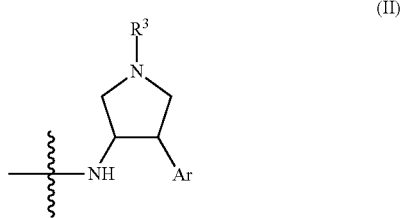

(II)

The term "1-alkyl-4-aryl-pyrolidin-3-ylamine" as used herein refers to a fragment of formula II wherein $R^3$ is $C_{1-3}$ alkyl optionally substituted by a phenyl ring and Ar is optionally substituted phenyl. 4-Aryl-pyrrolidin-3-ylamine refers to a fragment of formula II wherein $R^3$ is hydrogen and aryl is as defined above.

The terms "treat" and "treatment" refer to therapeutic treatment wherein the object is to slow down (lessen) an undesired physiological change or disorder, such as the spread of cancer. For purposes of this invention, beneficial or desired clinical results include, but are not limited to, alleviation of symptoms, limiting the extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment.

The phrase "therapeutically effective amount" means an amount of a compound of the present invention that (i) treats the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug may prevent growth and/or kill existing cancer cells, it may be cytostatic and/or cytotoxic. For cancer therapy, efficacy can be measured, for example, by assessing the time to disease progression (TTP) and/or determining the response rate (RR).

The terms "cancer" and "cancerous" refer to or describe the physiological condition in mammals that is typically characterized by unregulated cell growth. A "tumor" comprises one or more cancerous cells. Examples of cancer include, but are not limited to, carcinoma, lymphoma, blastoma, sarcoma, and leukemia or lymphoid malignancies. More particular examples of such cancers include squamous cell cancer (e.g., epithelial squamous cell cancer), lung cancer including small-cell lung cancer, non-small cell lung cancer ("NSCLC"), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

A "chemotherapeutic agent" is a chemical compound useful in the treatment of cancer. Examples of chemotherapeutic agents include erlotinib (TARCEVA®, Genentech/OSI Pharm.), bortezomib (VELCADE®, Millennium Pharm.), fulvestrant (FASLODEX®, AstraZeneca), sunitib (SUTENT®, Pfizer/Sugen), letrozole (FEMARA®, Novartis), imatinib mesylate (GLEEVEC®, Novartis), finasunate (VATALANIB®, Novartis), oxaliplatin (ELOXATIN®, Sanofi), 5-FU (5-fluorouracil), leucovorin, Rapamycin (Sirolimus, RAPAMUNE®, Wyeth), Lapatinib (TYKERB®, GSK572016, Glaxo Smith Kline), Lonafamib (SCH 66336), sorafenib (NEXAVAR®, Bayer Labs), gefitinib (IRESSA®, AstraZeneca), AG1478, alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including the synthetic analog topotecan); bryostatin; callystatin; CC-1065 (including its adozelesin, carzelesin and bizelesin synthetic analogs); cryptophycins (particularly cryptophycin 1 and cryptophycin 8); dolastatin; duocarmycin (including the synthetic analogs, KW-2189 and CB1-TM1); eleutherobin; pancratistatin; a sarcodictyin; spongistatin; nitrogen mustards such as chlorambucil, chlomaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, especially calicheamicin γ1I and calicheamicin ω1I (*Angew Chem. Intl. Ed. Engl.* 1994 33:183-186); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® (doxorubicin), morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfomithine; elliptinium acetate; an epothilone; etoglucid; gallium nitrate; hydroxyurea; lentinan; lonidainine; maytansinoids such as maytansine and ansamitocins; mitoguazone; mitoxantrone; mopidamnol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL (paclitaxel; Bristol-Myers Squibb Oncology, Princeton, N.J.), ABRAXANE® (Cremophor-free), albumin-engineered nanoparticle formulations of paclitaxel (American Pharmaceutical Partners, Schaumberg, Ill.), and TAXOTERE® (docetaxel, doxetaxel; Sanofi-Aventis); chloranmbucil; GEMZAR® (gemcitabine); 6-thioguanine; mercaptopurine; methotrexate; platinum analogs such as cisplatin and carboplatin; vinblastine; etoposide (VP-16); ifosfamide; mitoxantrone; vincristine; NAVELBINE® (vinorelbine); novantrone; teniposide; edatrexate; daunomycin; aminopterin; capecitabine (XELODA®); ibandronate; CPT-11; topoisomerase inhibitor RFS 2000; difluoromethylornithine (DMFO); retinoids such as retinoic acid; and pharmaceutically acceptable salts, acids and derivatives of any of the above.

Also included in the definition of "chemotherapeutic agent" are: (i) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, 4-hydroxytamoxifen, trioxifene, keoxifene, LY117018, onapristone, and FARESTON® (toremifine citrate); (ii) aromatase inhibitors that inhibit the enzyme aromatase, which regulates estrogen production in the adrenal glands, such as, for example, 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) anti-androgens such as flutamide, nilutamide, bicalutamide, leuprolide, and goserelin; as well as troxacitabine (a 1,3-dioxolane nucleoside cytosine analog); (iv) protein kinase inhibitors; (v) lipid kinase inhibitors; (vi) antisense oligonucleotides, particularly those which inhibit expression of genes in signaling pathways implicated in aberrant cell proliferation, such as, for example, PKC-alpha, Raf and H-Ras; (vii) ribozymes such as VEGF expression inhibitors (e.g., ANGIOZYME®) and HER2 expression inhibitors; (viii) vaccines such as gene therapy vaccines, for example, ALLOVECTIN®, LEUVECTIN®, and VAXID®; PRO-LEUKIN®, rIL-2; a topoisomerase 1 inhibitor such as LUR-TOTECAN®; ABARELIX® rmRH; (ix) anti-angiogenic agents such as bevacizumab (AVASTIN®), Genentech); and (x) pharmaceutically acceptable salts, acids and derivatives of any of the above.

In one embodiment of the present invention there is provided a compound of formula I wherein $R^1$, $R^2$, Ar, X and Z are as defined hereinabove. The terms "as defined above" and "as defined herein above" when referring to a variable incorporates by reference the broadest definition of the variable provided in the Summary of the Invention or the broadest claim.

In another embodiment of the present invention there is provided a compound according to formula I wherein X is N and $R^1$, $R^2$, Ar and Z are as defined hereinabove.

In another embodiment of the present invention there is provided a compound according to formula I wherein X is CH and $R^1$, $R^2$, Ar and Z are as defined hereinabove.

In another embodiment of the present invention there is provided a compound according to formula I wherein X is N or CH, Z is NHCH$_2$CHR$^1$Ar and $R^1$, $R^2$ and Ar are as defined hereinabove.

In another embodiment of the present invention there is provided a compound according to formula I wherein X is N, Z is NHCH$_2$CHR$^1$Ar and $R^1$, $R^2$ and Ar are as defined hereinabove.

In another embodiment of the present invention there is provided a compound according to formula I wherein X is CH, Z is NHCH$_2$CHR$^1$Ar and $R^1$, $R^2$ and Ar are denied hereinabove.

In another embodiment of the present invention there is provided a compound according to formula I wherein X is N or CH, $R^1$ is (a) hydrogen, (b) $C_{1-6}$ alkyl optionally substituted with one to three hydroxyl or $C_{1-6}$ alkoxy groups, (c) a pyrrolidinyl group optionally substituted by halogen, or (d) a pyrazolyl or imidazolyl moiety optionally substituted with 1 to 3 $C_{1-6}$ alkyl moieties and Ar is optionally substituted phenyl.

In another embodiment of the present invention there is provided a compound according to formula I wherein X is N, $R^1$ is (a) hydrogen, (b) $C_{1-6}$ alkyl optionally substituted with one or more hydroxyl or $C_{1-6}$ alkoxy groups, (c) a pyrrolidinyl group optionally substituted by halogen, or (d) a pyrazolyl or imidazolyl moiety optionally substituted with 1 to 3 $C_{1-6}$ alkyl moieties and Ar is optionally substituted phenyl.

In another embodiment of the present invention there is provided a compound according to formula I wherein X is CH, $R^1$ is (a) hydrogen, (b) $C_{1-6}$ alkyl optionally substituted with one or more hydroxyl or $C_{1-6}$ alkoxy groups, (c) a pyrrolidinyl group optionally substituted by halogen, or (d) a pyrazolyl or imidazolyl moiety optionally substituted with 1 to 3 $C_{1-6}$ alkyl moieties and Ar is optionally substituted phenyl.

In another embodiment of the present invention there is provided a compound according to formula I wherein X is N or CH, Z is NHCHR$^1$Ar, R$^1$ is (a) hydrogen, (b) $C_{1-6}$ alkyl optionally substituted with one or more hydroxyl or $C_{1-6}$ alkoxy groups, (c) a pyrrolidinyl group optionally substituted by halogen, or (d) a pyrazolyl or imidazolyl moiety optionally substituted with 1 to 3 $C_{1-6}$ alkyl moieties; and Ar is optionally substituted phenyl. In one subembodiment X is N. In another subembodiment X is CH.

In another embodiment of the present invention there is provided a compound according to formula I wherein X is N or CH, Z is NHCHR$^1$Ar, R$^1$ is (a) $C_{1-6}$ alkyl, (b) $C_{1-6}$ alkyl substituted by a hydroxy group or (c) pyrazolyl optionally substituted by 1 or 2 $C_{1-6}$ alkyl moieties; and Ar is optionally substituted phenyl. In one subembodiment X is N. In another subembodiment X is CH.

In another embodiment of the present invention there is provided a compound according to formula I wherein X is N or CH, Z is NHCHR$^1$Ar, R$^1$ is (a) (R)—$C_{1-4}$ alkyl, (b) (S)—$C_{1-6}$ hydroxyalkyl or (c) (S)-1-$C_{1-6}$ alkyl-1H-pyrazol-4-yl; and Ar is optionally substituted phenyl. In one subembodiment X is N. In another subembodiment X is CH.

In another embodiment of the present invention there is provided a compound according to formula I wherein X is N or CH, Z is, R$^1$ is (a) (R)-ethyl, (b) hydroxymethyl or (c) (S)-1-methyl-1H-pyrazol-4-yl; and Ar is optionally substituted phenyl. In one subembodiment X is N. In another subembodiment X is CH.

In certain embodiments, R$^1$ is selected from (a) hydrogen; (b) $C_1$-$C_6$ alkyl optionally substituted with one or more hydroxyl or $C_{1-6}$ alkoxy groups; (c) a 4 to 6 membered heterocycle with one or two heteroatoms selected from N and O and wherein the heterocycle is optionally substituted with one or more groups selected from hydroxyl, $C_{1-6}$ alkoxy, $C_{1-6}$ alkyl and halogen; and (d) a 5 to 6 membered heteroaryl with one or two heteroatoms selected from N and O and wherein the heteroaryl is optionally substituted with one or more groups selected from hydroxyl, $C_{1-6}$ alkoxy, $C_{1-6}$ alkyl and halogen. In certain embodiments, R$^1$ is selected from (a) hydrogen; (b) $C_1$-$C_6$ alkyl optionally substituted with one or two hydroxyl or $C_{1-6}$ alkoxy groups; (c) a 4 to 6 membered heterocycle with one or two heteroatoms selected from N and O and wherein the heterocycle is optionally substituted with one or two groups selected from hydroxyl, $C_{1-6}$ alkoxy, $C_{1-6}$ alkyl and halogen; and (d) a 5 to 6 membered heteroaryl with one or two heteroatoms selected from N and O and wherein the heteroaryl is optionally substituted with one or two groups selected from hydroxyl, $C_{1-6}$ alkoxy, $C_{1-6}$ alkyl and halogen. In certain embodiments, R$^1$ is selected from (a) hydrogen; (b) $C_1$-$C_6$ alkyl optionally substituted with one hydroxyl group; (c) a 4 to 6 membered heterocycle with one or two heteroatoms selected from N and O and wherein the heterocycle is optionally substituted with halogen; and (d) a 5 to 6 membered heteroaryl with one or two heteroatoms selected from N and O and wherein the heteroaryl is optionally substituted with $C_{1-6}$ alkyl. In certain embodiments, R$^1$ is selected from (a) hydrogen; (b) $C_1$-$C_6$ alkyl optionally substituted with one hydroxyl group; (c) a 4 to 6 membered heterocycle with one N heteroatom and wherein the heterocycle is optionally substituted with halogen; and (d) a 5 to 6 membered heteroaryl with two N heteroatoms and wherein the heteroaryl is optionally substituted with $C_{1-6}$ alkyl.

In certain embodiments, R$^1$ is selected from hydrogen, hydroxymethyl, (S)-hydroxymethyl, (R)-hydroxymethyl, ethyl, (S)-ethyl, (R)-ethyl, 2-hydroxyethyl, (R)-2-hydroxyethyl, (S)-2-hydroxyethyl, 1-hydroxyethyl, 3-fluoropyrrolidin-3-yl, (R)-3-fluoropyrrolidin-3-yl, (S)-3-fluoropyrrolidin-3-yl, 1-methyl-1H-pyrazol-4-yl, (S)-1-methyl-1H-pyrazol-4-yl, (R)-1-methyl-1H-pyrazol-4-yl, 1-methyl-1H-pyrazol-5-yl, (S)-1-methyl-1H-pyrazol-5-yl, (R)-1-methyl-1H-pyrazol-5-yl, 1-methyl-1H-imidazol-5-yl, (S)-1-methyl-1H-imidazol-5-yl, (R)-1-methyl-1H-imidazol-5-yl, 1-methyl-1H-pyrazol-3-yl, (S)-1-methyl-1H-pyrazol-3-yl and (R)-1-methyl-1H-pyrazol-3-yl, In certain embodiments, R$^1$ is selected from hydrogen, hydroxymethyl, (S)-hydroxymethyl, ethyl, (S)-ethyl, 2-hydroxyethyl, (R)-2-hydroxyethyl, 1-hydroxyethyl, 3-fluoropyrrolidin-3-yl, (R)-3-fluoropyrrolidin-3-yl, (S)-3-fluoropyrrolidin-3-yl, 1-methyl-1H-pyrazol-4-yl, (S)-1-methyl-1H-pyrazol-4-yl, 1-methyl-1H-pyrazol-5-yl, (S)-1-methyl-1H-pyrazol-5-yl, 1-methyl-1H-imidazol-5-yl, (S)-1-methyl-1H-imidazol-5-yl, (R)-1-methyl-1H-imidazol-5-yl, 1-methyl-1H-pyrazol-3-yl, (S)-1-methyl-1H-pyrazol-3-yl and (R)-1-methyl-1H-pyrazol-3-yl, In certain embodiments, R$^1$ is selected from hydrogen, hydroxymethyl, ethyl, 2-hydroxyethyl, 1-hydroxyethyl, 3-fluoropyrrolidin-3-yl, 1-methyl-1H-pyrazol-4-yl, 1-methyl-1H-pyrazol-5-yl, 1-methyl-1H-imidazol-5-yl and 1-methyl-1H-pyrazol-3-yl.

In certain embodiments, R$^1$ is selected from (a) $C_1$-$C_6$ alkyl optionally substituted with one or more hydroxyl or $C_{1-6}$ alkoxy groups; (b) a 4 to 6 membered heterocycle with one or two heteroatoms selected from N and O and wherein the heterocycle is optionally substituted with one or more groups selected from hydroxyl, $C_{1-6}$ alkoxy, $C_{1-6}$ alkyl and halogen; and (c) a 5 to 6 membered heteroaryl with one or two heteroatoms selected from N and O and wherein the heteroaryl is optionally substituted with one or more groups selected from hydroxyl, $C_{1-6}$ alkoxy, $C_{1-6}$ alkyl and halogen. In certain embodiments, R$^1$ is selected from (a) $C_1$-$C_6$ alkyl optionally substituted with one or two hydroxyl or $C_{1-6}$ alkoxy groups; (b) a 4 to 6 membered heterocycle with one or two heteroatoms selected from N and O and wherein the heterocycle is optionally substituted with one or two groups selected from hydroxyl, $C_{1-6}$ alkoxy, $C_{1-6}$ alkyl and halogen; and (c) a 5 to 6 membered heteroaryl with one or two heteroatoms selected from N and O and wherein the heteroaryl is optionally substituted with one or two groups selected from hydroxyl, $C_{1-6}$ alkoxy, $C_{1-6}$ alkyl and halogen. In certain embodiments, R$^1$ is selected from (a) $C_1$-$C_6$ alkyl optionally substituted with one hydroxyl group; (b) a 4 to 6 membered heterocycle with one or two heteroatoms selected from N and O and wherein the heterocycle is optionally substituted with halogen; and (c) a 5 to 6 membered heteroaryl with one or two heteroatoms selected from N and O and wherein the heteroaryl is optionally substituted with $C_{1-6}$ alkyl. In certain embodiments, R$^1$ is selected from (a) $C_1$-$C_6$ alkyl optionally substituted with one hydroxyl group; (b) a 4 to 6 membered heterocycle with one N heteroatom and wherein the heterocycle is optionally substituted with halogen; and (c) a 5 to 6 membered heteroaryl with two N heteroatoms and wherein the heteroaryl is optionally substituted with $C_{1-6}$ alkyl.

In certain embodiments, R$^1$ is selected from hydroxymethyl, (S)-hydroxymethyl, (R)-hydroxymethyl, ethyl, (S)-ethyl, (R)-ethyl, 2-hydroxyethyl, (R)-2-hydroxyethyl, (S)-2-hydroxyethyl, 1-hydroxyethyl, 3-fluoropyrrolidin-3-yl, (R)-3-fluoropyrrolidin-3-yl, (S)-3-fluoropyrrolidin-3-yl, 1-methyl-1H-pyrazol-4-yl, (S)-1-methyl-1H-pyrazol-4-yl, (R)-1-methyl-1H-pyrazol-4-yl, 1-methyl-1H-pyrazol-5-yl, (S)-1-methyl-1H-pyrazol-5-yl, (R)-1-methyl-1H-pyrazol-5-yl, 1-methyl-1H-imidazol-5-yl, (S)-1-methyl-1H-imidazol-5-yl, (R)-1-methyl-1H-imidazol-5-yl, 1-methyl-1H-pyrazol- 3-yl, (S)-1-methyl-1H-pyrazol-3-yl and (R)-1-methyl-1H-pyrazol-3-yl, In certain embodiments, $R^1$ is selected from hydroxymethyl, (S)-hydroxymethyl, ethyl, (S)-ethyl, 2-hydroxyethyl, (R)-2-hydroxyethyl, 1-hydroxyethyl, 3-fluoropyrrolidin-3-yl, (R)-3-fluoropyrrolidin-3-yl, (S)-3-fluoropyrrolidin-3-yl, 1-methyl-1H-pyrazol-4-yl, (S)-1-methyl-1H-pyrazol-4-yl, 1-methyl-1H-pyrazol-5-yl, (S)-1-methyl-1H-pyrazol-5-yl, 1-methyl-1H-imidazol-5-yl, (S)-1-methyl-1H-imidazol-5-yl, (R)-1-methyl-1H-imidazol-5-yl, 1-methyl-1H-pyrazol-3-yl, (S)-1-methyl-1H-pyrazol-3-yl and (R)-1-methyl-1H-pyrazol-3-yl, In certain embodiments, $R^1$ is selected from hydroxymethyl, ethyl, 2-hydroxyethyl, 1-hydroxyethyl, 3-fluoropyrrolidin-3-yl, 1-methyl-1H-pyrazol-4-yl, 1-methyl-1H-pyrazol-5-yl, 1-methyl-1H-imidazol-5-yl and 1-methyl-1H-pyrazol-3-yl.

In certain embodiments, $R^2$ is selected from (a) $C_{1-10}$ hydroxyalkyl; (b) $C_{1-6}$ haloalkyl; (c) heterocyclyl wherein said heterocyclyl is selected from the group consisting of tetrahydropyranyl, tetrahydrofuranyl, 2-oxabicyclo[2.2.1]heptan-5-yl and pyrrolidinyl and wherein said heterocyclyl is optionally substituted by 1 to 3 groups independently selected from the group consisting of halogen, $C_{1-3}$ hydroxyalkyl and oxo; (d) heteroaryl wherein said heteroaryl is selected from the group consisting of pyrazolyl and pyridinyl and wherein said heteroaryl is optionally substituted with 1 or 2 $C_{1-3}$ alkyl groups; and (e) $C_{3-7}$ cycloalkyl-$C_{1-6}$ alkyl optionally substituted with hydroxyl. In certain embodiments, $R^2$ is selected from (a) $C_{1-10}$ hydroxyalkyl; (b) $C_{1-6}$ haloalkyl; (c) heterocyclyl wherein said heterocyclyl is selected from the group consisting of tetrahydropyranyl, tetrahydrofuranyl, 2-oxabicyclo[2.2.1]heptan-5-yl and pyrrolidinyl and wherein said heterocyclyl is optionally substituted by 1 to 3 groups independently selected from the group consisting of halogen, $C_{1-3}$ hydroxyalkyl and oxo; (d) heteroaryl wherein said heteroaryl is selected from the group consisting of pyrazolyl and pyridinyl and wherein said heteroaryl is optionally substituted with 1 or 2 methyl groups; and (e) $C_{3-7}$ cycloalkyl-$C_{1-6}$ alkyl optionally substituted with hydroxyl. In certain embodiments, $R^2$ is selected from the group consisting of 1-hydroxypropan-2-yl, (S)-1-hydroxypropan-2-yl, 3-hydroxy-3-methylbutan-2-yl, (S)-3-hydroxy-3-methylbutan-2-yl, (R)-3-hydroxy-3-methylbutan-2-yl, 3-fluoropropyl, 5-oxopyrrolidin-3-yl, tetrahydropyran-4-yl, 3-fluorotetrahydropyran-4-yl, (3S,4S)-3-fluorotetrahydropyran-4-yl, (3R,4R)-3-fluorotetrahydropyran-4-yl, 2-(hydroxymethyl)tetrahydropyran-4-yl, (2S,4R)-2-(hydroxymethyl)tetrahydropyran-4-yl, 2-oxabicyclo[2.2.1]heptan-5-yl, tetrahydrofuran-3-yl, 1-methyl-1H-pyrazol-5-yl, 2-methylpyridin-4-yl, 1,3-dimethyl-1H-pyrazol-5-yl, 1-(1-hydroxycyclopropyl)ethyl and (S)-1-(1-hydroxycyclopropyl)ethyl.

In another embodiment of the present invention there is provided a compound according to formula I wherein X is N or CH and $R^2$ is (a) $C_{1-10}$ hydroxyalkyl, (b) heterocyclyl wherein said heterocyclyl is tetrahydropyranyl or tetrahydropyranyl, optionally substituted by 1 to 3 groups independently selected from $C_{1-6}$ alkyl, halogen, or $C_{1-3}$ hydroxyalkyl or (c) heteroaryl wherein said heteroaryl is pyrazolyl or pyridinyl optionally substituted by 1 to 3 $C_{1-6}$ alkyl moieties. In one subembodiment X is N. In another subembodiment X is CH. In another subembodiment $R^2$ is N—$C_{1-3}$ alkyl-pyrazolyl optionally substituted by 1 to 3 $C_{1-6}$ alkyl moieties. In yet another subembodiment $R^2$ is N-methyl-pyrazolyl optionally substituted by 1 to 3 $C_{1-6}$ alkyl moieties.

In another embodiment of the present invention there is provided a compound according to formula I wherein X is N or CH and $R^2$ is 1-methyl-1H-pyrazol-4-yl, 2-methyl-2H-pyrazol-3-yl, 2,5-dimethyl-2H-pyrazol-3-yl, tetrahydropyran-4-yl, 3-fluoro-tetrahydropyran-4-yl, tetrahydrofuran-3-yl or 2-hydroxy-1-methyl-ethyl.

In another embodiment of the present invention there is provided a compound according to formula I wherein X is N or CH; $R^2$ is 1-methyl-1H-pyrazol-4-yl, 2-methyl-2H-pyrazol-3-yl, 2,5-dimethyl-2H-pyrazol-3-yl, tetrahydropyran-4-yl, 3-fluoro-tetrahydropyran-4-yl, tetrahydrofuran-3-yl or 2-hydroxy-1-methyl-ethyl; and, Ar is phenyl optionally substituted by 1 or 2 groups independently selected from $C_{1-6}$ alkoxy, halogen, $C_{1-6}$ haloalkoxy or cyano. In one subembodiment X is N. In another subembodiment X is CH.

In another embodiment of the present invention there is provided a compound according to formula I, wherein X is N or CH and Ar is phenyl optionally substituted by 1 or 2 groups independently selected from $C_{1-6}$ alkoxy, halogen, $C_{1-6}$ haloalkoxy or cyano. In one subembodiment X is N. In another subembodiment X is CH.

In another embodiment of the present invention there is provided a compound according to formula I, wherein X is N or CH and $R^1$ is (R)-ethyl, (S)-2-hydroxymethyl or (S)-1-methyl-1H-pyrazol-4-yl; $R^2$ is 1-methyl-1H-pyrazol-4-yl, 2-methyl-2H-pyrazol-3-yl, 2,5-dimethyl-2H-pyrazol-3-yl, tetrahydropyran-4-yl, 3-fluoro-tetrahydropyran-4-yl, tetrahydrofuran-3-yl or 2-hydroxy-1-methyl-ethyl; and, Ar is phenyl optionally substituted by 1 or 2 groups independently selected from $C_{1-6}$ alkoxy, halogen, $C_{1-6}$ haloalkoxy or cyano. In one subembodiment X is N. In another subembodiment X is CH.

In another embodiment of the present invention there is provided a compound according to formula I, wherein X is N or CH and $R^1$ is (R)-ethyl, (S)-2-hydroxymethyl or (S)-1-methyl-1H-pyrazol-4-yl; $R^2$ is 1-methyl-1H-pyrazol-4-yl, 2-methyl-2H-pyrazol-3-yl, or 2,5-dimethyl-2H-pyrazol-3-yl; and, Ar is phenyl optionally substituted by 1 or 2 groups independently selected from $C_{1-6}$ alkoxy, halogen, $C_{1-6}$ haloalkoxy or cyano. In one subembodiment X is N. In another subembodiment X is CH.

In certain embodiments, Ar is selected from phenyl, 3-fluorophenyl, 3-fluoro-4-methoxyphenyl, 4-chloro-3-fluorophenyl, 4-trifluoromethoxyphenyl, 3-chloro-4-cyanophenyl, 2-bromophenyl, 4-bromophenyl, 3-bromophenyl, 4-(1-methyl-1H-pyrazol-4-yl)phenyl, 4-(4-methylpyridin-3-yl)phenyl, 3-(4-methylpyridin-3-yl)phenyl, 3-(1-methyl-1H-pyrazol-4-yl)phenyl, 3-benzylphenyl, 4-(pyrimidin-5-yl)phenyl, 4-(pyrazin-5-yl)phenyl, 4-(pyridin-4-yl)phenyl, 3-(pyridin-4-yl)phenyl, 3-(pyrazin-2-yl)phenyl, 2-(1-methyl-1H-pyrazol-4-yl)phenyl, 3-phenoxyphenyl, 4-methoxyphenyl, 3-chloro-4-fluorophenyl, 4-(difluoromethoxy)phenyl, pyridin-2-yl, pyridin-3-yl, pyridin-4-yl, 5-benzylpyridin-3-yl, 4-benzylpyridin-2-yl, 4-(4-methylpiperazin1-yl)pyridin-2-yl, 4-phenoxypyridin-2-yl, 2-benzylpyridin-3-yl, 4-(o-tolyl)pyridin-2-yl, 4-(2-chlorophenoxy)pyridin-2-yl and 4-fluoro-1H-indol-2-yl. In certain embodiments, Ar is selected from phenyl, 3-fluorophenyl, 3-fluoro-4-methoxyphenyl, 4-chloro-3-fluorophenyl, 4-trifluoromethoxyphenyl, 3-chloro-4-cyanophenyl, 2-bromophenyl, 4-bromophenyl, 3-bromophenyl, 4-(1-methyl-1H-pyrazol-4-yl)phenyl, 4-(4-methylpyridin-3-yl)phenyl, 3-(4-methylpyridin-3-yl)phenyl, 3-(1-methyl-1H-pyrazol-4-yl)phenyl, 3-benzylphenyl, 4-(pyrimidin-5-yl)phenyl, 4-(pyrazin-5-yl)phenyl, 4-(pyridin-4-yl)phenyl, 3-(pyridin-4-yl)phenyl, 3-(pyrazin-2-yl)phenyl, 2-(1-methyl-1H-pyrazol-4-yl)phenyl, 3-phenoxyphenyl, 4-methoxyphenyl, 3-chloro-4-fluorophenyl and 4-(difluoromethoxy)phenyl. In certain embodiments, Ar is selected from pyridin-2-yl, pyridin-3-yl, pyridin-4-yl, 5-benzylpyridin-3-yl, 4-benzylpyridin-2-yl, 4-(4-methylpiperazin1-yl)pyridin-2-yl, 4-phenoxypyridin-2-yl, 2-benzylpyridin-3-yl, 4-(o-tolyl)pyridin-2-yl and 4-(2-chlorophenoxy)pyridin-2-yl. In certain embodiments, Ar is selected from 4-fluoro-1H-indol-2-yl.

In another embodiment of the present invention there is provided a compound according to formula I, wherein Ar is selected from 3-fluorophenyl, 3-fluoro-4-methoxy-phenyl, 4-chloro-3-fluoro-phenyl, 4-trifluoromethoxy-phenyl, 3-chloro-4-cyano-phenyl, 4-methoxy-phenyl and 4-difluoromethoxy-phenyl.

In another embodiment of the present invention there is provided a compound according to formula I, wherein X is N or CH and $R^1$ is (R)-ethyl, (S)-2-hydroxymethyl or (S)-1-methyl-1H-pyrazol-4-yl; $R^2$ is 1-methyl-1H-pyrazol-4-yl, 2-methyl-2H-pyrazol-3-yl, or 2,5-dimethyl-2H-pyrazol-3-yl; and, Ar is 3-fluorophenyl, 3-fluoro-4-methoxy-phenyl, 4-chloro-3-fluoro-phenyl, 4-trifluoromethoxy-phenyl, 3-chloro-4-cyano-phenyl, 4-methoxy-phenyl or 4-difluoromethoxy-phenyl. In one subembodiment X is N. In another subembodiment X is CH.

In another embodiment of the present invention there is provided a compound according to formula I wherein X is N or CH and Z is $NH(CH_2)_n CHR^1 Ar$ wherein n is 0. In one subembodiment X is N. In another subembodiment X is CH.

In another embodiment of the present invention there is provided a compound according formula I wherein $R^1$ is 1-alkyl-4-aryl-pyrrolidin-3-ylamine. In one subembodiment X is N. In another subembodiment X is CH. In another subembodiment X is N and alkyl is methyl. In another subembodiment X is CH and alkyl is methyl.

In certain embodiments, Z is $NH(CH_2)_n CHR^1 Ar$, n is 1, and $R^1$ is hydrogen. In certain embodiments, X is N, Z is $NH(CH_2)CHR^1 Ar$, n is 1, and $R^1$ is hydrogen.

In certain embodiments, X is CH, Z is (i) NH $(CH_2)_n CHR^1 Ar$ wherein n is 0, or (ii) 1-alkyl-4-aryl-pyrrolidin-3-ylamine or 4-aryl-pyrrolidin-3-ylamine, wherein alkyl is $C_{1-3}$ alkyl optionally substituted by a phenyl ring and aryl is optionally substituted phenyl.

In certain embodiments:

$R^1$ is selected from (a) hydrogen; (b) $C_1$-$C_6$ alkyl optionally substituted with one hydroxyl group; (c) a 4 to 6 membered heterocycle with one or two heteroatoms selected from N and O and wherein the heterocycle is optionally substituted with halogen; and (d) a 5 to 6 membered heteroaryl with one or two heteroatoms selected from N and O and wherein the heteroaryl is optionally substituted with $C_{1-6}$ alkyl;

$R^2$ is selected from (a) $C_{1-10}$ hydroxyalkyl; (b) $C_{1-6}$ haloalkyl; (c) heterocyclyl wherein said heterocyclyl is selected from the group consisting of tetrahydropyranyl, tetrahydrofuranyl, 2-oxabicyclo[2.2.1]heptan-5-yl and pyrrolidinyl and wherein said heterocyclyl is optionally substituted with halogen, $C_{1-3}$ hydroxyalkyl or oxo; (d) heteroaryl wherein said heteroaryl is selected from the group consisting of pyrazolyl and pyridinyl and wherein said heteroaryl is optionally substituted with 1 or 2 $C_{1-3}$ alkyl groups; and (e) $C_{3-7}$ cycloalkyl-$C_{1-6}$ alkyl optionally substituted with hydroxyl.

In certain embodiments:

$R^1$ is selected from hydrogen, hydroxymethyl, (S)-hydroxymethyl, ethyl, (S)-ethyl, 2-hydroxyethyl, (R)-2-hydroxyethyl, 1-hydroxyethyl, 3-fluoropyrrolidin-3-yl, (R)-3-fluoropyrrolidin-3-yl, (S)-3-fluoropyrrolidin-3-yl, 1-methyl-1H-pyrazol-4-yl, (S)-1-methyl-1H-pyrazol-4-yl, 1-methyl-1H-pyrazol-5-yl, (S)-1-methyl-1H-pyrazol-5-yl, 1-methyl-1H-imidazol-5-yl, (S)-1-methyl-1H-imidazol-5-yl, (R)-1-methyl-1H-imidazol-5-yl, 1-methyl-1H-pyrazol-3-yl, (S)-1-methyl-1H-pyrazol-3-yl and (R)-1-methyl-1H-pyrazol-3-yl;

$R^2$ is selected from the group consisting of 1-hydroxypropan-2-yl, (S)-1-hydroxypropan-2-yl, 3-hydroxy-3-methylbutan-2-yl, (S)-3-hydroxy-3-methylbutan-2-yl, (R)-3-hydroxy-3-methylbutan-2-yl, 3-fluoropropyl, 5-oxopyrrolidin-3-yl, tetrahydropyran-4-yl, 3-fluorotetrahydropyran-4-yl, (3S,4S)-3-fluorotetrahydropyran-4-yl, (3R,4S)-3-fluorotetrahydropyran-4-yl, 2-(hydroxymethyl)tetrahydropyran-4-yl, (2S,4R)-2-(hydroxymethyl)tetrahydropyran-4-yl, 2-oxabicyclo [2.2.1]heptan-5-yl, tetrahydrofuran-3-yl, 1-methyl-1H-pyrazol-5-yl, 2-methylpyridin-4-yl, 1,3-dimethyl-1H-pyrazol-5-yl, 1-(1-hydroxycyclopropyl)ethyl and (S)-1-(1-hydroxycyclopropyl)ethyl.

In another embodiment of the present invention there is provided a compound is selected from compounds I-1 to I-61 in TABLE I and II-1 to II-69 in TABLE II or a pharmaceutically acceptable salt thereof. In another embodiment of the present invention there is provided a compound is selected from compounds I-1 to I-61 in TABLE I or a pharmaceutically acceptable salt thereof. In another embodiment of the present invention there is provided a compound is selected from compounds II-1 to II-69 in TABLE II or a pharmaceutically acceptable salt thereof.

In another embodiment of the present invention there is provided a pharmaceutical composition containing a compound according to formula I wherein $R^2$, Ar, X and Z are as defined hereinabove and at least one pharmaceutically acceptable carrier, excipient or diluent.

In another embodiment of the present invention there is provided a method of inhibiting ERK protein kinase activity in a cell comprising treating the cell with a compound according to formula I wherein $R^1$, $R^2$, Ar, X and Z are as defined hereinabove and at least one pharmaceutically acceptable carrier, excipient or diluent.

In another embodiment of the present invention there is provided a method of inhibiting ERK protein kinase activity in a patient in need thereof comprising administering to the patient a compound according to formula I wherein $R^1$, $R^2$, Ar, X and Z are as defined hereinabove and at least one pharmaceutically acceptable carrier, excipient or diluent.

In another embodiment of the present invention there is provided a method of treating or ameliorating the severity of a hyperproliferative disorder in a patient in need thereof comprising administering to the patient a compound according to formula I wherein $R^1$, $R^2$, Ar, X and Z are as defined hereinabove and at least one pharmaceutically acceptable carrier, excipient or diluent.

In another embodiment of the present invention there is provided a method of treating or ameliorating the severity of a hyperproliferative disorder selected from the group consisting of adenoma, bladder cancer, brain cancer, breast cancer, colon cancer, epidermal carcinoma, follicular carcinoma, cancer of the genitourinary tract, glioblastoma, Hodgkin's disease, head and neck cancers, hepatoma, keratoacanthoma, kidney cancer, large cell carcinoma, leukemias, lung adenocarcinoma, lung cancer, lymphoid disorders, melanoma and non-melanoma skin cancer, myelodysplastic syndrome, neuroblastoma, non-Hodgkins lymphoma, ovarian cancer, papillary carcinoma, pancreatic cancer, prostate cancer, rectal cancer, sarcoma, small cell carcinoma, testicular cancer, tetracarcinomas, thyroid cancer, and undifferentiated carcinoma in a patient in need thereof comprising administering to the patient a compound according to formula I wherein $R^1 R^2$, Ar, X and Z are as defined hereinabove and at least one pharmaceutically acceptable carrier, excipient or diluent.

In another embodiment of the present invention there is provided a method of treating or ameliorating the severity of a hyperproliferative disorder selected from the group consisting of melanoma, pancreatic cancer, thyroid cancer colorectal cancer, lung cancer, breast cancer and ovarian cancer in a patient in need thereof comprising administering to the patient a compound according to formula I wherein $R^1$, $R^2$, Ar, X and Z are as defined hereinabove and at least one pharmaceutically acceptable carrier, excipient or diluent.

In another embodiment of the present invention there is provided a method of treating or ameliorating the severity of a hyperproliferative disorder selected from the group consisting of acute myelogenous leukemia, chronic myelomonocytic leukemia, chronic myelogenous leukemia, multiple myeloma and myeloid leukemia in a patient in need thereof comprising administering to the patient a compound according to formula I wherein $R^1$, $R^2$, Ar, X and Z are as defined hereinabove and at least one pharmaceutically acceptable carrier, excipient or diluent.

In another embodiment of the present invention there is provided a method of treating or ameliorating the severity of a hyperproliferative disorder in a patient in need thereof comprising co-administering to the patient a compound according to formula I wherein $R^1$, $R^2$, Ar, X and Z are as defined hereinabove and at least one other chemotherapeutic agent used.

Another embodiment of the present invention provides the use a compound of formula I wherein $R^1$, $R^2$, Ar, X and Z are as defined hereinabove in the manufacture of a medicament for the treatment of a hyperproliferative disease.

Another embodiment of the present invention provides the use a compound of formula I wherein $R^1$, $R^2$, Ar, X and Z are as a medicament.

Another embodiment of the present invention provides the use a compound of formula I wherein $R^1$, $R^2$, Ar, X and Z in therapy.

Another embodiment of the present invention provides the use a compound of formula I wherein $R^1$, $R^2$, Ar, X and Z in the treatment of a cancer.

In another embodiment of the present invention there is provided a pharmaceutical composition for use in the treatment of a hyperproliferative disease containing a compound according to formula I wherein $R^1$, $R^2$, Ar, X and Z are as defined hereinabove and at least one pharmaceutically acceptable carrier, excipient or diluent.

Commonly used abbreviations include: acetyl (Ac), aqueous (aq.), atmospheres (Atm), 2,2'-bis(diphenylphosphino)-1,1'-binaphthyl (BINAP), tert-butoxycarbonyl (Boc), di-tert-butyl pyrocarbonate or boc anhydride ($BOC_2O$), benzyl (Bn), butyl (Bu), Chemical Abstracts Registration Number (CASRN), benzyloxycarbonyl (CBZ or Z), carbonyl diimidazole (CDI), 1,5-diazabicyclo[4.3.0]non-5-ene (DBN), 1,8-diazabicyclo[5.4.0]undec-7-ene (DBU), N,N'-dicyclohexyl-carbodiimide (DCC), 1,2-dichloroethane (DCE), dichloromethane (DCM), diethyl azodicarboxylate (DEAD), di-iso-propylazodicarboxylate (DIAD), di-iso-butylaluminumhydride (DIBAL or DIBAL-H), di-iso-propylethylamine (DIPEA), diphenylphosphoryl azide (DPPA)N,N-dimethyl acetamide (DMA), 4-N,N-dimethylaminopyridine (DMAP), N,N-dimethylformamide (DMF), dimethyl sulfoxide (DMSO), 1-(3-dimethylaminopropyl)-3-ethylcarbodiimide hydrochloride (EDCI), ethyl (Et), ethyl acetate (EtOAc), ethanol (EtOH), 2-ethoxy-2H-quinoline-1-carboxylic acid ethyl ester (EEDQ), diethyl ether ($Et_2O$), O-(7-azabenzotriazole-1-yl)-N,N,N'N'-tetramethyluronium hexafluorophosphate acetic acid (HATU), acetic acid (HOAc), 1-hydroxy-7-aza-benzotriazole (HOAt), 1-N-hydroxybenzotriazole (HOBt), high pressure liquid chromatography (HPLC), isopropanol (IPA), lithium diisopropylamide (LDA), methanol (MeOH), melting point (mp), $MeSO_2$— (mesyl or Ms), methyl (Me), acetonitrile (MeCN), m-chloroperbenzoic acid (MCPBA), mass spectrum (ms), methyl tert-butyl ether (MTBE), N-methylmorpholine (NMM), N-methylpyrrolidone (NMP), not available (N/A), phenyl (Ph), propyl (Pr), iso-propyl (i-Pr), pounds per square inch (psi), pyridine (pyr), room temperature (rt or RT), saturated (satd.), tert-butyldimethylsilyl or t-$BuMe_2Si$ (TBDMS), tetrabutyl ammonium fluoride (TBAF), triethylamine (TEA or $Et_3N$), triflate or $CF_3SO_2$— (Tf), trifluoroacetic acid (TFA), O-benzotriazol-1-yl-N,N,N',N'-tetramethyluronium tetrafluoroborate (TBTU), thin layer chromatography (TLC), tetrahydrofuran (THF), tetramethylethylenediamine (TMEDA), trimethylsilyl or $Me_3Si$ (TMS), p-toluenesulfonic acid monohydrate (TsOH or pTsOH), 4-Me-$C_6H_4SO_2$— or tosyl (Ts), N-urethane-N-carboxyanhydride (UNCA). Conventional nomenclature including the prefixes normal (n-), iso (i-), secondary (sec-), tertiary (tert-) and neo- have their customary meaning when used with an alkyl moiety. (J. Rigaudy and D. P. Klesney, Nomenclature in Organic Chemistry, IUPAC 1979 Pergamon Press, Oxford.).

Compounds and Preparation

Examples of representative compounds within the scope of the invention are provided in the following Tables. These examples and preparations which follow are provided to enable those skilled in the art to more clearly understand and to practice the present invention. They should not be considered as limiting the scope of the invention, but merely as being illustrative and representative thereof.

If there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it. The following numbering system is used herein.

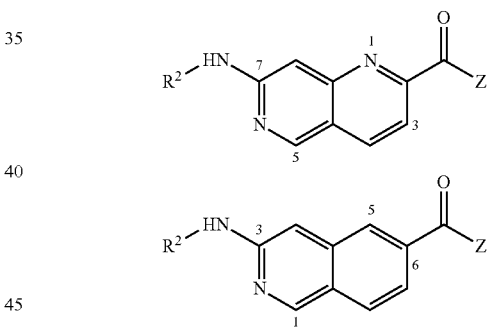

Table I depicts examples naphthyridines within the scope of the present claims.

TABLE I

| Cpd. No. | Structure | Retention Time (conditions) | mass spec |
|---|---|---|---|
| I-1 | (structure shown) | 9.26 (G) | 435.2 |

TABLE I-continued

| Cpd. No. | Structure | Retention Time (conditions) | mass spec |
|---|---|---|---|
| I-2 | 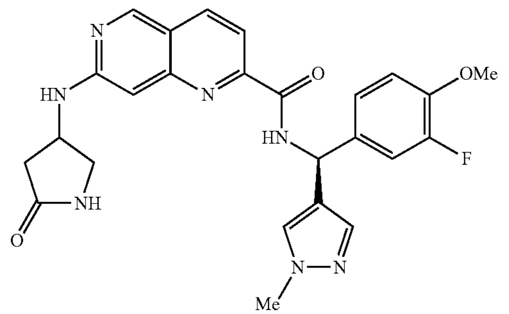 [SMILES: COc1ccc([C@H](NC(=O)c2ccc3cnc(NC4CNC(=O)C4)cc3n2)c2cnn(C)c2)cc1F] | 3.77 (E) | 490.1 |
| I-3 | 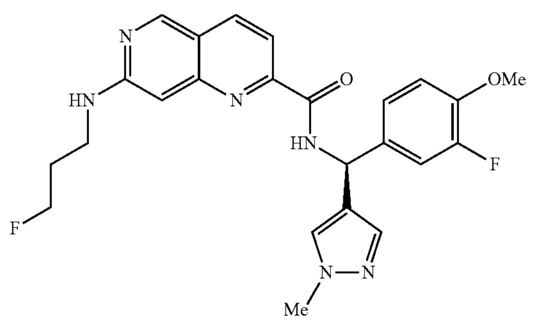 [SMILES: COc1ccc([C@H](NC(=O)c2ccc3cnc(NCCCF)cc3n2)c2cnn(C)c2)cc1F] | 4.33 (E) | 467.13 |
| I-4 | 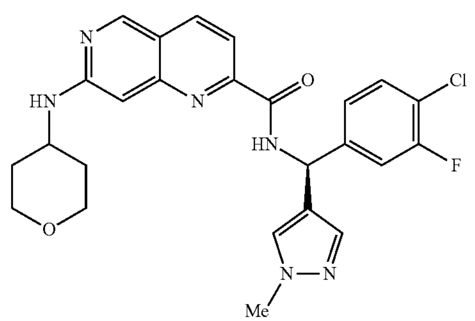 [SMILES: Cn1cc([C@@H](NC(=O)c2ccc3cnc(NC4CCOCC4)cc3n2)c2ccc(Cl)c(F)c2)cn1] | 4.59 (E) | 495.1 |
| I-5 | 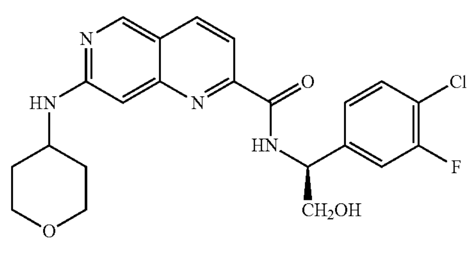 | 10.51 (G) | 445.1 |
| I-6 | 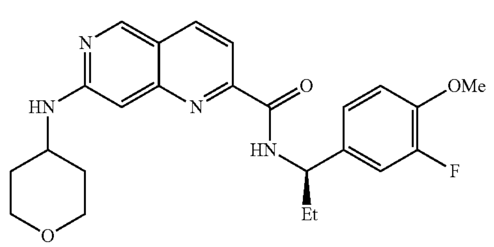 [SMILES: CC[C@@H](NC(=O)c1ccc2cnc(NC3CCOCC3)cc2n1)c1ccc(OC)c(F)c1] | 4.71 (E) | 439.1 |

TABLE I-continued

| Cpd. No. | Structure | Retention Time (conditions) | mass spec |
|---|---|---|---|
| I-7 | 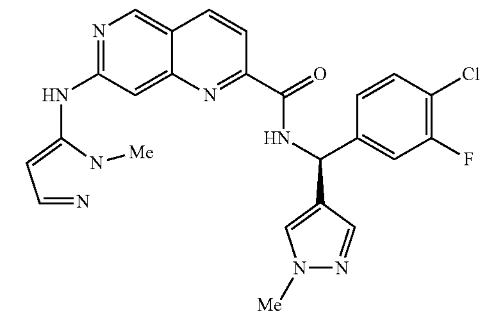 [SMILES: CN/C(=C\C=N)Nc1cc2nc(C(=O)N[C@@H](c3ccc(Cl)c(F)c3)c3cnn(C)c3)ccc2cn1] | 4.52 (E) | 491.0 |
| I-8 | 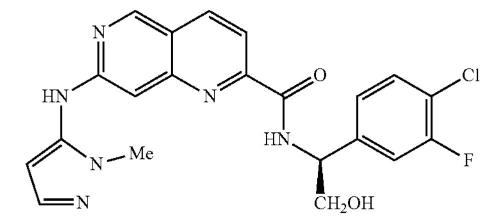 [SMILES: CN/C(=C\C=N)Nc1cc2nc(C(=O)N[C@H](CO)c3ccc(Cl)c(F)c3)ccc2cn1] | 4.22 (E) | 441.0 |
| I-9 | 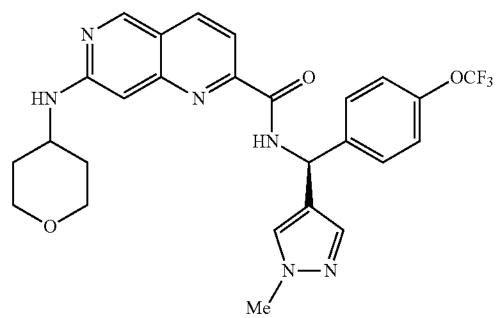 [SMILES: Cn1cc([C@@H](NC(=O)c2ccc3cnc(NC4CCOCC4)cc3n2)c2ccc(OC(F)(F)F)cc2)cn1] | 4.76 (E) | 527.11 |
| I-10 | 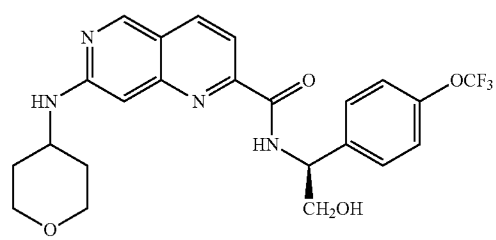 [SMILES: O=C(N[C@H](CO)c1ccc(OC(F)(F)F)cc1)c1ccc2cnc(NC3CCOCC3)cc2n1] | 4.45 (E) | 477.1 |
| I-11 | 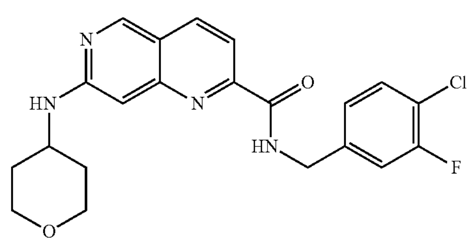 [SMILES: O=C(NCc1ccc(Cl)c(F)c1)c1ccc2cnc(NC3CCOCC3)cc2n1] | 4.70 (E) | 415.0 |
| I-12 | 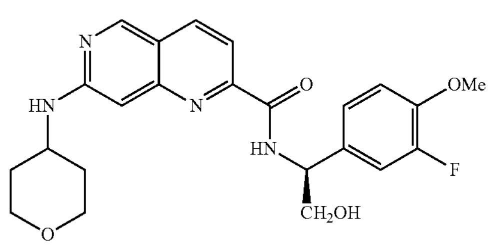 [SMILES: COc1ccc([C@@H](CO)NC(=O)c2ccc3cnc(NC4CCOCC4)cc3n2)cc1F] | 8.52 (E) | 441.2 |

TABLE I-continued

| Cpd. No. | Structure | Retention Time (conditions) | mass spec |
|---|---|---|---|
| I-13 | 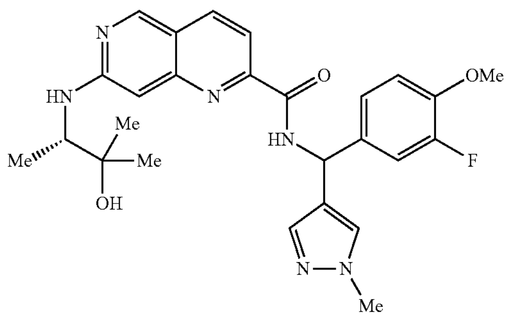 [SMILES: COc1ccc(C(NC(=O)c2ccc3cnc(N[C@@H](C)C(C)(C)O)cc3n2)c2cnn(C)c2)cc1F] | 9.92 (G) | 493.2 |
| I-14 | 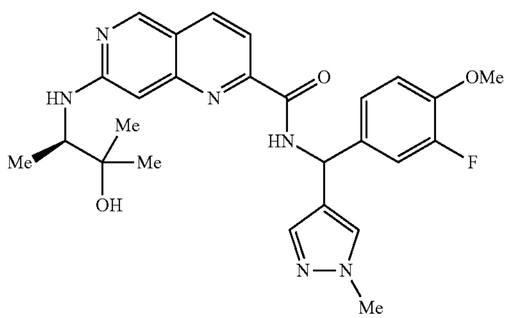 [SMILES: COc1ccc(C(NC(=O)c2ccc3cnc(N[C@H](C)C(C)(C)O)cc3n2)c2cnn(C)c2)cc1F] | 9.86 (G) | 493.2 |
| I-15 | 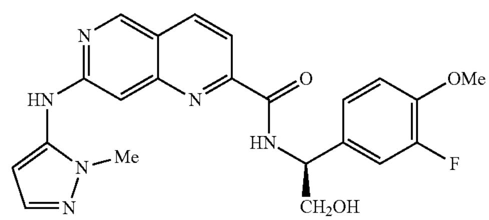 [SMILES: COc1ccc([C@@H](CO)NC(=O)c2ccc3cnc(Nc4ccnn4C)cc3n2)cc1F] | 3.79 (E) | 437.1 |
| I-16 | Isomer A | 10.10 (G) | 503.2 |
| I-17 | 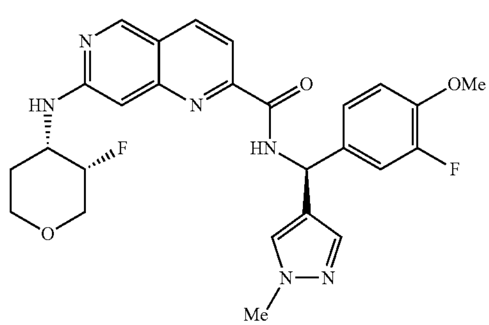 [SMILES: COc1ccc([C@H](NC(=O)c2ccc3cnc(N[C@H]4CCOC[C@H]4F)cc3n2)c2cnn(C)c2)cc1F] | 10.69 (G) | 509.2 |

TABLE I-continued

| Cpd. No. | Structure | Retention Time (conditions) | mass spec |
|---|---|---|---|
| I-18 | 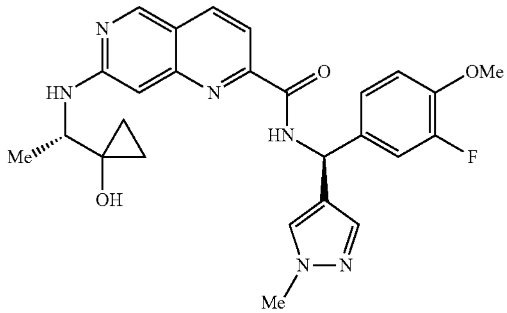 [SMILES: COc1ccc([C@H](NC(=O)c2ccc3cnc(N[C@@H](C)C4(O)CC4)cc3n2)c2cnn(C)c2)cc1F] | 6.12 (G) | 491.2 |
| I-19 | 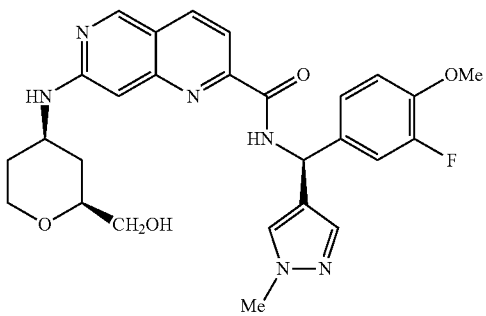 [SMILES: COc1ccc([C@H](NC(=O)c2ccc3cnc(N[C@@H]4CCO[C@H](CO)C4)cc3n2)c2cnn(C)c2)cc1F] | 5.46 (G) | 521.2 |
| I-20 | 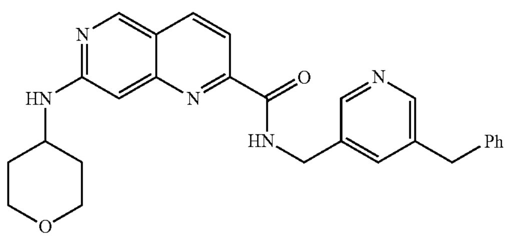 [SMILES: O=C(NCc1cncc(Cc2ccccc2)c1)c1ccc2cnc(NC3CCOCC3)cc2n1] | 3.58 (E) | 454.2 |
| I-21 | 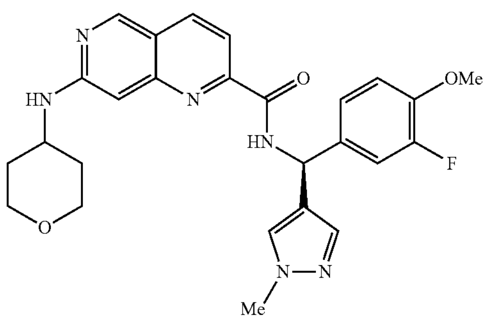 [SMILES: COc1ccc([C@H](NC(=O)c2ccc3cnc(NC4CCOCC4)cc3n2)c2cnn(C)c2)cc1F] | 9.97 (G) | 491.0 |
| I-22 | 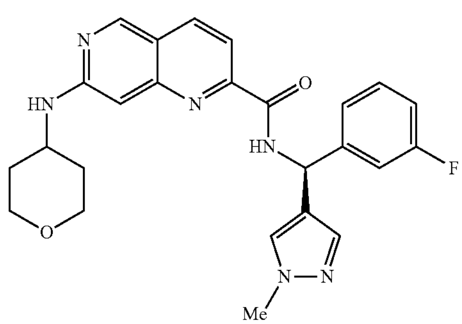 [SMILES: Cn1cc([C@@H](NC(=O)c2ccc3cnc(NC4CCOCC4)cc3n2)c2cccc(F)c2)cn1] | 10.21 (G) | 461.2 |

TABLE I-continued

| Cpd. No. | Structure | Retention Time (conditions) | mass spec |
|---|---|---|---|
| I-23 | Isomer B | | |
| I-24 | 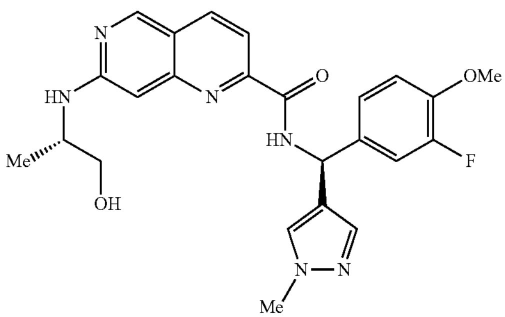 [SMILES: COc1ccc([C@H](NC(=O)c2ccc3cnc(N[C@@H](C)CO)cc3n2)c2cnn(C)c2)cc1F] | 8.97 (G) | 465.2 |
| I-25 | 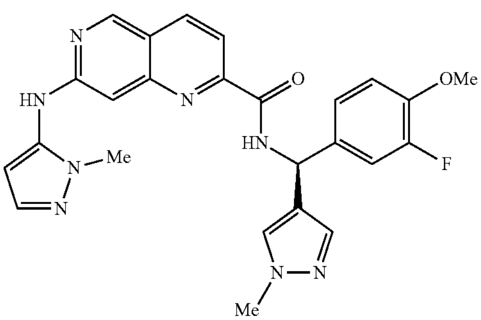 [SMILES: COc1ccc([C@H](NC(=O)c2ccc3cnc(Nc4ccnn4C)cc3n2)c2cnn(C)c2)cc1F] | 4.14 (E) | 487 |
| I-26 | 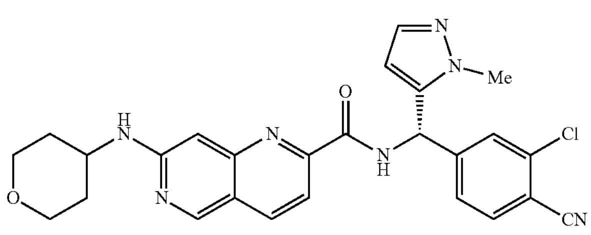 [SMILES: Cn1nccc1[C@@H](NC(=O)c1ccc2cnc(NC3CCOCC3)cc2n1)c1ccc(C#N)c(Cl)c1] | 5.41 (E) | 502.3 |
| I-27 | 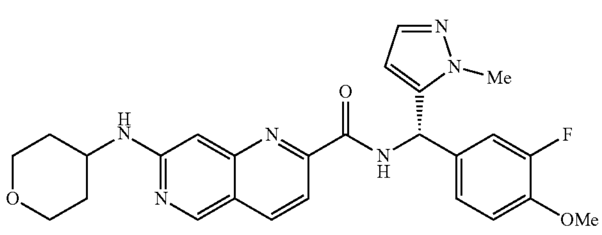 [SMILES: COc1ccc([C@H](NC(=O)c2ccc3cnc(NC4CCOCC4)cc3n2)c2ccnn2C)cc1F] | 5.27 (M) | 491.2 |

TABLE I-continued

| Cpd. No. | Structure | Retention Time (conditions) | mass spec |
|---|---|---|---|
| I-28 | 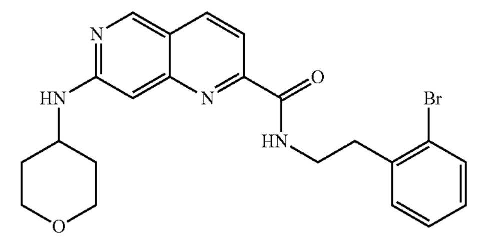 [SMILES: O=C(NCCc1ccccc1Br)c1ccc2cnc(NC3CCOCC3)cc2n1] | 4.70 (E) | 455.1 |
| I-29 | 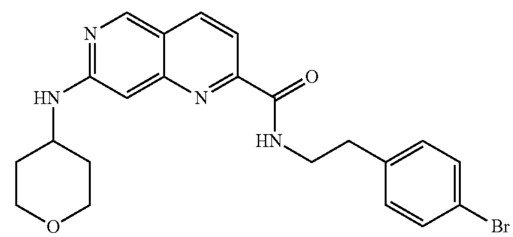 [SMILES: O=C(NCCc1ccc(Br)cc1)c1ccc2cnc(NC3CCOCC3)cc2n1] | 4.75 (E) | 455.1 |
| I-30 | 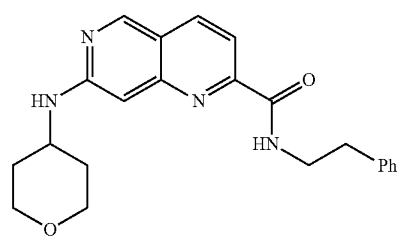 [SMILES: O=C(NCCc1ccccc1)c1ccc2cnc(NC3CCOCC3)cc2n1] | 4.33 (E) | 377.2 |
| I-31 | 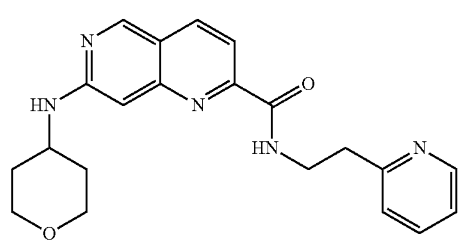 [SMILES: O=C(NCCc1ccccn1)c1ccc2cnc(NC3CCOCC3)cc2n1] | 2.81 (E) | 378.2 |
| I-32 | 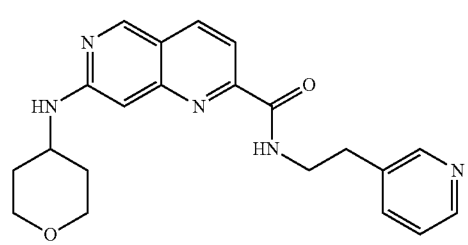 [SMILES: O=C(NCCc1cccnc1)c1ccc2cnc(NC3CCOCC3)cc2n1] | 2.80 (E) | 378.2 |
| I-33 | 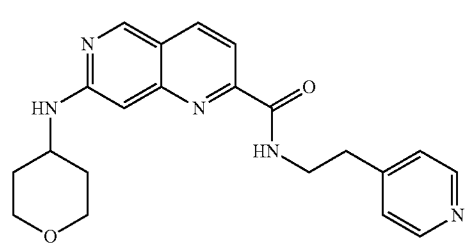 [SMILES: O=C(NCCc1ccncc1)c1ccc2cnc(NC3CCOCC3)cc2n1] | 2.80 (E) | 378.2 |

TABLE I-continued

| Cpd. No. | Structure | Retention Time (conditions) | mass spec |
|---|---|---|---|
| I-34 | 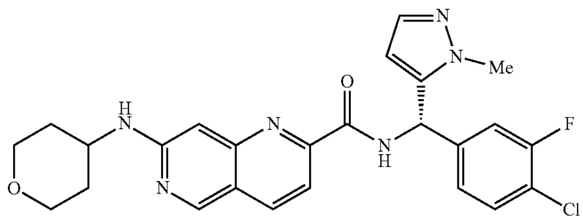 [SMILES: Cn1nccc1[C@@H](NC(=O)c1ccc2cnc(NC3CCOCC3)cc2n1)c1ccc(Cl)c(F)c1] | 5.87 (M) | 495.3 |
| I-35 | 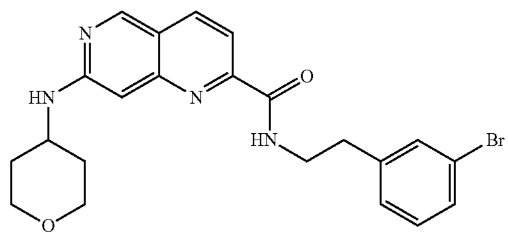 [SMILES: O=C(NCCc1cccc(Br)c1)c1ccc2cnc(NC3CCOCC3)cc2n1] | 4.72 (E) | 455.1 457.1 |
| I-36 | 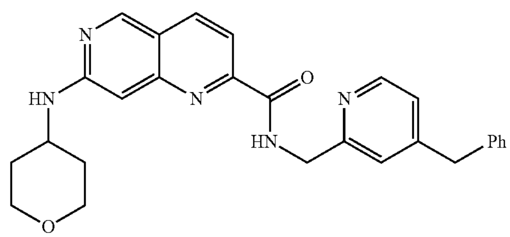 [SMILES: O=C(NCc1cc(Cc2ccccc2)ccn1)c1ccc2cnc(NC3CCOCC3)cc2n1] | 3.49 (E) | 454.2 |
| I-37 | 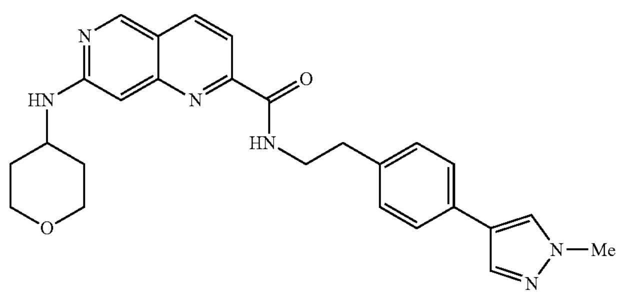 [SMILES: Cn1cc(-c2ccc(CCNC(=O)c3ccc4cnc(NC5CCOCC5)cc4n3)cc2)cn1] | 4.12 (E) | 457.2 |
| I-38 | 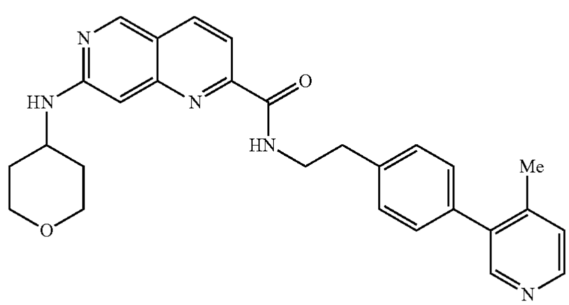 [SMILES: Cc1ccncc1-c1ccc(CCNC(=O)c2ccc3cnc(NC4CCOCC4)cc3n2)cc1] | 3.49 (E) | 468.2 |
| I-39 | 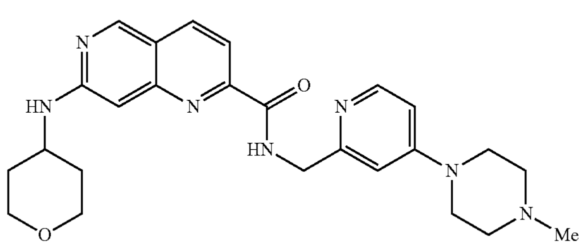 [SMILES: CN1CCN(c2ccnc(CNC(=O)c3ccc4cnc(NC5CCOCC5)cc4n3)c2)CC1] | | 462.2 |

TABLE I-continued

| Cpd. No. | Structure | Retention Time (conditions) | mass spec |
|---|---|---|---|
| I-40 | 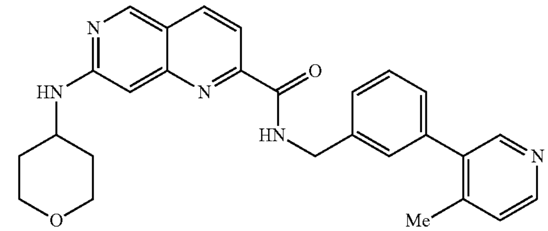 [SMILES: Cc1ccncc1-c1cccc(CNC(=O)c2ccc3cnc(NC4CCOCC4)cc3n2)c1] | 3.45 (E) | 454.2 |
| I-41 | 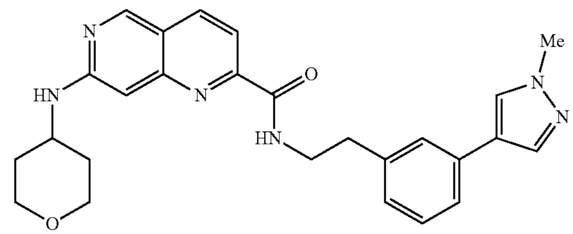 [SMILES: Cn1cc(-c2cccc(CCNC(=O)c3ccc4cnc(NC5CCOCC5)cc4n3)c2)cn1] | 4.13 (E) | 457.2 |
| I-42 | 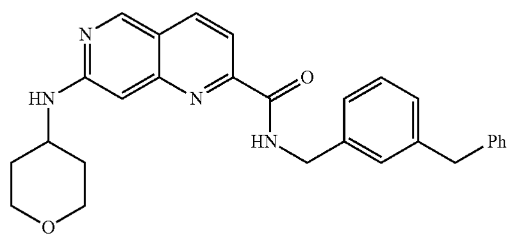 [SMILES: O=C(NCc1cccc(Cc2ccccc2)c1)c1ccc2cnc(NC3CCOCC3)cc2n1] | 5.18 (E) | 453.2 |
| I-43 | 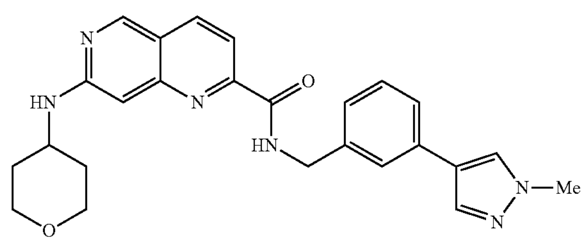 [SMILES: Cn1cc(-c2cccc(CNC(=O)c3ccc4cnc(NC5CCOCC5)cc4n3)c2)cn1] | 4.05 (E) | 443.2 |
| I-44 | 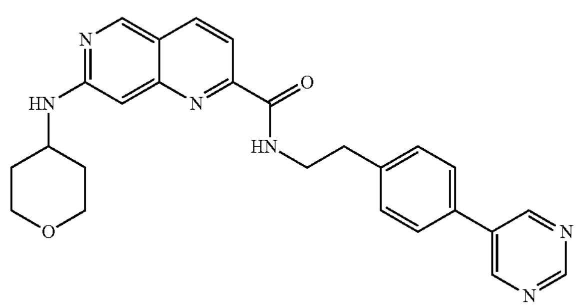 [SMILES: O=C(NCCc1ccc(-c2cncnc2)cc1)c1ccc2cnc(NC3CCOCC3)cc2n1] | 3.99 (E) | 455.2 |
| I-45 | 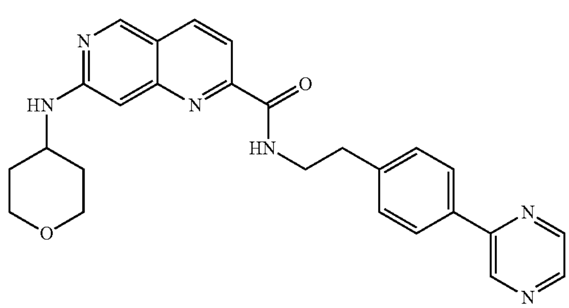 [SMILES: O=C(NCCc1ccc(-c2cnccn2)cc1)c1ccc2cnc(NC3CCOCC3)cc2n1] | 4.10 (E) | 455.2 |

TABLE I-continued

| Cpd. No. | Structure | Retention Time (conditions) | mass spec |
|---|---|---|---|
| I-46 | 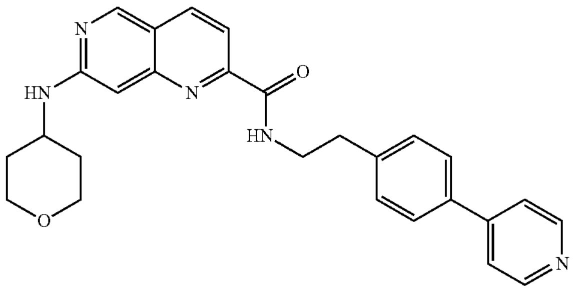 [SMILES: O=C(NCCc1ccc(-c2ccncc2)cc1)c1ccc2cnc(NC3CCOCC3)cc2n1] | 3.40 (E) | 454.2 |
| I-47 | 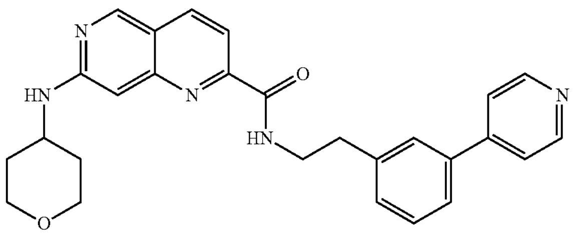 [SMILES: O=C(NCCc1cccc(-c2ccncc2)c1)c1ccc2cnc(NC3CCOCC3)cc2n1] | 3.44 (E) | 454.2 |
| I-48 | 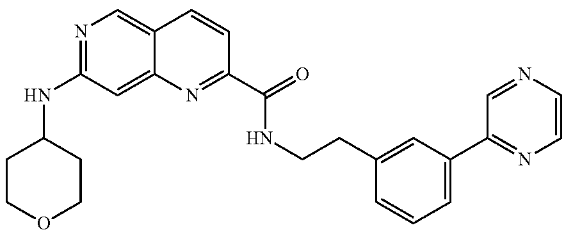 [SMILES: O=C(NCCc1cccc(-c2cnccn2)c1)c1ccc2cnc(NC3CCOCC3)cc2n1] | 4.08 (E) | 455.2 |
| I-49 | 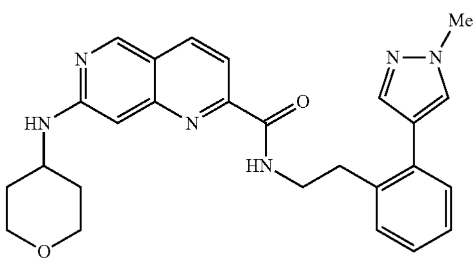 [SMILES: Cn1cc(-c2ccccc2CCNC(=O)c2ccc3cnc(NC4CCOCC4)cc3n2)cn1] | 4.20 (E) | 451.2 |
| I-50 | 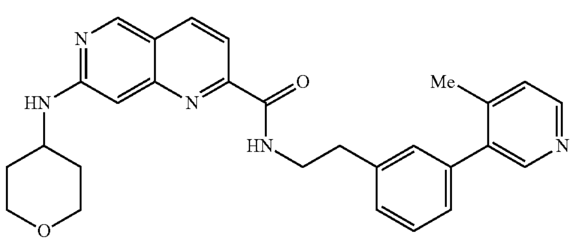 [SMILES: Cc1ccncc1-c1cccc(CCNC(=O)c2ccc3cnc(NC4CCOCC4)cc3n2)c1] | 3.54 (E) | 468.2 |
| I-51 | 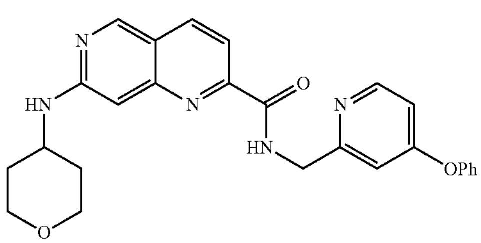 [SMILES: O=C(NCc1cc(Oc2ccccc2)ccn1)c1ccc2cnc(NC3CCOCC3)cc2n1] | 3.63 (E) | 456.2 |

TABLE I-continued
| Cpd. No. | Structure | Retention Time (conditions) | mass spec |
|---|---|---|---|
| I-52[1] | 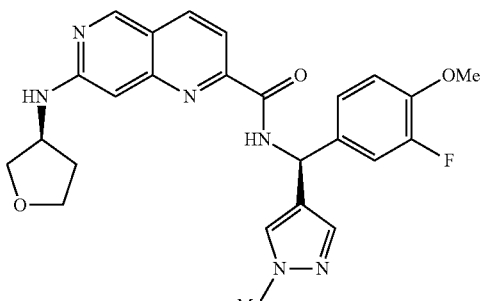 | 9.82 (G) | 477.2 |
| I-53[1] | 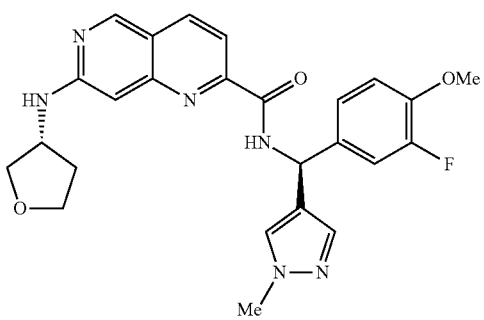 [SMILES: COc1ccc([C@H](NC(=O)c2ccc3cnc(N[C@@H]4CCOC4)cc3n2)c2cnn(C)c2)cc1F] | 9.77 (G) | 477.2 |
| I-54 | 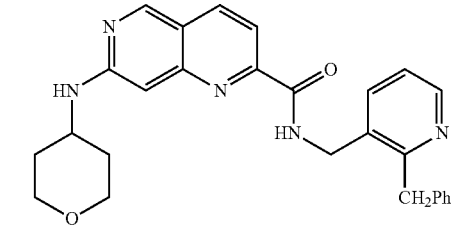 | 3.49 (E) | 454.2 |
| I-55 | 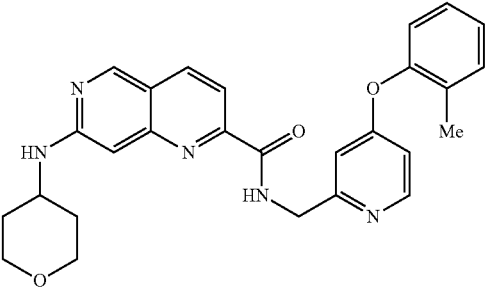 [SMILES: Cc1ccccc1Oc1ccnc(CNC(=O)c2ccc3cnc(NC4CCOCC4)cc3n2)c1] | 3.03 (E) | 470.2 |
| I-56 | 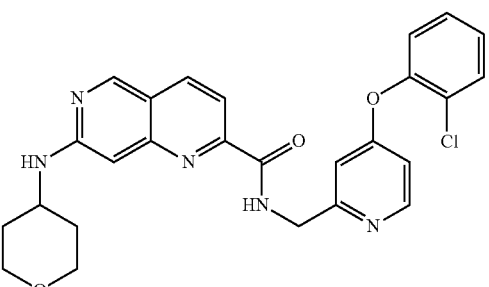 | 3.08 (E) | 455.2 |

TABLE I-continued

| Cpd. No. | Structure | Retention Time (conditions) | mass spec |
|---|---|---|---|
| I-57 | 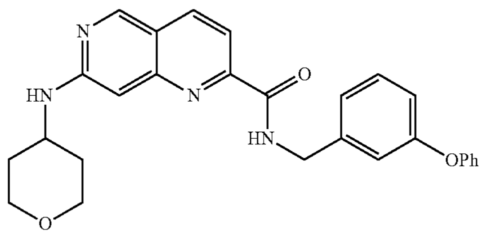 [SMILES: O=C(NCc1cccc(Oc2ccccc2)c1)c1ccc2cnc(NC3CCOCC3)cc2n1] | 4.48 (E) | 455.2 |
| I-58 | 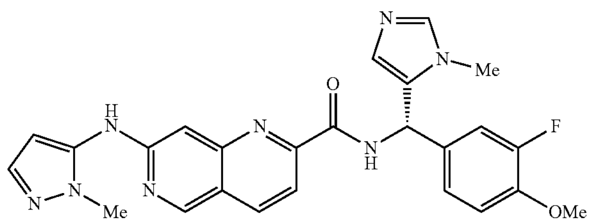 [SMILES: COc1ccc([C@H](NC(=O)c2ccc3cnc(Nc4ccnn4C)cc3n2)c2cncn2C)cc1F] | N/A | |
| I-59 | 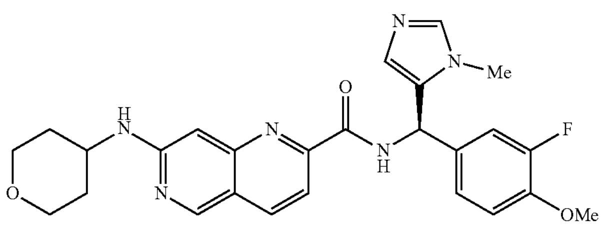 [SMILES: COc1ccc([C@@H](NC(=O)c2ccc3cnc(NC4CCOCC4)cc3n2)c2cncn2C)cc1F] | N/A | |
| I-60 | 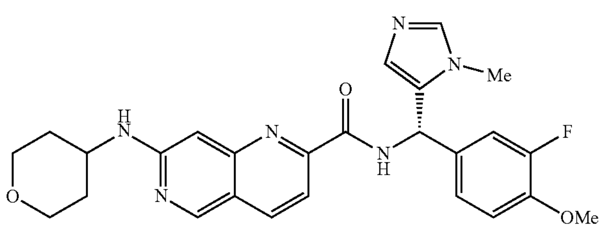 [SMILES: COc1ccc([C@H](NC(=O)c2ccc3cnc(NC4CCOCC4)cc3n2)c2cncn2C)cc1F] | N/A | |
| I-61 | 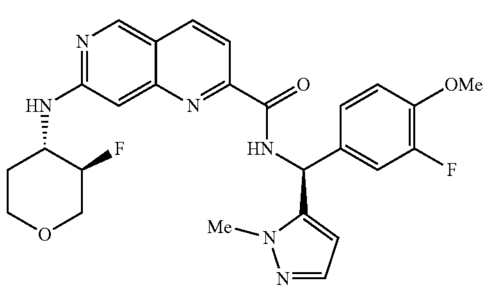 [SMILES: COc1ccc([C@H](NC(=O)c2ccc3cnc(N[C@H]4CCOC[C@@H]4F)cc3n2)c2ccnn2C)cc1F] | | 509.3 |

[1] Diasteromers-stereochemical assignment arbitrary

Table II depicts examples of isoquinolines within the scope of the present claims.
TABLE II
| | | | |
|---|---|---|---|
| II-1 | 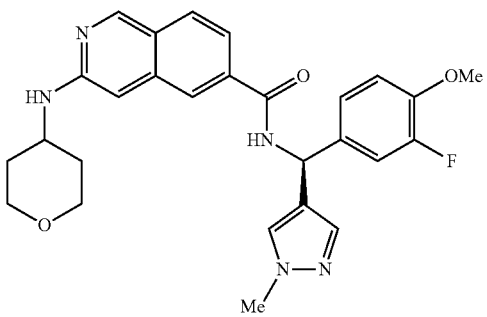 | 3.69 (E) | 490.2 |
| II-2 | 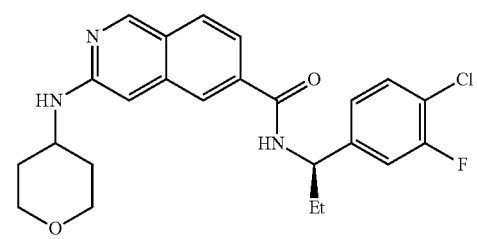 [SMILES: CC[C@@H](NC(=O)c1ccc2cnc(NC3CCOCC3)cc2c1)c1ccc(Cl)c(F)c1] | 3.74 (E) | 442.1 |
| II-3 | 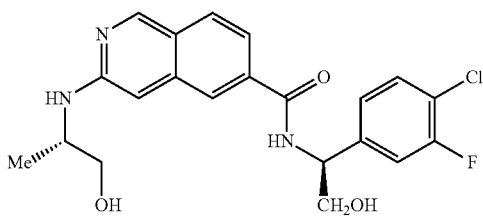 | 3.62 (E) | 418.1<br>420.1 |
| II-4 | 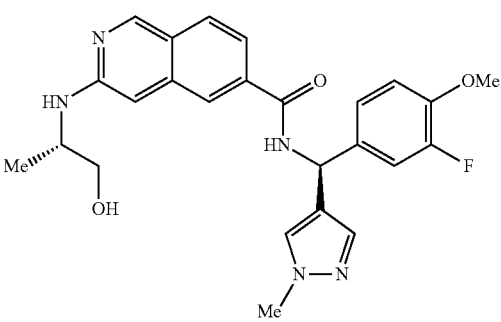 [SMILES: COc1ccc([C@H](NC(=O)c2ccc3cnc(N[C@@H](C)CO)cc3c2)c2cnn(C)c2)cc1F] | N/A | N/A |
| II-5 | 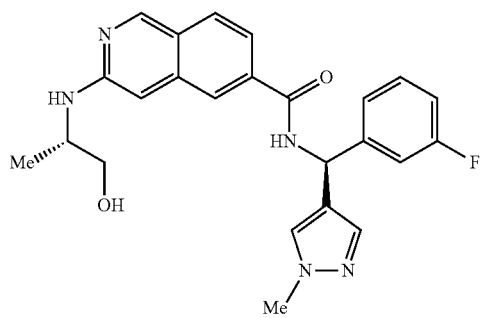 [SMILES: C[C@@H](CO)Nc1cc2cc(C(=O)N[C@@H](c3cccc(F)c3)c3cnn(C)c3)ccc2cn1] | 3.59 (E) | 434.4 |

TABLE II-continued
| | | | |
|---|---|---|---|
| II-6 | 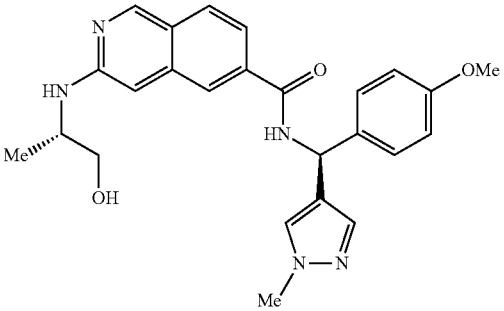 [SMILES: COc1ccc([C@H](NC(=O)c2ccc3cnc(N[C@@H](C)CO)cc3c2)c2cnn(C)c2)cc1] | 3.50 (E) | 445.514 |
| II-7 | 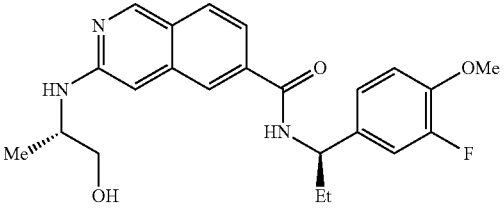 [SMILES: CC[C@@H](NC(=O)c1ccc2cnc(N[C@@H](C)CO)cc2c1)c1ccc(OC)c(F)c1] | 2.68 (H) | 412.2 |
| II-8 | 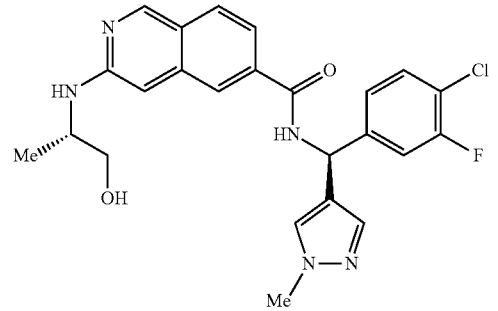 [SMILES: C[C@@H](CO)Nc1cc2cc(C(=O)N[C@@H](c3ccc(Cl)c(F)c3)c3cnn(C)c3)ccc2cn1] | 2.67 (H) | 468.1 470.1 |
| II-9 | 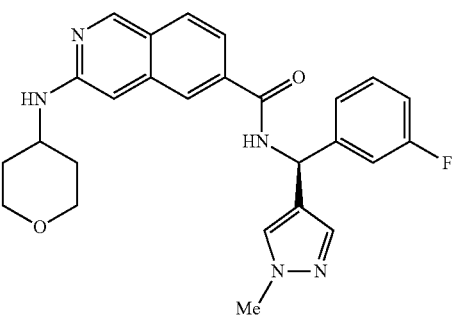 | 3.76 (E) | 460.1 |
| II-10 | 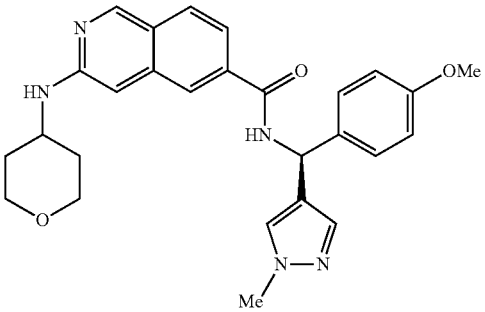 [SMILES: COc1ccc([C@H](NC(=O)c2ccc3cnc(NC4CCOCC4)cc3c2)c2cnn(C)c2)cc1] | 3.67 (G) | 472.1 |

TABLE II-continued
| | | | |
|---|---|---|---|
| II-11 | 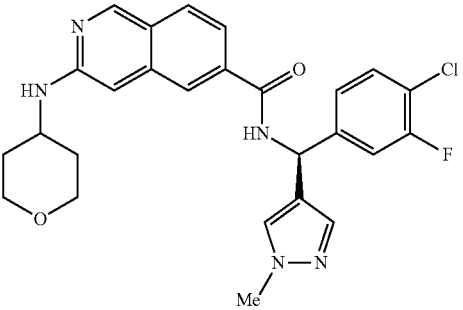 [SMILES: Cn1cc([C@@H](NC(=O)c2ccc3cnc(NC4CCOCC4)cc3c2)c2ccc(Cl)c(F)c2)cn1] | 4.06 (G) | 494.1 496.1 |
| II-12 | 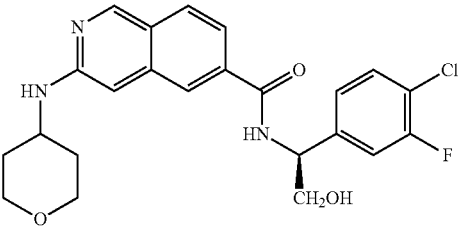 | 3.79 (E) | 444.0 446.0 |
| II-13 | 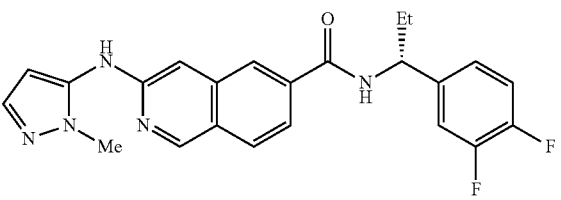 [SMILES: CC[C@@H](NC(=O)c1ccc2cnc(Nc3ccnn3C)cc2c1)c1ccc(F)c(F)c1] | 4.79 (E) | 438.0 |
| II-14 | 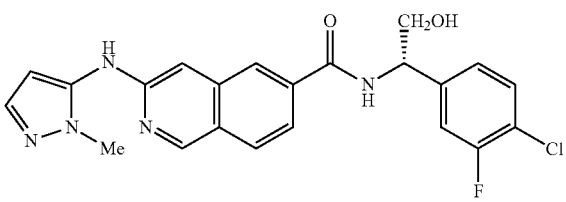 [SMILES: Cn1nccc1Nc1cc2cc(C(=O)N[C@H](CO)c3ccc(Cl)c(F)c3)ccc2cn1] | 4.04 (E) | 440.0 |
| II-15 | 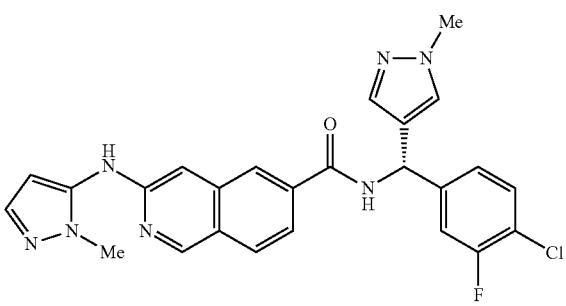 [SMILES: Cn1cc([C@@H](NC(=O)c2ccc3cnc(Nc4ccnn4C)cc3c2)c2ccc(Cl)c(F)c2)cn1] | 4.33 (E) | 490.0 |
| II-16 | 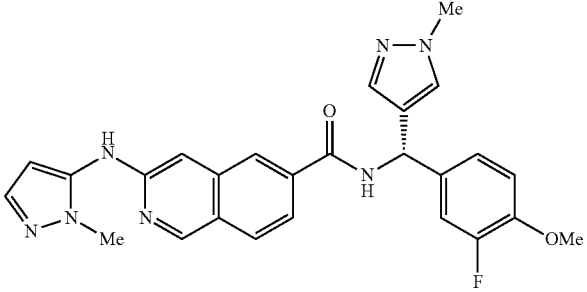 [SMILES: COc1ccc([C@H](NC(=O)c2ccc3cnc(Nc4ccnn4C)cc3c2)c2cnn(C)c2)cc1F] | 3.98 (E) | 486.1 |

TABLE II-continued

| ID | Structure | Data |
|---|---|---|
| II-17 | (isoquinoline-6-carboxamide with tetrahydropyran-4-ylamino substituent and N-[(S)-1-(3-fluoro-4-methoxyphenyl)-2-hydroxyethyl]) | 4.64 (M) 440.2 |
| II-18 | (isoquinoline-6-carboxamide with (S)-1-hydroxypropan-2-ylamino and N-[(S)-1-(3-fluoro-4-methoxyphenyl)-2-hydroxyethyl]) | 4.16 (L) 414.2 |
| II-19 | (isoquinoline-6-carboxamide with 1-methyl-1H-pyrazol-5-ylamino and N-[(S)-1-(3-chloro-4-fluorophenyl)propyl]) | 4.77 (E) 438.0 |
| II-20 | (isoquinoline-6-carboxamide with tetrahydrofuran-3-ylamino and N-[(S)-1-(3-fluorophenyl)-2-hydroxyethyl]) | 4.45 (M) 396.2 |
| II-21 | (isoquinoline-6-carboxamide with tetrahydrofuran-3-ylamino and N-[(S)-1-(4-methoxyphenyl)-2-hydroxyethyl]) | 4.28 (M) 408.2 |
| II-22 | (isoquinoline-6-carboxamide with (S)-1-hydroxypropan-2-ylamino and N-[(S)-1-(3-fluorophenyl)-2-hydroxyethyl]) | 4.29 (M) 384.3 |
| II-23 | (isoquinoline-6-carboxamide with (S)-1-hydroxypropan-2-ylamino and N-[(4-fluoro-1H-indol-2-yl)methyl]) | 5.17 (M) 393.3 |

TABLE II-continued
| | | | |
|---|---|---|---|
| II-24 | 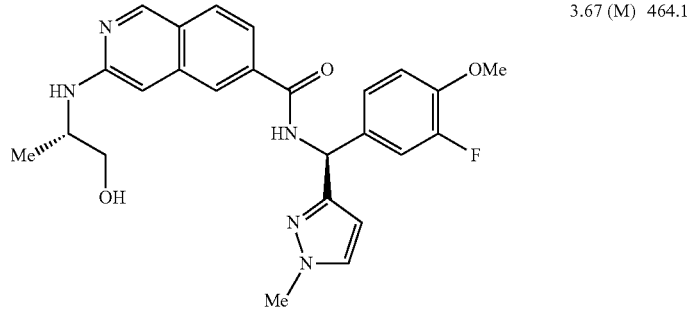 | 3.67 (M) | 464.1 |
| II-25 | 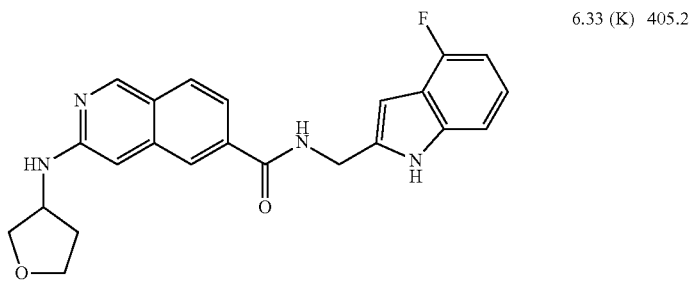 | 6.33 (K) | 405.2 |
| II-26 | 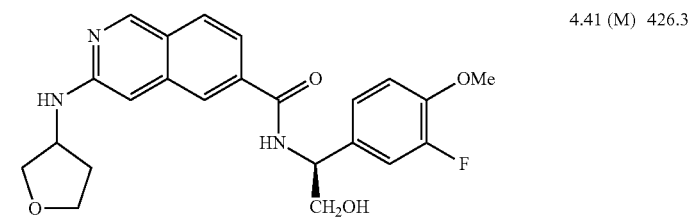 | 4.41 (M) | 426.3 |
| II-27 | 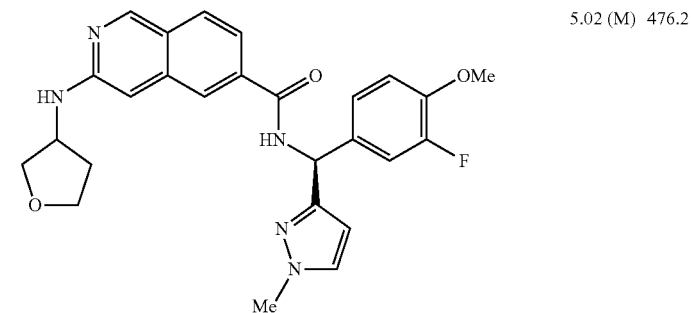 | 5.02 (M) | 476.2 |
| II-28 | 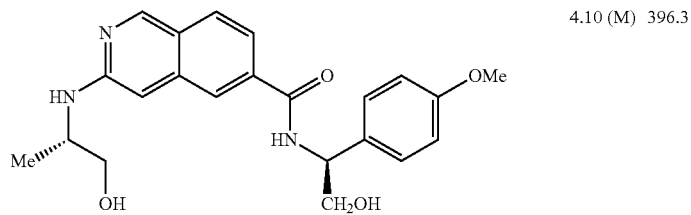 | 4.10 (M) | 396.3 |
| II-29 | 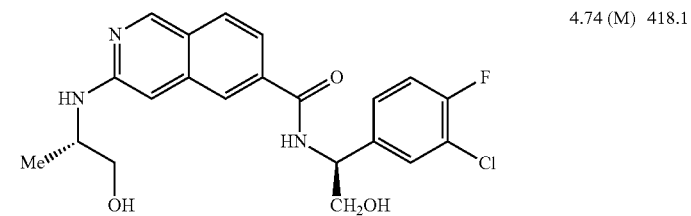 | 4.74 (M) | 418.1 |

TABLE II-continued
| | | | |
|---|---|---|---|
| II-30 | 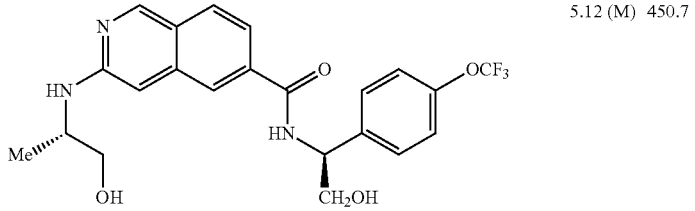 | 5.12 (M) | 450.7 |
| II-31 | 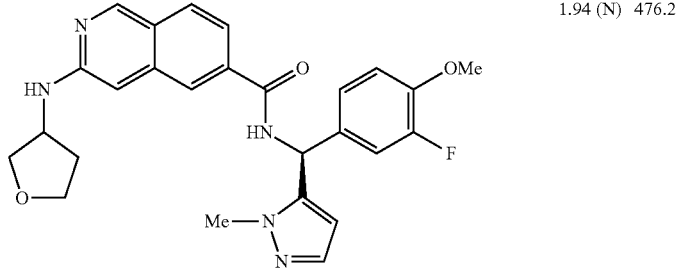 | 1.94 (N) | 476.2 |
| II-32 | 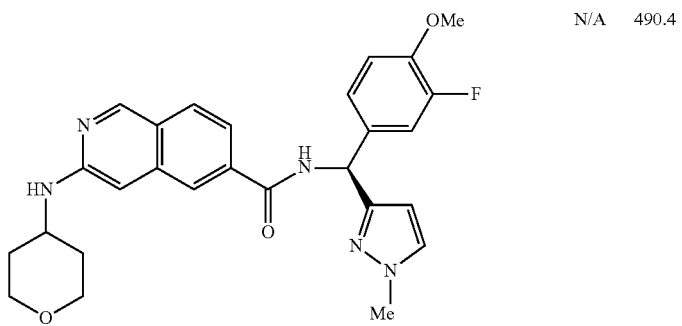 | N/A | 490.4 |
| II-33 | 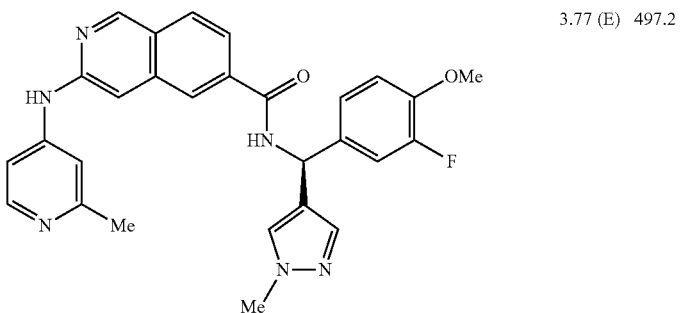 | 3.77 (E) | 497.2 |
| II-34 | 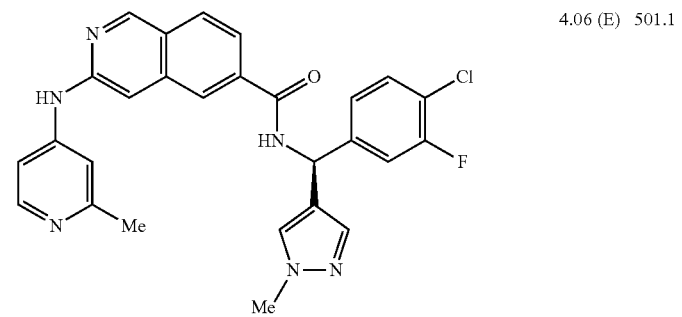 | 4.06 (E) | 501.1 |

TABLE II-continued
| | | | |
|---|---|---|---|
| II-35 | 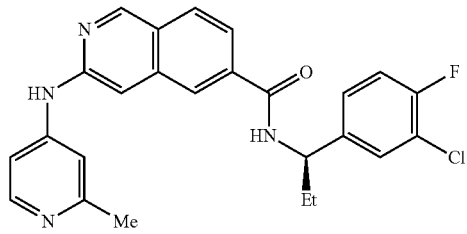 [SMILES: CC[C@@H](NC(=O)c1ccc2cnc(Nc3ccnc(C)c3)cc2c1)c1ccc(F)c(Cl)c1] | 4.42 (E) | 449.1 |
| II-36 | 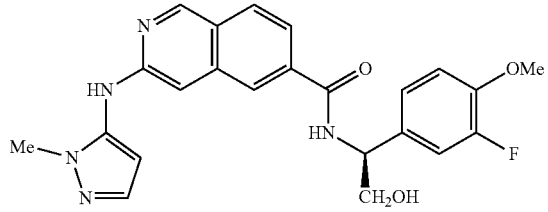 [SMILES: COc1ccc([C@@H](CO)NC(=O)c2ccc3cnc(Nc4ccnn4C)cc3c2)cc1F] | N/A | 436.11 |
| II-37 | 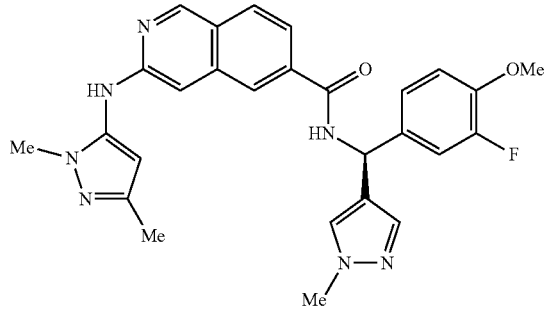 [SMILES: COc1ccc([C@H](NC(=O)c2ccc3cnc(Nc4cc(C)nn4C)cc3c2)c2cnn(C)c2)cc1F] | 3.88 (E) | 500.2 |
| II-38 | 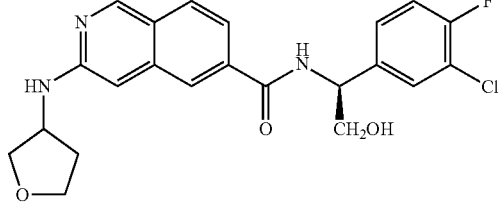 | 4.96 (M) | 430.1 |
| II-39 | 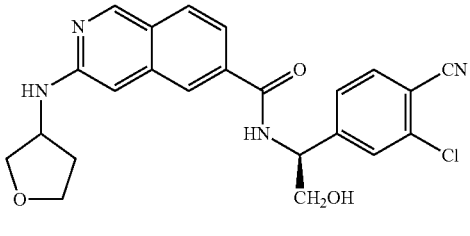 [SMILES: N#Cc1ccc([C@@H](CO)NC(=O)c2ccc3cnc(NC4CCOC4)cc3c2)cc1Cl] | 4.65 (M) | 437.2 |
| II-40 | 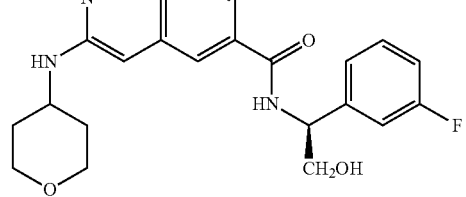 | 4.64 (M) | 410.3 |

TABLE II-continued

| ID | Structure | Data |
|---|---|---|
| II-41 | (isoquinoline-6-carboxamide with 3-(tetrahydropyran-4-ylamino) and N-[(S)-1-(4-methoxyphenyl)-2-hydroxyethyl]) | 4.43 (M) 422.2 |
| II-42 | (isoquinoline-6-carboxamide with 3-(tetrahydropyran-4-ylamino) and N-[(S)-1-(3-chloro-4-cyanophenyl)-2-hydroxyethyl]) | 4.79 (M) 451.3 |
| II-43 | (isoquinoline-6-carboxamide with 3-(3-fluoro-tetrahydropyran-4-ylamino) and N-[(S)-1-(4-methoxyphenyl)-2-hydroxyethyl]) | 4.50 (M) 440.2 |
| II-44 | (isoquinoline-6-carboxamide with 3-(1,3-dimethylpyrazol-5-ylamino) and N-[(S)-1-(3-fluoro-4-methoxyphenyl)-2-hydroxyethyl]) | N/A 450.2 |
| II-45 | (isoquinoline-6-carboxamide with 3-(1,3-dimethylpyrazol-5-ylamino) and N-[(S)-1-(4-chloro-3-fluorophenyl)-2-hydroxyethyl]) | 3.95 (E) 454.1 |
| II-46 | (isoquinoline-6-carboxamide with 3-(1,3-dimethylpyrazol-5-ylamino) and N-[(S)-1-(4-chloro-3-fluorophenyl)propyl]) | 4.61 (E) 451.924 |

TABLE II-continued
| | | | |
|---|---|---|---|
| II-47 | 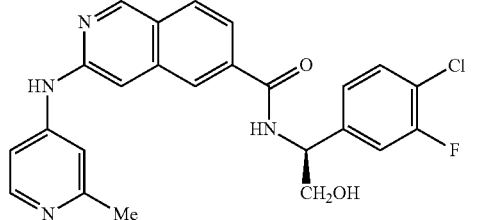 [SMILES: Cc1cc(Nc2cc3cc(C(=O)N[C@H](CO)c4ccc(Cl)c(F)c4)ccc3cn2)ccn1] | N/A | 451.1 |
| II-48 | 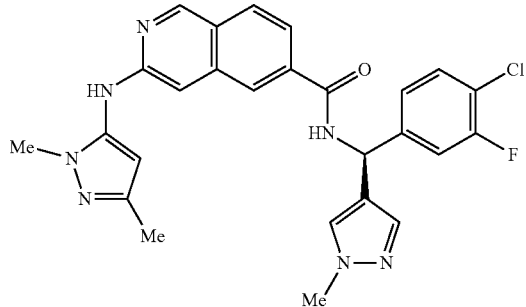 [SMILES: Cc1cc(Nc2cc3cc(C(=O)N[C@@H](c4ccc(Cl)c(F)c4)c4cnn(C)c4)ccc3cn2)n(C)n1] | 4.21 (E) | 504.1 |
| II-49 | 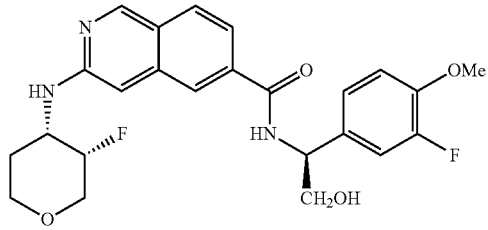 [SMILES: COc1ccc([C@@H](CO)NC(=O)c2ccc3cnc(N[C@H]4CCOC[C@H]4F)cc3c2)cc1F] | 4.61 (M) | 458.3 |
| II-50 | 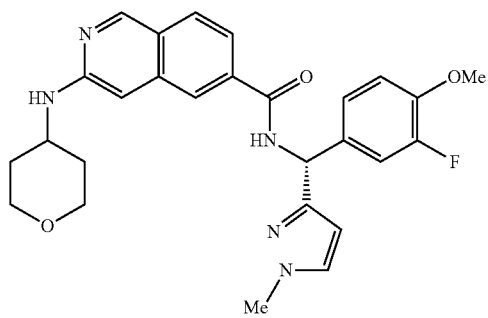 [SMILES: CN/C=C\C(=N)[C@H](NC(=O)c1ccc2cnc(NC3CCOCC3)cc2c1)c1ccc(OC)c(F)c1] | 4.86 (K) | 490.2 |
| II-51 | 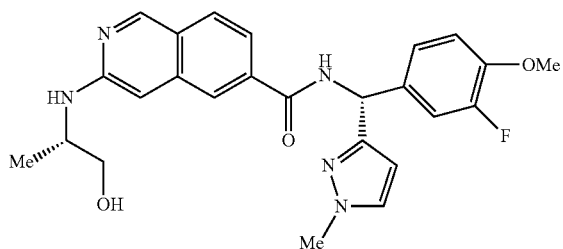 [SMILES: COc1ccc([C@@H](NC(=O)c2ccc3cnc(N[C@@H](C)CO)cc3c2)c2ccn(C)n2)cc1F] | 4.86 (K) | 464.1 |

TABLE II-continued

| II-52 | (structure) | N/A | 476.2 |
| II-53 | (structure) | | |
| II-54 | (structure) | | |
| II-55 | (structure) | N/A | 469.3 |
| II-56 | (structure) | | 444.2 |
| II-57 | (structure) | | 432 |

TABLE II-continued

| | | | |
|---|---|---|---|
| II-58 | (structure) | N/A | 432.2 |
| II-59 | (structure) | N/A | 519.2 |
| II-60 | (structure) | N/A | 432 |
| II-61 | (structure) | N/A | 45833 |
| II-62 | (structure) | N/A | N/A |
| II-63 | (structure) | N/A | 547.3 |

TABLE II-continued

| | | | |
|---|---|---|---|
| II-64 | (structure) | N/A | 471.2 |
| II-65 | (structure) | N/A | 501.2 |
| II-66 | (structure) | N/A | 501.2 |
| II-67 | (structure) | N/A | 437.2 |
| II-68 | (structure) | N/A | 508.3 |

Compounds of the present invention can be made by a variety of methods depicted in the illustrative synthetic reaction schemes shown and described below. The starting materials and reagents used in preparing these compounds generally are either available from commercial suppliers, such as Sigma Aldrich Chemical Co., or are prepared by methods known to those skilled in the art. Generally applicable synthetic procedures have been described in treatises are set forth in references such as *Fieser and Fieser's Reagents for Organic Synthesis*; Wiley & Sons: New York, Volumes 1-21; R. C. LaRock, *Comprehensive Organic Transformations*, 2nd edition Wiley-VCH, New York 1999; *Comprehensive Organic Synthesis*, B. Trost and I. Fleming (Eds.) vol. 1-9 Pergamon, Oxford, 1991; *Comprehensive Heterocyclic Chemistry*, A. R. Katritzky and C. W. Rees (Eds) Pergamon, Oxford 1984, vol. 1-9; *Comprehensive Heterocyclic Chem-* istry II, A. R. Katritzky and C. W. Rees (Eds) Pergamon, Oxford 1996, vol. 1-11; and *Organic Reactions*, Wiley & Sons: New York, 1991, Volumes 1-40. The following synthetic reaction schemes are merely illustrative of some methods by which the compounds of the present invention can be synthesized, and various modifications to these synthetic reaction schemes can be made and will be suggested to one skilled in the art having referred to the disclosure contained herein.

The starting materials and the intermediates of the synthetic reaction schemes can be isolated and purified if desired using conventional techniques. One skilled in the art will apply techniques most likely to achieve the desired separation. Typically such separations involve multiphase extraction, crystallization from a solvent or solvent mixture, distillation, sublimation, or chromatography. Chromatography can involve any number of methods including, for example: chiral, reverse-phase and normal phases; size exclusion; ion exchange; high, medium and low pressure liquid chromatography methods and apparatus; supercritical fluid chromatography; small scale analytical; simulated moving bed (SMB) and preparative thin or thick layer chromatography, as well as techniques of small scale thin layer and flash chromatography. Such materials can be characterized using conventional means, including physical constants and spectral data.

Unless specified to the contrary, the reactions described herein preferably are conducted under an inert atmosphere at atmospheric pressure at a reaction temperature range of from about −78° C. to about 150° C., more preferably from about 0° C. to about 125° C., and most preferably and conveniently at about room (or ambient) temperature, e.g., about 20° C.

Diastereomeric mixtures can be separated into their individual diastereomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereoisomers to the corresponding pure enantiomers. Enantiomers can also be separated by use of a chiral HPLC column.

A single stereoisomer, e.g., an enantiomer, substantially free of its stereoisomer may be obtained by resolution of the racemic mixture using a method such as formation of diastereomers using optically active resolving agents (Eliel, E. and Wilen, S. "Stereochemistry of Organic Compounds," John Wiley & Sons, Inc., New York, 1994; Lochmuller, C. H., *J. Chromatogr.*, 1975 113(3):283-302). Racemic mixtures can be separated and isolated by any suitable method, including: (1) formation of ionic, diastereomeric salts with chiral compounds and separation by fractional crystallization or other methods, (2) converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereoisomers to the corresponding pure enantiomers, and (3) separation of the substantially pure or enriched stereoisomers directly under chiral conditions. (see, e.g., *Drug Stereochemistry, Analytical Methods and Pharmacology*, Irving W. Wainer, Ed., Marcel Dekker, Inc., New York 1993).

Under method (1), diastereomeric salts can be formed by reaction of enantiomerically pure chiral bases such as brucine, quinine, ephedrine, strychnine, α-methyl-β-phenylethylamine (amphetamine), and the like with asymmetric compounds bearing acidic functionality, such as carboxylic acid and sulfonic acid. The diastereomeric salts may be induced to separate by fractional crystallization or ionic chromatography. For separation of the optical isomers of amino compounds, addition of chiral carboxylic or sulfonic acids, such as camphorsulfonic acid, tartaric acid, mandelic acid, or lactic acid can result in formation of the diastereomeric salts.

Alternatively, by method (2), the substrate to be resolved is reacted with one enantiomer of a chiral compound to form a diastereomeric pair (E. Eliel and S. Wilen, *Stereochemistry of Organic Compounds*, John Wiley & Sons, Inc., 1994, p. 322). Diastereomeric compounds can be formed by reacting asymmetric compounds with enantiomerically pure chiral derivatizing reagents, such as menthyl derivatives, followed by separation of the diastereomers and hydrolysis to yield the pure or enriched enantiomer. A method of determining optical purity involves making chiral esters, such as a menthyl ester, e.g., (−) menthyl chloroformate in the presence of base, or Mosher ester, α-methoxy-α-(trifluoromethyl)phenyl acetate (Jacob III. *J. Org. Chem.*, 1982 47:4165), of the racemic mixture, and analyzing the $^1$H NMR spectrum for the presence of the two atropisomeric enantiomers or diastereomers. Stable diastereomers of atropisomeric compounds can be separated and isolated by normal- and reverse-phase chromatography following methods for separation of atropisomeric naphthyl-isoquinolines (WO 96/15111). By method (3), a racemic mixture of two enantiomers can be separated by chromatography using a chiral stationary phase ("Chiral Liquid Chromatography" 1989 W. J. Lough, Ed., Chapman and Hall, New York; Okamoto, *J. Chromatogr.*, 1990 513:375-378). Enriched or purified enantiomers can be distinguished by methods used to distinguish other chiral molecules with asymmetric carbon atoms, such as optical rotation and circular dichroism.

Some compounds in the following schemes are depicted with generalized substituents; however, one skilled in the art will immediately appreciate that the nature of the R groups can be varied to afford the various compounds contemplated in this invention. Moreover, the reaction conditions are exemplary and alternative conditions are well known. The reaction sequences in the following examples are not meant to limit the scope of the invention as set forth in the claims.

SCHEME A

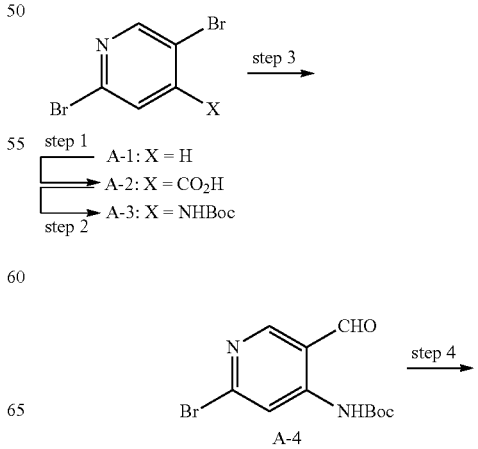

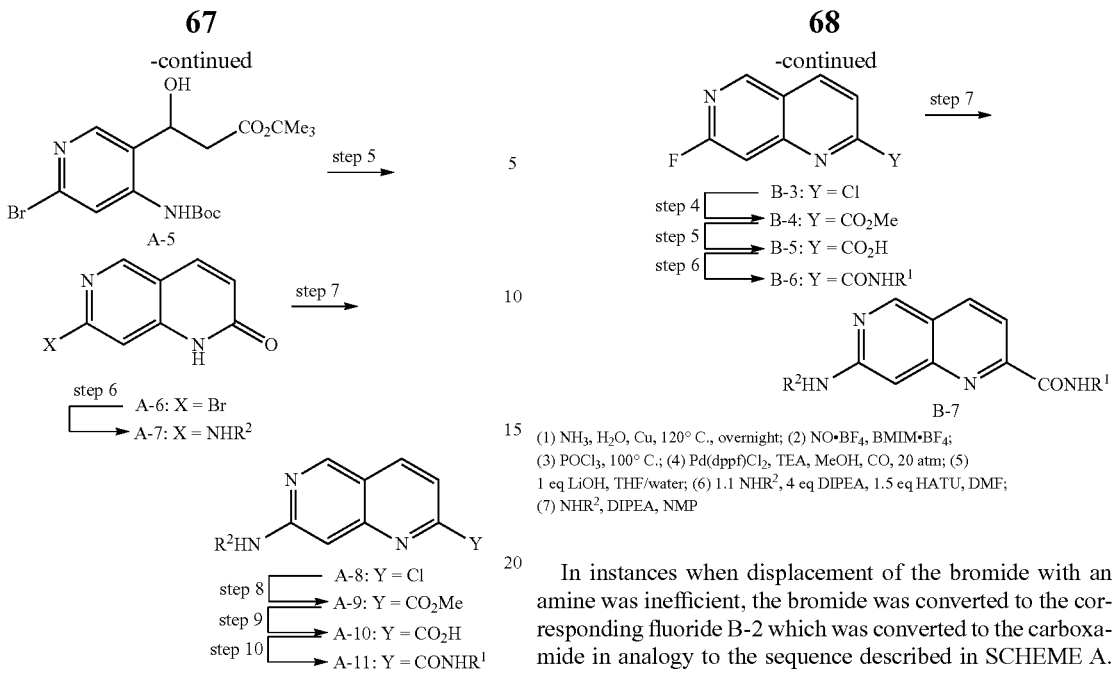

(1) LDA, CO₂, THF, -80° C.; (2) DPPA, TEA, t-BuOH, 80° C.; (3) (i) 1) n-BuLi, THF (ii) DMF, -78° C.; (4) 2.0 eq t-BuAc, 2.1 eq LDA, Et₂O/THF, -60° C.; (5) HCl, water/dioxane, reflux, overnight; (6) R²—NH₂, Pd(OAc)₂, Xantphos, LiHMDS, THF, reflux, 2 h; (7) POCl₃, 100° C.; (8) Pd(dppf)Cl₂, TEA, MeOH, CO, 20 atm; (9) 1 eq LiOH, THF/H₂O; (10) 1.1 NHR¹, 4 eq DIPEA, 1.5 eq HATU, DMF 7-Bromo-1H-[1,6]naphthyridin-2-one (A-6) can be prepared by two-step amination of 2,5-dibromo-pyridine. Metallation and quenching of the resulting organolithium intermediate with CO₂ afforded A-2. Conversion of A-2 to the corresponding acyl azide with diphenylphosphoryl azide in tert-butanol and subsequent Curtius rearrangement afforded tert-butyl(2,5-dibromo-pyridin-4-yl)-carbamate A-3. Formylation of A-3 by metallation and quenching with DMF afforded A-4 which was treated with the lithium salt of tert-butyl acetate to afford A-5. Exposing A-5 to aqueous acid resulted with deprotection of the amine and intramolecular cyclization and dehydration to afford A-6.

Palladium-catalyzed displacement of the bromide with an amine afforded A-7. The desired carboxamide was elaborated by chlorination of the lactam which was subsequently subjected to palladium-catalyzed carbonylation in MeOH which afforded the corresponding ester which was hydrolyzed to the corresponding acid A-10 which was converted to the amide using amidation protocols developed for peptide synthesis. Compounds described herein where R² is tetrahydropyran-4-yl were prepared by the procedure in SCHEME A.

SCHEME B

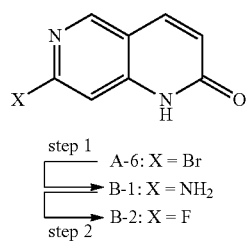

(1) NH₃, H₂O, Cu, 120° C., overnight; (2) NO•BF₄, BMIM•BF₄; (3) POCl₃, 100° C.; (4) Pd(dppf)Cl₂, TEA, MeOH, CO, 20 atm; (5) 1 eq LiOH, THF/water; (6) 1.1 NHR², 4 eq DIPEA, 1.5 eq HATU, DMF; (7) NHR², DIPEA, NMP In instances when displacement of the bromide with an amine was inefficient, the bromide was converted to the corresponding fluoride B-2 which was converted to the carboxamide in analogy to the sequence described in SCHEME A. Displacement of the fluoride with the requisite amine afforded the desired amine B-7. The referential examples include the preparation of some amines within the scope of the present invention. Other amines which were obtained from commercial sources including: (3S)-3-amino-2-methyl-butanol (CASRN 74608-26-7), 3-amino-2-methyl-butanol (CASRN 6291-17-4), 1,3-dimethyl-1H-pyrazol-5-amine (CASRN 3524-32-1), 2-methyl-pyridin-4-amine (CASRN18437-58-6), 1-methyl-1H-pyrazol-5-amine (CASRN 1192-21-8), tetrahydro-3-furanamine (CASRN 88675-24-5), (3S)-tetrahydro-3-furanamine (CASRN 104530-79-2), (3R)-tetrahydro-3-furanamine (CASRN 111769-26-7) and 3-fluoro-1-propanamine (CASRN 462-41-9).

SCHEME C

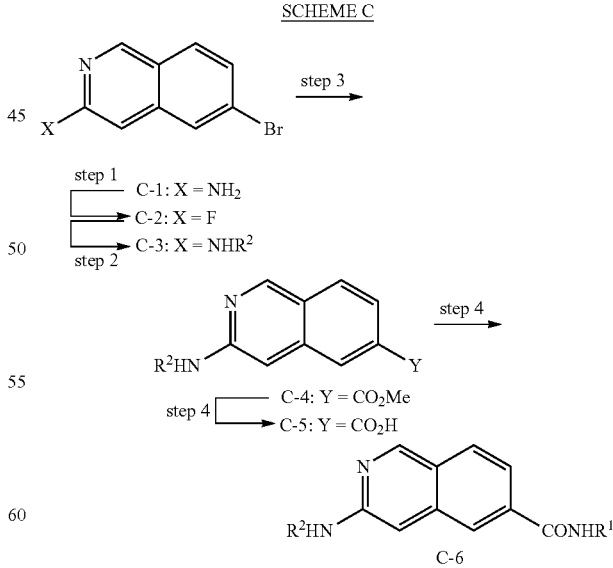

Isoquinolines encompassed with the present invention can be prepared as depicted in SCHEME C. 3-Amino-6-bromo-isoquinoline was converted to –6-bromo-3-fluoro-isoquinoline which underwent displacement of the fluorine by an amine to afford C-3. Carboxymethylation, saponification of the ester and condensation with a requisite amine afforded the desired isoquinolinecarboxamides.

The requisite amines may be prepared as described in SCHEME D, where aryl-heteroaryl amines (D-3; R=heteroaryl) may be prepared by steps 1 through 2. Addition of an aryl Grignard or aryl lithium reagent to the N-tert-butylsulfinyl imines (D-2) afforded amines (C-3) after hydrolysis of the intermediate sulfinamides. Chiral amines are prepared by addition of an aryl Grignard or lithium to a chiral sulfinamide. (D. A. Cogan et al., Tetrahedron 1999 55:8883-8904). The sulfinyl imines D-2 are, in turn, available from the large pool of aldehydes which can be easily prepared or purchased.

SCHEME D

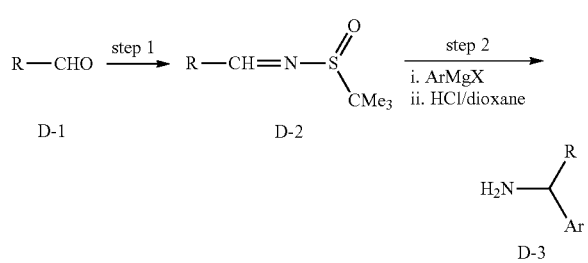

4-Aryl-1-benzyl-pyrrolin-3-carboxylic acids were prepared from readily available substituted benzaldeydes E-1 by Knoevenagel condensation with malonic acid to afford a substituted acrylic acid. Condensation of the corresponding acid chloride with (R)-4-phenyloxazolidin-2-one introduces a chiral auxiliary, which affords chiral E-4 after a 1,3-dipolar addition of an azomethine methylide. Hydrolysis of the amide affords a carboxylic acid, which can be converted to the isocyanate and condensed with an amine and deprotected to afford compounds within the scope of the present invention.

SCHEME E

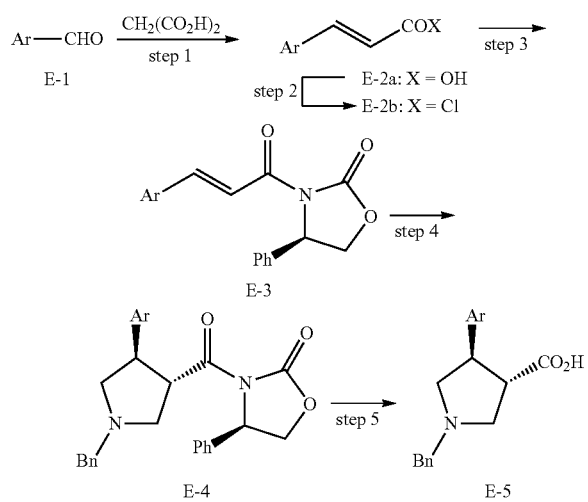

The SCHEMES described above provide general procedures which have been applied to compounds encompassed in the present invention. The examples which follow containing additional details which are useful to introduce the various structural features found in specific compounds.

Biological Activity

Determination of the activity of ERK activity of a compound of formula I is possible by a number of direct and indirect detection methods. Certain exemplary compounds described herein were assayed for their ERK inhibition assay (Example 18). The range of ERK binding activities was less than 1 nM (nanomolar) to about 10 μM (micromolar). A cell-based function assay (Example 20) was used to determine the effect of ERK inhibitors on down-stream signaling by assaying phosphorylation of P90RSK.

The cytotoxic or cytostatic activity of formula I exemplary compounds was measured by: establishing a proliferating mammalian tumor cell line in a cell culture medium, adding a formula I compound, culturing the cells for a period from about 6 h to about 5 d; and measuring cell viability (Example 19). Cell-based in vitro assays were used to measure viability, i.e. proliferation ($IC_{50}$), cytotoxicity ($EC_{50}$).

Dosage & Administration

The present invention provides pharmaceutical compositions or medicaments containing the compounds of the invention and at least one therapeutically inert carrier, diluent or excipient, as well as methods of using the compounds of the invention to prepare such compositions and medicaments. In one example, compounds of Formula I with the desired degree of purity may be formulated by mixing with physiologically acceptable carriers, i.e., carriers that are non-toxic to recipients at the dosages and concentrations employed into a dosage form at ambient temperature and at the appropriate pH. The pH of the formulation depends mainly on the particular use and the concentration of compound, but typically ranges anywhere from about 3 to about 8. In one example, a compound of Formula I is formulated in an acetate buffer, at pH 5. In another embodiment, the compounds of Formula I are sterile. The compound may be stored, for example, as a solid or amorphous composition, as a lyophilized formulation or as an aqueous solution.

Compositions are formulated, dosed, and administered in a fashion consistent with good medical practice. Factors for consideration in this context include the particular disorder being treated, the severity of the disorder, the particular patient being treated, the clinical condition of the individual patient, the cause of the disorder, the site of delivery of the agent, the method of administration, the scheduling of administration, and other factors known to medical practitioners. The "effective amount" of the compound to be administered will be governed by such considerations, and is the minimum amount necessary to inhibit ERK activity. Typically such amount may be below the amount that is toxic to normal cells, or the patient as a whole.

The pharmaceutical composition (or formulation) for application may be packaged in a variety of ways depending upon the method used for administering the drug. Generally, an article for distribution includes a container having deposited therein the pharmaceutical formulation in an appropriate form. Suitable containers are well-known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

Sustained-release preparations may be prepared. Suitable examples of sustained-release preparations include semipermeable matrices of solid hydrophobic polymers containing a compound of Formula I, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides, copolymers of L-glutamic acid and gamma-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid.

A dose to treat human patients may range from about 0.1 mg to about 1000 mg of a compound of formula I. A typical dose may be about 1 mg to about 300 mg of the compound. A dose may be administered once a day (QD), twice per day (BID), or more frequently, depending on the pharmacokinetic and pharmacodynamic properties, including absorption, distribution, metabolism, and excretion of the particular compound. In addition, toxicity factors may influence the dosage and administration regimen. When administered orally, the pill, capsule, or tablet may be ingested daily or less frequently for a specified period of time. The regimen may be repeated for a number of cycles of therapy.

The compounds of the invention may be administered by any suitable means, including oral, topical (including buccal and sublingual), rectal, vaginal, transdermal, parenteral, subcutaneous, intraperitoneal, intrapulmonary, intradermal, intrathecal, epidural and intranasal, and, if desired for local treatment, intralesional administration. Parenteral infusions include intramuscular, intravenous, intraarterial, intraperitoneal, or subcutaneous administration.

The compounds of the present invention may be administered in any convenient administrative form, e.g., tablets, powders, capsules, solutions, dispersions, suspensions, syrups, sprays, suppositories, gels, emulsions, patches, etc. Such compositions may contain components conventional in pharmaceutical preparations, e.g., diluents, carriers, pH modifiers, sweeteners, bulking agents, and further active agents.

A typical formulation is prepared by mixing a compound of the present invention and a carrier or excipient. Suitable carriers and excipients are well known to those skilled in the art and are described in detail in, e.g., Ansel, H. C., et al., Ansel's *Pharmaceutical Dosage Forms and Drug Delivery Systems*. Philadelphia: Lippincott, Williams & Wilkins, 2004; Gennaro, Alfonso R., et al. *Remington: The Science and Practice of Pharmacy*. Philadelphia: Lippincott, Williams & Wilkins, 2000; and Rowe, R. C., *Handbook of Pharmaceutical Excipients*, Chicago, Pharmaceutical Press, 2005. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament).

For oral administration, tablets containing various excipients, such as citric acid may be employed together with various disintegrants such as starch, alginic acid and certain complex silicates and with binding agents such as sucrose, gelatin and acacia. Additionally, lubricating agents such as magnesium stearate, sodium lauryl sulfate and talc are often useful for tableting purposes. Solid compositions of a similar type may also be employed in soft and hard filled gelatin capsules. Preferred materials, therefore, include lactose or milk sugar and high molecular weight polyethylene glycols. When aqueous suspensions or elixirs are desired for oral administration the active compound therein may be combined with various sweetening or flavoring agents, coloring matters or dyes and, if desired, emulsifying agents or suspending agents, together with diluents such as water, ethanol, propylene glycol, glycerin, or combinations thereof.

An example of a suitable oral dosage form is a tablet containing about 25 mg, 50 mg, 100 mg, 250 mg or 500 mg of the compound of the invention compounded with about 90-30 mg anhydrous lactose, about 5-40 mg sodium croscarmellose, about 5-30 mg polyvinylpyrrolidone (PVP) K30, and about 1-10 mg magnesium stearate. The powdered ingredients are first mixed together and then mixed with a solution of the PVP. The resulting composition can be dried, granulated, mixed with the magnesium stearate and compressed to tablet form using conventional equipment. An example of an aerosol formulation can be prepared by dissolving the compound, for example 5-400 mg, of the invention in a suitable buffer solution, e.g. a phosphate buffer, adding a tonicifier, e.g. a salt such as sodium chloride, if desired. The solution may be filtered, e.g., using a 0.2 micron filter, to remove impurities and contaminants.

In one embodiment, the pharmaceutical composition also includes at least one additional anti-proliferative agent.

An embodiment, therefore, includes a pharmaceutical composition comprising a compound of Formula I, or a stereoisomer, tautomer or pharmaceutically acceptable salt thereof. A further embodiment includes a pharmaceutical composition comprising a compound of Formula I, or a stereoisomer, tautomer or pharmaceutically acceptable salt thereof, together with a pharmaceutically acceptable carrier or excipient.

The invention further provides veterinary compositions comprising at least one active ingredient as above defined together with a veterinary carrier therefore. Veterinary carriers are materials useful for the purpose of administering the composition and may be solid, liquid or gaseous materials which are otherwise inert or acceptable in the veterinary art and are compatible with the active ingredient. These veterinary compositions may be administered parenterally, orally or by any other desired route.

Combination Therapy

The compounds of formula I may be employed alone or in combination with other therapeutic agents for the treatment of a disease or disorder described herein, such as a hyperproliferative disorder (e.g., cancer). In certain embodiments, a compound of formula I is combined in a pharmaceutical combination formulation, or dosing regimen as combination therapy, with a second compound that has anti-hyperproliferative properties or that is useful for treating a hyperproliferative disorder (e.g., cancer). The second compound of the pharmaceutical combination formulation or dosing regimen preferably has complementary activities to the compound of formula I such that they do not adversely affect each other. The combination therapy may provide "synergy" and prove "synergistic", i.e., the effect achieved when the active ingredients used together is greater than the sum of the effects that results from using the compounds separately.

The combination therapy may be administered as a simultaneous or sequential regimen. When administered sequentially, the combination may be administered in two or more administrations. The combined administration includes co-administration, using separate formulations or a single pharmaceutical formulation, and consecutive administration in either order, wherein preferably there is a time period while both (or all) active agents simultaneously exert their biological activities.

Suitable dosages for any of the above co-administered agents are those presently used and may be lowered due to the combined action (synergy) of the newly identified agent and other chemotherapeutic agents or treatments.

Combination therapies according to the present invention thus comprise the administration of at least one compound of formula I, or a stereoisomer, geometric isomer, tautomer, or pharmaceutically acceptable salt and the use of at least one other cancer treatment method. The amounts of the compound(s) of formula I and the other pharmaceutically active chemotherapeutic agent(s) and the relative timings of administration will be selected in order to achieve the desired combined therapeutic effect.

Articles of Manufacture

In another embodiment of the invention, an article of manufacture, or "kit", containing materials useful for the treatment of the diseases and disorders described above is provided. In one embodiment, the kit comprises a container comprising a compound of formula I, or a stereoisomer, tautomer, or pharmaceutically acceptable salt thereof. The kit may further comprise a label or package insert on or associated with the container. The term "package insert" is used to refer to instructions customarily included in commercial packages of therapeutic products, that contain information about the indications, usage, dosage, administration, contraindications and/or warnings concerning the use of such therapeutic products. Suitable containers include, for example, bottles, vials, syringes, blister pack, etc. The container may be formed from a variety of materials such as glass or plastic. The container may hold a compound of formula I or a formulation thereof which is effective for treating the condition and may have a sterile access port (for example, the container may be an intravenous solution bag or a vial having a stopper pierceable by a hypodermic injection needle). At least one active agent in the composition is a compound of formula I. Alternatively, or additionally, the article of manufacture may further comprise a second container comprising a pharmaceutical diluent, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

In another embodiment, the kits are suitable for the delivery of solid oral forms of a compound of formula I, such as tablets or capsules. Such a kit can include a number of unit dosages. An example of such a kit is a "blister pack". Blister packs are well known in the packaging industry and are widely used for packaging pharmaceutical unit dosage forms.

According to one embodiment, a kit may comprise (a) a first container with a compound of formula I contained therein; and optionally (b) a second container with a second pharmaceutical formulation contained therein, wherein the second pharmaceutical formulation comprises a second compound with anti-hyperproliferative activity. Alternatively, or additionally, the kit may further comprise a third container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The following examples illustrate the preparation and biological evaluation of compounds within the scope of the invention. These examples and preparations which follow are provided to enable those skilled in the art to more clearly understand and to practice the present invention. They should not be considered as limiting the scope of the invention, but merely as being illustrative and representative thereof. The referential examples that follow illustrate procedures which prepare the amines required to assemble the ERK inhibitors encompassed in the present invention.

The following chromatography methods refer to the procedures listed in TABLES I and II.

Method A: Experiments were performed on Agilent or Shimadzu system using ESI as ionization source with an Xtimate C18 (3 μm), 30×2.1 mm column, at a 1.2 mL/minute flow rate. The solvent system was a gradient starting with 90% water with 0.0375% TFA (solvent A) and 10% acetonitrile with 0.01875% TFA (solvent B), ramping up to 20% solvent A and 80% solvent B over 2 minutes.

Method B: Experiments were performed on Agilent or Shimadzu system using ESI as ionization source with an Xtimate C18 (3 μm), 30×2.1 mm column, at a 1.2 mL/minute flow rate. The solvent system was a gradient starting with 100% water with 0.0375% TFA (solvent A) and 0% acetonitrile with 0.01875% TFA (solvent B), ramping up to 40% solvent A and 60% solvent B over 2 minutes.

Method C: Experiments were performed on Agilent or Shimadzu system using ESI as ionization source with an Xtimate C18 (3 μm), 30×2.1 mm column, at a 1.2 mL/minute flow rate. The solvent system was a gradient starting with 100% water with 0.0375% TFA (solvent A) and 0% acetonitrile with 0.01875% TFA (solvent B), ramping up to 70% solvent A and 30% solvent B over 2 minutes.

Method D: Experiments performed on an Agilent 1100 HPLC with Agilent MSD mass spectrometer using ESI as ionization source using an Agilent ZORBAX SB-C18 100× 3.0 mm column and a 0.7 mL/minute flow rate. The solvent system was a gradient starting with 98% water with 0.05% TFA (solvent A) and 2% acetonitrile with 0.05% TFA (solvent B), ramping up to 2% solvent A and 98% solvent B over 25.5 minutes. The final solvent system was held constant for a further 2.5 minutes.

Method E: Experiments performed on an Agilent 1100 HPLC with Agilent MSD mass spectrometer using ESI as ionization source using an Agilent ZORBAX SB-C18 30×2.1 mm column and a 0.4 mL/minute flow rate. The solvent system was a gradient starting with 97% water with 0.05% TFA (solvent A) and 3% acetonitrile with 0.05% TFA (solvent B), ramping up to 5% solvent A and 95% solvent B over 7 minutes. The final solvent system was held constant for a further 1.5 minute.

Method F: Experiments performed on a Waters Acquity UHPLC with Waters LCT Premier XE mass spectrometer using ESI as ionization source using an Acquity UPLC BEH C18, 1.7 um, 2.1*50 mm column and a 0.6 mL/minute flow rate. The solvent system was a gradient starting with 98% water with 0.05% TFA (solvent A) and 2% acetonitrile with 0.05% TFA (solvent B), ramping up to 2% solvent A and 98% solvent B over 2.5 minutes. The final solvent system was held constant for a further 0.5 minute.

Method G: Experiments performed on a Waters Acquity UHPLC with Waters LCT Premier XE mass spectrometer using ESI as ionization source using an Acquity UPLC BEH C18, 1.7 um, 2.1*50 mm column and a 0.6 mL/minute flow rate. The solvent system was a gradient starting with 98% water with 0.05% TFA (solvent A) and 2% acetonitrile with 0.05% TFA (solvent B), ramping up to 2% solvent A and 98% solvent B over 17 minutes. The final solvent system was held constant for a further 1.5 minutes.

Method H: Experiments performed on a Waters Acquity UHPLC with Waters LCT Premier XE mass spectrometer using ESI as ionization source using an Acquity UPLC BEH C18, 1.7 um, 2.1*50 mm column and a 0.6 mL/minute flow rate. The solvent system was a gradient starting with 98% water with 0.05% TFA (solvent A) and 2% acetonitrile with 0.05% TFA (solvent B), ramping up to 2% solvent A and 98% solvent B over 7.5 minutes. The final solvent system was held constant for a further 1.0 minutes.

Method I: Experiments were performed on Agilent or Shimadzu system using ESI as ionization source with an Xtimate C18 (3 μm), 30×2.1 mm column, at a 1.2 mL/minute flow rate. The solvent system was a gradient starting with 70% water with 0.0375% TFA (solvent A) and 30% acetonitrile with 0.01875% TFA (solvent B), ramping up to 10% solvent A and 90% solvent B over 2 minutes.

Method J: Experiments were performed on Agilent or Shimadzu system using ESI as ionization source with an Xtimate C18 (3 μm), 30×2.1 mm column, at a 1.2 mL/minute flow rate. The solvent system was a gradient starting with 90% water with 0.0375% TFA (solvent A) and 10% acetonitrile with 0.01875% TFA (solvent B), ramping up to 20% solvent A and 80% solvent B over 7 minutes.

Method K: Experiments were performed on an Agilent 1200 HPLC with Agilent MSD mass spectrometer using ESI as ionization source using an Waters Sunfire C18 4.6×50 mm (or Agilent Poroshell 120 SB C18 4.6×30 mm) column and a 1.2 mL/minute flow rate. The solvent system was a gradient starting with 95% water with 0.01% TFA (solvent A) and 5% acetonitrile with 0.01% TFA (solvent B), ramping up to 5% solvent A and 95% solvent B over 8.0 minutes. The final solvent system was held constant for a further 2.0 minute.

Method L: Experiments performed on an Agilent 1200 HPLC with Agilent MSD mass spectrometer using ESI as ionization source using an Waters Xbridge C18 4.6×50 mm (or YMC Triart C18 4.6×50 mm) column and a 1.2 mL/minute flow rate. The solvent system was a gradient starting with 95% water with 0.01% ammonia (solvent A) and 5% acetonitrile (solvent B), ramping up to 5% solvent A and 95% solvent B over 8.0 minutes. The final solvent system was held constant for a further 2.0 minute Method M: Experiments performed on an Agilent 1200 HPLC with Agilent MSD mass spectrometer using ESI as ionization source using an Waters Xbridge C18 4.6×50 mm (or YMC Triart C18 4.6×50 mm) column and a 1.2 mL/minute flow rate. The solvent system was a gradient starting with 95% water with 10 mM ammonium hydrogen carbonate (solvent A) and 5% acetonitrile (solvent B), ramping up to 5% solvent A and 95% solvent B over 8.0 minutes. The final solvent system was held constant for a further 2.0 minute.

Method N: Experiments performed on an Agilent 1200 HPLC with Agilent MSD mass spectrometer using ESI as ionization source using an Waters Xbridge C18 4.6×50 mm (or YMC Triart C18 4.6×50 mm) column and a 1.2 mL/minute flow rate. The solvent system was a gradient starting with 95% water with 10 mM ammonium hydrogen carbonate (solvent A) and 5% acetonitrile (solvent B), ramping up to 5% solvent A and 95% solvent B over 1.6 minutes. The final solvent system was held constant for a further 2.0 minute.

Referential Example 1

2-Oxa-bicyclo[2.2.1]heptan-5-amine hydrochloride

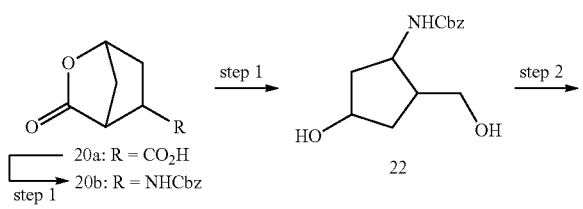

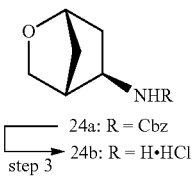

24a: R = Cbz
step 3 → 24b: R = H·HCl

Step 1:

To a solution of 3-oxo-2-oxa-bicyclo[2.2.1]heptane-5-carboxylic acid (20a, 0.50 g, 3.2 mmol) in toluene (5.0 mL) was added DPPA (0.97 g, 3.5 mmol) and TEA (384 mg, 3.80 mmol). The mixture was stirred at 100° C. under $N_2$ atmosphere and then phenylmethanol (1.0 g, 10 mmol) was added. The resulting mixture was stirred at 130° C. for another 2 h. The reaction was quenched with water (1.0 mL) and diluted with EtOAc (300 mL). The organic layer was washed with brine (3×50 mL), dried ($Na_2SO_4$), filtered and concentrated. The residue was purified by $SiO_2$ chromatography eluting with petroleum ether/EtOAc to afford 600 mg (72%) of 20b as a white solid. $^1$H NMR (500 MHz, $CDCl_3$) 7.39-7.31 (m, 5H), 5.08-5.00 (m, 3H), 3.87 (s, 1H), 2.78 (s, 1H), 2.20 (m, 1H), 2.14 (d, J=9 Hz, 1H), 1.97 (t, J=20.5 Hz, 1H), 1.71 (d, J=14 Hz, 1H).

Step 2:

To a solution of 20b (1.0 g, 3.8 mmol) and $CaCl_2$ (0.85 g, 7.6 mmol) in EtOH (50 mL) was added $NaBH_4$ (0.58 g, 15 mmol) at 0° C. The mixture was stirred at RT for 12 h. The excess reagent was decomposed with conc. HCl, and the solution was concentrated. The residue was extracted with $CHCl_3$ (3×100 mL), washed with water (50 mL), brine (50 mL), dried ($Na_2SO_4$). After concentration, the crude product was re-crystallized from petroleum ether to afford 750 mg (75%) of 22 as a white solid. $^1$H NMR (500 MHz, DMSO-$d_6$) δ 7.38-7.31 (m, 5H), 7.25 (d, J=13.5 Hz, 1H), 4.99 (s, 1H), 4.53 (d, J=4.0 Hz, 1H), 4.48 (t, J=10.0 Hz, 1H), 4.09 (d, J=4.0 Hz, 1H), 3.73 (t, J=15.5 Hz, 1H), 3.44 (m, 1H), 3.30 (m, 1H), 1.99 (d, J=7.0 Hz, 1H), 1.80-1.74 (m, 2H), 1.57 (t, J=12.5 Hz, 1H), 1.26 (s, 1H).

Step 3:

To a solution of 22 (100 mg, 0.380 mmol) and pyridine (3.0 mL) in toluene (6.0 mL) at 0° C. was added dropwise a solution of TsCl (290 mg, 1.52 mmol) in toluene (3.0 mL). The mixture was warmed to RT and stirred for 2 d. Then, the reaction mixture was heated at 120° C. for 16 h. The reaction was cooled, and the solvent removed in vacuo. The residue was purified by reverse phase Combi-flash chromatography eluting with a MeCN/$H_2O$ (0.3% $NH_4HCO_3$) gradient (5 to 95% MeCN) to afford 58 mg (62%) of 24a as a white solid. $^1$H NMR (500 MHz, DMSO-$d_6$) δ 7.37-7.31 (m, 5H), 5.09 (s, 1H), 4.33 (s, 1H), 3.73 (d, J=5.5 Hz, 1H), 3.63-3.61 (m, 2H), 3.48 (d, J=7.5 Hz, 1H), 2.53 (s, 1H), 2.07-2.04 (m, 2H), 1.72 (d, J=10.5 Hz, 1H), 1.61 (d, J=11.0 Hz, 1H), 1.42 (d, J=14 Hz, 1H).

Step 4:

A mixture of 24a (0.50 g, 2.0 mmol) and Pd/C (50 mg) in MeOH (20 mL) was stirred under hydrogen atmosphere at RT for 16 h. The mixture was adjusted to pH about 4 with 1N HCl/methanol. The resulting mixture was filtered through Celite®, and the filtrate was concentrated under reduced pressure to afford 300 mg (100%) of 24b as a white solid. $^1$H NMR (500 MHz, DMSO-$d_6$) δ 4.43 (s, 1H), 3.72-3.70 (m, 2H), 3.54 (d, J=7.5 Hz, 1H), 3.50-3.48 (m, 2H), 2.76 (s, 1H), 2.20-2.15 (m, 2H), 1.96 (d, J=11.0 Hz, 1H), 1.78 (d, J=11.0 Hz, 1H), 1.61 (d, J=11.0 Hz, 1H).

Referential Example 2

(S)-1-(1-Aminoethyl)cyclopropanol

Step 1:

To a solution of (S)-ethyl 2-aminopropanoate hydrochloride (4.59 g, 30.0 mmol) and K₂CO₃ (12.4 g, 90.0 mmol) in MeCN was added (bromomethyl)benzene (12.9 g, 75.0 mmol) at RT. The mixture was stirred at 70° C. for 14 h. The reaction mixture was quenched with aq. NH₄Cl. After concentration, the aqueous layer was extracted with EtOAc. The combined organic layers were dried (MgSO₄), filtered and concentrated in vacuo. The crude product was purified by SiO₂ chromatography eluting with petroleum ether/EtOAc (100:1) to afford 8.8 g (98%) of (S)-ethyl 2-(dibenzylamino) propanoate (26): LCMS (ESI) m/z: 298.2 [M+11]⁺.

Step 2:

To a solution of 26 (8.80 g, 29.5 mmol) and titanium tetraisopropoxide (1.28 g, 5.90 mmol) in dry THF (100 mL) was added EtMgBr (30 mL, 90 mmol, 3.0 N in THF) at 0° C. After stirring at RT overnight, the mixture was cooled to 0° C. and quenched with NH₄Cl solution. The solid was filtered off and filtrate was extracted with EtOAc. The combined organic layers were dried (MgSO₄), filtered and concentrated in vacuo. The crude product was purified by SiO₂ chromatography eluting with petroleum ether/EtOAc (20:1) to afford 7.5 g (90%) of 7.5 g (90%) of (S)-1-(1-(dibenzylamino)ethyl) cyclopropanol (28). LCMS (ESI) m/z: 282.1 [M+H]⁺.

Step 3:

To a solution of 28 (7.50 g, 26.6 mmol) in MeOH (80 mL) was added Pd(OH)₂/C (1.50 g) at RT. The mixture was stirred under H₂ atmosphere (1 atm) at RT for 15 h. After filtration and concentration, the residue was purified with SiO₂ chromatography eluting with DCM/MeOH (15:1) to afford 1.4 g (54%) of (S)-1-(1-aminoethyl)cyclopropanol (30). ¹H NMR (500 MHz, CDCl₃) δ 2.58 (q, J=6.5 Hz, 1H), 2.18 (s, 3H), 1.17 (d, J=6.5 Hz, 3H), 0.80-0.74 (m, 2H), 0.70-0.51 (m, 2H).

Referential Example 3

(4-Fluoro-1H-indol-2-yl)methanamine (38)

Step 1:

Sodium (2.30 g, 100 mmol) was added to anhydrous EtOH (80 mL) at 0-5° C. for 10 min to prepare a fresh sodium ethoxide solution. A solution of 1-fluoro-2-methyl-3-nitrobenzene (14.4 g, 93.0 mmol) and diethyl oxalate (15.3 g, 105 mmol) in EtOH (80 mL) was added to the above solution, and the resulting mixture was then refluxed for 45 min. After cooling down, the red dark solution was diluted with water (100 mL). After removal of the ethanol, the residue was extracted with EtOAc. The aqueous layer was acidified with 2N HCl to pH around 3 to 4, and extracted with DCM. The organic layers were washed with water, dried, and concentrated to afford 4.5 g (21%) of 3-(2-fluoro-6-nitrophenyl)-2-oxopropanoic acid (32) as red oil. LCMS (ESI) m/z: 245.1 [M+NH₄]⁺.

Step 2:

A solution of 32 (4.8 g, 31 mmol) in 4% NH₄OH (60 mL) was added to a suspension of ferrous hydroxide that was prepared from ferrous sulfate heptahydrate (52.45 g, 188.7 mmol) and concentrated NH₄OH (23 mL) in water (200 mL). The mixture was maintained at the boiling point for five minutes. The ferric hydroxide was separated by filtration and washed repeatedly with dilute NH₄OH and water. The filtrate was acidified with dilute HCl. The resulting solid was collected by filtration to afford 1.2 g (22%) of 4-fluoro-1H-indole-2-carboxylic acid (34) as a white solid, which was used in the next step without further purification.

Step 3:

To a solution of 34 (179 mg, 1.00 mmol) in anhydrous DMF (2.0 mL) were added NH₄Cl (160 mg, 3.00 mmol), EDCI (395 mg, 2.20 mmol), HOBt (297 mg, 2.20 mmol) and TEA (303 mg, 3.00 mmol) at RT. After stirring at RT for 3 h, the mixture was quenched with H₂O (10 mL) the resulting mixture was extracted with EtOAc (3×6 mL). The combined extracts were dried and concentrated. The residue was purified by SiO₂ chromatography eluting with petroleum ether/EtOAc (5:1 to 3:1) to afford 130 mg (73%) of 4-fluoro-1H-indole-2-carboxamide (36) as a white solid. LCMS (ESI) m/z: 179.1 [M+H]⁺.

Step 4:

To a solution of 36 (130 mg, 0.730 mmol) in anhydrous THF (5.0 mL) was added LiAlH₄ (138 mg, 3.65 mmol) at 0-5° C. The reaction mixture was heated at 80° C. overnight. After cooling to RT, the mixture was treated with aq. Na₂SO₄. The resulting mixture was extracted with EtOAc (3×10 mL). The combined organic layers were dried and concentrated. The residue was purified by SiO₂ chromatography eluting with petroleum ether/EtOAc/TEA (10:10:0.5) to afford 40 mg (33%) of (4-fluoro-1H-indol-2-yl)methanamine (38) as a pale yellow solid. ¹H NMR (500 MHz, DMSO-d₆) δ 11.22 (s, 1H), 7.14 (d, J=8.0 Hz, 1H), 6.97 (m, 1H), 6.70 (m, 1H), 6.28 (s, 1H), 3.82 (s, 2H). LCMS (ESI) m/z: 148.1 [M+H−17]⁺.

Referential Example 4

(S)-4-(Amino(1-methyl-1H-pyrazol-4-yl)methyl)-2-chlorobenzonitrile hydrochloride (44)

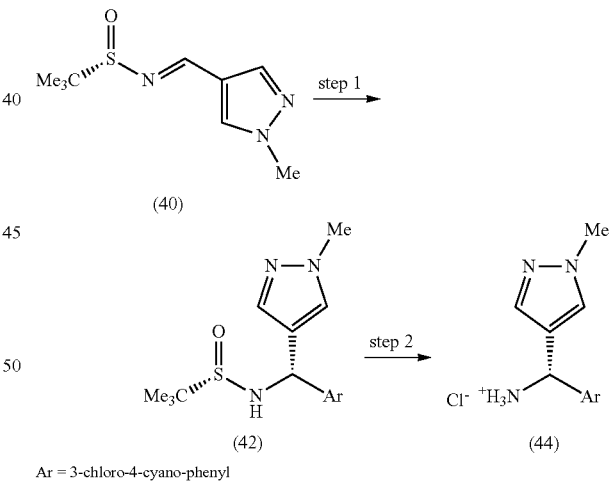

Ar = 3-chloro-4-cyano-phenyl

Step 1:

To a solution of 1-methyl-1H-pyrazole-4-carbaldehyde (3.0 g, 27 mmol) in THF (100 mL) was added (S)-2-methyl-propane-2-sulfinamide (6.6 g, 54 mmol) and Ti(OEt)₄ (22.3 g, 98.0 mmol). The reaction mixture was heated at 65° C. for 12 h. After cooling, the mixture was poured into water. The solid was filtered, and the filtrate was extracted with EtOAc (3×100 mL). The organic layer was washed with water (3×50 mL), dried (Na₂SO₄), filtered and concentrated in vacuo. The residue was purified by SiO₂ chromatography eluting with petroleum ether/EtOAc (4:1) to afford 5.6 g (98%) of (S,E)-2- methyl-N-((1-methyl-1H-pyrazol-4-yl)methylene)propane-2-sulfinamide 40 as colorless oil. LCMS (ESI) m/z: 214.1 [M+H]$^+$.

Step 2:

To a suspension of LiCl (920 mg, 22.0 mmol) in THF (20 mL) was added isopropylmagnesium chloride (2.0 N in THF, 11 mL, 22 mmol) at RT. The resultant mixture was stirred at 40° C. for 30 min. The mixture was cooled to −78° C. and 4-bromo-2-chlorobenzonitrile (4.00 g, 18.5 mmol) in THF (50 mL) was added. The resulting mixture was stirred at 0° C. for 1 h then cooled to −78° C. 40 (2.8 g, 13 mmol) in THF (50 mL) was then added. The reaction was stirred at 0° C. for 4 h then quenched with water (50 mL). The resulting mixture was extracted with EtOAc (3×100 mL). The organic layer was washed with sat. NaCl (3×50 mL), dried (Na$_2$SO$_4$), filtered and concentrated in vacuo. The residue was purified by SiO$_2$ chromatography eluting with DCM/MeOH (100:1) to afford 1.0 g (19%) of 42 as a yellow solid. LCMS (ESI) m/z: 351.2 [M+H]$^+$.

Step 3:

To a solution of 42 (1.0 g, 3.0 mmol) in EtOAc (20 mL) was added 3N HCl/EtOAc (2.2 mL) at RT. After stirring for 1 h, the solid was filtered to afford 500 mg (68%) of 44 as a white solid. $^1$H NMR (500 MHz, CD$_3$OD) δ 7.96 (d, J=8.0 Hz, 1H), 7.84-7.82 (m, 2H), 7.67-7.64 (m, 2H), 5.80 (s, 1H), 3.93 (s, 3H). LCMS (ESI) m/z: 247.1 [M+H]$^+$.

Referential Example 5

(S)-(4-Chloro-3-fluorophenyl)(1-methyl-1H-pyrazol-4-yl)methanamine hydrochloride (50a)

Step 1:

To a solution of 1-methyl-1H-pyrazole-4-carbaldehyde (2.2 g, 20 mmol) in THF (50 mL) was added (R)-2-methylpropane-2-sulfinamide (4.8 g, 40 mmol) and Ti(OEt)$_4$ (9.2 g, 40 mmol). The reaction mixture was heated at 65° C. for 14 h. After cooling, the mixture was poured into water. The solid was filtered off, and the filtrate was extracted with EtOAc. The organic layer was concentrated and purified by SiO$_2$ chromatography eluting with petroleum ether/EtOAc (5:1) to afford 4.0 g (83%) of (R,E)-2-methyl-N-((1-methyl-1H-pyrazol-4-yl)methylene)propane-2-sulfinamide (46). LCMS (ESI) m/z: 214.1 [M+$^{11}$]$^+$.

Step 2:

To a mixture of 4-bromo-1-chloro-2-fluorobenzene (11.7 g, 56.0 mmol) and magnesium turnings (2.1 g, 84 mmol) in THF (150 mL) at RT was added a few drops of 1,2-dibromoethane (1.1 g, 5.6 mmol). The mixture was stirred at RT for 1.5 h. After cooling to −78° C., (R,E)-2-methyl-N-((1-methyl-1H-pyrazol-4-yl)methylene)propane-2-sulfinamide (4.00 g, 18.7 mmol) was added and stirred at −78° C. for 6 h. The reaction was quenched with aq. NH$_4$Cl solution and extracted with EtOAc. The combined organic layers were dried (MgSO$_4$), filtered, and concentrated. The crude product was purified by SiO$_2$ chromatography eluting with DCM/MeOH (150:1) to afford the 2.9 g (45%) of (R)—N—((S)-(4-chloro-3-fluorophenyl)(1-methyl-1H-pyrazol-4-yl)methyl)-2-methylpropane-2-sulfinamide (48). LCMS (ESI) m/z: 344.1 [M+H]$^+$.

Step 3:

To a solution of 48 (2.9 g, 8.4 mmol) in MBTE (40 mL) was added 3N HCl/methanol (6.0 mL, 18 mmol). The mixture was stirred for 2 h at RT. The resulting solid was filtered and washed with MTBE to afford 650 mg (35%) of 50a. $^1$H NMR (500 MHz, CD$_3$OD) δ 7.46-7.43 (m, 2H), 7.38 (s, 1H), 7.31 (dd, J=10.5, 2.0 Hz, 1H), 7.21 (dd, J=8.5, 1.5 Hz, 1H), 5.13 (s, 1H), 3.85 (s, 3H). LCMS (ESI) m/z: 240.0 [M+H]$^+$.

(S)-(1-Methyl-1H-pyrazol-4-yl)(4-(trifluoromethoxy)phenyl)methanamine hydrochloride (50b) was prepared analogously except in step 2,4-trifluoromethoxy-bromobenzene replaced 4-bromo-1-chloro-2-fluorobenzene. $^1$H NMR (500 MHz, CD$_3$OD) δ 7.74 (s, 1H), 7.65-7.63 (m, 3H), 7.42 (d, J=8.5 Hz, 2H), 5.73 (s, 1H), 3.94 (s, 3H). LCMS (ESI) m/z: 272.1 [M+H−17]$^+$.

(S)-(3-Fluoro-4-methoxyphenyl)(1-methyl-1H-pyrazol-4-yl)methanamine hydrochloride (50c) was prepared analogously except in step 2,4-methoxy-3-fluoro-1-bromobenzene replaced 4-bromo-1-chloro-2-fluorobenzene. $^1$H NMR (500 MHz, CD$_3$OD) δ 7.58 (d, J=1.5 Hz, 1H), 7.24-7.17 (m, 3H), 6.55 (d, J=2.0 Hz 1H), 5.87 (s, 1H), 3.92 (s, 3H), 3.68 (s, 3H). LCMS (ESI) m/z: 236.3 [M+H]$^+$.

(S)-(3-Fluoro-4-methoxyphenyl)(1-methyl-1H-pyrazol-3-yl)methanamine hydrochloride (50d) was prepared analogously except in step 1,1-methyl-1H-pyrazole-4-carbaldehyde was replaced with 1-methyl-1H-pyrazole-3-carbaldehyde and in step 2, 4-methoxy-3-fluoro-1-bromobenzene replaced 4-bromo-1-chloro-2-fluorobenzene. $^1$H NMR (500 MHz, CD$_3$OD) δ 7.62 (s, 1H), 7.26-7.15 (m, 3H), 6.15 (s, 1H), 5.54 (s, 1H), 3.93 (s, 3H), 3.91 (s, 3H). LCMS m/z: 219.1 [M+H−17]$^+$.

(S)-(3-Fluoro-4-methoxyphenyl)(1-methyl-1H-pyrazol-5-yl)methanamine hydrochloride (50e) was prepared analogously except in step 1,1-methyl-1H-pyrazole-4-carbaldehyde was replaced with 1-methyl-1H-pyrazole-5-carbaldehyde and in step 2, 4-methoxy-3-fluoro-1-bromobenzene replaced 4-bromo-1-chloro-2-fluorobenzene.

(S)-(3-Fluoro-phenyl)(1-methyl-1H-pyrazol-5-yl)methanamine hydrochloride (50f) was prepared analogously except in step 1,1-methyl-1H-pyrazole-4-carbaldehyde was replaced with 1-methyl-1H-pyrazole-5-carbaldehyde and in step 2,4-methoxy-3-fluoro-1-bromobenzene replaced 1-bromo-3-fluorobenzene.

(S)-(4-Chloro-3-fluorophenyl)(1-methyl-1H-pyrazol-5-yl)methanamine hydrochloride (50 g) was prepared analogously except in step 1,1-methyl-1H-pyrazole-4-carbaldehyde was replaced with 1-methyl-1H-pyrazole-5-carbaldehyde.

(S)-(3-Fluoro-phenyl)(1-methyl-1H-pyrazol-4-yl)methanamine hydrochloride (50h) was prepared analogously except in step 2,4-methoxy-3-fluoro-1-bromobenzene replaced 1-bromo-3-fluorobenzene.

(S)-(4-Methoxy-phenyl)(1-methyl-1H-pyrazol-4-yl)methanamine hydrochloride (50i) was prepared analogously except in step 2,4-methoxy-1-bromobenzene replaced 1-bromo-3-fluorobenzene.

Referential Example 6

(S)-2-Amino-2-(3-fluorophenyl)ethanol hydrochloride 62a (Ar=3-fluorophenyl)

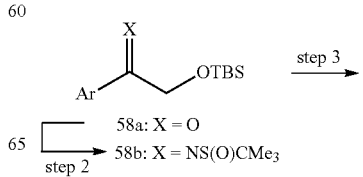

-continued

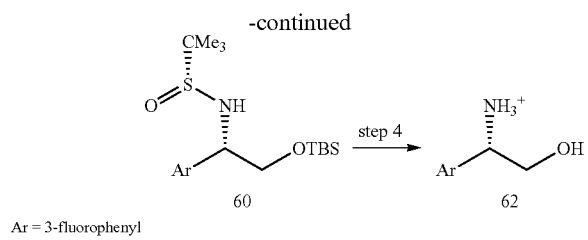

Ar = 3-fluorophenyl

Step 1:

To a suspension of magnesium turnings (2.10 g, 85.7 mmol) in anhydrous THY (120 mL), was added slowly at RT 1-bromo-3-fluorobenzene (10.0 g, 57.2 mmol) and 1,2-dibromoethane (0.10 mL). After stirring for 40 min under argon, the mixture was cooled to −78° C., and 2-(tert-butyldimethylsilyloxy)-N-methoxy-N-methylacetamide (9.3 g, 40 mmol) was added. The resulting mixture was warmed to 0° C. and stirred for 2 h. The reaction was quenched with saturated $NH_4Cl$ (5.0 mL), and the insoluble material was filtered. The filtrate was dried ($Na_2SO_4$), filtered and concentrated in vacuo. The residue was purified by $SiO_2$ chromatography eluting with petroleum ether/EtOAc (20:1) to afford 10.3 g (93%) of 2-(tert-butyldimethylsilyloxy)-1-(3-fluorophenyl)ethanone (58a) as oil. LCMS (ESI) m/z: 268.0[M+H]$^+$.

Step 2:

To a mixture of 58a (11.3 g, 42.1 mmol) and (R)-2-methylpropane-2-sulfinamide (6.60 g, 54.7 mmol) in THF (200 mL) at RT was added Ti(Oi-Pr)$_4$ (29.9 g, 105 mmol). The reaction mixture was heated to reflux under $N_2$ overnight. The mixture was cooled then treated with saturated $NH_4Cl$ (5.0 mL), and the insoluble material was filtered. The filtrate was dried ($Na_2SO_4$), filtered and concentrated in vacuo. The residue was purified by $SiO_2$ chromatography eluting with petroleum ether/EtOAc gradient (60:1 to 20:1) to afford 7.6 g (49%) of (R,E)-N-(2-(tert-butyldimethylsilyloxy)-1-(3-fluorophenyl)ethylidene)-2-methylpropane-2-sulfinamide (58b) as yellow oil. LCMS (ESI) m/z: 372.2 [M+H]$^+$.

Step 3:

To a solution of 58b (7.60 g, 20.5 mmol) in anhydrous THF (250 mL) at −78° C. was added DIBAL-H (51.1 mL, 51.1 mmol) under argon. After stirring at −78° C. for 1 h, the mixture was treated with brine (16 mL) at −78° C. and then warmed to RT. The insoluble material was filtered, and the filtrate was dried ($Na_2SO_4$), filtered and concentrated in vacuo. The residue was purified by $SiO_2$ chromatography eluting with a petroleum ether/EtOAc gradient (20:1 to 6:1) to afford 6.5 g (86%) of 60 as a yellow solid. LCMS (ESI) m/z: 374.2 [M+H]$^+$.

Step 4:

To a solution of 60 (3.0 g, 8.0 mmol) in MeOH (100 mL) was added 3N HCl/MeOH (8.0 mL, 24 mmol). After stirring at RT for 1 h, the mixture was concentrated in vacuo and diluted with EtOAc (30 mL). The solid was filtered and washed with EtOAc (20 mL) to afford 880 mg (57%) of 62a as a white solid. $^1$H NMR (500 MHz, CD$_3$OD) δ 7.50 (m, 1H), 7.32-7.28 (m, 2H), 7.19 (m, 1H), 7.41 (m, 1H), 3.93 (m, 1H), 3.82 (m, 1H). LCMS (ESI) m/z: 156.1 [M+11]$^+$.

(S)-2-Amino-2-(4-(trifluoromethoxy)phenyl)ethanol hydrochloride (62b) (Ar=4-trifluoromethoxyphenyl) was prepared analogously except in step 1,3-fluoro-bromobenzene was replaced with 4-fluoromethoxy-bromobenzene. $^1$H NMR (500 MHz, CD$_3$OD) δ 7.44 (d, J=8.5 Hz, 2H), 7.33 (d, J=8.5 Hz, 2H), 4.44 (m, 1H), 3.91-3.81 (m, 2H). LCMS (ESI) m/z: 222.1 [M+H]$^+$.

(S)-2-Amino-2-(4-methoxyphenyl)ethanol hydrochloride (62c) (Ar=4-methoxyphenyl) was prepared analogously except in step 1,3-fluoro-bromobenzene was replaced with 4-methoxy-bromobenzene. $^1$H NMR (500 MHz, DMSO-d$_6$) δ 8.49 (s, 3H), 7.43 (d, J=8.5 Hz, 2H), 6.97 (d, J=8.5 Hz, 2H), 5.50 (brs, 1H), 4.19 (m, 1H), 3.76 (s, 3H), 3.68-3.67 (m, 2H). LCMS (ESI) m/z: 151.3 [M+H−17]$^+$.

(S)-2-Amino-2-(3-fluoro-4-methoxyphenyl)ethanol hydrochloride (62d) (Ar=3-fluoro-4-methoxyphenyl) was prepared analogously except in step 1,3-fluoro-bromobenzene was replaced with 3-fluoro-4-methoxy-bromobenzene. $^1$H NMR (500 MHz, CD$_3$OD) δ 7.28-7.17 (m, 3H), 4.31 (m, 1H), 3.91-3.87 (m, 4H), 3.78 (m, 1H). LCMS (ESI) m/z: 169.3 [M+H−17]$^+$.

(S)-2-Amino-2-(4-chloro-3-fluoro-phenyl)ethanol hydrochloride (62e) (Ar=4-chloro-3-fluoro-phenyl) can be prepared analogously except in step 1,3-fluoro-bromobenzene is replaced with 4-chloro-3-fluoro-bromobenzene (S)-2-Amino-2-(3-chloro-4-fluoro-phenyl)ethanol hydrochloride (62l) (Ar=3-chloro-4-fluoro-4-phenyl) can be prepared analogously except in step 1,3-fluoro-bromobenzene is replaced with 3-chloro-4-fluoro-bromobenzene.

(S)-2-Amino-2-(4-fluorophenyl)ethanol (62g) (Ar=4-fluorophenyl) can be prepared analogously except in step 1,3-fluoro-bromobenzene is replaced with 4-fluoro-bromobenzene.

(S)-2-Amino-2-(4-difluoromethoxy-phenyl)ethanol (62h) (Ar=4-difluoromethoxy-phenyl) can be prepared analogously except in step 1,3-fluoro-bromobenzene is replaced with 4-difluoromethoxy-bromobenzene.

Referential Example 7

(S)-4-(1-Amino-2-(tert-butyldimethylsilyloxy)ethyl)-2-chlorobenzonitrile hydrochloride (62i; Ar=3-chloro-4-cyano-phenyl)

Step 1:

4-(2-(tert-Butyldimethylsilyloxy)acetyl)-2-chlorobenzonitrile—To a solution of 4-bromo-2-chlorobenzonitrile (15 g, 69 mmol) in THF (150 mL) at −78° C. was added LiCl (3.39 g, 81.0 mmol) and isopropylmagnesium chloride (1.3 N in THF, 62 mL, 81 mmol). After stirring at 0° C. for 30 min, the solution was cooled to −78° C., and a solution of 2-(tert-butyldimethylsilyloxy)-N-methoxy-N-methylacetamide (12 g, 57 mmol) in THF (150 mL) was added. The reaction was stirred at 0° C. for 2 h, then quenched with water (50 mL), and the resulting mixture was extracted with EtOAc (3×100 mL). The organic layer was washed with sat. NaCl (3×50 mL), dried ($Na_2SO_4$), filtered and concentrated in vacuo. The residues were purified by $SiO_2$ chromatography eluting with petroleum ether/EtOAc (50:1) to afford 37 g (88%) of 58 (Ar=3-chloro-4-cyanophenyl) as yellow oil. LCMS (ESI) m/z: 509.1 [M+H]$^+$.

Step 2:

(R,E)-N-(2-(tert-Butyldimethylsilyloxy)-1-(3-chloro-4-cyanophenyl)ethylidene)-2-methylpropane-2-sulfinamide was prepared in accord with the procedure in step 2 of referential example 6 except 58a (Ar=3-chloro-4-cyanophenyl) was the reactant. The residue was purified by $SiO_2$ chromatography eluting with petroleum ether/EtOAc (20:1) to afford 4.9 g (25%) of 58b (Ar=3-chloro-4-cyanophenyl) as a yellow solid. LCMS (ESI) m/z: 413.1 [M+H]$^+$.

Step 3:

To a solution of 58b (Ar=3-chloro-4-cyanophenyl) (4.90 g, 11.9 mmol) in THF (100 mL) was added NaBH$_4$ (700 mg, 14.2 mmol) at 0° C. After stirring for 30 min, the reaction mixture was treated with water (50 mL) and extracted with EtOAc (2×100 mL). The organic layer was washed with sat. NaCl (50 mL), dried (Na₂SO₄), filtered and concentrated in vacuo. The residue was purified by SiO₂ chromatography eluting with petroleum ether/EtOAc (20:1) to afford 1 g (22%) of 60 (Ar=3-chloro-4-cyanophenyl) as a white solid. LCMS (ESI) m/z: 415.3 [M+H]⁺.

Step 4:

To a solution of 60 (Ar=3-chloro-4-cyanophenyl) (500 mg, 1.20 mmol) in EtOAc (10 mL) was added 3N HCl/methanol (1.2 mL) at RT. After stirring for 1 h, the solid was filtered to afford 400 mg (100%) of 62i (Ar=3-chloro-4-cyanophenyl) as a white solid. LCMS (ESI) m/z: 311.3 [M+H]⁺.

Referential Example 8

(R)-1-(3-Fluoro-4-methoxyphenyl)propan-1-amine hydrochloride (70a)

Step 1:

To a solution of 3-fluoro-4-methoxybenzaldehyde (2.0 g, 13 mmol) in THF (40 mL) was added (S)-2-methylpropane-2-sulfinamide (2.84 g, 23.4 mmol) and Ti(OEt)₄ (5.92 g, 26.0 mmol). The reaction mixture was heated at 65° C. for 12 h. After cooling to RT, the mixture was poured into water. The solid was filtered, and the filtrate was extracted with EtOAc (3×100 mL). The filtrate was dried (Na₂SO₄), filtered and concentrated in vacuo. The residue was purified by SiO₂ chromatography eluting with EtOAc/petroleum ether (1:4) to afford 3.0 g (90%) of (S,E)-N-(3-fluoro-4-methoxybenzylidene)-2-methylpropane-2-sulfinamide (66). LCMS (ESI) m/z: 258.1 [M+H]⁺.

Step 2:

To a solution of 66 (3.0 g, 12 mmol) in THF (30 mL) at −78° C. was added a solution of ethylmagnesium bromide in THF (1N, 18 mL, 18 mmol). After stirring for 4 h, the reaction mixture was warmed to 25° C. and stirred at RT overnight. The mixture was treated with NH₄Cl, and diluted with EtOAc. The combined organic layers were dried (Na₂SO₄), filtered and concentrated in vacuo. The residue was purified by SiO₂ chromatography eluting with EtOAc/petroleum ether (1:1) to afford 1.5 g (45%) of (S)—N—((R)-1-(3-fluoro-4-methoxyphenyl)propyl)-2-methylpropane-2-sulfinamide (68). LCMS (ESI) m/z: 288.1 [M+H]⁺.

Step 3:

To a solution of 68 (1.5 g, 5.2 mmol) in Et₂O (20 mL) at 0° C. was added 3N HCl/MeOH (5.0 mL, 15 mmol). After being stirred for 1.5 h, the solid was filtered and dried in vacuo to afford 900 mg (80%) of 70a. ¹H NMR (500 MHz, DMSO-d₆) δ 8.56 (s, 3H), 7.44 (dd, J=12.5, 2.0 Hz, 1H), 7.29-7.20 (m, 2H), 4.08 (m, 1H), 3.84 (s, 3H), 1.97 (m, 1H), 1.78 (m, 1H), 0.73 (t, J=7.0 Hz, 3H). LCMS (ESI) m/z: 167.1 [M+H−17]⁺.

(R)-1-(4-Chloro-3-fluoro-phenyl)propan-1-amine hydrochloride (70b) can be prepared analogously except in step 1,3-fluoro-4-methoxy-benzaldehyde is replaced with 4-chloro-3-fluoro-benzaldehyde.

(R)-1-(3-Chloro-4-fluoro-phenyl)propan-1-amine hydrochloride (70c) can be prepared analogously except in step 1,3-fluoro-4-methoxy-benzaldehyde is replaced with 3-chloro-4-fluoro-benzaldehyde.

(R)-1-(4-Chloro-3-fluorophenyl)prop-2-en-1-amine hydrochloride (70d) can be prepared analogously except in step 1,3-fluoro-4-methoxy-benzaldehyde is replaced with 3-chloro-4-fluoro-benzaldehyde. In step 2, ethyl magnesium bromide is replaced with vinyl magnesium bromide. ¹H NMR (500 MHz, MeOH-d₄) δ 7.62 (t, J=7.0 Hz, 1H), 7.40 (m, 1H), 7.33 (dd, J=5.5, 2.5 Hz, 1H), 6.13 (m, 1H), 5.55-5.46 (m, 2H), 5.04 (d, J=6.0 Hz, 1H).

Referential Example 9

(3S,4S)-3-Fluorotetrahydro-2H-pyran-4-amine (71c) and (3R,4R)-3-fluorotetrahydro-2H-pyran-4-amine (71d)

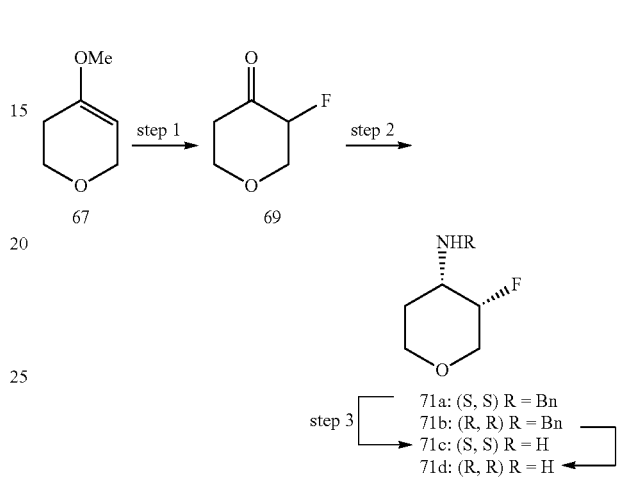

Step 1:

To a stirred solution of 1-chloromethyl-4-fluoro-1,4-diazoniabicyclo[2.2.2]octane bis-tetrafluoroborate (147 g, 414 mmol, Selectfluor®) in MeCN/H₂O (1:1, 800 mL) cooled to 0° C. under nitrogen in a 3 L round-bottom flask was added dropwise a solution of 67 (45.0 g, 394 mmol, CASRN 17327-22-9) in MeCN (120 mL). The reaction was stirred for 30 min. in an ice bath before the bath was removed, and the reaction was stirred for an additional 1 h. Solid NaCl (200 g) was then added to the reaction along with DCM (300 mL). A saturated Na₂CO₃ solution was added slowly until pH was 10. The mixture was transferred into a 4 L sep. funnel and thrice extracted into DCM. The aqueous layer was then placed in a continuous liquid-liquid extractor with DCM and heated to 58° C. for 18 h. The combined organic extracts were dried (MgSO₄), filtered and concentrated at 20° C. on the rotovap. The crude product was purified by SiO₂ chromatography eluting with DCM/MeOH gradient (500:3 to 500:5 DCM:MeOH) to afford 30 g (64.4%) of 3-fluorodihydro-2H-pyran-4(3H)-one (69).

Step 2:

To a solution of 69 (30 g, 254 mmol) and DCE (800 mL) cooled to 0° C. under nitrogen was added phenylmethanamine (29.8 mL, 267 mmol), and the solution was stirred for 10 min. To the reaction mixture was added NaBH(OAc)₃ (75.4 g, 356 mmol) followed by the dropwise addition of glacial HOAc (14.5 mL, 254 mmol). The reaction was stirred for 2 h and then poured into 1M NaOH and extracted with DCM. The combined organic fractions were dried (MgSO₄), filtered and concentrated. The crude product was purified by reverse phase column chromatography using a MeCN/H₂O gradient (0 to 40% MeCN) to afford 39 g (73.4%) of the racemic cis product [(3S,4S)— and (3R,4R)—N-benzyl-3-fluorotetrahydro-2H-pyran-4-amine (71a) and (71b) respectively].

The enantiomers can be separated by chromatography on a Chiralpak IC, 5×25 cm column eluting with 10% IPA (0.1%

NH$_4$OH)/90% CO$_2$ at a flow rate of 300 mL/min and a temperature of 40° C. The back pressure was 100 Bar.

Step 3:

To a solution of 71a (3.7 g, 18 mmol) and MeOH (40 mL) at RT was added Pd/C (3.8 g, 1.8 mmol), and the resulting suspension stirred under H$_2$ for 18 h. The catalyst was filtered and washed with MeOH. The solvent was concentrated to afford 2.1 g (100%) (3S,4S)-3-fluorotetrahydro-2H-pyran-4-amine (71c). $^1$H NMR (400 MHz, CDCl$_3$) δ 4.58-4.44 (m, 1H), 4.19-4.09 (m, 1H), 4.05-3.95 (m, 1H), 3.56-3.38 (m, 2H), 2.96-2.84 (m, 1H), 1.88-1.77 (m, 1H), 1.72-1.65 (m, 1H). The enantiomer, (3R,4R)-3-fluorotetrahydro-2H-pyran-4-amine (71d), can be prepared analogously by replacing 71a with 71b.

Referential Example 10

(3S,4R)-3-Fluorotetrahydro-2H-pyran-4-amine (77a) and (3R,4S)-3-fluorotetrahydro-2H-pyran-4-amine (77b)

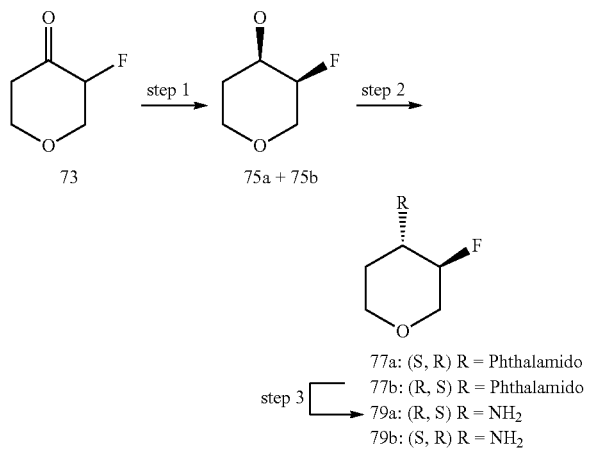

Step 1:

To a stirred solution of 73 (34.58 g, 292.8 mmol) and THF (350 mL) cooled to −78° C. under nitrogen was added dropwise L-selectride (307.4 mL, 307.4 mmol), and the reaction was stirred for 30 min. MeOH (35.58 mL, 878.4 mmol) and 1M NaOH (878.4 mL, 878.4 mmol) were then added, and the reaction was allowed to warm to 0° C. To the solution was added dropwise with care H$_2$O$_2$ (99.59 mL, 1464 mmol), and the reaction was stirred for an additional 30 min Saturated brine (50 mL) was then added, and the reaction was concentrated to remove THF. The solution was diluted with DCM (500 mL) and transferred to a liquid-liquid continuous extractor, which was heated at 58° C. for 24 h. The organic fraction was then separated, dried (MgSO$_4$), filtered and concentrated. The crude product was purified by SiO$_2$ chromatography eluting with a DCM/EtOAc gradient (5:1 to 3:1) to afford 21 g (60.2%) of the racemic cis product (3R,4S)— and (3S,4R)-3-fluorotetrahydro-2H-pyran-4-ol ((75a) and (75b) respectively).

Step 2:

To a stirred solution of 75a and 75b (15.0 g, 125 mmol), isoindoline-1,3-dione (20.2 g, 137 mmol) and 2-(diphenylphosphino)pyridine (42.7 g, 162 mmol) and THF (550 mL) cooled to 0° C. under nitrogen was added (E)-di-tert-butyl diazene-1,2-dicarboxylate (37.4 g, 162 mmol) and the reaction stirred at RT for 24 h. To the reaction mixture was added 4M HCl in dioxane (156 mL, 624 mmol), and the resulting solution stirred for 2 h then concentrated to dryness. The residue was dissolved in ether and washed six times with 4M HCl. The solids that did not dissolve in ether were set aside for later purification (batch 1). The organic solution was then dried (MgSO$_4$), filtered and concentrated. The crude material was suspended in THF and filtered, giving solid product (batch 2). The filtrate was next concentrated, re-suspended in DCM and filtered. The solid was discarded. The filtrate was combined with the first two batches of solids (batches 1 and 2), concentrated, and purified by SiO$_2$ chromatography eluting with a DCM/MeOH gradient (500:2 to 500:5) to afford 14 g (45%) of racemic 2-((3S,4R) and (3R,4S)-3-fluorotetrahydro-2H-pyran-4-yl)isoindoline-1,3-dione ((77a) and (77b) respectively).

The enantiomers were separated by chromatography on a Chiralpak IA, 5×25 cm column eluting with 10% MeOH: DCM (1:1)/90% CO$_2$ at a flow rate of 300 mL/min and a temperature of 40° C. The back pressure was 100 Bar.

Step 3:

To a solution of 77b (8.4 g, 34 mmol) and THF/MeOH (1:1, 160 mL) was added hydrazine monohydrate (17 g, 337 mmol), and the reaction was stirred at 50° C. for 6 h and then cooled to RT for 24 h. The resulting mixture was filtered, and the solid was washed with THF. The filtrate was concentrated, and the crude product was purified by SiO$_2$ chromatography eluting with a DCM:MeOH gradient (500:20 to 500:25) to afford 4.0 g (100%) of (3R,4S)-3-fluorotetrahydro-2H-pyran-4-amine (79a). $^1$H NMR (400 MHz, CDCl$_3$) δ 4.28-4.04 (m, 2H), 3.94-3.85 (m, 1H), 3.45-3.35 (m, 1H), 3.30-3.20 (m, 1H), 3.05-2.92 (m, 1H), 1.97-1.88 (m, 1H), 1.58-1.48 (m, 1H). The other enantiomer, (3R,4S)-3-fluorotetrahydro-2H-pyran-4-amine (79b), was prepared analogously from 77a.

Referential Example 11

(2S,4R)-2-(tert-Butyl-dimethyl-silanyloxymethyl)-tetrahydropyran-4-ylamine

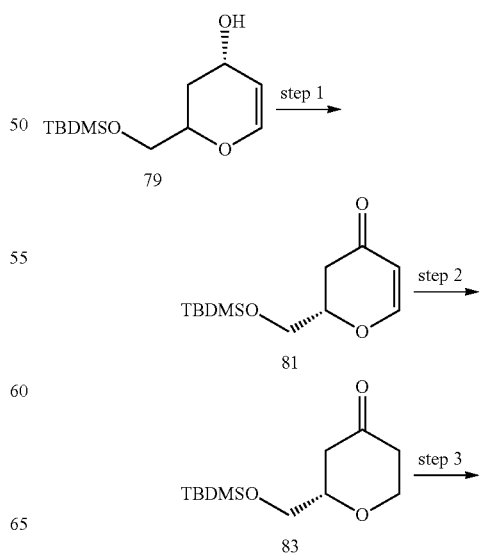

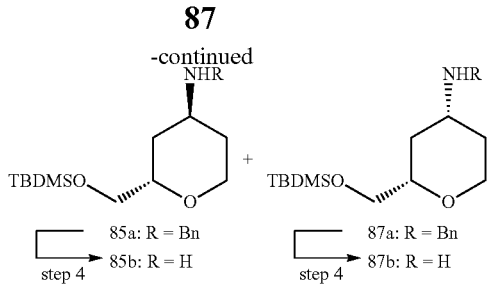

85a: R = Bn
step 4 → 85b: R = H

87a: R = Bn
step 4 → 87b: R = H

Step 1:

To a solution of (2S,4S)-2-((tert-butyldimethylsilyloxy)methyl)-3,4-dihydro-2H-pyran-4-ol (79, 3.565 g, 14.59 mmol) (prepared from (2R,3S,4R)-2-(hydroxymethyl)-3,4-dihydro-2H-pyran-3,4-diol according to the procedures in L. A. Paquette and J. A. Oplinger, *J. Org. Chem.* 1988 53:2953-2959) and DCM (25 mL) was added 4 Å molecular sieves (7 g) followed by N-methyl morpholine N-oxide (3.418 g, 29.17 mmol) and tetrapropylammonium perruthenate (0.2563 g, 0.7293 mmol). The reaction was stirred for 1.5 h at RT. The mixture was passed through a plug of $SiO_2$ and eluted with DCM. The filtrate was concentrated and the resulting residue was purified by $SiO_2$ chromatography eluting with 25% EtOAc/hexane to afford 3.097 g (87.6%) of 81.

Step 2:

A suspension of 81 (3.097 g, 12.78 mmol), Pd/C (0.5439 g, 0.2555 mmol) and EtOAc (30 mL) was stirred and maintained under hydrogen balloon pressure for 18 h. The reaction was filtered through a plug of Celite® and concentrated. The resulting residue was purified by $SiO_2$ chromatography eluting with 20% EtOAc/hexane to afford 2.035 g (65.17%) of 83.

Step 3:

To a solution of 83 (1.885 g, 7.713 mmol), phenylmethanamine (0.9470 mL, 8.484 mmol) and DCE (40 mL) was added $NaBH(OAc)_3$ (2.288 g, 10.80 mmol), and the reaction stirred for 1 h. The reaction mixture was poured into water and extracted with DCM. The combined organic extracts were washed with $NaHCO_3$, dried ($MgSO_4$), filtered and concentrated. The resulting residue was purified by $SiO_2$ eluting with a DCM/MeOH gradient (0 to 3% MeOH) to afford (2S,4R)—N-benzyl-2-((tert-butyldimethylsilyloxy)methyl)tetrahydro-2H-pyran-4-amine (87a, 1.686 g, 65.15% yield) and the trans (2S,4S)—N-benzyl-2-((tert-butyldimethylsilyloxy)methyl)tetrahydro-2H-pyran-4-amine (85a, 1.04 g, 40.18% yield).

Step 4:

To a solution of 85a (1.04 g, 3.10 mmol) and EtOH (20 mL) was added Pd/C (0.660 g, 0.310 mmol), and the reaction was stirred and maintained under balloon hydrogen pressure for 18 h. The mixture was filtered through a zap cap membrane filter. The filtrate was concentrated to afford 664 mg (87.3%) of 85b which was used without further purification.

The conversion of 87a to (2S,4R)-2-((tert-butyldimethylsilyloxy)methyl)tetrahydro-2H-pyran-4-amine (87b) was carried out analogously.

Referential Example 12

7-(Tetrahydro-2H-pyran-4-ylamino)-1,6-naphthyridine-2-carboxylic acid (72) [A-10, Scheme A, $R^1$=tetrahydropyran-4-yl)]

Step 1:

A 20-L 4-necked round-bottom flask purged and maintained under a $N_2$ atmosphere was charged with a solution of diisopropylamine (582 g, 5.76 mol, 1.05 equiv) in THF (4.2 L), followed by the dropwise addition over 30 min of n-BuLi (2.4 M, 2.4 L, 1.05 equiv) with stirring at −30° C. The resulting solution was stirred at −30° C. for 30 min then cooled to −80° C. To the LDA solution was added dropwise over 1 h with stirring a solution of 2,5-dibromopyridine (1.3 Kg, 5.49 mol, 1.00 equiv) in THF (5.2 L). The resulting solution was stirred at −70° C. for 30 min. To the mixture was added $CO_2$ (dry ice) (1267 g, 28.80 mol, 5.00 equiv) in several batches at −70° C. The resulting solution was stirred at −70° C. for 30 min, quenched by the addition of 5 L of water at −70° C., concentrated in vacuo and extracted with 3×4 L of EtOAc. The pH value of the aqueous layer was adjusted to 3-4 with HCl (12 mol/L). The precipitate was collected by filtration to afford 2,5-dibromoisonicotinic acid (A-2) white solid.

Step 2:

A 20-L 4-necked round-bottom flask purged and maintained under a $N_2$ atmosphere was charged with 2,5-dibromoisonicotinic acid (1.030 Kg, 3.67 mol, 1.00 equiv), TEA (484 g, 4.78 mol, 1.30 equiv), tert-butanol (10 L) followed by the addition of DPPA (1215 g, 4.41 mol, 1.20 equiv). The resulting solution was stirred overnight at 80° C. This reaction was repeated for 5 times. The resulting mixture was concentrated in vacuo, diluted with 20 L of water and extracted with 3×15 L of EtOAc. The organic layers were combined, washed with 2×15 L of brine, dried ($Na_2SO_4$), filtered and concentrated in vacuo. The residue was purified by $SiO_2$ chromatography eluting with an EtOAc/petroleum ether gradient (1:30 to 1:15) to afford 3.2 Kg (41%) of tert-butyl 2,5-dibromopyridine-4-ylcarbamate (A-3) as a white solid.

Step 3:

A 10-L 4-necked round-bottom flask was purged and maintained under $N_2$ atmosphere and then charged with A-3 (420 g, 1.19 mol, 1.00 equiv), MTBE (3.2 L), THF (1.4 L), then cooled to −80° C. and n-BuLi (2.5 M, 52 mL, 2.40 equiv) was added dropwise with stirring over 30 min. The resulting solution was stirred at −70° C. for 30 min, and then DMF (1400 mL, 5.00 equiv) was added dropwise with stirring at −70° C. The resulting solution was stirred at −70° C. for 30 min. The pH value of the solution was adjusted to 5-6 with HOAc. The resulting solution was extracted with 3×2.0 L of EtOAc. The organic layers were combined, washed with 2×3.0 L of brine, dried ($MgSO_4$), filtered and concentrated in vacuo. The residue was purified by $SiO_2$ chromatography eluting with an EtOAc:petroleum ether (1:30 to 1:10) to afford 200 g (56%) of A-4 as a white solid.

Step 4:

A 2 L 4-necked round-bottom flask purged and maintained under a $N_2$ atmosphere was charged with a solution of diisopropylamine (30.3 g, 299.44 mmol, 2.00 equiv) in THF (250 mL), and then n-butyllithium (125 mL, 2.00 equiv) was added dropwise with stirring at −60° C. The resulting solution was stirred at −20 to −30° C. for 1 h. To this stirred solution cooled to −60 to −70° was added dropwise a solution of tert-butyl acetate (34.8 g, 299.59 mmol, 2.00 equiv) in THF (100 mL). The resulting solution was stirred at −50° C. for 1 h. To the mixture was added a solution of A-4 (45 g, 149.43 mmol, 1.00 equiv) in THF (100 mL) at −60 to −70° C. The resulting solution was stirred at −50 to −60° C. for 1 h, quenched by the addition of 300 mL of satd. aq. $NH_4Cl$, concentrated in vacuo and extracted with 2×300 mL of EtOAc. The organic layers were combined, washed with brine (3×300 mL), dried ($Na_2SO_4$), filtered and concentrated in vacuo to afford 60 g (96%) of A-5 as a yellow oil.

Step 5:

A 2 L round-bottom flask was purged and maintained with a $N_2$ atmosphere was charged with A-5 (60 g, 143.78 mmol, 1.00 equiv), 6N HCl (360 mL) and 1,4-dioxane (240 mL). The resulting solution was heated to reflux overnight, cooled and concentrated in vacuo. The pH of the solution was adjusted to 8~9 with NaOH. The precipitate was collected by filtration and dried in an oven under reduced pressure to afford 20 g (62%) of A-6 as an off-white solid. (ES, m/z): 225 $[M+H]^+$. H NMR (DMSO, 300 MHz, ppm): 12.09 (s, 1H), 8.66 (s, 1H), 7.97~8.01 (d, 1H, J=9.6 Hz), 7.36 (s, 1H), 6.60~6.64 (dd, 1H, J=1.5, 9.6 Hz).

Step 6:

A 5 L 4-necked round-bottom flask purged and maintained with a $N_2$ atmosphere was charged with A-6 (100 g, 444.36 mmol, 1.00 equiv), $Pd(OAc)_2$ (10 mg, 0.04 mmol, 0.10 equiv), Xantphos (25.8 g, 44.56 mmol, 0.10 equiv), tetrahydro-2H-pyran-4-amine hydrochloride (67 g, 486.88 mmol, 1.10 equiv), and THF (1 L), and then a solution of LiHMDS (1 M on THF) (2000 mL, 4.50 equiv) was added. The resulting solution was heated to reflux for 2 h, concentrated in vacuo, diluted with 4 L of water and extracted with EtOAc (2×2 L). The aqueous layers were combined, and the pH adjusted to 8~9 with $NaHCO_3$ (solid). The precipitates were collected by filtration and dried in an oven in vacuo to afford 81.7 g (75%) of A-7 ($R^2$=tetrahydro-2H-pyran-4-yl) as a yellow solid.

Step 7:

A 2 L round-bottom flask was charged with A-7 ($R^2$=tetrahydro-2H-pyran-4-yl) (71.7 g, 289.94 mmol, 1.00 equiv) and $POCl_3$ (360 mL). The resulting solution was heated to reflux for 1 h, cooled to 0° C., quenched by the addition of 5 L of sat'd. aq. $NaHCO_3$ and extracted with EtOAc (3×3 L). The organic layers were combined, washed with brine (2×4 L), dried ($Na_2SO_4$), filtered and concentrated in vacuo. The residue was purified by $SiO_2$ chromatography eluting with a petroleum ether/EtOAc gradient (5:1 to 2:1) to afford 30 g (39%) of A-8 ($R^2$=tetrahydro-2H-pyran-4-yl) as a yellow solid.

Step 8:

A 1 L pressure tank reactor (20 atm) was charged with A-8 ($R^2$=tetrahydro-2H-pyran-4-yl) (30 g, 113.76 mmol, 1.00 equiv), $Pd(dppf)Cl_2$ (12.5 g, 17.08 mmol, 0.15 equiv), TEA (33.3 g, 329.08 mmol, 3.00 equiv), and MeOH (500 mL). CO (excess) was introduced. The resulting solution was stirred at 80° C. for 5 h and then cooled to RT. The solid was filtered, and the filtrate was concentrated in vacuo. The residue was purified by $SiO_2$ chromatography eluting with a petroleum ether/EtOAc gradient (2:1 to 0:1) to afford 29.5 g (90%) of A-9 ($R^2$=tetrahydro-2H-pyran-4-yl) as a yellow solid.

Step 9:

A 500-mL round-bottom flask was charged with A-9 ($R^2$=tetrahydro-2H-pyran-4-yl) (29.5 g, 102.68 mmol, 1.00 equiv), LiOH (2.75 g, 114.82 mmol, 1.10 equiv), and THF/water (300/60 mL). The resulting solution was stirred at RT for 1 h, concentrated in vacuo, diluted with 500 mL of water and extracted with DCM (3×150 mL). The pH value of the aqueous layer was adjusted to 5 with HCl (12 mol/L). The precipitate was collected by filtration and dried in an oven under reduced pressure to afford 27.26 g (97%) of A-10 ($R^2$=tetrahydro-2H-pyran-4-yl) as a red solid. (ES, m/z): 274 $[M+H]^+$. $^1$H NMR (DMSO, 300 MHz, ppm) δ 9.03 (s, 1H), 8.36~8.39 (d, 1H, J=8.4 Hz), 7.66~7.69 (d, 1H, J=8.4 Hz), 7.03~7.06 (d, 1H, J=7.8 Hz), 6.81 (s, 1H), 3.88~3.92 (m, 3H), 3.42~3.49 (m, 3H), 1.91~1.94 (d, 2H, J=10.8 Hz), 1.46~1.58 (m, 2H).

Referential Example 13

7-Fluoro-1,6-naphthyridine-2-carboxylic acid (74) (Scheme B, B-5)

Step 1:

A 2 L pressure tank reactor was charged with A-6 (93.5 g, 415.48 mmol, 1.00 equiv), ammonia (1 Kg), and Cu (10.7 g, 167.19 mmol, 0.40 equiv). The resulting solution was stirred at 120° C. overnight and then cooled to 25° C. The solids were collected by filtration and washed with 2×350 mL of ammonia to afford 48.8 g (73%) of B-1 as a yellow solid.

Step 2:

A 1 L 4-necked round-bottom flask was purged and maintained with a $N_2$ atmosphere then charged with B-1 (48.8 g, 302.80 mmol, 1.00 equiv) and $BMIM.BF_4$ (685 g, 3.03 mol, 10.00 equiv) followed by the addition of $NO.BF_4$ (53.2 g, 455.44 mmol, 1.50 equiv) in several batches. The resulting solution was stirred at RT for 1.5 h and then diluted with water (500 mL). The solids were collected by filtration and washed with water (2×200 mL). The filtrate was extracted with EtOAc (3×1.5 L). The combined organic layers were washed with brine (2×1.5 L), dried ($Na_2SO_4$), filtered and concentrated in vacuo. The residue was combined with the solids obtained earlier. The crude product was washed with $H_2O$ (2×20 mL) and dried to afford 35 g (70%) of B-2 as a yellow solid.

Step 3:

A 500 mL round-bottom flask was charged with B-2 (35 g, 213.24 mmol, 1.00 equiv) and $POCl_3$ (200 mL). The resulting solution was heated to reflux for 1 h, cooled to 30° C., quenched with cold sat'd. aq. $NaHCO_3$ (3 L) and extracted with EtOAc (3×2 L). The combined organic layers were washed with brine (2×4 L), dried ($Na_2SO_4$), filtered and concentrated in vacuo. The residue was by $SiO_2$ chromatography eluting with an EtOAc/hexane gradient (20 to 25% EtOAc) to afford 24 g (62%) of B-3 as an off-white solid.

Step 4:

A 1 L pressure tank reactor (20 atm) was charged with B-3 (18 g, 98.59 mmol, 1.00 equiv), MeOH (360 mL), TEA (28.4 g, 280.66 mmol, 3.00 equiv) and $Pd(dppf)Cl_2CH_2Cl_2$ (13.4 g, 16.46 mmol, 0.15 equiv). Excess CO was introduced, and the resulting solution was stirred at 60° C. for 2 h and then overnight at 70° C. The reaction mixture was cooled to 30° C. and concentrated in vacuo. The residue was purified by $SiO_2$ eluting with petroleum ether/EtOAc (3:1) to afford 15.8 g (78%) of B-4 as an off-white solid.

Step 5:

A 1 L 3-necked round-bottom flask was charged with B-4 (16.2 g, 78.57 mmol, 1.00 equiv) and THF (230 g, 3.19 mol, 40.59 equiv) and then a solution of LiOH (2.1 g, 87.50 mmol, 1.10 equiv) in water (40 mL) was added dropwise with stirring. The resulting solution was stirred at RT for 1.5 h, concentrated in vacuo, diluted with $H_2O$ (500 mL) and extracted with EtOAc (2×200 mL). The pH of the aqueous layer was adjusted to 3 with aq. HCl (12 mol/L). The precipitate was collected by filtration, washed with $H_2O$ (2×50 mL) and dried in a vacuum oven to afford 13.8 g (91%) of B-5 as a white solid. MS (ES, m/z): 193 $[M+H]^+$. H NMR (300 MHz, DMSO) δ 13.88 (1H, s), 9.35 (1H, s), 8.84~8.81 (1H, d, J=8.7 Hz), 8.20~8.17 (1H, d, J=8.7 Hz), 7.81 (1H, s).

Referential Example 14

(R)-3-Amino-3-(3-fluoro-4-(trifluoromethyl)phenyl)propan-1-ol (91a) and (R)-3-amino-3-(4-chloro-3-fluorophenyl)propan-1-ol (91b)

Step 1:
A solution of 3-fluoro-4-(trifluoromethyl)benzaldehyde (4.8 g, 25 mmol), malonic acid (2.6 g, 25 mmol), ammonium acetate (0.85 g, 50 mmol) and EtOH (30 mL) was heated at 80° C. for 18 h. The reaction was cooled, diluted with Et$_2$O (50 mL) and filtered to afford 2.0 g (16%) of 3-amino-3-(3-fluoro-4-(trifluoromethyl)phenyl)propanoic acid (93) as a white solid which was used without further purification.

Step 2:
To a stirred suspension of 93 (2.0 g, 8.0 mmol) and THF (25 mL) under N$_2$ at 0° C. was added dropwise 1M LiAlH$_4$ in THF (12 mL, 12 mmol), and the reaction stirred at 0° C. in an ice bath for 1.5 h. The cold reaction mixture was quenched by carefully adding the reaction mixture to a satd. solution of Rochelle's salt (50 mL) that was cooled in an ice bath and adequately vented. The resulting mixture was stirred for 18 h while warming to RT slowly as the ice bath melted. The mixture was diluted with EtOAc (50 mL) and filtered through CELITE® to remove solids which were rinsed several times with EtOAc. The phases were separated, and the aqueous phase re-extracted with EtOAc (30 mL). The combined organic extracts were washed with brine (50 mL), dried (MgSO$_4$), filtered, and concentrated in vacuo. The crude product was purified by SiO$_2$ chromatography eluting with 5% 7N NH$_3$ in MeOH in DCM (500 mL to pre-wash column, followed by 500 mL of eluent, then 500 mL of 7.5% 7N NH$_3$ in MeOH in DCM) to afford 0.43 g (22%) of 3-amino-3-(3-fluoro-4-(trifluoromethyl)phenyl)propan-1-ol (91a).

(R)-3-Amino-3-(4-chloro-3-fluorophenyl)propan-1-ol (91b) was prepared analogously except in step 1,3-fluoro-4-trifluoromethylbenzaldehyde was replaced with 4-chloro-3-fluorobenzaldehyde.

Example 1

(S)—N-((3-Fluoro-4-methoxyphenyl)(1-methyl-1H-pyrazol-4-yl)methyl)-7-(tetrahydro-2H-pyran-4-ylamino)-1,6-naphthyridine-2-carboxamide (I-21)

Method A

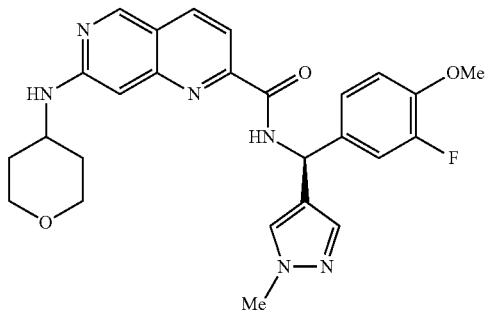 [SMILES: COc1ccc([C@H](NC(=O)c2ccc3cnc(NC4CCOCC4)cc3n2)c2cnn(C)c2)cc1F]

A mixture of 72 (720 mg, 2.63 mmol), HATU (1503 mg, 3.95 mmol), and DIPEA (1.38 mL, 7.90 mmol) in DMF (6.14 mL, 79.03 mmol) was stirred at RT for 5 min (solution turns dark brown). After 5 min 50c (859.0 mg, 3.16 mmol) was added as a solid in one portion, and the reaction mixture was stirred at RT for 1 h. The reaction mixture was diluted with EtOAc (200 mL) and washed with water (200 mL). The organic layer was separated, dried (Na$_2$SO$_4$), filtered and concentrated in vacuo. The crude product was purified by SiO$_2$ chromatography eluting with a EtOAc/heptane gradient (0 to 100% EtOAc). Product-containing fractions were combined and evaporated in vacuo to afford the desired product as a yellow/orange foam that was further purified by supercritical fluid chromatography (SFC) to afford 1.38 g (93%) of I-21 as a yellow solid. $^1$H NMR (400 MHz, DMSO-d$_6$) δ 9.01 (d, J=6.7 Hz, 2H), 8.38 (d, J=8.3 Hz, 1H), 7.72 (d, J=8.3 Hz, 1H), 7.28 (dd, J=12.7, 1.9 Hz, 1H), 7.19-7.14 (m, 1H), 7.11 (t, J=8.6 Hz, 1H), 6.98 (d, J=8.0 Hz, 1H), 6.80 (s, 1H), 5.07 (t, J=5.4 Hz, 1H), 5.03 (m, 1H), 3.95-3.83 (m, 3H), 3.81 (s, 3H), 3.79-3.71 (m, 2H), 3.47 (m, 2H), 1.93 (d, J=10.5 Hz, 2H), 1.51 (m, 2H); LCMS (Method G): R$_T$=9.97 min, M+H$^+$=491.0.

7-(Tetrahydro-pyran-4-ylamino)-[1,6]naphthyridine-2-carboxylic acid [(S)-1-(4-chloro-3-fluoro-phenyl)-2-hydroxy-ethyl]-amide (I-5) was prepared analogously except 50c was replaced with (S)-2-amino-2-(4-chloro-3-fluorophenyl)ethanol hydrochloride (62e). $^1$H NMR (400 MHz, DMSO) δ 9.10 (d, J=8.1 Hz, 1H), 9.02 (s, 1H), 8.38 (d, J=8.4 Hz, 1H), 7.71 (d, J=8.3 Hz, 1H), 7.54 (t, J=8.1 Hz, 1H), 7.47 (dd, J=10.6, 1.9 Hz, 1H), 7.28 (dd, J=8.3, 1.9 Hz, 1H), 6.97 (d, J=7.9 Hz, 1H), 6.81 (s, 1H), 5.14 (t, J=5.4 Hz, 1H), 5.08 (m, 1H), 3.91 (m, 2H), 3.47 (m, 2H), 1.94 (m, 2H), 1.54 (m, 2H).

7-(Tetrahydro-pyran-4-ylamino)-[1,6]naphthyridine-2-carboxylic acid [(R)-1-(3-fluoro-4-methoxy-phenyl)-propyl]-amide (I-6) analogously except 50c was replaced with 70a. $^1$H NMR (400 MHz, DMSO) δ 8.99 (d, J=10.4 Hz, 2H), 8.36 (d, J=8.3 Hz, 1H), 7.70 (d, J=8.3 Hz, 1H), 7.35 (dd, J=12.7, 2.0 Hz, 1H), 7.20 (d, J=8.4 Hz, 1H), 7.11 (t, J=8.7 Hz, 1H), 6.97 (d, J=8.0 Hz, 1H), 6.80 (s, 1H), 4.89 (dd, J=15.5, 8.4 Hz, 1H), 3.95-3.88 (m, 2H), 3.85 (m, 1H), 3.46 (m, 2H), 2.03-1.80 (m, 4H), 1.54 (m, 2H), 0.87 (t, J=7.3 Hz, 3H).

7-(Tetrahydro-pyran-4-ylamino)-[1,6]naphthyridine-2-carboxylic acid [(S)-(1-methyl-1H-pyrazol-4-yl)-(4-trifluoromethoxy-phenyl)-methyl]-amide (I-9) was prepared analogously except 50c was replaced with 50b. $^1$H NMR (400 MHz, DMSO-d$_6$) δ 9.27 (d, J=8.6 Hz, 1H), 9.01 (s, 1H), 8.38 (d, J=8.3 Hz, 1H), 7.72 (d, J=8.3 Hz, 1H), 7.64 (s, 1H), 7.56 (m, 2H), 7.43 (s, 1H), 7.35 (d, J=8.3 Hz, 2H), 6.97 (d, J=8.0 Hz, 1H), 6.78 (s, 1H), 6.33 (d, J=8.5 Hz, 1H), 3.93-3.87 (m, 2H), 3.87-3.81 (m, 1H), 3.45 (m, 2H), 1.91 (d, J=12.1 Hz, 2H), 1.52 (m, 2H).

(S)—N-(2-Hydroxy-1-(4-(trifluoromethoxy)phenyl)ethyl)-7-(tetrahydro-2H-pyran-4-ylamino)-1,6-naphthyridine-2-carboxamide (I-10) was prepared analogously except 50c was replaced with 62b. $^1$H NMR (400 MHz, DMSO) δ 9.12 (d, J=8.2 Hz, 1H), 9.02 (s, 1H), 8.38 (d, J=8.3 Hz, 1H), 7.72 (d, J=8.3 Hz, 1H), 7.53 (m, 2H), 7.33 (d, J=8.2 Hz, 2H), 6.99 (d, J=8.0 Hz, 1H), 6.81 (s, 1H), 5.13 (m, 2H), 3.86 (m, 5H), 3.47 (m, 2H), 1.94 (d, J=10.5 Hz, 2H), 1.54 (m, 2H).

7-(Tetrahydro-pyran-4-ylamino)-[1,6]naphthyridine-2-carboxylic acid 4-chloro-3-fluoro-benzylamide (I-11) was prepared analogously except in step 2, 50c was replaced with 4-chloro-3-fluoro-benzyl amine. $^1$H NMR (400 MHz, DMSO-d$_6$) δ 9.46 (t, J=6.5 Hz, 1H), 9.02 (s, 1H), 8.38 (d, J=8.3 Hz, 1H), 7.74 (d, J=8.3 Hz, 1H), 7.54 (t, J=8.0 Hz, 1H), 7.37 (dd, J=10.4, 1.8 Hz, 1H), 7.22 (d, J=8.3 Hz, 1H), 7.01 (d, J=7.8 Hz, 1H), 6.75 (s, 1H), 4.52 (d, J=6.4 Hz, 2H), 3.91 (m, 3H), 3.45 (m, 2H), 1.93 (d, J=10.4 Hz, 2H), 1.53 (m, 2H).

7-(Tetrahydro-pyran-4-ylamino)-[1,6]naphthyridine-2-carboxylic acid [(S)-1-(3-fluoro-4-methoxy-phenyl)-2-hydroxy-ethyl]-amide (I-12) was prepared analogously except 50c was replaced with 62d. $^1$H NMR (400 MHz, DMSO) δ 9.01 (d, J=6.7 Hz, 2H), 8.38 (d, J=8.3 Hz, 1H), 7.72 (d, J=8.3

Hz, 1H), 7.28 (dd, J=12.7, 1.9 Hz, 1H), 7.19-7.14 (m, 1H), 7.11 (t, J=8.6 Hz, 1H), 6.98 (d, J=8.0 Hz, 1H), 6.80 (s, 1H), 5.07 (t, J=5.4 Hz, 1H), 5.03 (m, 1H), 3.95-3.83 (m, 3H), 3.81 (s, 3H), 3.79-3.71 (m, 2H), 3.47 (m, 2H), 1.93 (d, J=10.5 Hz, 2H), 1.51 (m, 2H).

7-(Tetrahydro-pyran-4-ylamino)-[1,6]naphthyridine-2-carboxylic acid [(S)-(4-chloro-3-fluoro-phenyl)-(1-methyl-1H-pyrazol-4-yl)-methyl]-amide (I-4) was prepared analogously except 50c was replaced with 50a. $^1$H NMR (400 MHz, DMSO-d$_6$) δ 9.30 (d, J=8.5 Hz, 1H), 9.01 (s, 1H), 8.38 (d, J=8.3 Hz, 1H), 7.71 (d, J=8.3 Hz, 1H), 7.64 (s, 1H), 7.57 (t, J=8.1 Hz, 1H), 7.52 (dd, J=10.6, 1.9 Hz, 1H), 7.43 (s, 1H), 7.32 (dd, J=8.4, 1.8 Hz, 1H), 6.98 (d, J=8.0 Hz, 1H), 6.78 (s, 1H), 6.30 (d, J=8.5 Hz, 1H), 3.93-3.87 (m, 2H), 3.87-3.81 (m, 1H), 3.80 (s, 3H), 3.45 (m, 2H), 1.92 (m, 2H), 1.59-1.46 (m, 2H).

7-(Tetrahydro-pyran-4-ylamino)-[1,6]naphthyridine-2-carboxylic acid [(S)-(3-fluoro-phenyl)-(1-methyl-1H-pyrazol-4-yl)-methyl]-amide (I-22) was prepared analogously except 50c was replaced with 50h. $^1$H NMR (400 MHz, DMSO-d$_6$) δ 9.30 (d, J=8.5 Hz, 1H), 9.01 (s, 1H), 8.38 (d, J=8.3 Hz, 1H), 7.71 (d, J=8.3 Hz, 1H), 7.64 (s, 1H), 7.57 (t, J=8.1 Hz, 1H), 7.52 (dd, J=10.6, 1.9 Hz, 1H), 7.43 (s, 1H), 7.32 (dd, J=8.4, 1.8 Hz, 1H), 6.98 (d, J=8.0 Hz, 1H), 6.78 (s, 1H), 6.30 (d, J=8.5 Hz, 1H), 3.93-3.87 (m, 2H), 3.87-3.81 (m, 1H), 3.80 (s, 3H), 3.45 (m, 2H), 1.92 (m, 2H), 1.59-1.46 (m, 2H).

7-(Tetrahydro-pyran-4-ylamino)-[1,6]naphthyridine-2-carboxylic acid [(S)-(3-chloro-4-cyano-phenyl)-(2-methyl-2H-pyrazol-3-yl)-methyl]-amide (I-26) was prepared analogously except 50c was replaced with 44. $^1$H NMR (500 MHz, DMSO-d$_6$) δ 9.77 (d, J=9.0 Hz, 1H), 9.03 (s, 1H), 8.39 (d, J=8.5 Hz, 1H), 8.03 (d, J=8.0 Hz, 1H), 7.96 (s, 1H), 7.74-7.70 (m, 2H), 7.36 (d, J=1.5, 1H), 7.05 (d, J=7.5 Hz, 1H), 6.78 (s, 1H), 6.69 (d, J=8.5 Hz, 1H), 5.94 (d, J=1.5 Hz, 1H), 3.89-3.80 (m, 6H), 3.46-3.42 (m, 2H), 1.92-1.90 (m, 2H), 1.53-1.51 (m, 2H).

(S)—N-((3-Fluoro-4-methoxyphenyl)(1-methyl-1H-pyrazol-5-yl)methyl)-7-(tetrahydro-2H-pyran-4-ylamino)-1,6-naphthyridine-2-carboxamide (I-27) was prepared analogously except 50c was replaced with 50e. $^1$H NMR (500 MHz, DMSO-d$_6$) δ 9.48 (d, J=8.5, 1H), 9.02 (s, 1H), 8.38 (d, J=8.0 Hz, 1H), 7.71 (d, J=8.0 Hz, 1H), 7.42 (d, 1H), 7.34 (d, J=1.5 Hz, 1H), 7.27 (m, 1H), 7.18 (m, 1H), 7.00 (d, J=8.0 Hz, 1H), 6.78 (s, 1H), 6.50 (d, J=9.0 Hz, 1H), 6.03 (d, J=2.0 Hz, 1H), 3.90-3.84 (m, 6H), 3.74 (s, 3H), 3.46-3.42 (m, 2H), 1.92-1.90 (m, 2H), 1.55-1.50 (m, 2H).

7-(Tetrahydro-pyran-4-ylamino)-[1,6]naphthyridine-2-carboxylic acid [2-(2-bromo-phenyl)-ethyl]-amide (I-28) was prepared analogously except 50c was replaced with 2-bromo-benzeneethanamine (CASRN 65185-58-2). $^1$H NMR (400 MHz, DMSO-d$_6$) δ 9.01 (s, 1H), 8.93 (t, J=6.0 Hz, 1H), 8.36 (d, J=8.3 Hz, 1H), 7.72 (d, J=8.3 Hz, 1H), 7.60 (d, J=7.9 Hz, 1H), 7.37 (d, J=6.3 Hz, 1H), 7.32 (t, J=7.4 Hz, 1H), 7.17 (t, J=7.6 Hz, 1H), 6.99 (d, J=7.8 Hz, 1H), 6.74 (s, 1H), 3.94-3.81 (m, 1H), 3.91 (d, J=11.7 Hz, 2H), 3.60 (q, J=7.0 Hz, 2H), 3.45 (t, J=10.8 Hz, 2H), 3.04 (t, J=7.3 Hz, 2H), 1.93 (d, J=11.1 Hz, 2H), 1.53 (qd, J=11.8, 4.3 Hz, 2H).

7-(Tetrahydro-pyran-4-ylamino)-[1,6]naphthyridine-2-carboxylic acid [2-(4-bromo-phenyl)-ethyl]-amide (I-29) was prepared analogously except 50c was replaced with 4-bromo-benzeneethanamine (CASRN 73918-56-6). $^1$H NMR (400 MHz, DMSO) δ 9.00 (s, 1H), 8.87 (t, J=5.8 Hz, 1H), 8.36 (d, J=8.3 Hz, 1H), 7.72 (d, J=8.3 Hz, 1H), 7.48 (d, J=8.3 Hz, 2H), 7.23 (d, J=8.3 Hz, 2H), 6.99 (d, J=7.8 Hz, 1H), 6.73 (s, 1H), 3.94-3.80 (m, 1H), 3.91 (d, J=11.4 Hz, 2H), 3.56 (q, J=7.0 Hz, 2H), 3.45 (t, J=10.7 Hz, 2H), 2.88 (t, J=7.3 Hz, 2H), 1.93 (d, J=10.8 Hz, 2H), 1.59-1.47 (m, 2H).

7-(Tetrahydro-pyran-4-ylamino)-[1,6]naphthyridine-2-carboxylic acid phenethyl-amide benzeneethaneamine (I-30) was prepared analogously except 50c was replaced with benzeneethanamine (CASRN 64-04-0). $^1$H NMR (400 MHz, DMSO-d$_6$) δ 9.01 (s, 1H), 8.87 (t, J=6.0 Hz, 1H), 8.37 (d, J=8.3 Hz, 1H), 7.73 (d, J=8.3 Hz, 1H), 7.34-7.24 (m, 4H), 7.21 (t, J=7.0 Hz, 1H), 7.00 (d, J=7.8 Hz, 1H), 6.74 (s, 1H), 3.94-3.82 (m, 1H), 3.91 (d, J=11.3 Hz, 3H), 3.57 (q, J=7.2 Hz, 2H), 3.45 (t, J=10.8 Hz, 2H), 2.90 (t, J=7.5 Hz, 2H), 1.93 (d, J=10.8 Hz, 2H), 1.53 (qd, J=11.8, 4.2 Hz, 2H).

7-(Tetrahydro-pyran-4-ylamino)-[1,6]naphthyridine-2-carboxylic acid (2-pyridin-2-yl-ethyl)-amide (I-31) was prepared analogously except 50c was replaced with 2-pyridineethanamine (CASRN 2706-56-1). $^1$H NMR (400 MHz, DMSO-d$_6$) δ 9.02-8.97 (m, 2H), 8.53 (d, J=4.7 Hz, 1H), 8.36 (d, J=8.4 Hz, 1H), 7.75-7.69 (m, 2H), 7.31 (d, J=7.7 Hz, 1H), 7.24 (dd, J=7.4, 5.0 Hz, 1H), 6.99 (d, J=7.8 Hz, 1H), 6.74 (s, 1H), 3.94-3.83 (m, 1H), 3.91 (d, J=11.4 Hz, 2H), 3.71 (q, J=6.9 Hz, 2H), 3.46 (t, J=10.8 Hz, 2H), 3.06 (t, J=7.3 Hz, 2H), 1.93 (d, J=11.2 Hz, 2H), 1.53 (qd, J=11.6, 4.4 Hz, 2H).

7-(Tetrahydro-pyran-4-ylamino)-[1,6]naphthyridine-2-carboxylic acid (2-pyridin-3-yl-ethyl)-amide (I-32) was prepared analogously except 50c was replaced with 3-pyridineethanamine (CASRN 20173-24-4). $^1$H NMR (400 MHz, DMSO-d$_6$) δ 9.01 (s, 1H), 8.92 (t, J=6.0 Hz, 1H), 8.47 (d, J=1.6 Hz, 1H), 8.41 (d, J=4.1 Hz, 1H), 8.36 (d, J=8.3 Hz, 1H), 7.71 (d, J=8.3 Hz, 1H), 7.68 (d, J=7.8 Hz, 1H), 7.31 (dd, J=7.7, 4.8 Hz, 1H), 7.00 (d, J=7.8 Hz, 1H), 6.74 (s, 1H), 3.94-3.81 (m, 1H), 3.91 (d, J=11.6 Hz, 2H), 3.60 (q, J=6.9 Hz, 2H), 3.45 (t, J=10.8 Hz, 2H), 2.93 (t, J=7.2 Hz, 2H), 1.93 (d, J=10.9 Hz, 2H), 1.53 (qd, J=11.8, 4.3 Hz, 2H).

7-(Tetrahydro-pyran-4-ylamino)-[1,6]naphthyridine-2-carboxylic acid (2-pyridin-4-yl-ethyl)-amide (I-33) was prepared analogously except 50c was replaced with 4-pyridineethanamine (CASRN 13258-63-4). $^1$H NMR (400 MHz, DMSO) δ 9.01 (s, 1H), 8.92 (t, J=6.0 Hz, 1H), 8.47 (d, J=5.8 Hz, 2H), 8.36 (d, J=8.3 Hz, 1H), 7.72 (d, J=8.3 Hz, 1H), 7.29 (d, J=5.7 Hz, 2H), 7.00 (d, J=7.8 Hz, 1H), 6.73 (s, 1H), 3.94-3.81 (m, 1H), 3.91 (d, J=11.5 Hz, 3H), 3.61 (q, J=6.9 Hz, 2H), 3.45 (dd, J=11.5, 10.0 Hz, 2H), 2.93 (t, J=7.3 Hz, 2H), 1.93 (d, J=10.8 Hz, 2H), 1.53 (ddd, J=15.5, 11.9, 4.2 Hz, 2H).

7-(Tetrahydro-pyran-4-ylamino)-[1,6]naphthyridine-2-carboxylic acid [(S)-(4-chloro-3-fluoro-phenyl)-(2-methyl-2H-pyrazol-5-yl)-methyl]-amide (I-34) was prepared analogously except 50c was replaced with 50 g. $^1$H NMR (500 MHz, DMSO-d$_6$) δ 9.64 (d, J=8.5 Hz, 1H), 9.02 (s, 1H), 8.38 (d, J=8.0 Hz, 1H), 7.71 (d, J=8.0 Hz, 1H), 7.64-7.61 (m, 2H), 7.41 (d, J=8.5, 1H), 7.35 (d, J=1.5 Hz, 1H), 7.03 (d, J=8.0 Hz, 1H), 6.78 (s, 1H), 6.59 (d, J=9.0 Hz, 1H), 5.98 (d, J=1.5 Hz, 1H), 3.91-3.78 (m, 6H), 3.46-3.42 (m, 2H), 1.92-1.90 (m, 2H), 1.53-1.51 (m, 2H).

Example 2

N—((S)-(3-Fluoro-4-methoxyphenyl)(1-methyl-1H-pyrazol-4-yl)methyl)-7-((S)-1-hydroxypropan-2-ylamino)-1,6-naphthyridine-2-carboxamide (I-24)
Method B Step 1:

A mixture of 74 (45 mg, 0.234 mmol), HATU (133.57 mg, 0.351 mmol), and DIPEA (0.123 mL, 0.703 mmol) in DMF (0.546 mL, 7.03 mmol) was stirred at RT for 5 min. To the solution was added in one portion (S)-(3-fluoro-4-methoxyphenyl)-(1-methylpyrazol-4-yl)methanamine hydrochloride (50c) (76.36 mg, 0.281 mmol) and the reaction mixture was stirred at RT for 1 h. The reaction mixture was diluted with EtOAc (30 mL) and washed with water (20 mL). The organic layer was separated, dried (Na$_2$SO$_4$), filtered and concentrated in vacuo. The residue that was purified by SiO$_2$ chromatography eluting a with an EtOAc/heptane gradient (0 to 100% EtOAc) to afford 80 mg (83%) of (S)-7-fluoro-N-((3-fluoro-4-methoxyphenyl)(1-methyl-1H-pyrazol-4-yl)methyl)-1,6-naphthyridine-2-carboxamide (76) as a yellow oil (80 mg, 83%), which was used in the next step without further purification.

Step 2:

A mixture of 76 (80 mg, 0.195 mmol), (S)-(+)-2-amino-1-propanol (75 mg, 0.977 mmol), and NMP (0.551 mL, 5.86 mmol) was mixed and heated at 110° C. for 48 h. The reaction mixture was diluted with EtOAc (50 mL) and washed with water (50 mL). The organic layer was separated, dried (Na$_2$SO$_4$), filtered and concentrated in vacuo. The residue was purified by reverse phase HPLC purification eluting with a MeCN/H$_2$O (containing 0.1% NH$_4$OH) gradient (5 to 85% MeCN) over 14 min to afford I-24 as a yellow solid. $^1$H NMR (400 MHz, DMSO) δ 9.19 (d, J=8.7 Hz, 1H), 8.99 (s, 1H), 8.37 (d, J=8.3 Hz, 1H), 7.70 (d, J=8.3 Hz, 1H), 7.61 (s, 1H), 7.39 (s, 1H), 7.32 (d, J=12.4 Hz, 1H), 7.21 (d, J=8.6 Hz, 1H), 7.13 (t, J=8.6 Hz, 1H), 6.76 (s, 1H), 6.67 (d, J=8.1 Hz, 1H), 6.23 (d, J=8.6 Hz, 1H), 4.75 (t, J=5.5 Hz, 1H), 3.83 (m, 1H), 3.82 (s, 3H), 3.79 (s, 3H), 3.53 (m, 1H), 3.41-3.34 (m, 1H), 1.19 (d, J=6.5 Hz, 3H). LCMS (Method G): R$_T$=8.97 min, M+H$^+$=465.2.

7-((S)-2-Hydroxy-1-methyl-ethylamino)-[1,6]naphthyridine-2-carboxylic acid [(S)-(3-fluoro-phenyl)-(1-methyl-1H-pyrazol-4-yl)-methyl]-amide (I-1) was prepared analogously except in step 1, 50c with replaced with (S)-(3-fluorophenyl)(1-methyl-1H-pyrazol-5-yl)methanamine hydrochloride (50f). $^1$H NMR (400 MHz, DMSO) δ 9.27 (d, J=8.6 Hz, 1H), 9.00 (s, 1H), 8.37 (d, J=8.3 Hz, 1H), 7.70 (d, J=8.3 Hz, 1H), 7.64 (s, 1H), 7.42 (s, 1H), 7.41-7.36 (m, 1H), 7.33-7.26 (m, 2H), 7.10 (m, 1H), 6.77 (s, 1H), 6.68 (d, J=8.1 Hz, 1H), 6.30 (d, J=8.6 Hz, 1H), 4.74 (t, J=5.6 Hz, 1H), 3.83 (s, 1H), 3.80 (s, 3H), 3.53 (m, 1H), 3.42-3.31 (m, 1H), 1.19 (d, J=6.5 Hz, 3H).

7-(5-Oxo-pyrrolidin-3-ylamino)-[1,6]naphthyridine-2-carboxylic acid [(3-fluoro-4-methoxy-phenyl)-(1-methyl-1H-pyrazol-4-yl)-methyl]-amide (I-2) was prepared analogously except in step 2, (S)-(+)-2-amino-1-propanol was replaced with 4-amino-pyrrolidin-2-one (CASRN88016-17-5, (S)-160806-40-6, (R)-1292324-66-3). $^1$H NMR (400 MHz, DMSO) δ 9.21 (d, J=8.7 Hz, 1H), 9.04 (s, 1H), 8.41 (d, J=8.4 Hz, 1H), 7.75 (d, J=8.3 Hz, 1H), 7.66 (s, 1H), 7.61 (s, 1H), 7.39 (d, J=8.5 Hz, 1H), 7.32 (dd, J=12.6, 2.0 Hz, 1H), 7.21 (d, J=10.2 Hz, 1H), 7.13 (t, J=8.6 Hz, 1H), 6.78 (s, 1H), 6.72 (s, 1H), 6.23 (d, J=8.6 Hz, 1H), 4.48 (m, 1H), 3.82 (s, 3H), 3.79 (s, 3H), 3.68 (dd, J=9.9, 6.9 Hz, 1H), 3.18 (dd, J=10.0, 4.1 Hz, 1H), 2.64 (dd, J=16.7, 8.1 Hz, 1H), 2.20 (dd, J=16.7, 5.1 Hz, 1H).

7-(3-Fluoro-propylamino)-[1,6]naphthyridine-2-carboxylic acid [(S)-(3-fluoro-4-methoxy-phenyl)-(1-methyl-1H-pyrazol-4-yl)-methyl]-amide (I-3) was prepared analogously except in step 2, (S)-(+)-2-amino-1-propanol was replaced with 3-fluoro-propylamine. $^1$H NMR (400 MHz, DMSO) δ 9.20 (d, J=8.7 Hz, 1H), 9.01 (s, 1H), 8.39 (d, J=8.3 Hz, 1H), 7.73 (d, J=8.3 Hz, 1H), 7.61 (s, 1H), 7.39 (s, 1H), 7.32 (dd, J=12.6, 2.0 Hz, 1H), 7.21 (d, J=8.5 Hz, 1H), 7.16-7.07 (m, 2H), 6.73 (s, 1H), 6.23 (d, J=8.7 Hz, 1H), 4.63 (t, J=5.9 Hz, 1H), 4.52 (t, J=5.8 Hz, 1H), 3.82 (s, 3H), 3.79 (s, 3H), 3.38 (m, 2H), 2.07-1.91 (m, 2H).

7-(2-Hydroxy-1,2-dimethyl-propylamino)-[1,6]naphthyridine-2-carboxylic acid [(3-fluoro-4-methoxy-phenyl)-(1-methyl-1H-pyrazol-4-yl)-methyl]-amide (I-13 and I-14) was prepared analogously except in step 2, (S)-(+)-2-amino-1-propanol was replaced with 3-amino-2-methyl-butan-2-ol.

Diastereomer 1 (I-13): $^1$H NMR (400 MHz, DMSO) δ 9.16 (d, J=8.6 Hz, 1H), 8.98 (s, 1H), 8.35 (d, J=8.3 Hz, 1H), 7.69 (d, J=8.3 Hz, 1H), 7.61 (s, 1H), 7.38 (s, 1H), 7.32 (d, J=12.5 Hz, 1H), 7.21 (d, J=8.7 Hz, 1H), 7.13 (t, J=8.6 Hz, 1H), 6.81 (s, 1H), 6.43 (d, J=9.5 Hz, 1H), 6.22 (d, J=8.6 Hz, 1H), 4.45 (s, 1H), 3.84 (m, 1H), 3.82 (s, 3H), 3.79 (s, 3H), 1.15 (m, 9H). Retention time 0.52 sec.

Diastereomer 2 (I-14): $^1$H NMR (400 MHz, DMSO) δ 9.16 (d, J=8.6 Hz, 1H), 8.98 (s, 1H), 8.35 (d, J=8.3 Hz, 1H), 7.68 (d, J=8.3 Hz, 1H), 7.61 (s, 1H), 7.39 (s, 1H), 7.32 (d, J=12.6 Hz, 1H), 7.21 (d, J=8.7 Hz, 1H), 7.13 (t, J=8.6 Hz, 1H), 6.81 (s, 1H), 6.43 (d, J=9.4 Hz, 1H), 6.22 (d, J=8.6 Hz, 1H), 4.45 (s, 1H), 3.84 (m, 1H), 3.82 (s, 3H), 3.79 (s, 3H), 1.15 (m, 9H). Retention time 0.62 sec.

7-(2-Oxa-bicyclo[2.2.1]hept-5-ylamino)-[1,6]naphthyridine-2-carboxylic acid [(3-fluoro-4-methoxy-phenyl)-(1-methyl-1H-pyrazol-4-yl)-methyl]-amide (I-16 and I-23) were prepared analogously except in step 2, (S)-(+)-2-amino-1-propanol was replaced with 24b. $^1$H NMR (400 MHz, DMSO) δ 9.23 (d, J=8.7 Hz, 1H), 9.03 (s, 1H), 8.40 (d, J=8.3 Hz, 1H), 7.74 (d, J=8.3 Hz, 1H), 7.60 (s, 1H), 7.39 (s, 1H), 7.32 (d, J=14.2 Hz, 1H), 7.21 (d, J=8.6 Hz, 1H), 7.13 (m, 2H), 6.72 (s, 1H), 6.24 (d, J=8.6 Hz, 1H), 4.30 (s, 1H), 3.82 (s, 3H), 3.79 (s, 3H), 3.73 (m, 1H), 3.57 (dd, J=7.2, 3.1 Hz, 1H), 3.49 (d, J=7.2 Hz, 1H), 2.59 (s, 1H), 2.11-2.01 (m, 1H), 1.79 (d, J=10.1 Hz, 1H), 1.55 (m, 2H).

7-((3S,4S)-3-Fluoro-tetrahydro-pyran-4-ylamino)-[1,6]naphthyridine-2-carboxylic acid [(S)-(3-fluoro-4-methoxy-phenyl)-(1-methyl-1H-pyrazol-4-yl)-methyl]-amide (I-17) was prepared analogously except in step 2, (S)-(+)-2-amino-1-propanol was replaced with 71c. $^1$H NMR (400 MHz, DMSO) δ 9.18 (d, J=8.6 Hz, 1H), 9.04 (s, 1H), 8.41 (d, J=8.4 Hz, 1H), 7.74 (d, J=8.3 Hz, 1H), 7.60 (s, 1H), 7.39 (s, 1H), 7.32 (d, J=12.6 Hz, 1H), 7.21 (d, J=8.7 Hz, 1H), 7.13 (t, J=8.6 Hz, 1H), 7.04 (d, J=8.2 Hz, 1H), 6.97 (s, 1H), 6.23 (d, J=8.6 Hz, 1H), 4.78 (d, J=49.6 Hz, 1H), 4.26 (m, 1H), 4.01 (t, J=12.2 Hz, 1H), 3.92 (m, 1H), 3.82 (s, 3H), 3.80 (s, 3H), 3.63 (dd, J=39.3, 13.1 Hz, 1H), 3.52 (t, J=11.3 Hz, 1H), 1.91 (m, 1H), 1.73 (m, 1H).

7-[(S)-1-(1-Hydroxy-cyclopropyl)-ethylamino]-[1,6]naphthyridine-2-carboxylic acid [(S)-(3-fluoro-4-methoxy-phenyl)-(1-methyl-1H-pyrazol-4-yl)-methyl]-amide (I-18) was prepared analogously except in step 2, (S)-(+)-2-amino-1-propanol was replaced with 30. $^1$H NMR (400 MHz, DMSO-d$_6$) δ 9.16 (d, J=8.6 Hz, 1H), 8.98 (s, 1H), 8.36 (d, J=8.3 Hz, 1H), 7.70 (d, J=8.3 Hz, 1H), 7.60 (s, 1H), 7.39 (s, 1H), 7.32 (dd, J=12.6, 1.7 Hz, 1H), 7.21 (d, J=8.7 Hz, 1H), 7.13 (t, J=8.6 Hz, 1H), 6.77 (s, 1H), 6.64 (d, J=8.6 Hz, 1H), 6.22 (d, J=8.6 Hz, 1H), 5.38 (s, 1H), 3.82 (s, 3H), 3.79 (s, 3H), 3.67 (m, 1H), 1.28 (d, J=6.5 Hz, 3H), 0.62-0.42 (m, 4H).

7-((2S,4R)-2-Hydroxymethyl-tetrahydro-pyran-4-ylamino)-[1,6]naphthyridine-2-carboxylic acid [(S)-(3-fluoro-4-methoxy-phenyl)-(1-methyl-1H-pyrazol-4-yl)-methyl]-amide (I-19) was prepared analogously except in step 2, (S)-(+)-2-amino-1-propanol was replaced with 87b. $^1$H NMR (400 MHz, DMSO) δ 9.20 (d, J=8.6 Hz, 1H), 9.01 (s, 1H), 8.37 (d, J=8.3 Hz, 1H), 7.72 (d, J=8.3 Hz, 1H), 7.60 (s, 1H), 7.39 (s, 1H), 7.32 (d, J=12.5 Hz, 1H), 7.21 (d, J=8.1 Hz, 1H), 7.13 (t, J=8.6 Hz, 1H), 6.94 (d, J=8.1 Hz, 1H), 6.78 (s, 1H), 6.23 (d, J=8.6 Hz, 1H), 4.62 (t, J=5.6 Hz, 1H), 3.95 (m, 1H), 3.86 (m, 1H), 3.82 (s, 3H), 3.80 (s, 3H), 3.54-3.33 (m, 4H), 1.95 (dd, J=35.7, 11.6 Hz, 2H), 1.47 (m, 1H), 1.26-1.11 (m, 1H).

7-(Tetrahydro-pyran-4-ylamino)-[1,6]naphthyridine-2-carboxylic acid [4-(4-methyl-piperazin-1-yl)-pyridin-2-ylmethyl]-amide (I-39) was prepared analogously except in step 1, 50c was replaced with 4-(4-methyl-1-piperazinyl)-2-pyridinemethanamine. $^1$H NMR (400 MHz, DMSO) δ 9.23 (t, J=5.6 Hz, 1H), 9.03 (s, 1H), 8.39 (d, J=8.3 Hz, 1H), 8.14 (d, J=5.9 Hz, 1H), 7.76 (d, J=8.3 Hz, 1H), 7.04 (d, J=7.8 Hz, 1H), 6.85 (s, 1H), 6.77 (m, 2H), 4.52 (d, J=5.6 Hz, 2H), 3.90 (d, J=11.3 Hz, 3H), 3.46 (t, J=11.4 Hz, 2H), 3.31-3.24 (m, 4H), 2.39 (m, 4H), 2.20 (s, 3H), 1.93 (d, J=12.5 Hz, 2H), 1.52 (m, 2H).

Example 3

N—((S)-(3-Fluoro-4-methoxyphenyl)(1-methyl-1H-pyrazol-4-yl)methyl)-7-((S)-tetrahydrofuran-3-ylamino)-1,6-naphthyridine-2-carboxamide and N—((S)-(3-fluoro-4-methoxyphenyl)(1-methyl-1H-pyrazol-4-yl)methyl)-7-((R)-tetrahydrofuran-3-ylamino)-1,6-naphthyridine-2-carboxamide (I-52 and I-53)

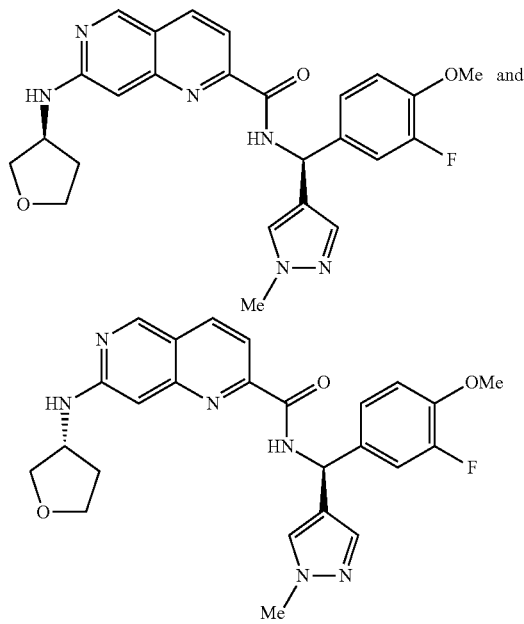

The title compounds were prepared as a racemate in accord with the procedure in example 2 except in step 2, (S)-(+)-2-amino-1-propanol was replaced with tetrahydrofuran-3-amine and subsequently resolved via chiral supercritical fluid chromatography (diastereomers are arbitrarily assigned).

Diastereomer 1: $^1$H NMR (400 MHz, DMSO) δ 9.21 (d, J=8.7 Hz, 1H), 9.03 (s, 1H), 8.40 (d, J=8.3 Hz, 1H), 7.74 (d, J=8.3 Hz, 1H), 7.61 (s, 1H), 7.39 (s, 1H), 7.32 (dd, J=12.6, 1.9 Hz, 1H), 7.21 (m, 2H), 7.13 (t, J=8.6 Hz, 1H), 6.76 (s, 1H), 6.23 (d, J=8.6 Hz, 1H), 4.33 (m, 1H), 3.94 (dd, J=8.8, 5.9 Hz, 1H), 3.87 (dd, J=15.4, 7.4 Hz, 1H), 3.82 (s, 3H), 3.79 (s, 3H), 3.78-3.71 (m, 1H), 3.64 (dd, J=8.8, 3.8 Hz, 1H), 2.24 (m, 1H), 1.90 (m, 1H). LCMS (Method G): $R_T$=9.82 min, M+H$^+$=477.2. ERK IC$_{50}$ 1.27 nM.

Diastereomer 2: $^1$H NMR (400 MHz, DMSO) δ 9.21 (d, J=8.7 Hz, 1H), 9.03 (s, 1H), 8.40 (d, J=8.3 Hz, 1H), 7.74 (d, J=8.3 Hz, 1H), 7.61 (s, 1H), 7.39 (s, 1H), 7.32 (dd, J=12.6, 1.9 Hz, 1H), 7.24-7.18 (m, 2H), 7.13 (t, J=8.6 Hz, 1H), 6.76 (s, 1H), 6.23 (d, J=8.6 Hz, 1H), 4.32 (m, 1H), 3.94 (dd, J=8.8, 5.9 Hz, 1H), 3.87 (dd, J=15.3, 7.4 Hz, 1H), 3.82 (s, 3H), 3.79 (s, 3H), 3.76 (m, 1H), 3.64 (dd, J=8.8, 3.8 Hz, 1H), 2.24 (m, 1H), 1.90 (m, 1H). LCMS (Method G): $R_T$=9.77 min, M+H$^+$=477.2. ERK IC$_{50}$ 2.75 nM.

Example 4

(S)—N-((3-Fluoro-4-methoxyphenyl)(1-methyl-1H-pyrazol-4-yl)methyl)-7-(1-methyl-1H-pyrazol-5-ylamino)-1,6-naphthyridine-2-carboxamide (I-25)

Step 1:
A mixture of 74 (300 mg, 1.56 mmol), 2-methylpyrazol-3-amine (182 mg, 1.874 mmol), and sodium hydride (60% w/w dispersion in mineral oil, 312 mg, 7.81 mmol) was diluted with DMF (3.64 mL, 46.84 mmol) and heated at 100° C. for 1 h. The reaction mixture was diluted with 10 mL of water, concentrated in vacuo to a black solid, and then dissolved in water (15 mL) water and washed with DCM (2×40 mL). The aqueous layer was separated, neutralized by addition of aq. HCl (11.6 mol/L) in water (0.81 mL, 9.37 mmol), and the resulting precipitate was collected via vacuum filtration to afford 300 mg (71%) of 7-(1-methyl-1H-pyrazol-5-ylamino)-1,6-naphthyridine-2-carboxylic acid (80) as a red/brown solid, which was used in the next step without further purification.

Step 2:
A mixture of 80 (50 mg, 0.186 mmol), HATU (212 mg, 0.557 mmol), and DIPEA (0.162 mL, 0.928 mmol) in DMF (0.72 mL) was stirred at RT for 5 min (the solution is dark brown). After 5 min, 50c (61 mg, 0.223 mmol) was added as a solid in one portion, and the reaction mixture was stirred at RT for 1 h. The reaction mixture was diluted with EtOAc (100 mL) and washed with water (100 mL). The organic layer was separated, dried (Na$_2$SO$_4$), filtered and concentrated in vacuo. The residue that was purified by SiO$_2$ chromatography eluting with a MeOH/DCM gradient (0 to 10% MeOH) to afford product as yellow/orange foam, which was further purified by reverse phase HPLC purification eluting with MeCN/H$_2$O gradient (containing 0.1% NH$_4$OH) (5 to 85% MeCN, 14 minutes) to afford I-25 as a bright yellow solid. $^1$H NMR (400 MHz, DMSO) δ 9.36 (d, J=8.9 Hz, 1H), 9.18 (s, 1H), 9.10 (s, 1H), 8.53 (d, J=8.4 Hz, 1H), 7.89 (d, J=8.4 Hz, 1H), 7.59 (s, 1H), 7.46 (d, J=1.9 Hz, 1H), 7.37 (s, 1H), 7.32 (dd, J=12.7, 2.1 Hz, 1H), 7.20 (d, J=10.3 Hz, 1H), 7.12 (t, J=8.7 Hz, 1H), 6.94 (s, 1H), 6.27 (d, J=1.9 Hz, 1H), 6.25 (d, J=8.9 Hz, 1H), 3.81 (s, 3H), 3.78 (s, 3H), 3.69 (s, 3H). LCMS (Method E): $R_T$=4.14 min, M+H$^+$=487.1.

7-(2-Methyl-2H-pyrazol-3-ylamino)-[1,6]naphthyridine-2-carboxylic acid [(S)-(4-chloro-3-fluoro-phenyl)-(1-methyl-1H-pyrazol-4-yl)-methyl]-amide (I-7) was prepared analogously except in step 2, 50c was replaced with 50a. $^1$H NMR (400 MHz, DMSO-d$_6$) δ 9.48 (d, J=8.7 Hz, 1H), 9.18 (s, 1H), 9.11 (s, 1H), 8.53 (d, J=8.4 Hz, 1H), 7.89 (d, J=8.4 Hz, 1H), 7.62 (s, 1H), 7.58-7.53 (t, J=8.7 Hz, 1H), 7.50 (d, J=1.9 Hz, 1H), 7.46 (d, J=1.9 Hz, 1H), 7.41 (s, 1H), 7.32 (dd, J=8.3, 1.8 Hz, 1H), 6.93 (s, 1H), 6.32 (d, J=8.7 Hz, 1H), 6.27 (d, J=1.9 Hz, 1H), 3.79 (s, 3H), 3.69 (s, 3H).

7-(2-Methyl-2H-pyrazol-3-ylamino)-[1,6]naphthyridine-2-carboxylic acid [(S)-1-(4-chloro-3-fluoro-phenyl)-2-hydroxy-ethyl]-amide (I-8) was prepared analogously except in step 2, 50c was replaced with 62e. $^1$H NMR (400 MHz, DMSO-$d_6$) δ 9.22 (d, J=8.2 Hz, 1H), 9.19 (s, 1H), 9.13 (s, 1H), 8.54 (d, J=8.4 Hz, 1H), 7.88 (d, J=8.4 Hz, 1H), 7.53 (t, J=8.1 Hz, 1H), 7.47 (dd, J=11.2, 1.9 Hz, 2H), 7.27 (dd, J=8.3, 1.7 Hz, 1H), 6.94 (s, 1H), 6.29 (d, J=1.9 Hz, 1H), 5.08 (m, 2H), 3.84-3.72 (m, 2H), 3.70 (s, 3H).

7-(2-Methyl-2H-pyrazol-3-ylamino)-[1,6]naphthyridine-2-carboxylic acid [(S)-1-(3-fluoro-4-methoxy-phenyl)-2-hydroxy-ethyl]-amide (I-15) was prepared analogously except in step 2, 50c was replaced with 62d. $^1$H NMR (400 MHz, DMSO-$d_6$) δ 9.19 (s, 1H), 9.12 (d, J=6.5 Hz, 2H), 8.53 (d, J=8.4 Hz, 1H), 7.88 (d, J=8.4 Hz, 1H), 7.48 (d, J=1.5 Hz, 1H), 7.28 (d, J=12.6 Hz, 1H), 7.16 (d, J=8.6 Hz, 1H), 7.10 (t, J=8.6 Hz, 1H), 6.94 (s, 1H), 6.65 (s, 1H), 6.29 (s, 1H), 5.02 (m, 2H), 3.80 (s, 3H), 3.78-3.72 (m, 1H), 3.70 (s, 3H).

Example 5

N—((S)-(3-Fluoro-4-methoxyphenyl)(1-methyl-1H-pyrazol-4-yl)methyl)-3-((S)-1-hydroxypropan-2-ylamino)isoquinoline-6-carboxamide (II-4) Method D Step 1:

To a cooled (0° C.), stirred suspension of C-1 (6.018 g, 26.98 mmol, 1.00 equiv.) in BMIM.BF$_4$ (50 mL, 0.26 mol, 9.7 equiv.) was added NO.BF$_4$ (3.90 g, 32.7 mmol, 1.21 equiv.) in several portions over 3 min. The mixture quickly changed in color from pale yellow-brown color to yellow-orange and warmed to ambient temperature with the evolution of nitrogen. After 15 min the effervescence subsided to produce a mobile yellow-orange suspension. After 60 min at RT the mixture was treated with sat'd. aq. NaHCO$_3$, diluted with water and extracted with EtOAc. The lower of the three layers was discarded, and the upper EtOAc phase separated. The orange-brown middle layer was diluted with sufficient water to become homogeneous and again extracted with EtOAc. The combined EtOAc phases were washed with water and brine, dried (Na$_2$SO$_4$), filtered and concentrated in vacuo to afford 6.792 g of a pale brown crystalline solid. The crude residue was absorbed onto silica gel and purified by SiO$_2$ chromatography eluting with an EtOAc/heptane gradient (0 to 30% EtOAc) to afford 4.248 g (70%) of 6-bromo-3-fluoroisoquinoline (C-2) as a white solid. $^1$H NMR (400 MHz, CDCl$_3$) δ 8.94 (s, 1H), 8.00 (s, 1H), 7.86 (d, J=8.8 Hz, 1H), 7.63 (dd, J=8.8, 1.6 Hz, 1H), 7.17 (s, 1H). LCMS: MH$^+$226.1/228.2.

Step 2:

A solution of C-2 (1.01 g, 4.47 mmol, 1.00 equiv.) in DMA (3.0 mL) was treated dropwise with (S)-2-aminopropan-1-ol (403 mg, 5.37 mmol, 1.20 equiv.) and DIPEA (1.17 mL, 6.70 mmol, 1.50 equiv.), and the mixture was heated to 100° C. for 22 h. LCMS analysis revealed a mixture of desired product (MH$^+$281/283) and starting material (MH$^+$ 226/228) in the ratio 1.5:1 (254 nm). The mixture was heated to 120° C. for 48 h and then cooled to RT. LCMS indicated a mixture of desired product and starting material in the ratio 9:1 (254 nm) contaminated by some O-arylated byproduct. The dark brown mixture was concentrated in vacuo to afford 1.56 g of a yellow-brown oily solid. The crude product was treated with EtOAc and washed twice with water then brine, dried (Na$_2$SO$_4$), filtered and concentrated in vacuo. The resulting green-yellow solid (1.08 g) by NMR was a 1:1.5 mixture of desired product to starting material. The crude was purified by automated SiO$_2$ flash chromatography eluting with an EtOAc/heptane gradient (0 to 100% EtOAc) to afford 388 mg (31%) of (S)-2-(6-bromoisoquinolin-3-ylamino)propan-1-ol (C-3, R$^2$=(S)-1-hydroxypropan-2-ylamino). $^1$H NMR (400 MHz, DMSO-$d_6$) δ 8.84 (s, 1H), 7.79 (s, 1H), 7.73 (d, J=8.7 Hz, 1H), 7.21 (dd, J=8.7, 1.7 Hz, 1H), 6.57 (s, 1H), 6.26 (d, J=8.1 Hz, 1H), 4.73 (t, J=5.6 Hz, 1H), 3.83 (septet, J=6 Hz, 1H), 3.51 (dt, J=10.4, 5.1 Hz, 1H), 3.45-3.3 (1H, obscured), 1.16 (d, J=6.5 Hz, 3H). LCMS: MH$^+$281.2/283.2.

Step 3:

A flask containing degassed DMF (5.0 mL) under nitrogen was charged with C-3 (R$^2$=(S)-1-hydroxypropan-2-ylamino) (377 mg, 1.34 mmol, 1.00 equiv.), Pd(OAc)$_2$ (31.9 mg, 0.142 mmol, 0.106 equiv.), 1,3-bis(dicyclohexylphosphino)-propane bis(tetrafluoroborate) (90.8 mg, 0.144 mmol, 0.107 equiv.) and K$_2$CO$_3$ (381 mg, 2.73 mmol, 2.04 equiv.) and treated with MeOH (0.55 mL, 14 mmol, 10 equiv.). The resulting yellow-orange mixture was heated to 100° C. while flushing with CO. LCMS analysis after 1 h indicated no starting material remained, and the mixture was a 3.3:1 mixture (254 nm) of the desired methyl ester (MH$^+$ 261) and carboxylic acid (MH$^+$ 247). The reaction was cooled, diluted with water and extracted twice with EtOAc. The combined organic phases were washed with brine, dried (Na$_2$SO$_4$), filtered through a pad of Celite® and concentrated in vacuo to afford 315 mg of a dark yellow-brown solid. The crude residue was absorbed onto SiO$_2$ and purified by flash chromatography eluting with an EtOAc/heptane gradient (0 to 100% EtOAc) to afford 0.1582 g (45%) of C-4 (R$^2$=(S)-1-hydroxypropan-2-ylamino). $^1$H NMR (400 MHz, CDCl$_3$) δ 8.89 (s, 1H), 8.28 (s, 1H), 7.80 (d, J=8.5 Hz, 1H), 7.76 (d, J=8.6 Hz, 1H), 6.71 (s, 1H), 4.60 (d, J=7.5 Hz, 1H), 4.02-3.91 (m, 1H), 3.97 (s, 3H), 3.85-3.76 (m, 1H), 3.68-3.61 (m, 1H), 2.82 (t, J=5.2 Hz, 1H), 1.31 (d, J=6.6 Hz, 3H).

Step 4:

A solution of C-4 (R$^2$=(S)-1-hydroxypropan-2-ylamino) (158 mg, 0.606 mmol, 1.00 equiv.) in THF (5.0 mL) was treated with 1.0 M aq. LiOH (0.73 mL, 0.73 mmol, 1.2 equiv.) at RT. When no trace of starting material remained the solution was adjusted to pH 4 with 2N aq. H$_2$SO$_4$ (400 µL), and brine, and extracted into EtOAc containing ca. 10% MeOH. The separated yellow aqueous phase was extracted twice more with EtOAc. The combined organic phases were dried (Na$_2$SO$_4$), filtered and concentrated in vacuo to afford 108.8 mg (73%) of C-5 (R$^2$=(S)-1-hydroxypropan-2-ylamino) as a yellow solid which was used without additional purification. LCMS m/s M+H$^+$=247.

Step 5:

A suspension of C-5 (R$^2$=(S)-1-hydroxypropan-2-ylamino) (36.2 mg, 0.147 mmol, 1.00 equiv.) and HATU (57.3 mg, 0.151 mmol, 1.03 equiv.) in DMF (2.0 mL) and was treated with DIPEA (78 pt, 0.45 mmol, 3.0 equiv.) at RT. After 10 min the resulting amber solution was added in one portion to a solution of 50c (47.4 mg, 0.174 mmol, 1.19 equiv.) and DIPEA (78 µL, 0.45 mmol, 3.0 equiv.) in DMF (1.0 mL) at RT. When starting material was consumed, the mixture was diluted with EtOAc and washed sequentially with water, satd. aq. NaHCO$_3$ and brine, dried (Na$_2$SO$_4$), filtered and concentrated in vacuo to afford 42.3 mg of a yellow oil (42.3 mg). The crude residue was purified by C-18 reverse phase HPLC eluting with a MeCN/H$_2$O (with 0.1% NH$_4$OH) gradient to afford 15.0 mg (22%) of II-4. $^1$H NMR (400 MHz, DMSO) δ 9.17 (d, J=8.6 Hz, 1H), 8.89 (s, 1H), 8.07 (s, 1H), 7.84 (d, J=8.6 Hz, 1H), 7.54 (s, 1H), 7.52 (d, J=9.8 Hz, 1H), 7.33 (s, 1H), 7.27 (d, J=12.7 Hz, 1H), 7.20 (d, J=10.1 Hz, 1H), 7.13 (t, J=8.6 Hz, 1H), 6.69 (s, 1H), 6.26 (d, J=8.5 Hz, 1H), 6.18 (d, J=7.9 Hz, 1H), 4.71 (t, J=5.5 Hz, 1H), 3.88-3.78 (m, 1H), 3.82 (s, 3H), 3.79 (s, 3H), 3.57-3.48 (m, 1H), 3.45-3.3 (obscured, 1H), 1.18 (d, J=6.5 Hz, 3H).

3-(Tetrahydro-pyran-4-ylamino)-isoquinoline-6-carboxylic acid [(S)-(3-fluoro-4-methoxy-phenyl)-(1-methyl-1H- pyrazol-4-yl)-methyl]-amide (II-1) was prepared analogously except in step 2, (S)-2-aminopropan-1-ol was replaced with 4-amino-tetrahydropyran. $^1$H NMR (400 MHz, DMSO-d$_6$) 9.20 (d, J=8.6 Hz, 1H), 8.91 (s, 1H), 8.08 (s, 1H), 7.84 (d, J=8.6 Hz, 1H), 7.56-7.50 (m, 2H), 7.33 (s, 1H), 7.28 (dd, J=12.6, 2.0 Hz, 1H), 7.22-7.17 (m, 1H), 7.13 (t, J=8.6 Hz, 1H), 6.72 (s, 1H), 6.52 (d, J=8.0 Hz, 1H), 6.26 (d, J=8.5 Hz, 1H), 3.93-3.86 (m, 2H), 3.82 (s, 3H), 3.86-3.76 (m, 1H), 3.79 (s, 3H), 3.44 (m, 2H), 1.91 (d, J=12.6 Hz, 2H), 1.49 (m, 2H).

3-(Tetrahydro-pyran-4-ylamino)-isoquinoline-6-carboxylic acid [(R)-1-(4-chloro-3-fluoro-phenyl)-propyl]-amide (II-2) was prepared analogously except in step 2 (S)-2-aminopropan-1-ol was replaced with 4-amino-tetrahydropyran and in step 5, 50c was replaced with (R)-1-(4-chloro-3-fluoro-phenyl)propan-1-amine hydrochloride (70b). $^1$H NMR (400 MHz, DMSO-d$_6$) δ 8.91 (s, 1H), 8.87 (d, J=8.2 Hz, 1H), 8.05 (s, 1H), 7.85 (d, J=8.5 Hz, 1H), 7.55 (t, J=8.1 Hz, 1H), 7.51 (d, J=8.5 Hz, 1H), 7.46 (dd, J=10.6, 1.5 Hz, 1H), 7.29 (d, J=8.3 Hz, 1H), 6.74 (s, 1H), 6.51 (d, J=7.9 Hz, 1H), 4.95 (dd, J=14.8, 8.3 Hz, 1H), 3.90 (m, 2H), 3.83 (m, 1H), 3.45 (t, J=10.7 Hz, 2H), 1.92 (m, 2H), 1.89-1.73 (m, 2H), 1.56-1.43 (m, 2H), 0.92 (t, J=7.3 Hz, 3H).

3-((S)-2-Hydroxy-1-methyl-ethylamino)-isoquinoline-6-carboxylic acid [(S)-1-(4-chloro-3-fluoro-phenyl)-2-hydroxy-ethyl]-amide (II-3) was prepared analogously except in step 2 (S)-2-aminopropan-1-ol was replaced with 62e. $^1$H NMR (400 MHz, DMSO-d$_6$) δ 8.90 (s, 1H), 8.87 (d, J=8 Hz, 1H), 8.09 (s, 1H), 7.85 (d, J=8.5 Hz, 1H), 7.54 (t, J=8.2 Hz, 1H), 7.53 (d, J=8.8 Hz, 1H), 7.46 (d, J=10.7 Hz, 1H), 7.29 (d, J=9.2 Hz, 1H), 6.71 (s, 1H), 6.24 (d, J=7.9 Hz, 1H), 5.09 (q, J=7 Hz, 1H), 3.84 (septet, J=7 Hz, 1H), 3.77-3.65 (m, 2H), 3.53 (dd, J=10.6, 4.8 Hz, 1H), 3.36 (dd, J=10.5, 6.2 Hz, 1H), 1.18 (d, J=6.5 Hz, 3H).

3-((S)-2-Hydroxy-1-methyl-ethylamino)-isoquinoline-6-carboxylic acid [(S)-(3-fluoro-phenyl)-(1-methyl-1H-pyrazol-4-yl)-methyl]-amide (II-5) was prepared analogously except in step 5, (S)-50c was replaced with 50h. $^1$H NMR (400 MHz, DMSO-d$_6$) δ 9.24 (d, J=8.5 Hz, 1H), 8.89 (s, 1H), 8.08 (s, 1H), 7.84 (d, J=8.5 Hz, 1H), 7.57 (s, 1H), 7.53 (d, J=8.5 Hz, 1H), 7.43-7.35 (m, 2H), 7.28 (d, J=8 Hz, 1H), 7.26 (d, J=10 Hz, 1H), 7.09 (t, J=8.5 Hz, 1H), 6.70 (s, 1H), 6.33 (d, J=8.5 Hz, 1H), 6.18 (d, J=8.0 Hz, 1H), 4.71 (t, J=5.6 Hz, 1H), 3.87-3.78 (m, 1H), 3.79 (s, 3H), 3.56-3.49 (1H), 3.45-3.35 (obscured), 1.18 (d, J=6.5 Hz, 3H).

3-((S)-2-Hydroxy-1-methyl-ethylamino)-isoquinoline-6-carboxylic acid [(S)-(4-methoxy-phenyl)-(1-methyl-1H-pyrazol-4-yl)-methyl]-amide (II-6) was prepared analogously except in step 5, 50c was replaced with 50i. $^1$H NMR (400 MHz, DMSO) δ 9.15 (d, J=8.5 Hz, 1H), 8.89 (s, 1H), 8.07 (s, 1H), 7.83 (d, J=8.5 Hz, 1H), 7.53 (d, J=10 Hz, 2H), 7.51 (s, 1H), 7.35 (d, J=8.6 Hz, 2H), 7.31 (s, 1H), 6.91 (d, J=8.7 Hz, 2H), 6.69 (s, 1H), 6.26 (d, J=8.6 Hz, 1H), 6.17 (d, J=7.9 Hz, 1H), 4.71 (t, J=5.5 Hz, 1H), 3.88-3.78 (m, 1H), 3.79 (s, 3H), 3.74 (s, 3H), 3.57-3.49 (m, 1H), 3.5-3.3 (obscured, 1H), 1.18 (d, J=6.5 Hz, 3H).

3-((S)-2-Hydroxy-1-methyl-ethylamino)-isoquinoline-6-carboxylic acid [(R)-1-(3-fluoro-4-methoxy-phenyl)-propyl]-amide (II-7) was prepared analogously except in step 5, 50c was replaced with 70a. $^1$H NMR (400 MHz, DMSO-d$_6$) δ 8.89 (s, 1H), 8.76 (d, J=8.4 Hz, 1H), 8.02 (s, 1H), 7.83 (d, J=8.5 Hz, 1H), 7.50 (dd, J=8.5, 1.4 Hz, 1H), 7.26 (dd, J=12.7, 1.9 Hz, 1H), 7.17 (dd, J=8.6, 1.9 Hz, 1H), 7.11 (t, J=8.6 Hz, 1H), 6.70 (s, 1H), 6.18 (d, J=8.0 Hz, 1H), 4.89 (q, J=8.0 Hz, 1H), 4.69 (t, J=5.5 Hz, 1H), 3.88-3.79 (m, 1H), 3.81 (s, 3H), 3.57-3.49 (m, 1H), 3.41-3.32 (m, 1H), 1.92-1.72 (m, 2H), 1.18 (d, J=6.5 Hz, 3H), 0.90 (t, J=7.3 Hz, 3H).

3-((S)-2-Hydroxy-1-methyl-ethylamino)-isoquinoline-6-carboxylic acid [(S)-(4-chloro-3-fluoro-phenyl)-(1-methyl-1H-pyrazol-4-yl)-methyl]-amide (II-8) was prepared analogously except in step 5, 50c was replaced with 50a. $^1$H NMR (400 MHz, DMSO-d$_6$) δ 9.24 (d, J=8.3 Hz, 1H), 8.89 (s, 1H), 8.08 (s, 1H), 7.84 (d, J=8.5 Hz, 1H), 7.57 (t, J=8.0 Hz, 1H), 7.57 (s, 1H), 7.52 (dd, J=8.6, 1.2 Hz, 1H), 7.47 (dd, J=10.6, 1.6 Hz, 1H), 7.37 (s, 1H), 7.32 (dd, J=8.3, 1.6 Hz, 1H), 6.70 (s, 1H), 6.32 (d, J=8.3 Hz, 1H), 6.19 (d, J=8.1 Hz, 1H), 4.70 (t, J=5.5 Hz, 1H), 3.87-3.77 (m, 1H), 3.79 (s, 3H), 3.57-3.49 (m, 1H), 3.40-3.33 (m, 1H), 1.18 (d, J=6.5 Hz, 3H).

3-(Tetrahydro-pyran-4-ylamino)-isoquinoline-6-carboxylic acid [(S)-(3-fluoro-phenyl)-(1-methyl-1H-pyrazol-4-yl)-methyl]-amide (II-9) was prepared analogously except in step 2, (S)-2-aminopropan-1-ol was replaced with 4-amino-tetrahydropyran and in step 5, 50c was replaced with (S)-(3-fluoro-phenyl)(1-methyl-1H-pyrazol-4-yl)methanamine hydrochloride (50h). $^1$H NMR (400 MHz, DMSO) δ 9.26 (d, J=8.5 Hz, 1H), 8.91 (s, 1H), 8.10 (s, 1H), 7.84 (d, J=8.6 Hz, 1H), 7.57 (s, 1H), 7.54 (dd, J=8.5, 1.4 Hz, 1H), 7.40 (td, J=8.0, 6.1 Hz, 1H), 7.36 (s, 1H), 7.30-7.24 (m, 2H), 7.09 (td, J=8.6, 2.5 Hz, 1H), 6.73 (s, 1H), 6.51 (d, J=8.0 Hz, 1H), 6.33 (d, J=8.5 Hz, 1H), 3.92-3.86 (m, 2H), 3.86-3.80 (m, 1H), 3.79 (s, 3H), 3.44 (td, J=11.8, 2.0 Hz, 2H), 1.92 (d, J=10.5 Hz, 2H), 1.49 (ddd, J=15.6, 12.0, 4.2 Hz, 2H).

3-(Tetrahydro-pyran-4-ylamino)-isoquinoline-6-carboxylic acid [(S)-(4-methoxy-phenyl)-(1-methyl-1H-pyrazol-4-yl)-methyl]-amide (II-10) was prepared analogously except in step 2, (S)-2-aminopropan-1-ol was replaced with 4-amino-tetrahydropyran and in step 5, 50c was replaced with (S)-(4-methoxy-phenyl)(1-methyl-1H-pyrazol-4-yl)methanamine hydrochloride (50i). $^1$H NMR (400 MHz, DMSO-d$_6$) δ 9.17 (d, J=8.6 Hz, 1H), 8.90 (s, 1H), 8.08 (s, 1H), 7.83 (d, J=8.6 Hz, 1H), 7.54 (dd, J=8.5, 1.4 Hz, 1H), 7.51 (s, 1H), 7.35 (d, J=8.6 Hz, 2H), 7.32 (s, 1H), 6.91 (d, J=8.6 Hz, 2H), 6.71 (s, 1H), 6.50 (d, J=8.0 Hz, 1H), 6.26 (d, J=8.6 Hz, 1H), 3.93-3.86 (m, 2H), 3.86-3.80 (m, 1H), 3.79 (s, 3H), 3.74 (s, 3H), 3.44 (td, J=11.5, 2.0 Hz, 2H), 1.92 (d, J=10.6 Hz, 2H), 1.49 (ddd, J=15.5, 12.0, 4.3 Hz, 2H).

3-(Tetrahydro-pyran-4-ylamino)-isoquinoline-6-carboxylic acid [(S)-(4-chloro-3-fluoro-phenyl)-(1-methyl-1H-pyrazol-4-yl)-methyl]-amide (II-11) was prepared analogously except in step 2, (S)-2-aminopropan-1-ol was replaced with 4-amino-tetrahydropyran and in step 5, 50c was replaced with (S)-(4-chloro-3-fluorophenyl)(1-methyl-1H-pyrazol-4-yl)methanamine hydrochloride (50a). $^1$H NMR (400 MHz, DMSO-d$_6$) δ 9.26 (d, J=8.4 Hz, 1H), 8.91 (s, 1H), 8.10 (s, 1H), 7.84 (d, J=8.6 Hz, 1H), 7.57 (t, J=8.4 Hz, 1H), 7.57 (s, 1H), 7.53 (dd, J=8.5, 1.4 Hz, 1H), 7.48 (dd, J=10.6, 1.9 Hz, 1H), 7.37 (s, 1H), 7.32 (dd, J=8.4, 1.8 Hz, 1H), 6.73 (s, 1H), 6.52 (d, J=7.9 Hz, 1H), 6.32 (d, J=8.3 Hz, 1H), 3.93-3.86 (m, 2H), 3.86-3.80 (m, 1H), 3.79 (s, 3H), 3.44 (td, J=11.5, 2.0 Hz, 2H), 1.92 (d, J=10.4 Hz, 2H), 1.49 (ddd, J=15.4, 12.0, 4.3 Hz, 2H).

3-(Tetrahydro-pyran-4-ylamino)-isoquinoline-6-carboxylic acid [(S)-1-(4-chloro-3-fluoro-phenyl)-2-hydroxy-ethyl]-amide (II-12) was prepared analogously except in step 2, (S)-2-aminopropan-1-ol was replaced with 4-amino-tetrahydropyran and in step 5, 50c was replaced with (S)-2-amino-2-(4-chloro-3-fluoro-phenyl)ethanol hydrochloride (62e). $^1$H NMR (400 MHz, DMSO-d$_6$) δ 8.91 (s, 1H), 8.83 (d, J=7.9 Hz, 1H), 8.10 (s, 1H), 7.85 (d, J=8.6 Hz, 1H), 7.55 (t, J=8.1 Hz, 1H), 7.53 (dd, J=8.6, 1.6 Hz, 1H), 7.47 (dd, J=10.6, 1.8 Hz, 1H), 7.29 (dd, J=8.3, 1.7 Hz, 1H), 6.74 (s, 1H), 6.53 (d, J=7.9 Hz, 1H), 5.10 (q, J=7.1 Hz, 1H), 5.03 (t, J=5.8 Hz, 1H), 3.94-3.87 (m, 2H), 3.87-3.78 (m, 1H), 3.78-3.64 (m, 2H), 3.45 (td, J=11.5, 2.0 Hz, 2H), 1.92 (d, J=12.4 Hz, 2H), 1.56-1.43 (m, 2H).

3-(Tetrahydro-pyran-4-ylamino)-isoquinoline-6-carboxylic acid [(S)-1-(3-fluoro-4-methoxy-phenyl)-2-hydroxy-ethyl]-amide (II-17) was prepared analogously except in step 2, (S)-2-aminopropan-1-ol was replaced with 4-amino-tetrahydropyran and in step 5, 50c was replaced with (S)-2-amino-2-(3-fluoro-4-methoxyphenyl)ethanol hydrochloride (62d). $^1$H NMR (500 MHz, DMSO-d$_6$) δ 8.91 (s, 1H), 8.76 (d, J=8.5 Hz, 1H), 8.08 (s, 1H), 7.85 (d, J=8.5 Hz, 1H), 7.53 (d, J=9.0 Hz, 1H), 7.27 (d, J=13.0 Hz, 1H), 7.17 (d, J=8.5 Hz, 1H), 7.11 (t, J=8.5 Hz, 1H), 6.73 (s, 1H), 6.55 (d, J=8.0 Hz, 1H), 5.06-5.02 (m, 1H), 4.96 (t, J=5.5 Hz, 1H), 3.91-3.89 (m, 2H), 3.81 (s, 3H), 3.70-3.61 (m, 2H), 3.46-3.42 (m, 3H), 1.94-1.91 (m, 2H), 1.52-1.45 (m, 2H).

3-((S)-2-Hydroxy-1-methyl-ethylamino)-isoquinoline-6-carboxylic acid [(S)-1-(3-fluoro-4-methoxy-phenyl)-2-hydroxy-ethyl]-amide (II-18) was prepared analogously except in step 5, (S)-(3-fluoro-4-methoxy-phenyl)-(1-methylpyrazol-4-yl)methanamine hydrochloride was replaced with (S)-2-amino-2-(3-fluoro-4-methoxyphenyl)ethanol hydrochloride (62d). $^1$H NMR (400 MHz, DMSO-d$_6$) δ 8.90 (s, 1H), 8.74 (d, J=8.2 Hz, 1H), 8.07 (s, 1H), 7.84 (d, J=8.5 Hz, 1H), 7.52 (dd, J=8.5, 1.4 Hz, 1H), 7.27 (dd, J=12.7, 1.9 Hz, 1H), 7.17 (dd, J=8.6, 1.8 Hz, 1H), 7.11 (t, J=8.6 Hz, 1H), 6.70 (s, 1H), 6.23 (d, J=8.0 Hz, 1H), 5.04 (td, J=7.9, 6.9 Hz, 1H), 4.93 (t, J=5.8 Hz, 1H), 4.72 (t, J=5.6 Hz, 1H), 3.88-3.80 (m, 1H), 3.81 (s, 3H), 3.74-3.60 (m, 2H), 3.53 (dt, J=10.4, 5.2 Hz, 1H), 3.36 (dt, J=10.6, 6.0 Hz, 1H), 1.18 (d, J=6.5 Hz, 3H).

N—((S)-1-(3-Fluorophenyl)-2-hydroxyethyl)-3-(tetrahydrofuran-3-ylamino)isoquinoline-6-carboxamide (II-20) was prepared analogously except in step 2, (S)-2-aminopropan-1-ol was replaced with 3-amino-tetrahydrofuran and in step 5, 50c was replaced with (S)-2-amino-2-(3-fluorophenyl)ethanol hydrochloride (62a). $^1$H NMR (500 MHz, DMSO-d$_6$) δ 8.94 (s, 1H), 8.87 (d, J=8 Hz, 1H), 8.13 (s, 1H), 7.88 (d, J=8.5 Hz, 1H), 7.56 (d, J=8.5 Hz, 1H), 7.38 (m, 1H), 7.26 (d, J=8.0 Hz, 2H), 7.08 (t, J=19.5 Hz, 1H), 6.84 (d, J=6 Hz, 1H), 6.72 (s, 1H), 5.12 (m, 1H), 5.02 (t, J=11.5 Hz, 1H), 4.32 (t, J=6.0, 1H), 3.96-3.93 (m, 1H), 3.87 (m, 1H), 3.78-3.67 (m, 3H), 3.61 (m, 1H), 2.23 (m, 1H), 1.98 (m, 1H).

N—((S)-2-Hydroxy-1-(4-methoxyphenyl)ethyl)-3-(tetrahydrofuran-3-ylamino)isoquinoline-6-carboxamide (II-21) was prepared analogously except in step 2, (S)-2-aminopropan-1-ol was replaced with 3-amino-tetrahydrofuran and in step 5, 50c was replaced with 62c. $^1$H NMR (500 MHz, DMSO-d$_6$) δ 8.93 (s, 1H), 8.78 (d, J=8 Hz, 1H), 8.10 (s, 1H), 7.86 (d, J=8.5 Hz, 1H), 7.55 (dd, J=8.5, 1.5 Hz, 1H), 7.33 (d, J=9.0 Hz, 2H), 6.89 (d, J=9.0 Hz, 2H), 6.82 (d, J=6.0 Hz, 1H), 6.70 (s, 1H), 5.04 (m, 1H), 4.91 (t, J=6.0 Hz, 1H), 4.30 (m, 1H), 3.95 (m, 1H), 3.86 (m, 1H), 3.77-3.64 (m, 5H), 3.62-3.60 (m, 2H), 2.23 (m, 1H), 1.87 (m, 1H).

3-((S)-2-Hydroxy-1-methyl-ethylamino)-isoquinoline-6-carboxylic acid [(S)-1-(3-fluoro-phenyl)-2-hydroxy-ethyl]-amide (II-22) was prepared analogously except in step 5, 50c was replaced with 62a. $^1$H NMR (500 MHz, DMSO-d$_6$) δ 8.91 (s, 1H), 8.86 (d, J=10.0 Hz, 1H), 8.10 (s, 1H), 7.85 (d, J=11.0 Hz, 1H), 7.53 (dd, J=10.5, 2.0 Hz, 1H), 7.37 (m, 1H), 7.27-7.25 (m, 2H), 7.07 (m, 1H), 6.70 (s, 1H), 6.29 (d, J=10.0 Hz, 1H), 5.11 (m, 1H), 5.03 (t, J=7.5 Hz, 1H), 4.76 (t, J=7.5 Hz, 1H), 3.83 (m, 1H), 3.76-3.64 (m, 2H), 3.53 (m, 1H), 3.31 (m, 1H), 1.18 (d, J=8.5 Hz, 3H).

3-((S)-2-Hydroxy-1-methyl-ethylamino)-isoquinoline-6-carboxylic acid (4-fluoro-1H-indol-2-ylmethyl)-amide (II-23) was prepared analogously except in step 5, 50c was replaced with 38. $^1$H NMR (500 MHz, DMSO-d$_6$) δ 11.31 (s, 1H), 9.14 (t, J=5.5 Hz, 1H), 8.90 (s, 1H), 8.06 (s, 1H), 7.86 (d, J=8.5 Hz, 1H), 7.57 (m, 1H), 7.20 (d, J=8.0 Hz, 1H), 7.01 (m, 1H), 6.75-6.70 (m, 2H), 6.38 (s, 1H), 6.26 (d, J=8.0 Hz, 1H), 4.73 (dd, J=5.5, 6.0 Hz, 1H), 4.65 (d, J=5.5 Hz, 2H), 3.84 (m, 1H), 3.52 (m, 1H), 3.35 (m, 1H), 1.17 (d, J=6.5 Hz, 3H).

3-(Tetrahydro-furan-3-ylamino)-isoquinoline-6-carboxylic acid (4-fluoro-1H-indol-2-ylmethyl)-amide (II-25) was prepared analogously except in step 2, (S)-2-aminopropan-1-ol was replaced with 3-amino-tetrahydrofuran and in step 5, 50c was replaced with 38. $^1$H NMR (500 MHz, DMSO-d$_6$) δ 11.32 (s, 1H), 9.16 (t, J=5.5 Hz, 1H), 8.94 (s, 1H), 8.12 (s, 1H), 7.89 (d, J=8.5 Hz, 1H), 7.59 (m, 1H), 7.20 (d, J=8.0 Hz, 1H), 7.01 (m, 1H), 6.83 (d, J=6.5 Hz, 1H), 6.75-6.70 (m, 2H), 6.39 (s, 1H), 4.66 (d, J=5.5 Hz, 2H), 4.32 (m, 1H), 3.94 (m, 1H), 3.85 (m, 1H), 3.75 (m, 1H), 3.59 (m, 1H), 2.22 (m, 1H), 1.87 (m, 1H).

3-((S)-2-Hydroxy-1-methyl-ethylamino)-isoquinoline-6-carboxylic acid [(S)-(3-fluoro-4-methoxy-phenyl)-(1-methyl-1H-pyrazol-3-yl)-methyl]-amide (II-24) was prepared analogously except in step 5, 50c was replaced with (S)-(3-fluoro-4-methoxyphenyl)(1-methyl-1H-pyrazol-3-yl)methanamine hydrochloride (50d). $^1$H NMR (500 MHz, DMSO-d$_6$) δ 9.25 (d, J=9.0 Hz, 1H), 8.89 (s, 1H), 8.09 (s, 1H), 7.84 (d, J=8.5 Hz, 1H), 7.62 (d, J=2.0 Hz, 1H), 7.53 (dd, J=8.5, 1.5 Hz, 1H), 7.27 (dd, J=12.5, 2.0 Hz, 1H), 7.18 (d, J=9.0 Hz, 1H), 7.12 (t, J=8.5 Hz, 1H), 6.70 (s, 1H), 6.32 (d, J=8.0 Hz, 1H), 6.26 (d, J=8.5 Hz, 1H), 6.20 (d, J=2.0 Hz, 1H), 4.75 (t, J=5.5 Hz, 1H), 3.85-3.78 (m, 8H), 3.52 (m, 1H), 1.17 (d, J=6.5 Hz, 3H).

N—((S)-1-(3-Fluoro-4-methoxyphenyl)-2-hydroxyethyl)-3-(tetrahydrofuran-3-ylamino)isoquinoline-6-carboxamide (II-26) was prepared analogously except in step 2, (S)-2-aminopropan-1-ol was replaced with 3-amino-tetrahydrofuran and in step 5, (S)-(3-fluoro-4-methoxy-phenyl)-(1-methylpyrazol-4-yl)methanamine hydrochloride was replaced with (S)-2-amino-2-(3-fluoro-4-methoxyphenyl)ethanol hydrochloride (62d) $^1$H NMR (500 MHz, CD$_3$OD) δ 8.89 (s, 1H), 8.09 (s, 1H), 7.89 (d, J=8.5 Hz, 1H), 7.59 (d, J=6.5 Hz, 1H), 7.22-7.19 (m, 2H), 7.09 (t, J=8.5 Hz, 1H), 6.80 (s, 1H), 5.18 (m, 1H), 4.42 (m, 1H), 4.07-3.99 (m, 2H), 3.92-3.85 (m, 6H), 3.76 (m, 1H), 2.38 (m, 1H), 1.98 (m, 1H).

N—((R)-(3-Fluoro-4-methoxyphenyl)(1-methyl-1H-pyrazol-3-yl)methyl)-3-(tetrahydrofuran-3-ylamino)isoquinoline-6-carboxamide (II-27) was prepared analogously except in step 2, (S)-2-aminopropan-1-ol was replaced with 3-amino-tetrahydrofuran and in step 5, 50c was replaced with (R)-(3-fluoro-4-methoxyphenyl)(1-methyl-1H-pyrazol-3-yl)methanamine hydrochloride (50d). $^1$H NMR (500 MHz, DMSO-d$_6$) δ 9.26 (d, J=9 Hz, 1H), 8.92 (s, 1H), 8.45 (s, 0.4H), 8.28 (s, 1H), 7.86 (d, J=8.5 Hz, 1H), 7.62 (d, J=2 Hz, 1H), 7.56 (dd, J=8.55, 1.5 Hz, 1H), 7.26 (dd, J=12.5, 1.5 Hz, 1H), 7.18 (d, J=9 Hz, 1H), 7.12 (t, J=9 Hz, 1H), 6.83 (d, J=6 Hz, 1H), 6.70 (s, 1H), 6.32 (d, J=9 Hz, 1H), 6.20 (d, J=2 Hz, 1H), 4.30 (m, 1H), 3.94 (m, 1H), 3.85 (q, J=7.5 Hz, 1H), 3.81 (s, 3H), 3.80 (s, 3H), 3.75 (m, 1H), 3.59 (dd, J=8.5, 3.5 Hz, 1H), 2.22 (m, 1H), 1.87 (m, 1H).

3-((S)-2-Hydroxy-1-methyl-ethylamino)-isoquinoline-6-carboxylic acid [(S)-2-hydroxy-1-(4-methoxy-phenyl)-ethyl]-amide (II-28) was prepared analogously except in step 5, (S)-(3-fluoro-4-methoxy-phenyl)-(1-methylpyrazol-4-yl)methanamine hydrochloride was replaced with 62c. $^1$H NMR (500 MHz, DMSO-d$_6$) δ 8.89 (s, 1H), 8.77 (d, J=7.5 Hz, 1H), 8.07 (s, 1H), 7.84 (d, J=8.5 Hz, 1H), 7.52 (d, J=9.0 Hz, 1H), 7.33 (d, J=8.5 Hz, 2H), 6.89 (d, J=9.0 Hz, 2H), 6.97 (s, 1H), 6.26 (d, J=8.0 Hz, 1H), 5.03 (m, 1H), 4.91 (t, J=5.5 Hz, 1H), 4.75 (t, J=5.5 Hz, 1H), 3.82 (m, 1H), 3.72-3.68 (m, 4H), 3.62 (m, 1H), 3.53 (m, 1H), 3.35 (m, 1H), 1.17 (d, J=6.0 Hz, 3H).

3-((S)-2-Hydroxy-1-methyl-ethylamino)-isoquinoline-6-carboxylic acid [(S)-1-(3-chloro-4-fluoro-phenyl)-2-hydroxy-ethyl]-amide (II-29) was prepared analogously except in step 5, 50c was replaced with 62f. $^1$H NMR (500 MHz, DMSO-$d_6$) δ 8.90 (s, 1H), 8.85 (d, J=8.0 Hz, 1H), 8.08 (s, 1H), 7.85 (d, J=8.5 Hz, 1H), 7.64 (m, 1H), 7.51 (d, J=8.5 Hz, 1H), 7.44-7.36 (m, 2H), 6.71 (s, 1H), 6.28 (d, J=8.0 Hz, 1H), 5.09-5.02 (m, 2H), 4.75 (t, J=4.4 Hz, 1H), 3.83 (t, J=6.3 Hz, 1H), 3.74-3.65 (m, 2H), 3.53 (dd, J=11, 5.5 Hz, 1H), 3.36 (dd, J=12, 6.0 Hz, 1H), 1.18 (d, J=6.0 Hz, 3H).

3-((S)-2-Hydroxy-1-methyl-ethylamino)-isoquinoline-6-carboxylic acid [(S)-2-hydroxy-1-(4-trifluoromethoxy-phenyl)-ethyl]-amide (II-30) was prepared analogously except in step 5, (S)-(3-fluoro-4-methoxy-phenyl)-(1-methylpyrazol-4-yl)methanamine hydrochloride was replaced with 62b. $^1$H NMR (500 MHz, DMSO-$d_6$) δ 8.90 (s, 1H), 8.78 (d, J=8.5 Hz, 1H), 8.09 (s, 1H), 7.55-7.52 (m, 3H), 7.33 (d, J=8.0 Hz, 2H), 6.70 (s, 1H), 6.27 (d, J=8.5, 1H), 5.12 (m, 1H), 5.01 (s, 1H), 4.74 (t, J=6.5 Hz, 1H), 3.83-3.67 (m, 3H), 3.52 (m, 1H), 3.32 (m, 1H), 1.78 (d, J=6.5 Hz, 3H).

N—((S)-(3-Fluoro-4-methoxyphenyl)(1-methyl-1H-pyrazol-5-yl)methyl)-3-(tetrahydrofuran-3-ylamino)isoquinoline-6-carboxamide (II-31) was prepared analogously except in step 2, (S)-2-aminopropan-1-ol was replaced with 3-amino-tetrahydrofuran and in step 5, (S)-(3-fluoro-4-methoxy-phenyl)-(1-methylpyrazol-4-yl)methanamine hydrochloride was replaced with (S)-(3-fluoro-4-methoxyphenyl)(1-methyl-1H-pyrazol-5-yl)methanamine hydrochloride (50f). $^1$H NMR (500 MHz, DMSO-$d_6$) δ 9.46 (s, J=6.5 Hz, 1H), 8.93 (s, 1H), 8.13 (s, 1H), 7.87 (d, J=8.0 Hz, 1H), 7.55 (d, J=7.5 Hz, 1H), 7.34-7.17 (m, 4H), 6.84 (d, J=6.0 Hz, 1H), 6.70 (s, 1H), 6.49 (d, J=8.5 Hz, 1H), 5.95 (d, J=1.5 Hz, 1H), 4.40 (m, 1H), 3.94 (m, 1H), 3.88-3.83 (m, 4H), 3.76-3.74 (m, 4H), 3.59 (m, 1H), 2.20 (m, 1H), 1.89 (m, 1H).

3-(Tetrahydro-pyran-4-ylamino)-isoquinoline-6-carboxylic acid [(S)-(3-fluoro-4-methoxy-phenyl)-(1-methyl-1H-pyrazol-3-yl)-methyl]-amide (II-32) was prepared analogously except in step 2, (S)-2-aminopropan-1-ol was replaced with 3-amino-tetrahydropyran and in step 5, (S)-(3-fluoro-4-methoxy-phenyl)-(1-methylpyrazol-4-yl)methanamine hydrochloride was replaced with (S)-(3-fluoro-4-methoxyphenyl)(1-methyl-1H-pyrazol-3-yl)methanamine hydrochloride (50d). $^1$H NMR (400 MHz, DMSO-$d_6$) δ 9.07 (s, 1H), 8.84 (s, 1H), 8.78 (d, J=8.1 Hz, 1H), 8.23 (s, 1H), 8.00 (d, J=8.6 Hz, 1H), 7.70 (d, J=8.5 Hz, 1H), 7.42 (d, J=1.7 Hz, 1H), 7.26 (d, J=12.7 Hz, 1H), 7.17 (d, J=8.6 Hz, 1H), 7.11 (t, J=8.6 Hz, 1H), 6.94 (s, 1H), 6.24 (d, J=1.7 Hz, 1H), 5.04 (dd, J=13.8, 7.7 Hz, 2H), 3.81 (s, 3H), 3.73-3.60 (m, 5H).

N—((S)-1-(3-Chloro-4-fluorophenyl)-2-hydroxyethyl)-3-(tetrahydrofuran-3-ylamino)isoquinoline-6-carboxamide (II-38) was prepared analogously except in step 2, (S)-2-aminopropan-1-ol was replaced with 3-amino-tetrahydrofuran and in step 5, 50c was replaced with (S)-2-amino-2-(3-chloro-4-fluoro-phenyl)ethanol hydrochloride 62f. $^1$H NMR (500 MHz, DMSO-$d_6$) δ 8.93 (s, 1H), 8.87 (d, J=8.5 Hz, 1H), 8.12 (s, 1H), 7.87 (d, J=8.5 Hz, 1H), 7.64 (dd, J=7.0, 2.0 Hz, 1H), 7.55 (d, J=8.5 Hz, 1H), 7.44-7.36 (m, 2H), 6.84 (d, J=6.5 Hz, 1H), 6.71 (s, 1H), 5.10-5.03 (m, 2H), 4.31 (m, 1H), 3.95 (m, 1H), 3.86 (m, 1H), 3.77-3.75 (m, 2H), 3.73 (m, 1H), 3.61 (m, 1H), 2.23 (m, 1H), 1.87 (m, 1H).

N—((S)-1-(3-Chloro-4-cyanophenyl)-2-hydroxyethyl)-3-(tetrahydrofuran-3-ylamino)isoquinoline-6-carboxamide (II-39) was prepared analogously except in step 2, (S)-2-aminopropan-1-ol was replaced with 3-amino-tetrahydrofuran and in step 5, 50c was replaced with 62i. $^1$H NMR (500 MHz, DMSO-$d_6$) δ 8.96 (d, J=7.5 Hz, 1H), 8.94 (s, 1H), 8.14 (s, 1H), 7.95 (d, J=8.0 Hz, 1H), 7.89 (d, J=8.5 Hz, 1H), 7.81 (s, 1H), 7.60 (d, J=7.5 Hz, 1H), 7.56 (d, J=8.5 Hz, 1H), 6.86 (d, J=6.5 Hz, 1H), 6.72 (s, 1H), 5.17-5.13 (m, 2H), 4.31 (t, J=2.8 Hz, 1H), 3.95 (m, 1H), 3.87 (dd, J=16.0, 8.0 Hz, 1H), 3.78-3.73 (m, 3H), 3.61 (dd, J=8.5, 3.5 Hz, 1H), 2.23 (m, 1H), 1.89 (m, 1H).

3-(Tetrahydro-pyran-4-ylamino)-isoquinoline-6-carboxylic acid [(S)-1-(3-fluoro-phenyl)-2-hydroxy-ethyl]-amide (II-40) was prepared analogously except in step 2, (S)-2-aminopropan-1-ol was replaced with 3-amino-tetrahydropyran and in step 5, 50c was replaced with (S)-2-amino-2-(4-fluorophenyl)ethanol (62g). $^1$H NMR (500 MHz, DMSO-$d_6$) δ 8.91 (s, 1H), 8.84 (d, J=8.5 Hz, 1H), 8.10 (s, 1H), 7.85 (d, J=8.5 Hz, 1H), 7.53 (d, J=8.5 Hz, 1H), 7.37 (m, 1H), 7.25 (d, J=7.5 Hz, 2H), 7.07 (m, 1H), 6.74 (s, 1H), 6.56 (d, J=8.0 Hz, 1H), 5.11 (m, 1H), 5.01 (t, J=5.5 Hz, 1H), 3.91-3.84 (m, 3H), 3.73-3.66 (m, 2H), 3.47-3.42 (m, 2H), 1.94-1.91 (m, 2H), 1.50-1.48 (m, 2H).

3-(Tetrahydro-pyran-4-ylamino)-isoquinoline-6-carboxylic acid [(S)-2-hydroxy-1-(4-methoxy-phenyl)-ethyl]-amide (II-41) was prepared analogously except in step 2, (S)-2-aminopropan-1-ol was replaced with 3-amino-tetrahydropyran and in step 5, 50c was replaced with (S)-2-amino-2-(4-fluorophenyl)ethanol 62c. $^1$H NMR (500 MHz, DMSO-$d_6$) δ 8.91 (s, 1H), 8.76 (d, J=8 Hz, 1H), 8.08 (s, 1H), 7.84 (d, J=8.5 Hz, 1H), 7.53 (d, J=8.5 Hz, 1H), 7.33 (d, J=8.5 Hz, 2H), 6.89 (d, J=8.0 Hz, 2H), 6.73 (s, 1H), 6.55 (d, J=8.5 Hz, 1H), 5.05 (m, 1H), 4.90 (t, J=5.5 Hz, 1H), 3.91-3.83 (m, 3H), 3.73-3.68 (m, 4H), 3.63 (m, 1H), 3.47-3.42 (m, 2H), 1.94-1.91 (m, 2H), 1.51-1.48 (m, 2H).

3-(Tetrahydro-pyran-4-ylamino)-isoquinoline-6-carboxylic acid [(S)-1-(3-chloro-4-cyano-phenyl)-2-hydroxy-ethyl]-amide (II-42) was prepared analogously except in step 2, (S)-2-aminopropan-1-ol was replaced with 3-amino-tetrahydropyran and in step 5, 50c was replaced with 62i. $^1$H NMR (500 MHz, DMSO-$d_6$) δ 8.95-8.92 (m, 2H), 8.11 (s, 1H), 7.96 (d, J=7.5 Hz, 1H), 7.86 (d, J=8.5 Hz, 1H), 7.81 (s, 1H), 7.60 (d, J=8.5 Hz, 1H), 7.53 (d, J=8.5 Hz, 1H), 6.74 (s, 1H), 6.58 (d, J=7.5 Hz, 1H), 5.15-5.11 (m, 2H), 3.92-3.70 (m, 5H), 3.47-3.42 (m, 2H), 1.94-1.91 (m, 2H), 1.51-1.48 (m, 2H).

3-((3S,4S)-3-Fluoro-tetrahydro-pyran-4-ylamino)-isoquinoline-6-carboxylic acid [(S)-2-hydroxy-1-(4-methoxy-phenyl)-ethyl]-amide (II-43) was prepared analogously except in step 2, (S)-2-aminopropan-1-ol was replaced with (3S,4S)-3-fluorotetrahydro-2H-pyran-4-amine (71c) and in step 5, 50c was replaced with (S)-2-amino-2-(4-methoxyphenyl)ethanol hydrochloride (62c). $^1$H NMR (500 MHz, DMSO-$d_6$): δ 8.93 (s, 1H), 8.80 (d, J=8.5 Hz, 1H), 8.09 (s, 1H), 7.87 (d, J=9.0 Hz, 1H), 7.56 (d, J=9.0 Hz, 1H), 7.33 (d, J=8.5 Hz, 2H), 6.90 (s, 1H), 6.89 (d, J=8.5 Hz, 2H), 6.67 (d, J=8.5 Hz, 1H), 5.07-5.02 (m, 1H), 4.92 (t, J=11.5 Hz, 1H), 4.78 (d, J=50.0 Hz, 1H), 4.30-4.20 (m, 1H), 4.05-3.99 (m, 1H), 3.94-3.90 (m, 1H), 3.73-3.50 (m, 7H), 1.92-1.80 (m, 1H), 1.75-1.70 (m, 1H).

3-(Tetrahydro-pyran-4-ylamino)-isoquinoline-6-carboxylic acid [(R)-(3-fluoro-4-methoxy-phenyl)-(1-methyl-1H-pyrazol-3-yl)-methyl]-amide (II-50) was prepared analogously except in step 2, (S)-2-aminopropan-1-ol was replaced with 3-amino-tetrahydropyran and in step 5, 50c was replaced with (S)-(3-fluoro-4-methoxyphenyl)(1-methyl-1H-pyrazol-3-yl)methanamine hydrochloride (50d). $^1$H NMR (500 MHz, DMSO-$d_6$): δ 9.23 (d, J=8.5 Hz, 1H), 8.91 (s, 1H), 8.10 (s, 1H), 7.84 (d, J=8.0 Hz, 1H), 7.62 (d, J=2.0 Hz, 1H), 7.54 (dd, J=8.5, 1.5 Hz, 1H), 7.27 (d, J=12.5, 1.5 Hz, 1H), 7.20-7.10 (m, 2H), 6.54 (d, J=8.0 Hz, 1H), 6.32 (d, J=8.5 Hz, 1H), 6.20 (d, J=2.5 Hz, 1H), 3.91-3.88 (m, 2H), 3.82-3.80 (m, 7H), 3.46-3.42 (m, 2H), 1.93-1.90 (m, 2H), 1.50-1.48 (m, 2H).

3-((S)-2-Hydroxy-1-methyl-ethylamino)-isoquinoline-6-carboxylic acid [(R)-(3-fluoro-4-methoxy-phenyl)-(1-methyl-1H-pyrazol-3-yl)-methyl]-amide (II-51) was prepared analogously except in step 5, (S)-(3-fluoro-4-methoxy-phenyl)-(1-methylpyrazol-4-yl)methanamine hydrochloride was replaced with (S)-(3-fluoro-4-methoxyphenyl)(1-methyl-1H-pyrazol-3-yl)methanamine hydrochloride (50d). $^1$H NMR (500 MHz, MeOH-$d_4$): δ 8.86 (s, 1H), 8.06 (s, 1H), 7.87 (d, J=8.5 Hz, 1H), 7.58-7.56 (m, 2H), 7.18-7.10 (m, 2H), 7.09-7.06 (m, 1H), 6.81 (s, 1H), 6.41 (s, 1H), 6.20 (s, 1H), 3.93-3.87 (m, 7H), 3.68-3.65 (m, 2H), 1.30 (s, 3H).

3-(Tetrahydro-furan-3-ylamino)-isoquinoline-6-carboxylic acid [(3-fluoro-4-methoxy-phenyl)-(1-methyl-1H-pyrazol-3-yl)-methyl]-amide (II-52) was prepared analogously except in step 2, (S)-2-aminopropan-1-ol was replaced with 3-amino-tetrahydrofuran and in step 5, (S)-(3-fluoro-4-methoxy-phenyl)-(1-methylpyrazol-4-yl)methanamine hydrochloride was replaced with (S)-(3-fluoro-4-methoxyphenyl)(1-methyl-1H-pyrazol-3-yl)methanamine hydrochloride (50d). $^1$H NMR (500 MHz, DMSO-$d_6$): δ 9.26 (d, J=9.0 Hz, 1H), 8.93 (s, 1H), 8.28 (s, 0.4H), 8.12 (s, 1H), 7.86 (d, J=8.5 Hz, 1H), 7.63 (s, 1H), 7.62-7.55 (m, 1H), 7.47-7.25 (m, 1H), 7.18 (d, J=9.0 Hz, 1H), 7.14-7.10 (m, 1H), 6.82 (d, J=6.0 Hz, 1H), 6.70 (s, 1H), 6.32 (d, J=9.0 Hz, 1H), 6.20 (s, 1H), 4.31-4.29 (m, 1H), 3.95-3.92 (m, 1H), 3.88-3.72 (m, 8H), 3.61-3.58 (m, 1H), 2.50-2.20 (m, 1H), 1.84-1.76 (m, 1H).

3-((3S,4S)-3-Fluoro-tetrahydro-pyran-4-ylamino)-isoquinoline-6-carboxylic acid [(S)-1-(3-chloro-4-fluoro-phenyl)-2-hydroxy-ethyl]-amide (II-53) was prepared analogously except in step 2, (S)-2-aminopropan-1-ol was replaced with (3S,4S)-3-fluorotetrahydro-2H-pyran-4-amine (71c) and in step 5, 50c was replaced with (S)-2-amino-2-(3-chloro-4-fluoro-phenyl)ethanol hydrochloride (62f). $^1$H NMR (500 MHz, MeOH-$d_4$): δ 8.90 (s, 1H), 8.08 (s, 1H), 7.90 (d, J=8.5 Hz, 1H), 7.60-7.57 (m, 2H), 7.43-7.30 (m, 1H), 7.27-7.23 (m, 1H), 6.93 (s, 1H), 5.21-5.18 (m, 1H), 4.86-4.73 (m, 1H), 4.27-4.12 (m, 2H), 4.05-4.02 (m, 1H), 3.91-3.86 (m, 2H), 3.75-3.62 (m, 2H), 2.04-1.96 (m, 1H), 1.90-1.87 (m, 1H), 3-((3S,4S)-3-Fluoro-tetrahydro-pyran-4-ylamino)-isoquinoline-6-carboxylic acid [(S)-1-(4-chloro-3-fluoro-phenyl)-2-hydroxy-ethyl]-amide (II-54) was prepared analogously except in step 2, (S)-2-aminopropan-1-ol was replaced with (3S,4S)-3-fluorotetrahydro-2H-pyran-4-amine (71c) and in step 5, 50c was replaced with (S)-2-amino-2-(4-chloro-3-fluoro-phenyl)ethanol hydrochloride (62e). $^1$H NMR (500 MHz, MeOH-$d_4$): δ 8.90 (s, 1H), 8.09 (s, 1H), 7.92-7.88 (m, 1H), 7.61-7.59 (m, 1H), 7.47-7.45 (m, 1H), 7.38-7.33 (m, 1H), 7.28-7.24 (m, 1H), 6.91 (d, J=9.0 Hz, 1H), 5.21 (t, J=6.5 Hz, 1H), 4.84-4.73 (m, 1H), 4.27-4.11 (m, 2H), 4.05-4.02 (m, 1H), 3.92-3.80 (m, 2H), 3.75-3.60 (m, 2H), 2.06-1.96 (m, 1H), 1.93-1.88 (m, 1H).

3-((3S,4S)-3-Fluoro-tetrahydro-pyran-4-ylamino)-isoquinoline-6-carboxylic acid [(S)-1-(3-chloro-4-cyano-phenyl)-2-hydroxy-ethyl]-amide (II-55) was prepared analogously except in step 2, (S)-2-aminopropan-1-ol was replaced with (3S,4S)-3-fluorotetrahydro-2H-pyran-4-amine (71c) and in step 5, 50c was replaced with 62i. $^1$H NMR (500 MHz, MeOD-$d_4$): δ 8.79 (s, 1H), 7.98 (s, 1H), 7.79 (d, J=8.5 Hz, 1H), 7.70 (d, J=8.5 Hz, 1H), 7.62 (s, 1H), 7.49-7.45 (m, 2H), 7.81 (s, 1H), 5.12 (t, J=5.5 Hz, 1H), 4.71-4.61 (m, 1H), 4.16-4.00 (m, 2H), 3.94-3.90 (m, 1H), 3.80-3.79 (m, 2H), 3.64-3.52 (m, 2H), 1.92-1.85 (m, 1H), 1.77-1.73 (m, 1H).

3-(Tetrahydro-furan-3-ylamino)-isoquinoline-6-carboxylic acid [1-(4-difluoromethoxy-phenyl)-2-hydroxy-ethyl]-amide (II-56) was prepared analogously except in step 2, 50c was replaced with 3-amino-tetrahydrofuran and in step 5, 50c was replaced with (S)-2-amino-2-(4-(trifluoromethoxy)phenyl)ethanol hydrochloride (62h).

3-((S)-2-Hydroxy-1-methyl-ethylamino)-isoquinoline-6-carboxylic acid [(S)-1-(4-difluoromethoxy-phenyl)-2-hydroxy-ethyl]-amide (II-58) was prepared analogously except in step 5, 58c was replaced with (S)-2-amino-2-(4-(trifluoromethoxy)phenyl)ethanol hydrochloride (62b). $^1$H NMR (500 MHz, MeOH-$d_4$): δ 8.84 (s, 1H), 8.07 (s, 1H), 7.86 (d, J=8.5 Hz, 1H), 7.57 (d, J=8.0 Hz, 1H), 7.49 (d, J=8.5 Hz, 2H), 7.15 (d, J=8.0 Hz, 2H), 6.82-6.79 (m, 2H), 5.26-5.22 (m, 1H), 3.93-3.89 (m, 3H), 3.68-3.59 (m, 2H), 1.24 (d, J=6.5 Hz, 3H).

3-((3S,4S)-3-Fluoro-tetrahydro-pyran-4-ylamino)-isoquinoline-6-carboxylic acid [(S)-(3-chloro-4-cyano-phenyl)-(1-methyl-1H-pyrazol-4-yl)-methyl]-amide (II-59) was prepared analogously except in step 2, (S)-2-aminopropan-1-ol was replaced with (3S,4S)-3-fluorotetrahydro-2H-pyran-4-amine (71c) and in step 5, 50c was replaced with (S)-4-(amino(1-methyl-1H-pyrazol-4-yl)methyl)-2-chlorobenzonitrile hydrochloride (44). $^1$H NMR (500 MHz, DMSO-$d_6$) δ 9.39 (d, J=8.0 Hz, 1H), 8.94 (s, 1H), 8.11 (s, 1H), 7.99 (d, J=8.5 Hz, 1H), 7.87 (d, J=9.0 Hz, 1H), 7.81 (s, 1H), 7.63-7.55 (m, 3H), 7.41 (s, 1H), 6.89 (s, 1H), 6.69 (d, J=8.0 Hz, 1H), 6.38 (d, J=8.0 Hz, 1H), 4.78 (d, J=49.5 Hz, 1H), 4.25-4.19 (m, 1H), 4.01 (t, J=13.0 Hz, 1H), 3.93-3.90 (m, 1H), 3.79 (s, 3H), 3.67-3.49 (m, 3H), 1.91-1.83 (m, 1H), 1.73-1.70 (m, 1H); LCMS (ESI) m/z: 519.2 [M+H]$^+$.

3-(Tetrahydro-pyran-4-ylamino)-isoquinoline-6-carboxylic acid [(S)-1-(4-difluoromethoxy-phenyl)-2-hydroxy-ethyl]-amide (II-61) was prepared analogously except in step 2, (S)-2-aminopropan-1-ol was replaced with 4-amino-tetrahydropyran and in step 5, (S)-(3-fluoro-4-methoxy-phenyl)-(1-methylpyrazol-4-yl)methanamine hydrochloride was replaced with (S)-2-amino-2-(4-difluoromethoxy-phenyl)ethanol (62h).

3-((3S,4S)-3-Fluoro-tetrahydro-pyran-4-ylamino)-isoquinoline-6-carboxylic acid (4-fluoro-1H-indol-2-ylmethyl)-amide (II-67) was prepared analogously except in step 2, 71c replaced (S)-2-aminopropan-1-ol and in step 5, 38 replaced 50c $^1$H NMR (500 MHz, DMSO-$d_6$) δ 11.33 (s, 1H), 9.18 (t, J=5.5 Hz, 1H), 8.94 (s, 1H), 8.11 (s, 1H), 7.89 (d, J=8.5 Hz, 1H), 7.60 (d, J=10.5 Hz, 1H), 7.19 (d, J=8.5 Hz, 1H), 7.02-6.98 (m, 1H), 6.89 (s, 1H), 6.75-6.69 (m, 2H), 6.38 (s, 1H), 4.78 (d, J=49.5 Hz, 1H), 4.66-4.65 (m, 2H), 4.27-4.21 (m, 1H), 4.03-3.90 (m, 2H), 3.67-3.49 (m, 2H), 1.91-1.81 (m, 1H), 1.73-1.70 (m, 1H); LCMS (ESI) m/z: 437.2 [M+H]$^+$.

3-((3S,4S)-3-Fluoro-tetrahydro-pyran-4-ylamino)-isoquinoline-6-carboxylic acid [(S)-(3-fluoro-4-methoxy-phenyl)-(1-methyl-1H-pyrazol-4-yl)-methyl]-amide (II-68) was prepared analogously except in step 2, 71c replaced (S)-2-aminopropan-1-ol. $^1$H NMR (500 MHz, DMSO-$d_6$) δ 9.25 (d, J=8.5 Hz, 1H), 8.93 (s, 1H), 8.09 (s, 1H), 7.86 (d, J=8.5 Hz, 1H), 7.57-7.53 (m, 2H), 7.33 (s, 1H), 7.28 (d, J=12.5 Hz, 1H), 7.20 (d, J=10 Hz, 1H), 7.19-7.12 (m, 1H), 6.88 (s, 1H), 6.67 (d, J=8.5 Hz, 1H), 6.26 (d, J=8.5 Hz, 1H), 4.78 (d, J=49.5 Hz, 1H), 4.25-4.19 (m, 1H), 4.01 (t, J=12 Hz, 1H), 3.93-3.90 (m, 1H), 3.67 (s, 3H), 3.64 (s, 3H), 3.59-3.49 (m, 2H), 1.91-1.83 (m, 1H), 1.73-1.70 (m, 1H); LCMS (ESI) m/z: 568.3 [M+H]$^+$.

Example 6

(S)-3-(1,3-Dimethyl-1H-pyrazol-5-ylamino)-N-(1-(3-fluoro-4-methoxyphenyl)-2-hydroxyethyl)isoquinoline-6-carboxamide (II-44)

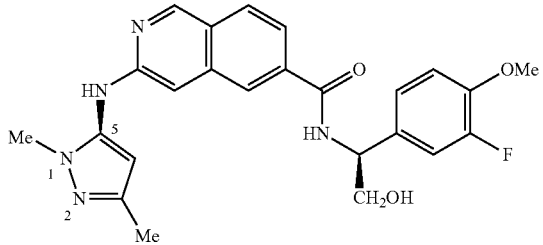

Step 1:

An oven dried 100 mL round bottomed flask equipped with a stirring bar was cooled under nitrogen and charged with 1,3-dimethyl-1H pyrazol-5-amine (491.7 mg, 4.42 mmol) and 45 mL of anhydrous THF (0.1M). The THF solution was treated with solid LiHMDS (1.481 g, 8.84 mmol) and stirred at RT for 5 min after which yellow solids formed. C-2 (500 mg, 2.21 mmol) was added in one portion. The flask was equipped with a reflux condenser, and the reaction mixture heated to 80° C. The reaction was monitored by LCMS and was 90% complete after 2 h at 80° C. The reaction mixture was cooled to RT, and the THF removed on a rotary evaporator. The crude residue was partitioned between DCM and water. The DCM layer was washed with brine, dried ($MgSO_4$) filtered and concentrated. The crude residue was absorbed onto Celite® and purified by $SiO_2$ chromatography eluting with an EtOAc/heptane gradient (50 to 100% EtOAc) to afford 328 mg (47%) of 6-bromo-N-(1,3 dimethyl-1H pyrazol-5-yl)-isoquinolin-3-amine (82).

Step 2:

Carbonylation of 82 (429 mg) was carbonylated using the procedure described in step 3 of Example 5 to afford 350 mg (87%) of methyl 3-(1,3-dimethyl-1H-pyrazol-5-ylamino) isoquinoline-6-carboxylate (84) as a yellow/brown solid, which was used in the next step without further purification.

Step 3:

A slurry of 84 (350 mg, 1.181 mmol) and LiOH (62.2 mg, 2.60 mmol) in THF (5.75 mL) and water (0.85 mL) was stirred at RT for 24 h. The THF was removed on a rotary evaporator. The reaction mixture was suspended in water (6 mL) and treated with 10M HCl in water (0.71 mL, 7.1 mmol). A yellow-brown colored precipitate formed and was collected by filtration to afford 3-(1,3-dimethyl-1H-pyrazol-5-ylamino)isoquinoline-6-carboxylic acid (86) which was used in the next step without further purification.

Step 4:

A 10 mL microwave tube was charged with 86 (29.7 mg, 0.105 mmol, 62d (15 mg, 0.081) and DMF (1.0 mL) and treated with HATU (47.6 mg, 0.121 mmol). The reaction mixture was stirred at RT for 30 min to pre-activate, then treated with TEA (0.046 mL, 0.324 mmol). The reaction mixture was filtered and then purified by preparative reverse phase HPLC chromatography (Varian HPLC using Gemini-NX C-18 (3.0×100 cm, 10 μm) at 60 mL/min, $NH_4OH$ 5-50% MeCN in 10 min) to afford 22.1 mg (60.7%) of II-45 as a yellow solid. $^1H$ NMR (400 MHz, DMSO) δ 9.06 (s, 1H), 8.86-8.69 (m, 2H), 8.24 (s, 1H), 7.99 (d, J=8.6 Hz, 1H), 7.69 (d, J=8.5 Hz, 1H), 7.33-7.22 (m, 1H), 7.14 (dt, J=17.2, 8.6 Hz, 2H), 6.93 (s, 1H), 6.03 (s, 1H), 5.04 (dd, J=13.8, 7.8 Hz, 1H), 4.94 (t, J=5.8 Hz, 1H), 3.81 (s, 3H), 3.75-3.61 (m, 2H), 3.61 (s, 3H), 2.15 (s, 3H). LCMS: $MH^+$ 450.2.

(S)-3-(1,3-Dimethyl-1H-pyrazol-5-ylamino)-N-((3-fluoro-4-methoxyphenyl)(1-methyl-1H-pyrazol-4-yl)methyl)isoquinoline-6-carboxamide (II-37) was prepared analogously except in step 4, 62d was replaced with (S)-(3-fluoro-4-methoxyphenyl)(1-methyl-1H-pyrazol-4-yl)methanamine hydrochloride (50c). $^1H$ NMR (400 MHz, DMSO-$d_6$) δ 9.20 (d, J=8.5 Hz, 1H), 9.05 (s, 1H), 8.78 (s, 1H), 8.24 (s, 1H), 7.98 (d, J=8.6 Hz, 1H), 7.70 (d, J=8.5 Hz, 1H), 7.53 (s, 1H), 7.32 (s, 1H), 7.30-7.23 (m, 1H), 7.16 (dt, J=17.2, 8.6 Hz, 2H), 6.92 (s, 1H), 6.26 (d, J=8.4 Hz, 1H), 6.02 (s, 1H), 3.80 (d, J=13.3 Hz, 6H), 3.60 (s, 3H), 2.14 (s, 3H).

(S)—N-(1-(4-Chloro-3-fluorophenyl)-2-hydroxyethyl)-3-(1,3-dimethyl-1H-pyrazol-5-ylamino)isoquinoline-6-carboxamide (II-45) was prepared analogously except in step 4, 62d was replaced with (S)-2-amino-2-(4-chloro-3-fluorophenyl)ethanol hydrochloride (62e). $^1H$ NMR (400 MHz, DMSO) δ 9.06 (s, 1H), 8.85 (d, J=8.0 Hz, 1H), 8.80 (s, 1H), 8.26 (s, 1H), 7.99 (d, J=8.5 Hz, 1H), 7.69 (d, J=8.5 Hz, 1H), 7.55 (t, J=8.0 Hz, 1H), 7.47 (d, J=10.6 Hz, 1H), 7.29 (d, J=8.3 Hz, 1H), 6.94 (s, 1H), 6.03 (s, 1H), 5.10 (dd, J=13.8, 7.2 Hz, 1H), 5.03 (t, J=5.8 Hz, 1H), 3.78-3.63 (m, 2H), 3.61 (s, 3H), 2.15 (s, 3H).

(R)—N-(1-(4-Chloro-3-fluorophenyl)propyl)-3-(1,3-dimethyl-1H-pyrazol-5-ylamino)isoquinoline-6-carboxamide (II-46) was prepared analogously except in step 4, 62 was replaced with (R)-1-(4-chloro-3-fluoro-phenyl)propan-1-amine hydrochloride (70b). $^1H$ NMR (400 MHz, DMSO) δ 9.06 (s, 1H), 8.89 (d, J=8.2 Hz, 1H), 8.79 (s, 1H), 8.21 (s, 1H), 7.99 (d, J=8.6 Hz, 1H), 7.67 (d, J=8.5 Hz, 1H), 7.55 (t, J=8.0 Hz, 1H), 7.49-7.40 (m, 1H), 7.28 (d, J=8.3 Hz, 1H), 6.94 (s, 1H), 6.03 (s, 1H), 4.95 (dd, J=14.8, 8.3 Hz, 1H), 3.61 (s, 3H), 2.15 (s, 3H), 1.82 (m, J=20.8, 13.8, 6.7 Hz, 2H), 0.92 (t, J=7.3 Hz, 3H).

(S)—N-((4-Chloro-3-fluorophenyl)(1-methyl-1H-pyrazol-4-yl)methyl)-3-(1,3-dimethyl-1H-pyrazol-5-ylamino)isoquinoline-6-carboxamide (II-48) was prepared analogously except in step 4, 62 was replaced with (S)-(4-chloro-3-fluorophenyl)(1-methyl-1H-pyrazol-4-yl)methanamine hydrochloride (50a). $^1H$ NMR (400 MHz, DMSO-$d_6$) δ 9.28 (d, J=8.3 Hz, 1H), 9.06 (s, 1H), 8.79 (s, 1H), 8.26 (s, 1H), 7.98 (d, J=8.6 Hz, 1H), 7.69 (d, J=8.5 Hz, 1H), 7.63-7.53 (m, 2H), 7.47 (d, J=10.6 Hz, 1H), 7.36 (s, 1H), 7.31 (d, J=8.3 Hz, 1H), 6.93 (s, 1H), 6.31 (d, J=8.2 Hz, 1H), 6.02 (s, 1H), 3.79 (s, 3H), 3.60 (s, 3H), 2.14 (s, 3H).

Example 7

(S)—N-(1-(3-Fluoro-4-methoxyphenyl)-2-hydroxyethyl)-3-(1-methyl-1H-pyrazol-5-ylamino)isoquinoline-6-carboxamide (II-36)

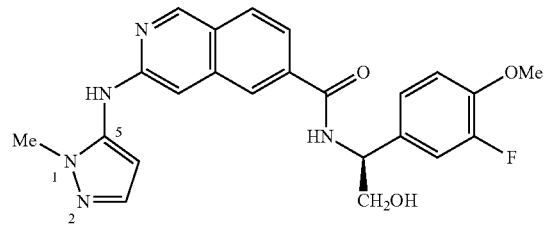 [SMILES: COc1ccc([C@@H](CO)NC(=O)c2ccc3cnc(Nc4ccnn4C)cc3c2)cc1F]

Step 1:

The carbonylation of C-2 (500 mg, 2.12 mmol) was carried out using the procedure described in step 3 of example 5 to afford 413 mg (91%) of methyl 3-fluoroisoquinoline-6-carboxylate (88) as a white solid, which was used in the next step without further purification.

Step 2:

A slurry of 88 (413 mg, 2.013 mmol) and LiOH (56 mg, 2.34 mmol) in THF (9.8 mL) and water (1.5 mL) was stirred at RT for 1.5 h. An additional 50 mg of LiOH was added (total: 106 mg, 4.43 mmol), and the reaction was stirred for an additional 2 h. The THF was removed on a rotary evaporator. The reaction mixture was suspended in water (10 mL) and treated with 10M HCl in water (0.604 mL, 6.04 mmol). A white cloudy precipitate was collected by vacuum filtration. The precipitate was washed with water (2×2 mL) and dried under house vacuum over night to afford 349 mg (100%) of 3-fluoroisoquinoline-6-carboxylic acid (90) as a white solid, which was used in the next step without further purification.

Step 3:

Under an atmosphere of nitrogen 1-methyl-1H-pyrazol-5-amine (284.5 mg, 2.93 mmol) was dissolved in THF (17.8 mL) at RT and treated with 1.0M LiHMDS in THF (5.86 mL, 5.86 mmol). The reaction was stirred vigorously for 10 min, and then 90 (280 mg, 1.4647 mmol) was added as a solid in one portion. The 100 mL round bottom reaction flask was equipped with a water cooled condenser and heated to 80° C. The reaction was 30% complete after 3.5 h, so additional 1.0M LiHMDS was added (8.86 mL, total: 14.72 mL, 14.72 mmol), and the reaction heated at 80° C. for another 2.5 hours (total time at 80° C.=6 h). The reaction mixture was diluted with water (20 mL), transferred to a separatory funnel and washed with DCM (4×30 mL). The DCM washings were combined, and the aqueous layer was neutralized via the addition 1.26 mL of 11.6 M aqueous HCl. The resulting precipitate was collected via vacuum filtration to afford 373 mg (94%) of 3-(1-methyl-1H-pyrazol-5-ylamino)isoquinoline-6-carboxylic acid (92), which was used without any further purification.

Step 4:

(S)—N-(1-(3-Fluoro-4-methoxyphenyl)-2-hydroxyethyl)-3-(1-methyl-1H-pyrazol-5-ylamino)isoquinoline-6-carboxamide was prepared from 92 (15 mg, 0.081 mmol 1.0 equiv) via a HATU mediated coupling as described step 4 of Example 7 using (S)-2-amino-(3-fluoro-4-methoxyphenyl)ethanol hydrochloride (62d) as the amine component to afford 8.3 mg (24%) of II-37 as a yellow solid. $^1$H NMR (400 MHz, DMSO) δ 9.07 (s, 1H), 8.84 (s, 1H), 8.23 (s, 1H), 8.00 (d, J=8.6 Hz, 1H), 7.70 (d, J=8.5 Hz, 1H), 7.53 (s, 2H), 7.42 (d, J=1.7 Hz, 1H), 7.26 (d, J=12.7 Hz, 1H), 7.17 (d, J=8.6 Hz, 1H), 6.94 (s, 1H), 6.24 (d, J=1.7 Hz, 1H), 5.04 (dd, J=13.8, 7.7 Hz, 2H), 3.81 (s, 3H), 3.73 (s, 3H), 3.66 (m, 2H). LCMS: MH+ 436.1.

(R)—N-(1-(4-Chloro-3-fluorophenyl)propyl)-3-(1-methyl-1H-pyrazol-5-ylamino)isoquinoline-6-carboxamide (II-13) was prepared analogously except in step 4, 62d was replaced with (R)-1-(4-chloro-3-fluoro-phenyl)propan-1-amine hydrochloride (70b). $^1$H NMR (400 MHz, DMSO) δ 9.07 (s, 1H), 8.89 (d, J=8.1 Hz, 1H), 8.83 (s, 1H), 8.20 (s, 1H), 7.99 (d, J=8.6 Hz, 1H), 7.67 (dd, J=8.5, 1.5 Hz, 1H), 7.54 (t, J=8.1 Hz, 1H), 7.50-7.36 (m, 2H), 7.28 (dd, J=8.3, 1.8 Hz, 1H), 6.94 (s, 1H), 6.23 (d, J=1.9 Hz, 1H), 4.95 (dd, J=14.8, 8.4 Hz, 1H), 3.69 (s, 3H), 1.83 (m, J=20.7, 13.7, 6.9 Hz, 2H), 0.92 (t, J=7.3 Hz, 3H).

(S)—N-(1-(4-Chloro-3-fluorophenyl)-2-hydroxyethyl)-3-(1-methyl-1H-pyrazol-5-ylamino)isoquinoline-6-carboxamide (II-14) was prepared analogously except in step 4, 62 was replaced with (S)-2-amino-2-(4-chloro-3-fluoro-phenyl)ethanol hydrochloride (62e). $^1$H NMR (400 MHz, DMSO) δ 9.07 (s, 1H), 8.83 (d, J=4.1 Hz, 2H), 8.23 (d, J=12.1 Hz, 1H), 8.00 (d, J=8.6 Hz, 1H), 7.70 (dd, J=8.5, 1.4 Hz, 1H), 7.54 (t, J=8.0 Hz, 1H), 7.51-7.38 (m, 2H), 7.29 (dd, J=8.3, 1.7 Hz, 1H), 6.94 (s, 1H), 6.24 (d, J=1.9 Hz, 1H), 5.14-4.97 (m, 2H), 3.69 (s, 3H), 3.82-3.60 (m, 2H).

(S)—N-((4-Chloro-3-fluorophenyl)(1-methyl-1H-pyrazol-4-yl)methyl)-3-(1-methyl-1H-pyrazol-5-ylamino)isoquinoline-6-carboxamide (II-15) was prepared analogously except in step 4, 62 was replaced with (S)-(4-chloro-3-fluorophenyl)(1-methyl-1H-pyrazol-4-yl)methanamine hydrochloride (50a). $^1$H NMR (400 MHz, DMSO) δ 9.27 (d, J=8.2 Hz, 1H), 9.07 (s, 1H), 8.83 (s, 1H), 8.25 (s, 1H), 7.99 (d, J=8.6 Hz, 1H), 7.70 (dd, J=8.6, 1.5 Hz, 1H), 7.62-7.52 (m, 2H), 7.47 (dd, J=0.6, 1.9 Hz, 1H), 7.41 (d, J=1.9 Hz, 1H), 7.36 (s, 1H), 7.31 (dd, J=8.3, 1.8 Hz, 1H), 6.93 (s, 1H), 6.31 (d, J=8.3 Hz, 1H), 6.23 (d, J=1.9 Hz, 1H), 3.79 (s, 3H), 3.69 (s, 3H).

(S)—N-((3-Fluoro-4-methoxyphenyl)(1-methyl-1H-pyrazol-4-yl)methyl)-3-(1-methyl-1H-pyrazol-5-ylamino)isoquinoline-6-carboxamide (II-16) was prepared analogously except in step 4, 62 was replaced with (S)-(3-fluoro-4-methoxyphenyl)(1-methyl-1H-pyrazol-4-yl)methanamine hydrochloride (50c). $^1$H NMR (400 MHz, DMSO) 9.20 (d, J=8.5 Hz, 1H), 9.06 (s, 1H), 8.82 (s, 1H), 8.23 (s, 1H), 7.99 (d, J=8.6 Hz, 1H), 7.70 (dd, J=8.6, 1.4 Hz, 1H), 7.53 (s, 1H), 7.41 (d, J=1.9 Hz, 1H), 7.32 (s, 1H), 7.27 (dd, J=12.6, 2.0, 1H), 7.27-7.17 (m, 1H), 7.13 (t, J=8.6 Hz, 1H), 6.93 (s, 1H), 6.24 (dd, J=11.5, 5.2 Hz, 2H), 3.82 (s, 3H), 3.79 (s, 3H), 2.49 (s, 3H).

(R)—N-(1-(3-Chloro-4-fluorophenyl)propyl)-3-(1-methyl-1H-pyrazol-5-ylamino)isoquinoline-6-carboxamide (II-15) was prepared analogously except in step 4, 62 was replaced with (R)-1-(3-chloro-4-fluoro-phenyl)propan-1-amine hydrochloride (70c). $^1$H NMR (400 MHz, DMSO) 9.07 (s, 1H), 8.88 (d, J=8.2 Hz, 1H), 8.83 (s, 1H), 8.19 (s, 1H), 7.99 (d, J=8.6 Hz, 1H), 7.67 (dd, J=8.6, 1.4 Hz, 1H), 7.64 (dd, J=7.2, 2.0 Hz, 1H), 7.45-7.33 (m, 3H), 6.94 (s, 1H), 6.24 (d, J=1.9 Hz, 1H), 4.94 (dd, J=14.9, 8.4 Hz, 1H), 3.69 (s, 3H), 1.83 (m, 2H), 0.91 (t, J=7.3 Hz, 3H).

Example 8

(S)—N-(1-(4-Chloro-3-fluorophenyl)-2-hydroxyethyl)-3-(2-methylpyridin-4-ylamino)isoquinoline-6-carboxamide Step 1:

A dry 40 mL scintillation vial equipped with a screw cap with a teflon insert was cooled under nitrogen, equipped with a stir bar and charged with 2-methylpyridine-4-amine (263 mg, 3.32 mmol) and anhydrous THF (27 mL) and maintained under a N$_2$ atmosphere. LiHMDS was added as a solid (0.925 g, 5.53 mmol). The reaction mixture was stirred at RT under nitrogen for 5 min. To the mixture was added 6-bromo-3-fluoro isoquinoline (500 mg, 2.21 mmol), the vial was flushed with N$_2$, tightly capped and placed in a pre-heated oil bath at 85° C. After 4 h at 85° C., additional 2-methylpyridine-4-amine (96 mg, total: 359 mg, 3.32 mmol) and LiHMDSi (185 mg, total: 1.11 g, 6.64 mmol) were added, and the reaction was heated an additional 2 h at 85° C. The reaction was cooled, and the THF was removed in vacuo. The crude reaction mixture was partitioned between water and DCM containing 10% MeOH. The organic layer was washed with brine, dried (Na$_2$SO$_4$), filtered and concentrated. The crude residue was absorbed onto Celite® and purified by SiO$_2$ chromatography eluting with a MeOH/DCM gradient (0 to 10% MeOH) to afford 196 mg (28%) of 6-bromo-N-(2-methylpyridin-4-yl)isoquinolin-3-amine (94) as a yellow solid, which was used in the next step without further purification.

Step 2:

Carbonylation of 94 (196 mg, 0.624 mmol) was carried out using the procedure described in step 3 of example 5 to afford 132 mg (72%) of methyl 3-(2-methylpyridin-4-ylamino)isoquinoline-6-carboxylate (96) as a yellow solid, which was used in the next step without further purification.

Step 3:

A slurry of 96 (132 mg, 0.45 mmol) in THF (2.19 mL) and water (0.324 mL) was treated with solid LiOH (24 mg, 0.99 mmol) and stirred for 3 h. THF was removed in vacuo, and the mixture was suspended in water (6.0 mL) and treated with aqueous HCl (10 M, 0.27 mL). A yellow-brown precipitate was collected by vacuum filtration to afford 3-(2-methylpyridin-4-ylamino)isoquinoline-6-carboxylic acid (98) as a yellow solid, which was used in subsequent steps without further purification.

Step 4:

(S)—N-(1-(4-Chloro-3-fluorophenyl)-2-hydroxyethyl)-3-(2-methylpyridin-4-ylamino)isoquinoline-6-carboxamide was prepared from 92 (15 mg, 0.081 mmol 1.0 equiv) via a HATU mediated coupling as described step 4 of Example 6 using (S)-2-amino-(4-chloro-3-fluoro-phenyl)ethanol hydrochloride (62e). The crude product from the coupling reaction and desilylation was purified by preparative reverse phase HPLC chromatography (Waters Mass-Directed HPLC using Gemini-NX C-18 (3.0×100 cm, 10 μm at 60 mL/min NH$_4$OH 20-60% MeCN in 10 min) to afford II-48 as a yellow solid (54 mg, 32%). $^1$H NMR (400 MHz, DMSO) δ 9.59 (s, 1H), 9.21 (s, 1H), 8.95 (d, J=7.9 Hz, 1H), 8.34 (s, 1H), 8.22-8.13 (m, 2H), 8.08 (d, J=8.6 Hz, 1H), 7.81 (d, J=8.5 Hz, 1H), 7.56 (t, J=8.1 Hz, 1H), 7.49 (d, J=10.6 Hz, 1H), 7.44-7.34 (m, 3H), 7.31 (d, J=8.3 Hz, 1H), 5.15-5.07 (m, 1H), 3.77-3.66 (m, 2H), 2.40 (s, 3H). LCMS [M+H]$^+$=451.1.

3-(2-Methyl-pyridin-4-ylamino)-isoquinoline-6-carboxylic acid [(S)-(3-fluoro-4-methoxy-phenyl)-(1-methyl-1H-pyrazol-4-yl)-methyl]-amide (II-33) was prepared analogously except 62e was replaced with (S)-(3-fluoro-4-methoxyphenyl)(1-methyl-1H-pyrazol-4-yl)methanamine hydrochloride (50c) in the coupling reaction. $^1$H NMR (400 MHz, DMSO-d$_6$) δ 9.56 (s, 1H), 9.30 (d, J=8.5 Hz, 1H), 9.20 (s, 1H), 8.33 (s, 1H), 8.18 (d, J=5.6 Hz, 1H), 8.06 (d, J=8.6 Hz, 1H), 7.80 (d, J=8.5 Hz, 1H), 7.55 (s, 1H), 7.42-7.33 (m, 4H), 7.29 (d, J=14.3 Hz, 1H), 7.22 (d, J=8.7 Hz, 1H), 7.14 (t, J=8.6 Hz, 1H), 6.28 (d, J=8.4 Hz, 1H), 3.81 (d, J=12.1 Hz, 6H), 2.39 (s, 3H).

3-(2-Methyl-pyridin-4-ylamino)-isoquinoline-6-carboxylic acid [(S)-(4-chloro-3-fluoro-phenyl)-(1-methyl-1H-pyrazol-4-yl)-methyl]-amide (II-34) was prepared analogously except 62e was replaced with (S)-(4-chloro-3-fluoro-phenyl)-(1-methyl-1H-pyrazol-4-yl)-methanamine hydrochloride (50a) in the coupling reaction. $^1$H NMR (400 MHz, DMSO) δ 9.57 (s, 1H), 9.38 (d, J=8.3 Hz, 1H), 9.20 (s, 1H), 8.35 (s, 1H), 8.18 (d, J=5.6 Hz, 1H), 8.08 (t, J=8.7 Hz, 1H), 7.80 (d, J=8.6 Hz, 1H), 7.63-7.53 (m, 2H), 7.50 (d, J=9.3 Hz, 1H), 7.43-7.29 (m, 5H), 6.34 (d, J=8.3 Hz, 1H), 3.80 (s, 3H), 2.39 (s, 3H).

3-(2-Methyl-pyridin-4-ylamino)-isoquinoline-6-carboxylic acid [(R)-1-(3-chloro-4-fluoro-phenyl)-propyl]-amide (II-35) was prepared analogously except 62e was replaced with (R)-1-(3-chloro-4-fluoro-phenyl)propan-1-amine hydrochloride (70c) in the coupling reaction. $^1$H NMR (400 MHz, DMSO) δ 9.56 (s, 1H), 9.20 (s, 1H), 8.98 (d, J=8.2 Hz, 1H), 8.29 (s, 1H), 8.18 (d, J=5.6 Hz, 1H), 8.07 (d, J=8.6 Hz, 1H), 7.78 (d, J=8.6 Hz, 1H), 7.65 (dd, J=7.2, 1.9 Hz, 1H), 7.42 (m, J=14.1, 8.8, 5.0 Hz, 5H), 4.96 (dd, J=14.9, 8.3 Hz, 1H), 2.40 (s, 3H), 1.86 (m, J=27.7, 13.9, 7.1 Hz, 2H), 0.93 (t, J=7.3 Hz, 3H).

Example 9

N-((5-Benzylpyridin-3-yl)methyl)-7-(tetrahydro-2H-pyran-4-ylamino)-1,6-naphthyridine-2-carboxamide (I-20)

Step 1:

N-((5-Bromopyridin-3-yl)methyl)-7-(tetrahydro-2H-pyran-4-ylamino)-1,6-naphthyridine-2-carboxamide (100) can be prepared in accord with the procedure in Example 1 using (5-bromopyridin-3-yl)methanamine in place of 50c. The product was in the next step without further purification.

Step 2:

A mixture of 100 (70 mg, 0.158 mmol), benzylzinc bromide (0.5 mol/L) in THF (0.9 mL, 0.475 mmol) and bis(di-tert-butyl(4-dimethylaminophenyl)phosphine)dichloropalladium(II) (11.2 mg, 0.0158 mmol) was heated at 80° C. for 3 h. The reaction mixture was diluted with EtOAc (50 mL) and washed with water (50 mL). The organic layer was separated, dried (Na$_2$SO$_4$), filtered and concentrated in vacuo to provide a residue that was purified by reverse phase HPLC chromatography eluting with a MeCN/H$_2$O gradient (containing 0.1% NH$_4$OH, 14 minutes) to afford 17.4 mg (24%) of I-20 as a yellow solid. $^1$H NMR (400 MHz, DMSO) δ 9.42 (t, J=6.3 Hz, 1H), 9.01 (s, 1H), 8.41 (d, J=2.0 Hz, 1H), 8.38 (s, 1H), 8.37 (d, J=5.3 Hz, 1H), 7.73 (d, J=8.3 Hz, 1H), 7.60 (s, 1H), 7.30-7.15 (m, 5H), 7.01 (d, J=7.8 Hz, 1H), 6.74 (s, 1H), 4.50 (d, J=6.2 Hz, 2H), 3.96 (s, 2H), 3.94-3.87 (m, 2H), 3.86 (s, 1H), 3.44 (td, J=11.5, 1.9 Hz, 2H), 1.92 (d, J=12.5 Hz, 2H), 1.59-1.46 (m, 2H). LCMS (Method E): R$_T$=3.58 min, [M+H]$^+$=454.2.

N-((4-Benzylpyridin-2-yl)methyl)-7-(tetrahydro-2H-pyran-4-ylamino)-1,6-naphthyridine-2-carboxamide (I-36) was as prepared analogously except in step 1, (5-bromopyridin-3-yl)methanamine was replaced with (4-bromopyridin-2-yl)methanamine. $^1$H NMR (400 MHz, DMSO) δ 9.33 (t, J=5.9 Hz, 1H), 9.03 (s, 1H), 8.42 (d, J=5.1 Hz, 1H), 8.39 (d, J=8.3 Hz, 1H), 7.75 (d, J=8.3 Hz, 1H), 7.30-7.15 (m, 5H), 7.13 (d, J=5.0 Hz, 1H), 7.00 (d, J=7.8 Hz, 1H), 6.77 (s, 1H), 4.61 (d, J=6.0 Hz, 2H), 3.95 (s, 2H), 3.91 (m, 3H), 3.45 (t, J=10.9 Hz, 2H), 1.93 (d, J=12.6 Hz, 2H), 1.53 (td, J=15.4, 4.2 Hz, 2H).

N-(3-Benzylbenzyl)-7-(tetrahydro-2H-pyran-4-ylamino)-1,6-naphthyridine-2-carboxamide (I-42) was prepared analogously except in step 1,3-bromo-benzylamine in place of 50i. $^1$H NMR (400 MHz, DMSO) δ 9.33 (t, J=6.4 Hz, 1H), 9.02 (s, 1H), 8.38 (d, J=8.3 Hz, 1H), 7.75 (d, J=8.3 Hz, 1H), 7.29-7.01 (m, 10H), 6.74 (s, 1H), 4.49 (d, J=6.3 Hz, 2H), 3.90 (d, J=12.7 Hz, 4H), 3.87-3.79 (m, 1H), 3.44 (t, J=11.1 Hz, 2H), 1.92 (d, J=12.5 Hz, 2H), 1.52 (ddd, J=15.2, 12.0, 4.2 Hz, 2H).

N-((2-Benzylpyridin-3-yl)methyl)-7-(tetrahydro-2H-pyran-4-ylamino)-1,6-naphthyridine-2-carboxamide (I-54) was prepared analogously except in step 1, (5-bromopyridin-3-yl)methanamine was replaced with (2-bromopyridin-3-yl)methanamine. $^1$H NMR (400 MHz, DMSO-d$_6$) δ 9.34 (t, J=6.2 Hz, 1H), 9.02 (s, 1H), 8.43 (d, J=4.8 Hz, 1H), 8.38 (d, J=8.3 Hz, 1H), 7.73 (d, J=8.3 Hz, 1H), 7.67 (d, J=7.7 Hz, 1H), 7.30-7.21 (m, 5H), 7.16 (m, 1H), 7.05 (d, J=7.8 Hz, 1H), 6.74 (s, 1H), 4.56 (d, J=6.2 Hz, 2H), 4.27 (s, 2H), 3.90 (d, J=11.7 Hz, 2H), 3.87-3.79 (m, 1H), 3.44 (t, J=11.3 Hz, 2H), 1.92 (d, J=13.2 Hz, 2H), 1.52 (m, 2H).

Example 10

7-(Tetrahydro-pyran-4-ylamino)-[1,6]naphthyridine-2-carboxylic acid [2-(3-bromo-phenyl)-ethyl]-amide (I-35) and N-(3-(1-methyl-1H-pyrazol-4-yl)phenethyl)-7-(tetrahydro-2H-pyran-4-ylamino)-1,6-naphthyridine-2-carboxamide (I-41)

Step 1:

N-[2-(3-Bromophenyl)ethyl]-7-(tetrahydropyran-4-ylamino)-1,6-naphthyridine-2-carboxamide (I-35) was prepared as described in Example 1 using 2-(3-bromophenyl)ethanamine in place of 50c. $^1$H NMR (400 MHz, DMSO-d$_6$) δ 9.01 (s, 1H), 8.87 (t, J=5.9 Hz, 1H), 8.37 (d, J=8.3 Hz, 1H), 7.72 (d, J=8.3 Hz, 1H), 7.49 (s, 1H), 7.43-7.38 (m, 1H), 7.29-7.23 (m, 2H), 7.00 (d, J=7.7 Hz, 1H), 6.74 (s, 1H), 3.94-3.81 (m, 1H), 3.91 (d, J=11.5 Hz, 2H), 3.57 (q, J=6.9 Hz, 2H), 3.45 (t, J=11.0 Hz, 2H), 2.91 (t, J=7.3 Hz, 2H), 1.93 (d, J=11.1 Hz, 2H), 1.53 (qd, J=11.7, 4.2 Hz, 2H).

Step 2:

A suspension of I-35 (63.1 mg, 0.139 mmol, 1.00 equiv.), 1-methylpyrazole-4-boronic acid pinacol ester (102, 120 mg, 0.550 mmol, 3.97 equiv.) and bis-(di-tert-butyl(4-dimethylaminophenyl)-phosphine)dichloropalladium(10 (20.8 mg, 0.029 mmol, 0.212 equiv.) in MeCN (3.0 mL) was treated with 1.0 M aq. $Na_2CO_3$ (1.0 mL, 1.0 mmol, 7.2 equiv.), and the mixture was irradiated in a microwave synthesizer (CEM, 300 watts) at 130° C. for 20 min. The cooled mixture was diluted with EtOAc and washed with aq. $NaHCO_3$ and brine, dried ($Na_2SO_4$), filtered and concentrated in vacuo to afford 90.3 mg of a yellow oil. The crude was purified by reverse phase HPLC (C18) using a MeCN/$H_2O$ (with 0.1% ammonium hydroxide) gradient to afford 43.8 mg (69%) of I-41 as a bright yellow solid (43.8 mg, 69%). $^1$H NMR (400 MHz, DMSO-$d_6$) δ 9.01 (s, 1H), 8.92 (t, J=6.0 Hz, 1H), 8.37 (d, J=8.4 Hz, 1H), 8.07 (s, 1H), 7.81 (s, 1H), 7.74 (d, J=8.3 Hz, 1H), 7.46 (s, 1H), 7.40 (d, J=7.7 Hz, 1H), 7.28 (t, J=7.6 Hz, 1H), 7.09 (d, J=7.5 Hz, 1H), 7.03 (d, J=7.8 Hz, 1H), 6.72 (s, 1H), 3.91 (d, J=11.6 Hz, 2H), 3.93-3.80 (m, 1H), 3.83 (s, 3H), 3.60 (dd, J=13.8, 6.8 Hz, 2H), 3.45 (t, J=11.3 Hz, 2H), 2.91 (t, J=7.3 Hz, 2H), 1.92 (d, J=12.7 Hz, 2H), 1.52 (qd, J=11.6, 4.2 Hz, 2H). LCMS (method E): $R_T$ 4.13 min, MH$^+$457.2.

N-(3-(Pyridin-4-yl)phenethyl)-7-(tetrahydro-2H-pyran-4-ylamino)-1,6-naphthyridine-2-carboxamide (I-47) was prepared analogously except in step 2, 102 was replaced with 4-(4,4,5,5-tetramethyl-1,3,2-dioxaborolan-2-yl)pyridine. $^1$H NMR (400 MHz, DMSO) 9.02 (s, 1H), 8.95 (t, J=5.9 Hz, 1H), 8.56 (d, J=5.6 Hz, 2H), 8.37 (d, J=8.3 Hz, 1H), 7.73 (d, J=8.3 Hz, 1H), 7.70-7.62 (m, 4H), 7.46 (t, J=7.6 Hz, 1H), 7.38 (d, J=7.5 Hz, 1H), 7.04 (d, J=7.9 Hz, 1H), 6.72 (s, 1H), 3.94-3.79 (m, 1H), 3.91 (d, J=11.6 Hz, 2H), 3.65 (q, J=6.8 Hz, 2H), 3.44 (t, J=11.0 Hz, 2H), 3.00 (t, J=7.2 Hz, 2H), 1.92 (d, J=11.8 Hz, 2H), 1.52 (qd, J=11.2, 4.2 Hz, 2H).

N-(3-(4-Methylpyridin-3-yl)phenethyl)-7-(tetrahydro-2H-pyran-4-ylamino)-1,6-naphthyridine-2-carboxamide (I-40) was prepared analogously except in step 2, 102 was replaced with 4-methyl-3-(4,4,5,5-tetramethyl-1,3,2-dioxaborolan-2-yl)pyridine. $^1$H NMR (400 MHz, DMSO) δ 9.01 (s, 1H), 8.90 (t, J=5.9 Hz, 1H), 8.40 (d, J=4.9 Hz, 1H), 8.36 (d, J=8.4 Hz, 1H), 8.34 (s, 1H), 7.72 (d, J=8.3 Hz, 1H), 7.42 (t, J=7.5 Hz, 1H), 7.35-7.27 (m, 3H), 7.24 (d, J=7.5 Hz, 1H), 7.02 (d, J=7.8 Hz, 1H), 6.71 (s, 1H), 3.94-3.80 (m, 1H), 3.91 (d, J=11.6 Hz, 2H), 3.63 (q, J=6.9 Hz, 2H), 3.44 (t, J=11.4 Hz, 2H), 2.98 (t, J=7.3 Hz, 2H), 2.20 (s, 3H), 1.92 (d, J=12.9 Hz, 2H), 1.52 (qd, J=11.1, 4.2 Hz, 2H).

N-(3-(Pyrazin-2-yl)phenethyl)-7-(tetrahydro-2H-pyran-4-ylamino)-1,6-naphthyridine-2-carboxamide (I-48) was prepared analogously except in step 2, 102 was replaced with 2-(4,4,5,5-tetramethyl-1,3,2-dioxaborolan-2-yl)pyrazine. $^1$H NMR (400 MHz, DMSO-$d_6$) δ 9.24 (s, 1H), 9.01 (s, 1H), 8.96 (t, J=6.0 Hz, 1H), 8.70 (s, 1H), 8.60 (s, 1H), 8.36 (d, J=8.4 Hz, 1H), 8.06 (s, 1H), 7.99 (d, J=7.7 Hz, 1H), 7.73 (d, J=8.3 Hz, 1H), 7.48 (t, J=7.6 Hz, 1H), 7.41 (d, J=7.5 Hz, 1H), 7.02 (d, J=7.7 Hz, 1H), 6.71 (s, 1H), 3.94-3.79 (m, 1H), 3.91 (d, J=11.5 Hz, 2H), 3.64 (q, J=6.9 Hz, 2H), 3.45 (t, J=11.4 Hz, 2H), 3.01 (t, J=7.4 Hz, 2H), 1.92 (d, J=12.9 Hz, 2H), 1.52 (qd, J=11.2, 4.4 Hz, 2H).

N-(2-(1-Methyl-1H-pyrazol-4-yl)phenethyl)-7-(tetrahydro-2H-pyran-4-ylamino)-1,6-naphthyridine-2-carboxamide (I-49) was prepared analogously except in step 2, I-35 was replaced with I-28. $^1$H NMR (400 MHz, DMSO-$d_6$) δ 9.05-8.99 (m, 1H), 9.02 (s, 1H), 8.38 (d, J=8.4 Hz, 1H), 8.06 (s, 1H), 7.75 (d, J=8.3 Hz, 1H), 7.71 (s, 1H), 7.37-7.31 (m, 2H), 7.27-7.21 (m, 2H), 7.04 (d, J=7.8 Hz, 1H), 6.75 (s, 1H), 3.95-3.88 (m, 1H), 3.94-3.80 (m, 1H), 3.90 (s, 3H), 3.58-3.50 (m, 2H), 3.46 (t, J=11.3 Hz, 2H), 3.02-2.94 (m, 2H), 1.93 (d, J=12.4 Hz, 2H), 1.53 (qd, J=11.2, 4.1 Hz, 2H).

N-(4-(1-Methyl-1H-pyrazol-4-yl)phenethyl)-7-(tetrahydro-2H-pyran-4-ylamino)-1,6-naphthyridine-2-carboxamide (I-37) was prepared analogously except in step 2, I-35 was replaced with I-29. $^1$H NMR (400 MHz, DMSO-$d_6$) δ 9.01 (s, 1H), 8.87 (t, J=6.0 Hz, 1H), 8.37 (d, J=8.3 Hz, 1H), 8.07 (s, 1H), 7.81 (s, 1H), 7.73 (d, J=8.3 Hz, 1H), 7.48 (d, J=8.0 Hz, 2H), 7.24 (d, J=8.0 Hz, 2H), 6.99 (d, J=7.8 Hz, 1H), 6.73 (s, 1H), 3.94-3.81 (m, 1H), 3.90 (d, J=11.5 Hz, 2H), 3.85 (s, 3H), 3.57 (q, J=7.0 Hz, 2H), 3.45 (t, J=10.9 Hz, 2H), 2.88 (t, J=7.4 Hz, 2H), 1.92 (d, J=12.7 Hz, 2H), 1.52 (qd, J=11.4, 4.2 Hz, 2H).

N-(4-(4-Methylpyridin-3-yl)phenethyl)-7-(tetrahydro-2H-pyran-4-ylamino)-1,6-naphthyridine-2-carboxamide (I-38) was prepared analogously except in step 2, I-35 was replaced with I-29, and 1-methylpyrazole-4-boronic acid pinacol ester was replaced with 4-methyl-3-(4,4,5,5-tetramethyl-1,3,2-dioxaborolan-2-yl)pyridine. $^1$H NMR (400 MHz, DMSO) δ 9.01 (s, 1H), 8.93 (t, J=5.8 Hz, 1H), 8.41 (d, J=5.0 Hz, 1H), 8.38 (d, J=8.4 Hz, 1H), 8.36 (s, 1H), 7.75 (d, J=8.3 Hz, 1H), 7.39 (d, J=8.1 Hz, 2H), 7.34 (d, J=8.1 Hz, 2H), 7.32 (d, J=5.0 Hz, 1H), 7.00 (d, J=7.7 Hz, 1H), 6.74 (s, 1H), 3.94-3.80 (m, 1H), 3.91 (d, J=11.7 Hz, 2H), 3.63 (q, J=6.9 Hz, 2H), 3.45 (t, J=11.0 Hz, 2H), 2.97 (t, J=7.5 Hz, 2H), 2.26 (s, 3H), 1.93 (d, J=12.5 Hz, 2H), 1.53 (qd, J=11.4, 4.2 Hz, 2H).

N-(4-(Pyrazin-2-yl)phenethyl)-7-(tetrahydro-2H-pyran-4-ylamino)-1,6-naphthyridine-2-carboxamide (I-45) was prepared analogously except in step 2, I-35 was replaced with I-29, and 1-methylpyrazole-4-boronic acid pinacol ester was replaced with 2-(4,4,5,5-tetramethyl-1,3,2-dioxaborolan-2-yl)pyrazine. $^1$H NMR (400 MHz, DMSO-$d_6$) δ 9.24 (s, 1H), 9.01 (s, 1H), 8.95 (t, J=6.0 Hz, 1H), 8.70 (s, 1H), 8.59 (d, J=2.1 Hz, 1H), 8.37 (d, J=8.4 Hz, 1H), 8.09 (d, J=8.0 Hz, 2H), 7.74 (d, J=8.3 Hz, 1H), 7.44 (d, J=8.0 Hz, 2H), 7.03 (d, J=7.8 Hz, 1H), 6.74 (s, 1H), 3.94-3.80 (m, 1H), 3.90 (d, J=11.8 Hz, 2H), 3.63 (q, J=6.8 Hz, 2H), 3.44 (t, J=11.3 Hz, 2H), 2.99 (t, J=7.3 Hz, 2H), 1.92 (d, J=12.2 Hz, 2H), 1.58-1.46 (m, 2H).

N-(4-(Pyridin-4-yl)phenethyl)-7-(tetrahydro-2H-pyran-4-ylamino)-1,6-naphthyridine-2-carboxamide (I-46) was prepared analogously except in step 2, I-35 was replaced with I-29, and 1-methylpyrazole-4-boronic acid pinacol ester was replaced with 4-(4,4,5,5-tetramethyl-1,3,2-dioxaborolan-2-yl)pyridine. $^1$H NMR (400 MHz, DMSO-$d_6$) 9.01 (s, 1H), 8.95 (t, J=5.9 Hz, 1H), 8.62 (d, J=5.0 Hz, 2H), 8.37 (d, J=8.4 Hz, 1H), 7.76 (d, J=8.5 Hz, 2H), 7.74 (d, J=8 Hz, 1H), 7.70 (d, J=5.0 Hz, 2H), 7.42 (d, J=7.8 Hz, 2H), 7.03 (d, J=7.8 Hz, 1H), 6.74 (s, 1H), 3.94-3.80 (m, 1H), 3.90 (d, J=11.6 Hz, 2H), 3.61 (q, J=6.8 Hz, 2H), 3.44 (t, J=11.3 Hz, 2H), 2.97 (t, J=7.4 Hz, 2H), 1.92 (d, J=12.7 Hz, 2H), 1.52 (qd, J=11.0, 4.2 Hz, 2H).

N-(4-(Pyrimidin-5-yl)phenethyl)-7-(tetrahydro-2H-pyran-4-ylamino)-1,6-naphthyridine-2-carboxamide (I-44) as prepared analogously except in step 2, I-35 was replaced with I-29 and 1-methylpyrazole-4-boronic acid pinacol ester was replaced with 5-(4,4,5,5-tetramethyl-1,3,2-dioxaborolan-2-yl)pyrimidine. $^1$H NMR (400 MHz, DMSO-$d_6$) 9.17 (s, 1H), 9.14 (s, 2H), 9.02 (s, 1H), 8.95 (t, J=6.0 Hz, 1H), 8.38 (d, J=8.3 Hz, 1H), 7.77 (d, J=7.9 Hz, 2H), 7.74 (d, J=8.6 Hz, 1H), 7.44 (d, J=7.9 Hz, 2H), 7.04 (d, J=7.8 Hz, 1H), 6.74 (s, 1H), 3.94-3.79 (m, 1H), 3.91 (d, J=11.9 Hz, 2H), 3.62 (q, J=6.9 Hz, 2H), 3.44 (t, J=11.3 Hz, 2H), 2.98 (t, J=7.3 Hz, 2H), 1.92 (d, J=12.4 Hz, 2H), 1.52 (q, J=11.2, 4.2 Hz, 2H).

N-(3-(1-Methyl-1H-pyrazol-4-yl)benzyl)-7-(tetrahydro-2H-pyran-4-ylamino)-1,6-naphthyridine-2-carboxamide (I-43) was prepared analogously except in step 1, (2-bromophenyl)methylamine replaced 2-(3-bromophenyl)ethanamine. $^1$H NMR (400 MHz, DMSO) δ 9.35 (t, J=6.3 Hz, 1H), 9.02 (s, 1H), 8.39 (d, J=8.3 Hz, 1H), 8.10 (s, 1H), 7.82 (s, 1H), 7.76 (d, J=8.3 Hz, 1H), 7.54 (s, 1H), 7.44 (d, J=7.6 Hz, 1H), 7.31 (t, J=7.6 Hz, 1H), 7.17 (d, J=7.6 Hz, 1H), 7.03 (d, J=7.7 Hz, 1H), 6.76 (s, 1H), 4.54 (d, J=6.2 Hz, 2H), 3.90 (d, J=11.5 Hz, 2H), 3.85 (s, 4H), 3.44 (t, J=11.2 Hz, 2H), 1.92 (d, J=13.8 Hz, 2H), 1.52 (qd, J=12.5, 4.4 Hz, 2H).

N-(3-(4-Methylpyridin-3-yl)phenethyl)-7-(tetrahydro-2H-pyran-4-ylamino)-1,6-naphthyridine-2-carboxamide (I-50) was prepared analogously except in step 2,4-methyl-3-(4,4,5,5-tetramethyl-1,3,2-dioxaborolan-2-yl)-pyridine (CASRN 1171891-31-8) replaced 1-methylpyrazole-4-boronic acid pinacol ester. $^1$H NMR (400 MHz, DMSO-d$_6$) δ 9.01 (s, 1H), 8.90 (t, J=5.9 Hz, 1H), 8.40 (d, J=4.9 Hz, 1H), 8.36 (d, J=8.4 Hz, 1H), 8.34 (s, 1H), 7.72 (d, J=8.3 Hz, 1H), 7.42 (t, J=7.5 Hz, 1H), 7.35-7.27 (m, 3H), 7.24 (d, J=7.5 Hz, 1H), 7.02 (d, J=7.8 Hz, 1H), 6.71 (s, 1H), 3.94-3.80 (m, 1H), 3.91 (d, J=11.6 Hz, 2H), 3.63 (q, J=6.9 Hz, 2H), 3.44 (t, J=11.4 Hz, 2H), 2.98 (t, J=7.3 Hz, 2H), 2.20 (s, 3H), 1.92 (d, J=12.9 Hz, 2H), 1.52 (qd, J=11.1, 4.2 Hz, 2H).

Example 11

N-((4-Phenoxypyridin-2-yl)methyl)-7-(tetrahydro-2H-pyran-4-ylamino)-1,6-naphthyridine-2-carboxamide (I-51)

Step 1:
N-((4-Chloropyridin-2-yl)methyl)-7-(tetrahydro-2H-pyran-4-ylamino)-1,6-naphthyridine-2-carboxamide (104) was prepared in accord with the procedure in example 1 except 50c was replaced with (5-bromopyridin-3-yl)methanamine. The product was used without further purification.

Step 2:
A mixture of 104 (50 mg, 0.126 mmol), phenol (17.8 mg, 0.189 mmol), potassium tert-butoxide (43.6 mg, 0.377 mmol) and NMP (0.25 mL) was heated at 120° C. overnight. The cooled reaction mixture was diluted with EtOAc (50 mL) and washed with water (50 mL). The organic layer was separated, dried (Na$_2$SO$_4$), filtered and concentrated in vacuo to provide a residue that was purified by reverse phase HPLC purification using a MeCN/H$_2$O (containing 0.1% NH$_4$OH) gradient (5 to 85%, 14 min). Desired fractions were combined and evaporated in vacuo to afford 17.6 mg (31%) of I-51 as a yellow solid. $^1$H NMR (400 MHz, DMSO-d$_6$) δ 9.39 (t, J=6.0 Hz, 1H), 9.03 (s, 1H), 8.45-8.36 (m, 2H), 7.73 (d, J=8.3 Hz, 1H), 7.44 (t, J=7.7 Hz, 2H), 7.24 (t, J=7.4 Hz, 1H), 7.15 (d, J=8.1 Hz, 2H), 7.05 (d, J=7.9 Hz, 1H), 6.91 (s, 1H), 6.77 (m, 2H), 4.59 (d, J=6.0 Hz, 2H), 3.91 (d, J=11.3 Hz, 3H), 3.46 (t, J=11.3 Hz, 2H), 1.93 (d, J=11.8 Hz, 2H), 1.53 (m, 2H).

7-(Tetrahydro-2H-pyran-4-ylamino)-N-((4-(o-tolyloxy)pyridin-2-yl)methyl)-1,6-naphthyridine-2-carboxamide (I-55) was prepared analogously except in step 2, phenol was replaced by 2-methylphenol. $^1$H NMR (400 MHz, DMSO-d$_6$) δ 9.38 (t, J=6.1 Hz, 1H), 9.04 (s, 1H), 8.42-8.36 (m, 2H), 7.73 (d, J=8.2 Hz, 1H), 7.32 (d, J=7.4 Hz, 1H), 7.25 (t, J=7.7 Hz, 1H), 7.16 (t, J=7.3 Hz, 1H), 7.06 (dd, J=7.8, 3.4 Hz, 2H), 6.81 (s, 1H), 6.76 (s, 1H), 6.66 (d, J=5.8 Hz, 1H), 4.58 (d, J=6.0 Hz, 2H), 3.91 (d, J=11.2 Hz, 3H), 3.46 (t, J=11.2 Hz, 2H), 2.08 (s, 3H), 1.93 (d, J=12.6 Hz, 2H), 1.53 (m, 2H).

N-((4-(2-Chlorophenoxy)pyridin-2-yl)methyl)-7-(tetrahydro-2H-pyran-4-ylamino)-1,6-naphthyridine-2-carboxamide (I-56) was prepared analogously except in step 2, phenol was replaced with ortho-chlorophenol. $^1$H NMR (400 MHz, DMSO-d$_6$) δ 9.40 (s, 1H), 9.03 (t, J=6.1 Hz, 1H), 8.45-8.36 (m, 2H), 7.73 (d, J=8.5 Hz, 1H), 7.62 (d, J=8.1 Hz, 1H), 7.48-7.38 (m, 1H), 7.37-7.27 (m, 2H), 7.05 (d, J=7.7 Hz, 1H), 6.88 (s, 1H), 6.76 (m, 1H), 6.70 (s, 1H), 4.60 (d, J=6.1 Hz, 2H), 3.91 (d, J=11.6 Hz, 3H), 3.45 (t, J=11.0 Hz, 2H), 1.93 (d, J=10.3 Hz, 2H), 1.53 (m, 2H).

7-(Tetrahydro-pyran-4-ylamino)-[1,6]naphthyridine-2-carboxylic acid 3-phenoxy-benzylamide (I-57) was prepared analogously except in step 1, (5-bromopyridin-3-yl)methanamine was replaced with 3-phenoxy-benzyl amine and step 2 was omitted. $^1$H NMR (400 MHz, DMSO-d$_6$) δ 9.41 (t, J=6.4 Hz, 1H), 9.02 (s, 1H), 8.38 (d, J=8.3 Hz, 1H), 7.74 (d, J=8.3 Hz, 1H), 7.40-7.30 (m, 3H), 7.15-6.96 (m, 6H), 6.87 (d, J=8.1 Hz, 1H), 6.74 (s, 1H), 4.51 (d, J=6.3 Hz, 2H), 3.90 (d, J=11.5 Hz, 2H), 3.87-3.78 (m, 1H), 3.44 (t, J=11.2 Hz, 2H), 1.92 (d, J=12.8 Hz, 2H), 1.52 (m, 2H).

Example 12

3-((S)-2-Hydroxy-1-methyl-ethylamino)-isoquinoline-6-carboxylic acid [(R)-1-(4-chloro-3-fluoro-phenyl)-3-hydroxy-propyl]-amide (II-57) and N-((1S)-1-(4-chloro-3-fluorophenyl)-2-hydroxypropyl)-3-((S)-1-hydroxypropan-2-ylamino)isoquinoline-6-carboxamide (II-60)

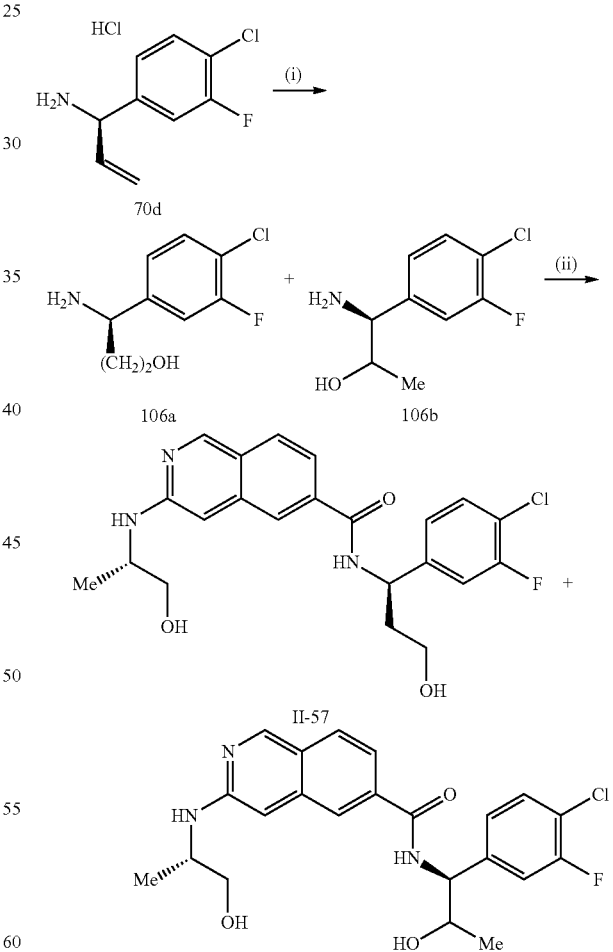

(i) BH$_3$, THF; (ii) C-4, R$^2$ = (S)-2-hydroxypropan-2-yl), HATU, DIPEA

Step 1:
To a solution of 70d (50 mg, 0.27 mmol) in THF (1.0 mL) was added BH$_2$.THF (1N, 1.0 mL) at −78° C. The mixture was then stirred at 0° C. for 4 h. H₂O₂ (30%, 0.31 mL) and NaOH (2 N, 1.4 mL) were added sequentially, and the mixture was further stirred for 1 h. The mixture was extracted with EtOAc, dried and concentrated in vacuo. The residue was purified by Combiflash (0.5% NH₃HCO₃/CH₃CN) to afford 25 mg (45%) of a mixture of (R)-3-amino-3-(4-chloro-3-fluorophenyl)propan-1-ol (106a) and (1S)-1-amino-1-(4-chloro-3-fluorophenyl)propan-2-ol (106b): LCMS (ESI): m/z 204 [M+H]⁺.

Step 2:

To a solution of a mixture of 106a and 106b, C-5 (R²=(S)-1-hydroxypropan-2-ylamino) (60 mg, 0.25 mmol), HATU (93.6 mg, 0.25 mmol) in DMF (2.0 mL) was added TEA (1.0 mL). The mixture was stirred at RT for 3 h. The mixture was diluted with EtOAc (100 mL) was washed with water (3×20 mL), dried (Na₂SO₄) and concentrated in vacuo. The residue was purified by preparative HPLC to afford 15 mg (14%) of II-57 and 5 mg (4.6%) of II-60.

N—((R)-1-(4-Chloro-3-fluorophenyl)-3-hydroxypropyl)-3-((S)-1-hydroxypropan-2-ylamino)isoquinoline-6-carboxamide (II-57): ¹H NMR (500 MHz, MeOH-d₄) δ 8.86 (s, 1H), 8.03 (s, 1H), 7.86 (d, J=9.0 Hz, 1H), 7.54 (dd, J=8.5, 1.5 Hz, 1H), 7.47 (m, 1H), 7.34 (dd, J=10.5, 2.5 Hz, 1H), 7.26 (dd, J=8.5, 1.5 Hz, 1H), 6.80 (s, 1H), 5.31 (m, 1H), 3.92 (m, 1H), 3.96-3.59 (m, 4H), 2.15-2.10 (m, 2H), 1.29 (d, J=7.0 Hz, 3H); LCMS (ESI): m/z 432 [M+H]⁺.

N—((1S)-1-(4-Chloro-3-fluorophenyl)-2-hydroxypropyl)-3-((S)-1-hydroxypropan-2-ylamino)isoquinoline-6-carboxamide (II-60): ¹H NMR (500 MHz, MeOH-d₄) δ 8.74 (s, 1H), 7.91 (s, 1H), 7.76 (d, J=8.5 Hz, 1H), 7.41 (m, 1H), 7.34 (t, J=7.5 Hz, 1H), 7.28 (dd, J=10, 1.5 Hz, 1H), 7.17 (d, J=1.5 Hz, 1H), 6.69 (s, 1H), 4.87 (d, J=7.0 Hz, 1H), 4.05 (m, 1H), 3.80 (m, 1H), 3.55-3.49 (m, 2H), 1.20-1.14 (m, 6H); LCMS (ESI): m/z 432 [M+H]⁺.

Example 13

3-((S)-2-Hydroxy-1-methyl-ethylamino)-isoquinoline-6-carboxylic acid [(S)-1-(4-difluoromethoxyphenyl)-2-hydroxy-ethyl]-amide (II-61)

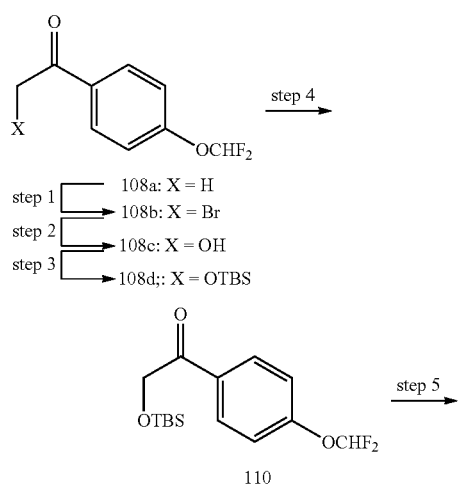

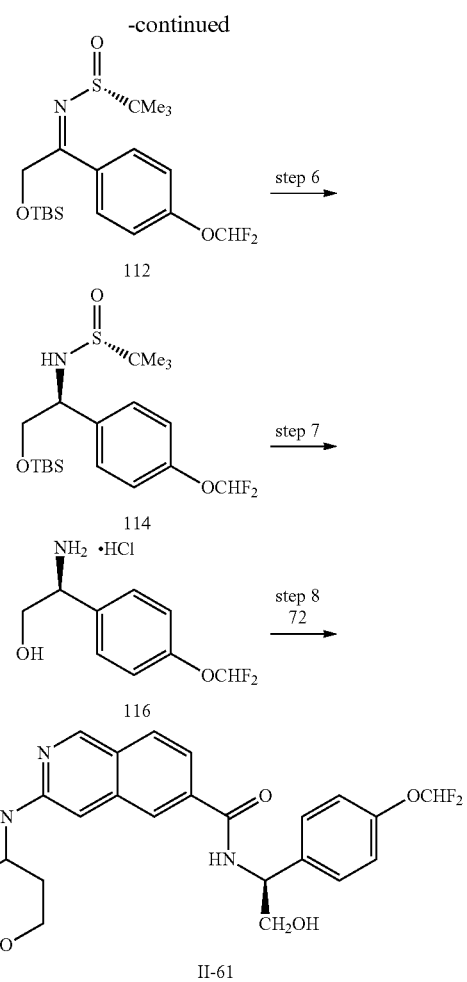

(1) Br₂, DCM, dioxane; (2) CsOCOH, MeOH; (3) TBSCl, imidazole, DCM; (4)(R)—Me₃CS(=O)NH₂, Ti(OEt)₄, THF (5) DIBAL—H, THF; (6) HATU, TEA, DMF Step 1:

To a solution of 108a (1.0 g, 5.4 mmol) in dioxane (5 mL) and ether (3 mL) was added bromine (1.1 g, 7.0 mmol) dropwise with stirring over 30 min. After stirring at RT for another 30 min, the mixture was poured into water. The organic layer was separated, washed with water, and dried (Na₂SO₄). The solvent was evaporated in vacuo, and the residue was re-crystallized from hexane to afford 1.2 g (85% yield) of 108b.

Step 2:

A mixture of 108b (1.8 g, 6.8 mmol) and CsOCHO (3.6 g, 20 mmol) in MeOH (10 mL) was stirred at 80° C. for 1 h. The solid was filtered off, and the filtrate was concentrated. The residue was purified by SiO₂ chromatography eluting with petroleum ether/EtOAc (1:3) to afford 0.90 g (65%) of 108c. LCMS (ESI) m/z: 203.1 [M+H]⁺.

Step 3:

To a solution of 108c (850 mg, 4.20 mmol) and imidazole (428 mg, 6.30 mmol) in dry DCM (10 mL) at 0° C. was added dropwise a solution of TBSCl (953 mg, 6.30 mmol) in dry DCM (4.0 mL). The mixture was stirred at RT for 4 h. The reaction mixture was washed with saturated Na₂CO₃, dried (Na₂SO₄), filtered and concentrated. The residue was purified by SiO₂ chromatography eluting with petroleum ether/EtOAc (100:6) to afford 850 mg (62%) of 108d. LCMS (ESI) m/z: 317.3 [M+H]⁺.

Step 4:

A solution of 108d (1.6 g, 5.1 mmol), Ti(OEt)$_4$ (5.8 g, 20 mmol), and (R)-2-methylpropane-2-sulfinamide (1.20 g, 10.2 mmol) in dry THF (10 mL) was stirred at 80° C. for 4 h. After removal of the solvent, the residue was diluted with EtOAc, washed with brine, dried, and concentrated. The residue was purified by SiO$_2$ chromatography eluting with petroleum ether/ethyl acetate (100:15) to afford 0.80 g (42%) of 110. LCMS (ESI) m/z: 420.2 [M+H]$^+$.

Step 5:

To a solution of 110 (100 mg, 0.240 mmol) in dry THF (5.0 mL) at −78° C. was added dropwise a solution of DIBAL-H (0.60 mL, 0.60 mmol) in dry hexane dropwise. The mixture was stirred at −78° C. for another 1 h. MeOH was added dropwise at −78° C. to quench the reaction. The mixture was warmed to RT, filtered, dried (Na$_2$SO$_4$), filtered and concentrated to afford 32 mg (32%) of 112 as off-yellow oil. LCMS (ESI) m/z: 422.2 [M+H]$^+$.

Step 6:

A solution of 112 (100 mg, 0.24 mmol) in 1N HCl in methanol (5.0 mL) was stirred at RT for 1 h. After concentration, the residue was diluted with EtOAc (10 mL). The resulting solid was collected to afford 40 mg (81%) of 114. $^1$H NMR (500 MHz, DMSO-d$_6$) δ 7.40 (d, J=8.5 Hz, 2H), 7.18 (t, J=74.5 Hz, 1H), 7.10 (d, J=8.5 Hz, 2H), 4.78 (brs, 1H), 3.86 (m, 1H), 3.42 (brs, 1H), 3.33-3.25 (m, 2H), 2.04 (brs, 2H); LCMS (ESI) m/z: 204.1 [M+H]$^+$.

Step 7:

A mixture of 72 (55 mg, 0.20 mmol), 114 (40 mg, 0.20 mmol), HATU (76 mg, 0.20 mmol) and DIPEA (0.50 mL) in DMF (1.5 mL) was stirred at RT for 3 h. After being diluted with EtOAc (100 mL) the resulting mixture was washed with water (3×20 mL) and dried (Na$_2$SO$_4$), filtered and concentrated under vacuum. The residue was purified by prep-HPLC to afford 3.5 mg (4%) of II-61 as a yellow solid. $^1$H NMR (500 MHz, DMSO-d$_6$) δ 8.91 (s, 1H), 8.85 (d, J=8.5 Hz, 1H), 8.10 (s, 1H), 7.84 (d, J=9.0 Hz, 1H), 7.53 (m, 1H), 7.46 (d, J=8.5 Hz, 2H), 7.20 (t, J=74.0 Hz, 1H), 7.15-7.12 (m, 1H), 6.73 (s, 1H), 6.57 (d, J=7.5 Hz, 1H), 5.08 (m, 1H), 4.99 (m, 1H), 3.91-3.82 (m, 3H), 3.75-3.63 (m, 2H), 3.46-3.42 (m, 2H), 1.91 (d, J=13.5 Hz, 2H), 1.53-1.45 (m, 2H); LCMS (ESI) m/z: 458.3 [M+H]$^+$.

Example 14

3-(Tetrahydro-pyran-4-ylamino)-isoquinoline-6-carboxylic acid [(4-chloro-3-fluoro-phenyl)-(3-fluoro-pyrrolidin-3-yl)-methyl]-amide (II-65)

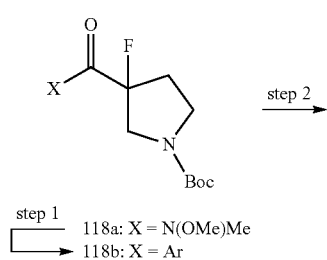

118a: X = N(OMe)Me
118b: X = Ar

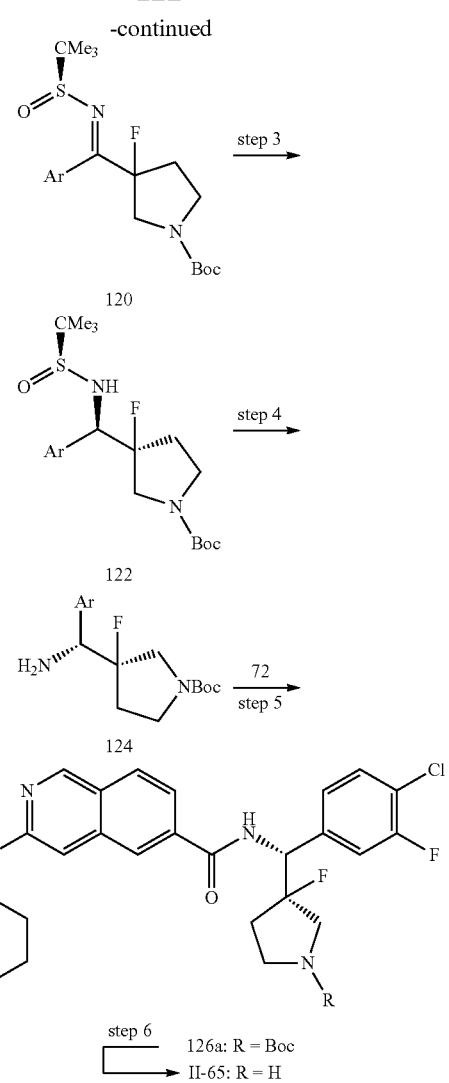

126a: R = Boc
II-65: R = H (1) 4-chloro-3-fluorophenyl magnesium bromide, THF; (2) (S)—CMe$_3$S(=O)NH$_2$, Ti(OEt)$_4$, THF; (3) DIBAL—H; (4) HCl, MeOH, EtOAc; (5) HATU, TEA, DMF; (6) HCl, MeOH Ar = 4-chloro-3-fluoro-phenyl Step 1:

tert-Butyl 3-(4-chloro-3-fluorobenzoyl)-3-fluoropyrrolidine-1-carboxylate: To a solution of 4-bromo-1-chloro-2-fluorobenzene (12 g, 58 mmol) in THF (100 mL) was added magnesium (1.4 g, 58 m mol). The mixture was degassed with nitrogen, and a small amount of 1,2-dibromoethane was added. The reaction was stirred for 1 h, and a solution of tert-butyl 3-fluoro-3-(methoxy(methyl)carbamoyl)pyrrolidine-1-carboxylate (8.0 g, 29 m mol) in THF (50 mL) was added to the above mixture at −78° C. After 10 min, the reaction mixture was allowed to warm up to 0° C. and stirred for 3 h. The reaction was quenched with NH$_4$Cl, and the resulting mixture was extracted with EtOAc (3×100 mL). The combined organic layers were washed with brine, dried (Na$_2$SO$_4$), filtered and concentrated. The residue was purified by SiO$_2$ chromatography eluting with a petroleum ether/EtOAc gradient (20:1 to 8:1) to afford 8.8 g (88%) of 118b. LCMS (ESI) m/z: 290 [M+H−56]$^+$.

Step 2:

A mixture of 118b (6.30 g, 18.3 mmol), (S)-2-methylpropane-2-sulfinamide (3.31 g 27.4 mmol), and Ti(OEt)$_4$ (11 mL 46 mmol) in THF (100 mL) was heated at 65° C. for 12 h. After cooling, the mixture was poured into water. The solid was filtered, and the filtrate was extracted with EtOAc (3×100 mL). The organic layer was washed with water (50 mL×3), dried (Na$_2$SO$_4$), filtered and concentrated under vacuum. The residues were purified by SiO$_2$ chromatography eluting with petroleum ether/EtOAc (5:1) to afford 5.6 g (68%) of 120 as a colorless oil.

Step 3:

To a solution of 120 (5.60 g, 12.5 mmol) in dry THF (100 mL) at −65° C. was added DIBAL-H (37.5 mL, 37.5 mmol). After being stirred for 1 h at −65° C., the reaction was quenched with water (2.0 mL). The insoluble material was filtered, and the filtrate was concentrated. The residue was purified by SiO$_2$ chromatography eluting with petroleum ether/EtOAc (2:1) to afford 240 mg (4.3%) of 124 (the absolute configuration was assigned arbitrarily) and 400 mg (7.1%) of the other isomer and 1.8 g (32%) of a mixture of the two isomers. LCMS (ESI) m/z: 395.1 [M+H−56]$^+$.

Step 4:

To a solution of 124 (240 mg, 0.50 mmol) in EtOAc (3.0 mL) was added 4 M HCl in methanol (0.4 mL) at RT. After being stirred for 30 min, the solid was collected by filtration to afford 130 mg (76%) of 124 as a white solid. LCMS (ESI) m/z: 291.1[M+H−56]$^+$.

Step 5:

A mixture of 124 (70 mg, 0.20 mmol), HATU (152 mg, 0.400 mmol), 72 (50 mg, 0.20 mmol), and TEA (80 mg, 0.80 mmol) in DMF (2.0 mL) was stirred at RT for 1 h. The resulting mixture was diluted with EtOAc (2×20 mL), washed with brine, dried, and concentrated to afford 120 mg (100%) of 126a as yellow oil, which was used in the next step without further purification. LCMS (ESI) m/z: 601.4 [M+H]$^+$.

Step 6:

A solution of 126a (120 mg, 0.200 mmol) in 4 M HCl in methanol (2.0 mL) was stirred for 30 min at RT. The pH of the resulting mixture was adjusted to ca. 10 with sat'd. NaHCO$_3$, extracted with EtOAc (2×10 mL), washed with brine, dried, and concentrated in vacuo. The residue was purified by prep-HPLC (0.5% NH$_4$HCO$_3$/MeCN) to afford 8.0 mg (8.0%) of II-65 as a yellow solid. $^1$H NMR (500 MHz, DMSO-d$_6$) δ 9.20 (d, J=9.0 Hz, 1H), 8.91 (s, 1H), 8.08 (s, 1H), 7.84 (d, J=8.0 Hz, 1H), 7.71 (d, J=11.0 Hz, 1H), 7.58 (m, 1H), 7.49-7.44 (m, 2H), 6.75 (s, 1H), 6.57 (d, J=7.5 Hz, 1H), 5.50 (m, 1H), 3.91-3.89 (m, 3H), 3.47-3.42 (m, 3H), 2.99-2.86 (m, 3H), 2.02-1.91 (m, 4H), 1.59 (d, J=11.0 Hz, 2H); LCMS (ESI) m/z: 501.2 [M+H]$^+$.

The other diastereomer was II-66 and also could be isolated. $^1$H NMR (500 MHz, DMSO-d$_6$) δ 9.20 (d, J=9.0 Hz, 1H), 8.91 (s, 1H), 8.10 (s, 1H), 7.86-7.83 (m, 1H), 7.73 (d, J=10.5 Hz, 1H), 7.61-7.58 (m, 1H), 7.48-7.46 (m, 2H), 6.76 (d, J=10.0 Hz, 1H), 6.57 (d, J=8.0 Hz, 1H), 5.53-5.45 (m, 1H), 3.91-3.82 (m, 3H), 3.47-3.42 (m, 3H), 3.00-2.90 (m, 4H), 1.93-1.91 (m, 3H), 1.53-1.46 (m, 3H); LCMS (ESI) m/z: 501.2 [M+H]$^+$.

Example 15

N-((3S,4R)-1-Benzyl-4-(4-methoxyphenyl)pyrrolidin-3-yl)-3-((1-methyl-1H-pyrazol-5-yl)amino)isoquinoline-6-carboxamide (II-62)

A 2-5 mL microwave vial equipped with a stirring bar was charged with 92 (94 mg, 0.3506 mmol, 1.1 equiv), (3S,4R)-1-benzyl-4-(4-methoxyphenyl)pyrrolidin-3-amine (90 mg, 0.3187 mmol, 1.0 mmol, CASRN 114616-86-5), DMF (2.0 mL) and HATU (187.4 mg, 0.4780 mmol, 1.5 equiv). The reaction mixture was stirred 20 min at RT and treated with TEA (0.1347 mL, 0.956 mmol, 3.0 equiv). The microwave vial was capped, and the reaction was stirred for 2 h at RT. The DMF solution was partitioned between EtOAc and water (120 mL/40 mL). The EtOAc layer was washed twice with brine, dried, filtered, and concentrated to give a crude oil. A portion of the crude (20%) was purified by RP HPLC to give 3.5 mg of N-((3S,4R)-1-benzyl-4-(4-methoxyphenyl)pyrrolidin-3-yl)-3-((1-methyl-1H-pyrazol-5-yl)amino)isoquinoline-6-carboxamide (purity=100%, 254 nM). The remainder of the crude (80%) was purified on a SiO$_2$ column (ISCO) eluting with a MeOH/DCM gradient (2 to 8% MeOH) to afford an additional 48 mg (total 51.5 mg, 30%). $^1$H NMR (400 MHz, DMSO-d$_6$) δ 9.05 (s, 1H), 8.87 (s, 1H), 8.80 (d, J=7.5 Hz, 1H), 8.16 (s, 1H), 7.96 (d, J=8.6 Hz, 1H), 7.64 (d, J=8.4 Hz, 1H), 7.42 (s, 1H), 7.34 (q, J=7.7 Hz, 4H), 7.26 (d, J=8.1 Hz, 3H), 6.92 (s, 1H), 6.86 (d, J=8.4, 2H), 6.23 (s, 1H), 4.49-4.43 (m, 1H), 3.76 (s, 3H), 3.70 (s, 3H), 3.62 (d, J=10.4 Hz, 1H), 3.43 (q, J=7.5 Hz, 1H), 3.04 (m, 2H), 2.60 (m, 2H). LCMS M+H+=534.

Example 16

N-((3S,4R)-1-Benzyl-4-(4-methoxyphenyl)pyrrolidin-3-yl)-3-((1,3-dimethyl-1H-pyrazol-5-yl)amino)isoquinoline-6-carboxamide (II-63) and 3-((1,3-dimethyl-1H-pyrazol-5-yl)amino)-N-((3S,4R)-4-(4-methoxyphenyl)-1-methylpyrrolidin-3-yl)isoquinoline-6-carboxamide (II-64)

N-((3S,4R)-1-Benzyl-4-(4-methoxyphenyl)pyrrolidin-3-yl)-3-((1,3-dimethyl-1H-pyrazol-5-yl)amino)isoquinoline-6-carboxamide was prepared from 3-(1,3-dimethyl-1H-pyrazol-5-ylamino)isoquinoline-6-carboxylic acid (99 mg, 0.3506 mmol, 1.1 equiv) via a HATU mediated coupling with (3S,4R)-1-benzyl-4-(4-methoxyphenyl)pyrrolidin-3-amine (90 mg, 0.3187 mmol, 1.0 equiv) as the amine. The procedure and workup followed was the same as used for the preparation of N-((3S,4R)-1-benzyl-4-(4-methoxyphenyl)pyrrolidin-3-yl)-3-((1-methyl-1H-pyrazol-5-yl)amino)isoquinoline-6-carboxamide. A portion of the crude product (~30% of the material) was purified via prep RP HPLC to yield 9.4 mg of II-63 (purity=100%, uv 254 nM). The remainder of the crude was used without further purification in the hydrogenation reaction to remove the N-benzyl. $^1$H NMR (400 MHz, DMSO) δ 9.04 (s, 1H), 8.81 (s, 1H), 8.79 (m, 1H), 8.17 (s, 1H), 7.96 (d, J=8.6 Hz, 1H), 7.64 (d, J=8.6 Hz, 1H), 7.34 (q, J=8.0 Hz, 4H), 7.26 (d, J=8.2 Hz, 3H), 6.92 (s, 1H), 6.86 (d, J=8.4, 2H), 6.03 (s, 1H), 4.52-4.41 (m, 1H), 3.70 (s, 3H), 3.70 (t, J=7.3 Hz, 1H), 3.62 (d, J=10.4 Hz, 1H), 3.60 (s, 3H), 3.43 (q, J=7.3 Hz, 1H), 3.03 (m, 2H), 2.57 (m, 2H), 2.15 (s, 3H). LCMS M+H+=547.3.

A suspension of II-63 (48 mg, 0.0878 mmol), 10% Pd/C (56 mg, 6.0 equiv) and MeOH (4 mL) was thrice degassed and stirred for 24 h under 1 atm of hydrogen (balloon) atmosphere. The N-benzyl group cleaved to give the N-methylated product. The reaction mixture was filtered through a pad of Celite®, and the Celite® pad was washed with methanol. The methanol was concentrated, and the residue purified by prep RP HPLC to afford 2.4 mg (5.8%) of II-64 (purity=98% uv @ 254 nM). $^1$H NMR (400 MHz, DMSO) 9.05 (s, 1H), 8.81 (s, 1H), 8.79 (m, 1H), 8.21 (d, J=18.7 Hz, 1H), 7.96 (d, J=8.6 Hz, 1H), 7.66 (d, J=8.5 Hz, 1H), 7.25 (d, J=8.4 Hz, 2H), 6.93 (s, 1H), 6.86 (d, J=8.4, 2H), 6.03 (s, 1H), 4.49-4.42 (m, 1H), 3.71 (s, 3H), 3.60 (s, 3H), 3.41 (q, J=7.3 Hz, 1H), 3.02 (t, J=8.5 Hz, 2H), 2.93 (t, J=8.5 Hz, 2H), 2.60 (m, 1H), 2.31 (s, 3H), 2.15 (s, 3H). LCMS M+H+=471.2.

Example 17

(S)—N-((3-Fluoro-4-methoxyphenyl)(1-methyl-1H-imidazol-5-yl)methyl)-7-((tetrahydro-2H-pyran-4-yl)amino)-1,6-naphthyridine-2-carboxamide (I-60)

Step 1:
A solution of 1-methyl-1H-imidazole-5-carbaldehyde (1.46 g, 13.26 mmol), (R)-2-methylpropane-2-sulfinamide (2.893 g, 23.87 mmol), and tetraethoxytitanium (10.89 g, 47.73 mmol) in THF (100 mL) was heated to 65° C. for 12 h. The reaction was cooled and poured onto water. The solids were filtered off, and the filtrate was extracted with EtOAc. The layers were separated, and the organic layer was concentrated. The resulting residue was purified by $SiO_2$ eluting with a DCM/MeOH gradient (1.5 to 2% MeOH) to afford 1.444 g (51.1%) of (R,E)-2-methyl-N-((1-methyl-1H-imidazol-5-yl)methylene)propane-2-sulfinamide (128).
Step 2:
A solution of 128 (1.444 g, 6.770 mmol) and THF (20 mL) was cooled to −10° C., and (3-fluoro-4-methoxyphenyl)magnesium bromide (2.717 g, 11.85 mmol) was added via addition funnel. The reaction was stirred at −10° C. for 1 h. Water was added, and the mixture was extracted with EtOAc. The organic layer was concentrated, and the resulting residue was purified by reverse phase chromatography (eluting with 0-65% MeCN/water) to afford 0.203 g (8.83%) of (R)—N#R)-(3-fluoro-4-methoxyphenyl)(1-methyl-1H-imidazol-5-yl)methyl)-2-methylpropane-2-sulfinamide (130a) and 315 mg (13.71%) of (R)—N—((S)-(3-fluoro-4-methoxyphenyl)(1-methyl-1H-imidazol-5-yl)methyl)-2-methylpropane-2-sulfinamide (130b).
Step 3:
To a solution of 130b (160 mg, 0.471 mmol) in DCM (15 mL) was added 4 N HCl in dioxane (3 mL), and the reaction was stirred for 15 min. Ether was added to the mixture, and the solids were filtered off to afford 106 mg (82.8%) of (S)-(3-fluoro-4-methoxyphenyl)(1-methyl-1H-imidazol-5-yl)methanamine hydrochloride (132).
Step 4:
To a solution of 132 (49.7 mg, 0.183 mmol), and DIPEA (31.9 µL, 0.183 mmol) in DMF (5 mL) was added 72 (50 mg, 0.183 mmol) and HBTU (76.3 mg, 0.201 mmol), and the reaction was stirred at RT for 18 h. The reaction was poured into water and extracted with EtOAc. The organic layer was concentrated, and the resulting residue was purified by reverse phase chromatography (SP4, eluting with a 0-50% MeCN:$H_2O$ gradient) to afford 62.1 mg (69.2%) of I-61. $^1$H NMR (400 MHz, $CDCl_3$) δ 8.90 (s, 1H), 8.79 (d, 1H), 8.20 (d, 1H), 7.98 (d, 1H), 7.51 (s, 1H), 7.16 (m, 2H), 6.97 (m, 2H), 6.81 (s, 1H), 6.73 (s, 1H), 6.43 (d, 2H), 4.45 (d, 2H), 4.06 (m, 2H), 3.90 (s, 3H), 3.77 (m, 1H), 3.62 (m, 2H), 3.59 (s, 3H), 2.15 (m, 2H), 1.65 (m, 2H); m/z (APCI-pos) M+1=491.1.

(R)—N-((3-Fluoro-4-methoxyphenyl)(1-methyl-1H-imidazol-5-yl)methyl)-7-((tetrahydro-2H-pyran-4-yl)amino)-1,6-naphthyridine-2-carboxamide (I-59) was prepared analogously except in step 3, 130b was replaced with (R)—N-4R)-(3-fluoro-4-methoxyphenyl)(1-methyl-1H-imidazol-5-yl)methyl)-2-methylpropane-2-sulfinamide (130a) which ultimately afforded 69 mg (77%) of I-59 after coupling with 72. $^1$H NMR (400 MHz, $CDCl_3$) δ 8.90 (s, 1H), 8.79 (d, 1H), 8.20 (d, 1H), 7.98 (d, 1H), 7.51 (s, 1H), 7.16 (m, 2H), 6.81 (s, 1H), 6.73 (s, 1H), 6.43 (d, 2H), 4.45 (d, 2H), 4.06 (m, 2H), 3.90 (s, 3H), 3.77 (m, 1H), 3.62 (m, 2H), 3.59 (s, 3H), 2.15 (m, 2H), 1.65 (m, 2H); m/z (APCI-pos) M+1=491.1.

(S)—N-((3-Fluoro-4-methoxyphenyl)(1-methyl-1H-imidazol-5-yl)methyl)-7-((1-methyl-1H-pyrazol-5-yl)amino)-1,6-naphthyridine-2-carboxamide (I-58) was prepared analogously except in step 4, 72 was replaced with 80. $^1$H NMR (400 MHz, $CDCl_3$) δ 9.03 (s, 1H), 8.61 (m, 1H), 8.31 (d, 1H), 8.12 (d, 1H), 7.59 (m, 1H), 7.48 (s, 1H), 7.13 (m, 2H), 6.96 (m, 1H), 6.87 (s, 1H), 6.80 (s, 1H), 6.43 (m, 2H), 6.29 (m, 1H), 3.89 (s, 3H), 3.82 (s, 3H), 3.56 (s, 3H); m/z (APCI-pos) M+1=487.2.

Biological Example 1

ERK-2 Enzymatic Assay

Compounds were tested in an enzymatic assay using human ERK-2 (Mitogen Activated Kinase 1), recombinantly expressed as an n-terminal 6-His fusion protein in *E. coli* and corresponding to a 8-360. The substrate used was the fluorescent Omnia peptide S/T17 (Invitrogen of Carlsbad, Calif.; Cat. KNZ1171C). Test compounds were diluted in DMSO in 3-fold serial dilutions at 100× final concentrations. In addition to compound, the assay contained 50 mM HEPES [pH 7.3], 10 mM $MgCl_2$, 2 mM DTT, 0.005% Triton-X100, 5 nM ERK-2 enzyme, 6.25 µM S/T17 peptide substrate and 25 uM ATP (corresponding to the observed $K_m$) for a total reaction volume of 25 µL. The assay was run at ambient temperature in a white 384-well polypropylene plate (Nunc, Inc of Naperville, Ill.; Cat. 267462) collecting data every 50 seconds for approximately 30 minutes on an Envision plate reader (PerkinElmer, Inc. of Waltham, Mass.); Excitation 340 nm/Emission 495 nm. The data collected from each well was fit to a straight line, and the resulting rates were used to calculate percent of control. Percent of control was plotted against compound concentration, and $IC_{50}$ values were determined using a four-parameter fit. Table 3 contains representative data for compounds disclosed herein. Representative data is in TABLE 3 (infra).

Biological Example 2

Cellular P90RSK(Ser380) Phosphorylation Assay

Inhibition of PMA-stimulated P90RSK(Ser380) phosphorylation was determined by the following in vitro cellular mechanistic assay, which comprises incubating cells with a compound for 1.5 hours and quantifying fluorescent pP90RSK(Ser380) signal on fixed cells and normalizing to GAPDH signal.

Materials and Methods: HepG2 cells were obtained from ATCC and grown in DMEM supplemented with 10% fetal bovine serum. Cells were plated in 96-well plates at 35,000 cells/well and allowed to attach overnight at 37° C./5% $CO_2$. Diluted compounds were then added at a final concentration of 0.5% DMSO. After 1.5 hour compound incubation, cells were stimulated with the addition of PMA (phorbol 12-myristate 13-acetate) at a final concentration of 100 ng/mL; the PMA stimulation was a 30-minute incubation at 37° C./5% $CO_2$. After the 30-minute PMA stimulation, cells were washed with PBS and fixed in 3.7% formaldehyde in PBS at room temperature for 15-20 minutes. This was followed by another wash in PBS and then permeabilization in 100% MeOH at room temperature for 10-15 minutes. Following the permeabilization incubation, cells were washed in PBS/0.05% Tween-20, followed by a block in Odyssey blocking buffer (LI-COR Biosciences) for at least 1 hour. Antibodies to phosphorylated P90RSK(Ser380) (Cell Signaling #9335, rabbit monoclonal) and GAPDH (Fitzgerald 10R-G109a, mouse monoclonal) were added to the cells and incubated overnight at 4° C. pP90RSK(Ser380) antibody was used at a 1:250 dilution; GAPDH was used at a 1:10,000 dilution. After washing with PBS/0.05% Tween-20, the cells were incubated with fluorescently-labeled secondary antibodies (Anti-rabbit-Alexa Flour680, Invitrogen Cat#A21109; Anti-mouse-IRDye800CW, Rockland Inc. Cat#610-131-121) for 1 hour. Both secondary antibodies were used at a 1:1000 dilution. Cells were then washed and analyzed for fluorescence at both wavelengths using the Odyssey Infrared Imaging System (LI-COR Biosciences). Phosphorylated P90RSK(Ser380) signal was normalized to GAPDH signal. Representative date is in TABLE III (infra).

TABLE III

| Cpd. No. | Erk Enzymatic Assay[1] $IC_{50}$ (μM) | Cellular P90RSK (Ser380) Phosphorylation Assay[2] $IC_{50}$ (μM) |
| --- | --- | --- |
| I-21 | 0.00186 | 0.0187 |
| I-24 | 0.00115 | 0.0378 |
| I-5 | 0.00404 | 0.0163 |
| I-6 | 0.0021 | 0.00596 |
| I-8 | 0.000748 | 0.00984 |
| I-11 | 0.00343 | 0.0989 |
| I-30 | 0.00595 | 0.476 |
| II-2 | 0.0025 | 0.0085 |
| II-15 | 0.00229 | 0.00997 |
| II-12 | 0.0028 | 0.0148 |
| II-23 | 0.0202 | 0.0651 |
| II-37 | 0.0046 | 0.0304 |
| II-46 | 0.0065 | 0.0157 |
| II-64 | 0.00268 | 0.00547 |

[1]Biological Example 1
[2]Biological Example 2

Formulation Example 21

Pharmaceutical compositions of the subject Compounds for administration via several routes were prepared as described in this Example.

Composition for Oral Administration (A)

| Ingredient | % wt./wt. |
| --- | --- |
| Active ingredient | 20.0% |
| Lactose | 79.5% |
| Magnesium stearate | 0.5% |

The ingredients are mixed and dispensed into capsules containing about 100 mg each.

Composition for Oral Administration (B)

| Ingredient | % wt./wt. |
| --- | --- |
| Active ingredient | 20.0% |
| Magnesium stearate | 0.5% |
| Croscarmellose sodium | 2.0% |
| Lactose | 76.5% |
| PVP (polyvinylpyrrolidine) | 1.0% |

The ingredients are combined and granulated using a solvent such as methanol. The formulation is then dried and formed into tablets (containing about 20 mg of active compound) with an appropriate tablet machine.

Composition for Oral Administration (C)

| Ingredient | % wt./wt. |
| --- | --- |
| Active compound | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum K (Vanderbilt Co.) | 1.0 g |
| Flavoring | 0.035 mL |
| Colorings | 0.5 mg |
| Distilled water | q.s. to 100 mL |

The ingredients are mixed to form a suspension for oral administration.

Parenteral Formulation (D)

| Ingredient | % wt./wt. |
| --- | --- |
| Active ingredient | 0.25 g |
| Sodium Chloride | qs to make isotonic |
| Water for injection to | 100 mL |

The active ingredient is dissolved in a portion of the water for injection. A sufficient quantity of sodium chloride is then added with stirring to make the solution isotonic. The solution is made up to weight with the remainder of the water for injection, filtered through a 0.2 micron membrane filter and packaged under sterile conditions.

Suppository Formulation (E)

| Ingredient | % wt./wt. |
| --- | --- |
| Active ingredient | 1.0% |
| Polyethylene glycol 1000 | 74.5% |
| Polyethylene glycol 4000 | 24.5% |

The ingredients are melted together and mixed on a steam bath, and poured into molds containing 2.5 g total weight.

Topical Formulation (F)

| Ingredients | grams |
| --- | --- |
| Active compound | 0.2-2 |
| Span 60 | 2 |
| Tween 60 | 2 |
| Mineral oil | 5 |
| Petrolatum | 10 |
| Methyl paraben | 0.15 |
| Propyl paraben | 0.05 |
| BHA (butylated hydroxy anisole) | 0.01 |
| Water | q.s. 100 |

All of the ingredients, except water, are combined and heated to about 60° C. with stirring. A sufficient quantity of water at about 60° C. is then added with vigorous stirring to emulsify the ingredients, and water then added q.s. about 100 g.

The features disclosed in the foregoing description, or the following claims, expressed in their specific forms or in terms of a means for performing the disclosed function, or a method or process for attaining the disclosed result, as appropriate, may, separately, or in any combination of such features, be utilized for realizing the invention in diverse forms thereof.

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

The patents, published applications, and scientific literature referred to herein establish the knowledge of those skilled in the art and are hereby incorporated by reference in their entirety to the same extent as if each was specifically and individually.

We claim:
1. A compound selected from the group consisting of:

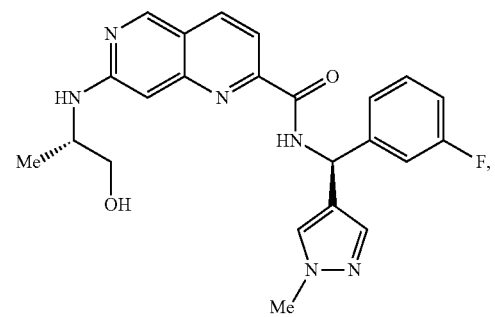

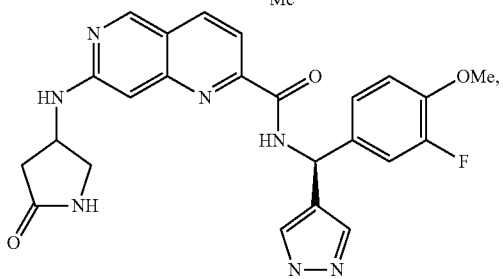

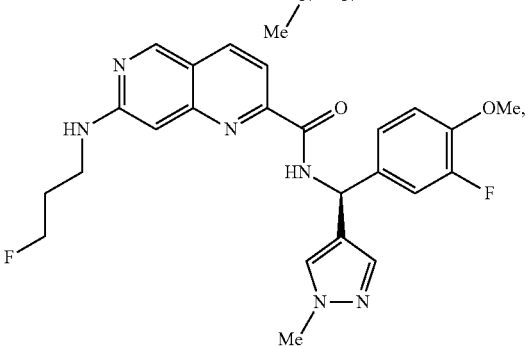

-continued

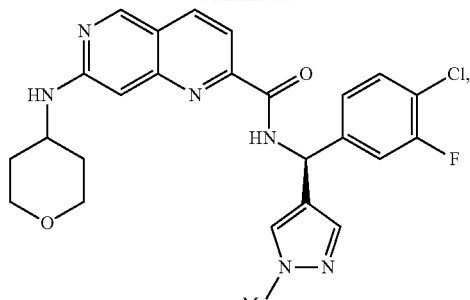

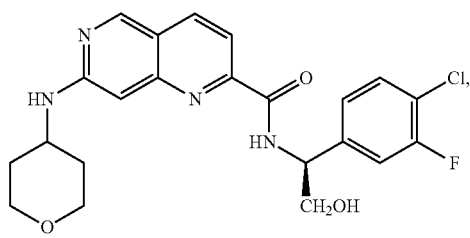

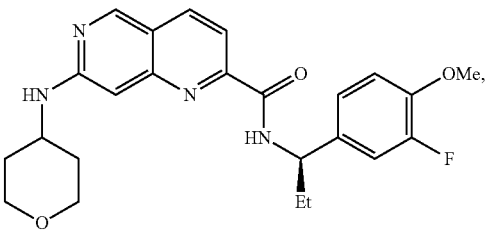

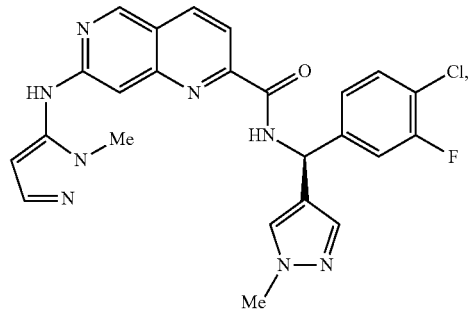

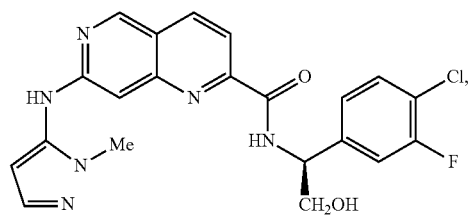

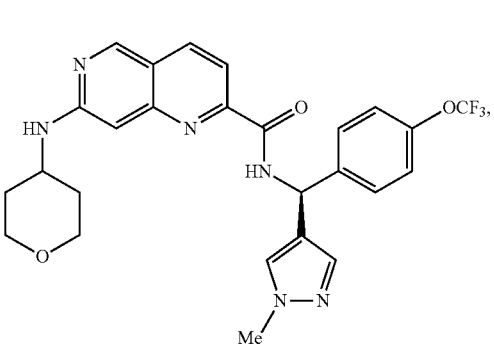

131
-continued
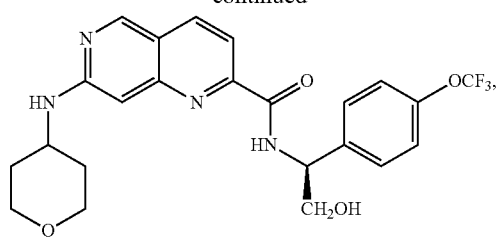
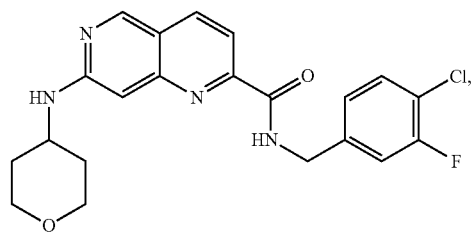
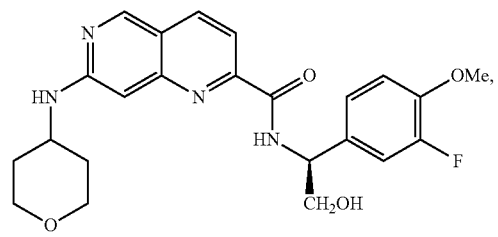
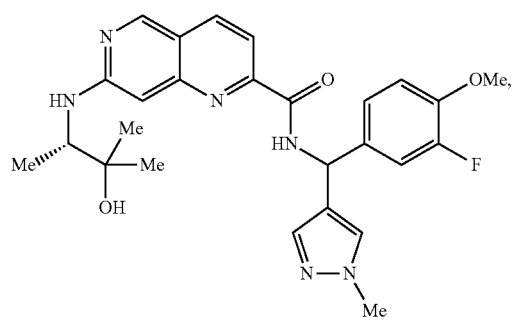
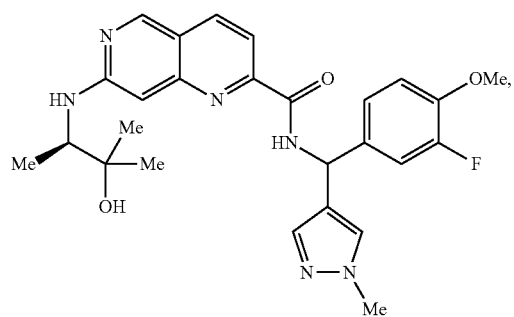
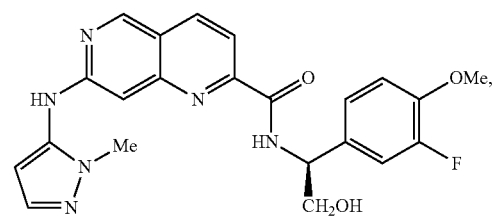
132
-continued
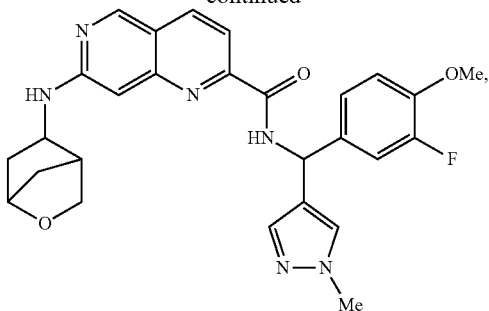
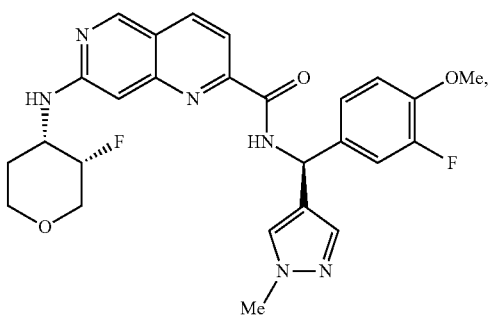
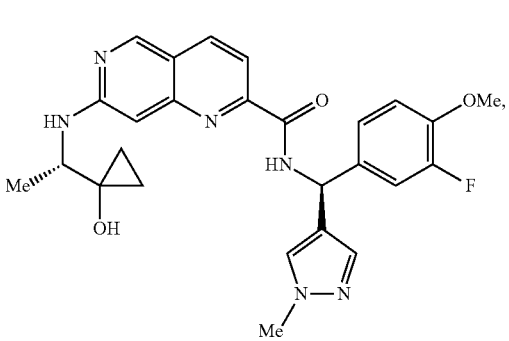
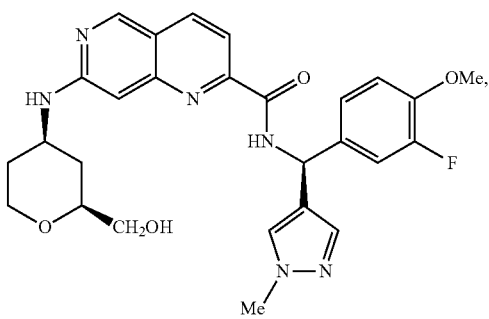
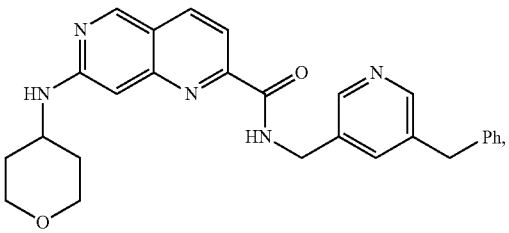

133
-continued
134
-continued
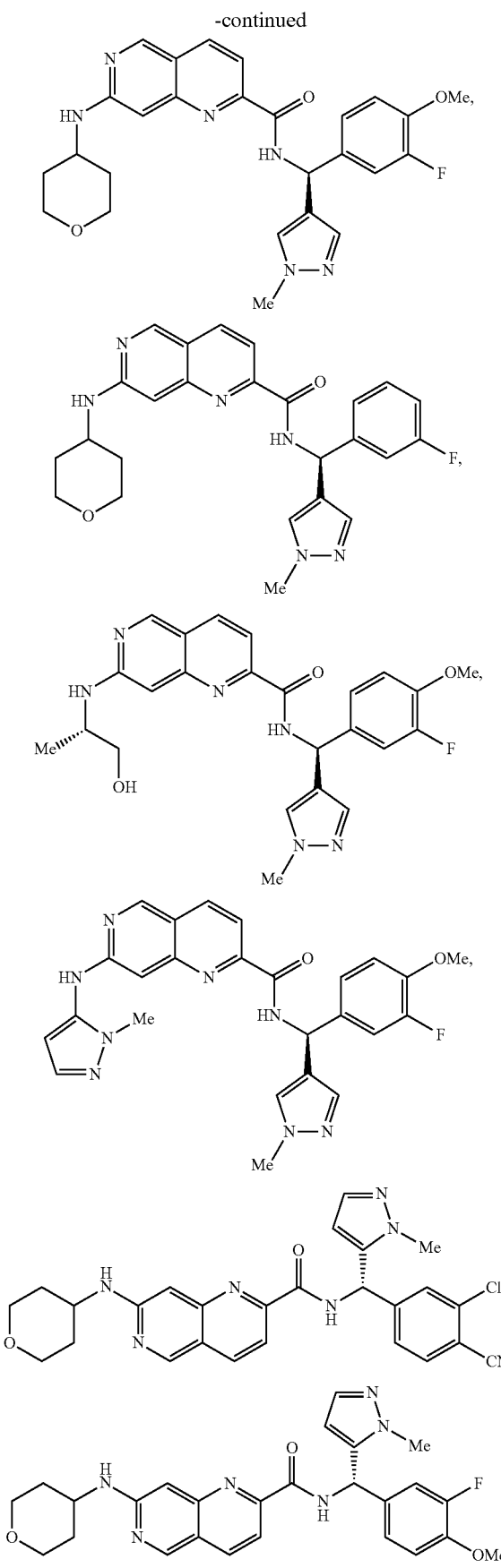
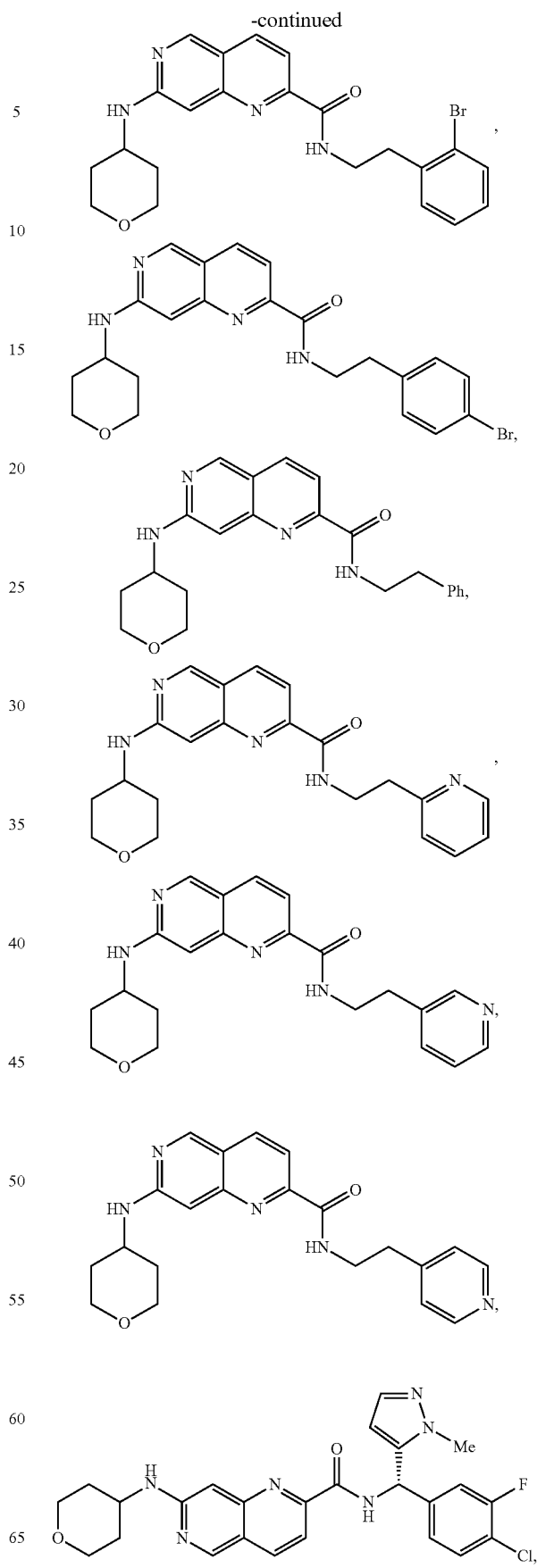

-continued
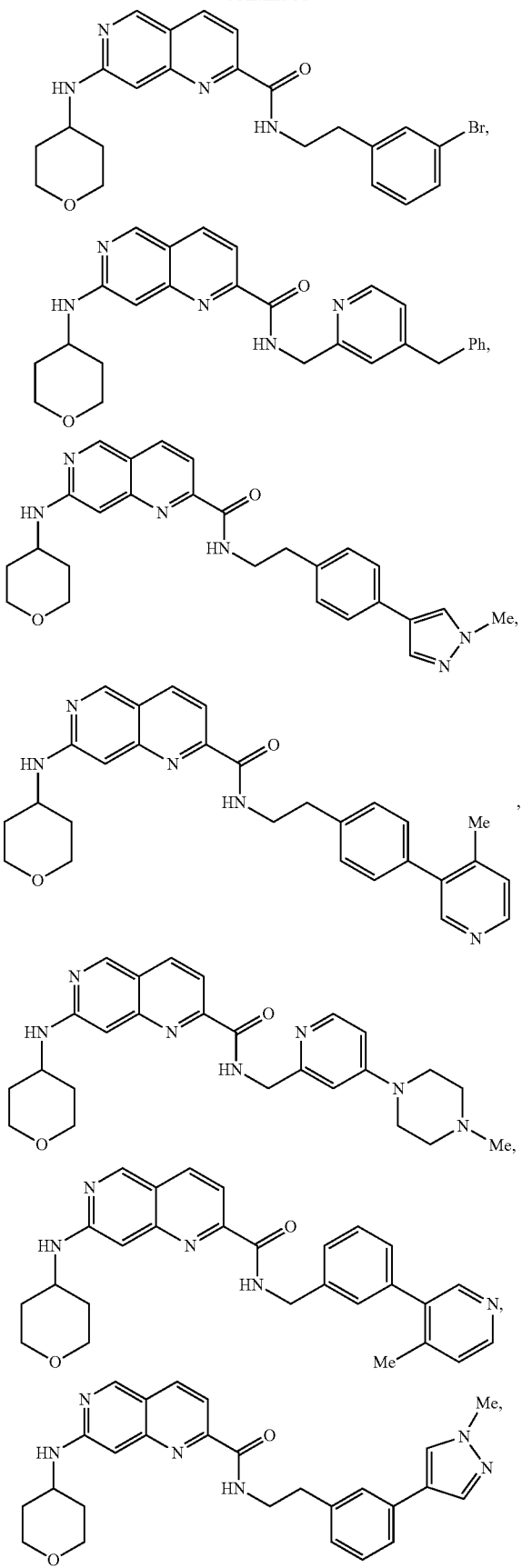
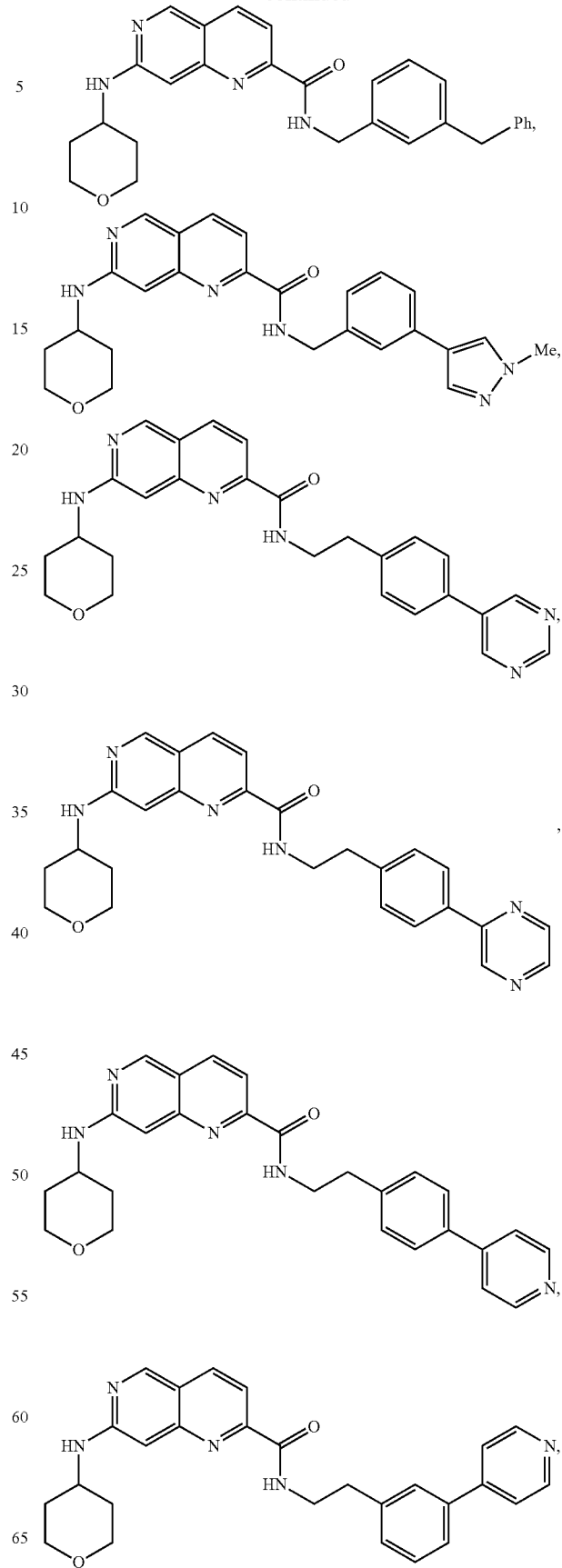

137
-continued
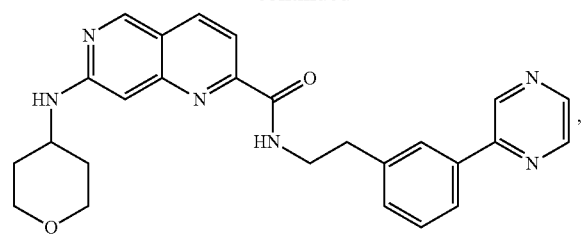
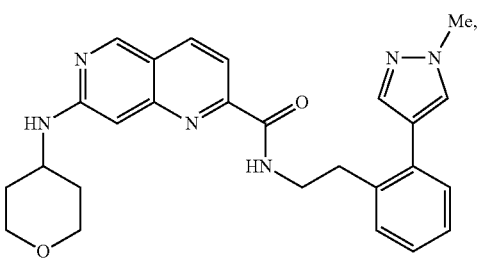
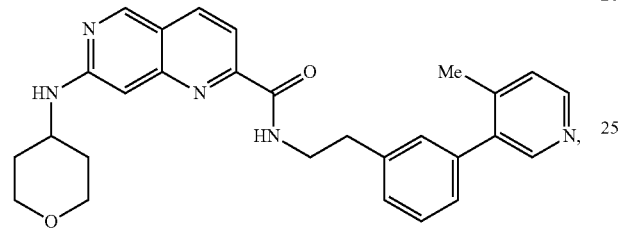
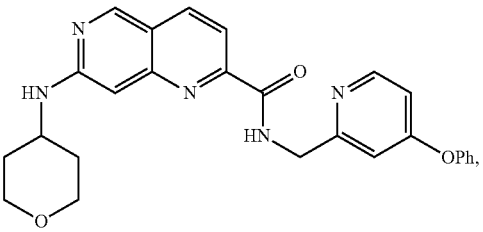
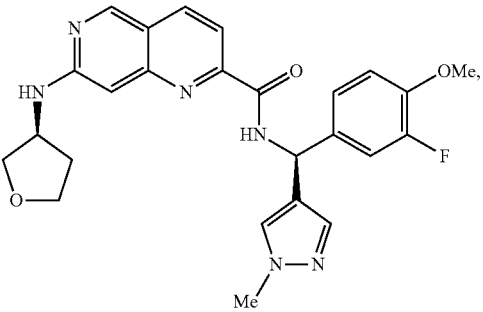
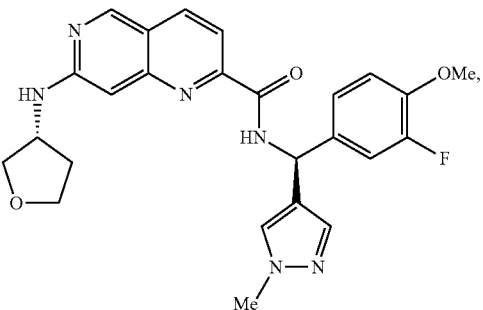
138
-continued
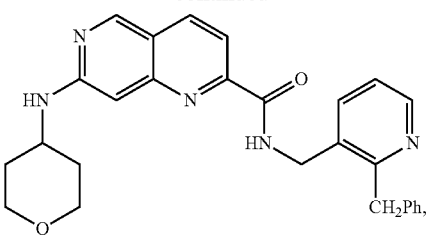
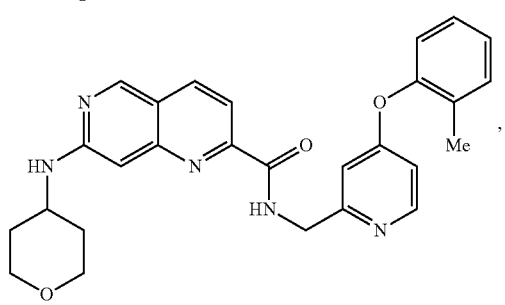
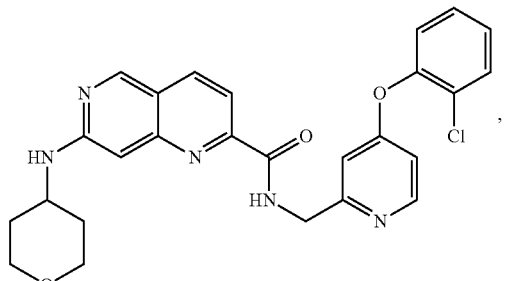
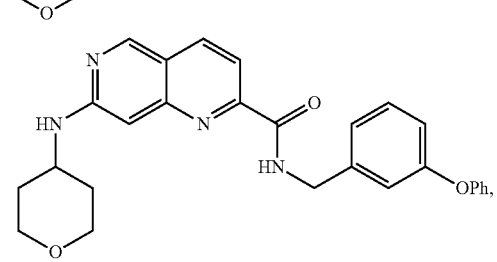
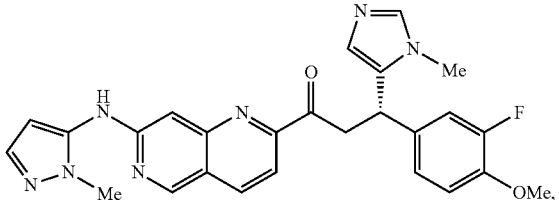
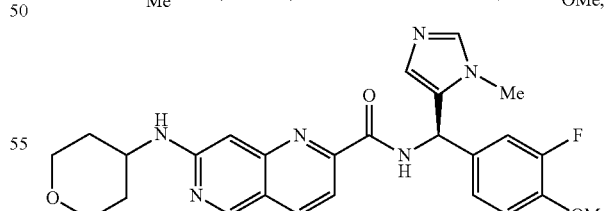
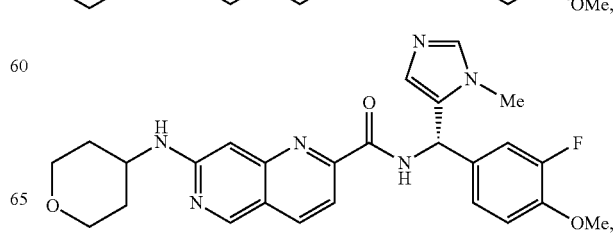

139
-continued
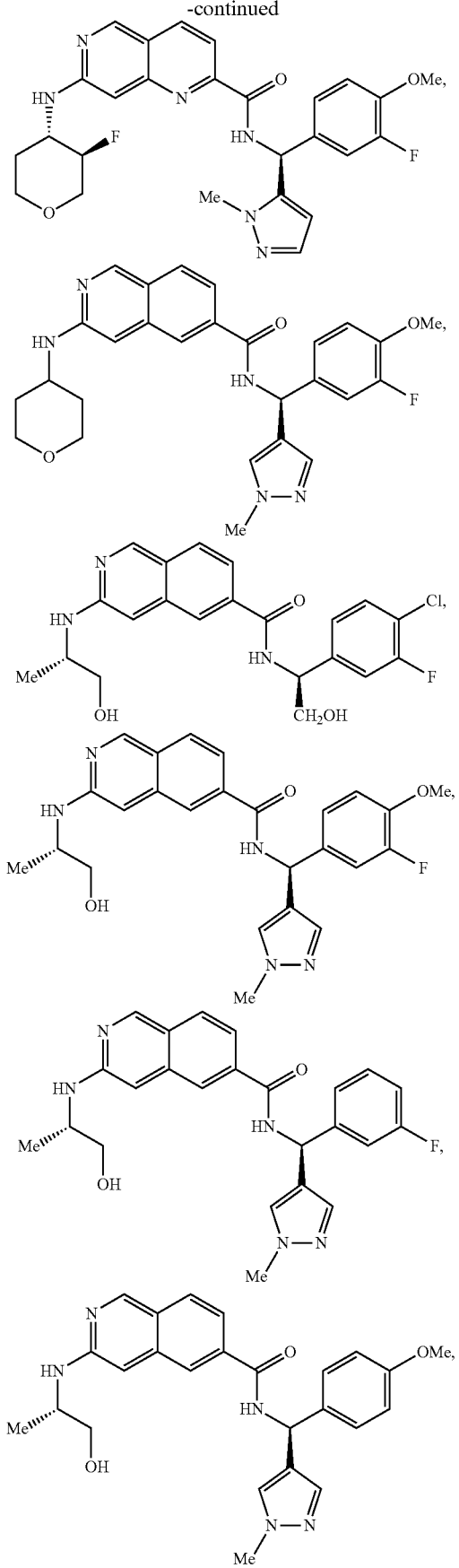
140
-continued
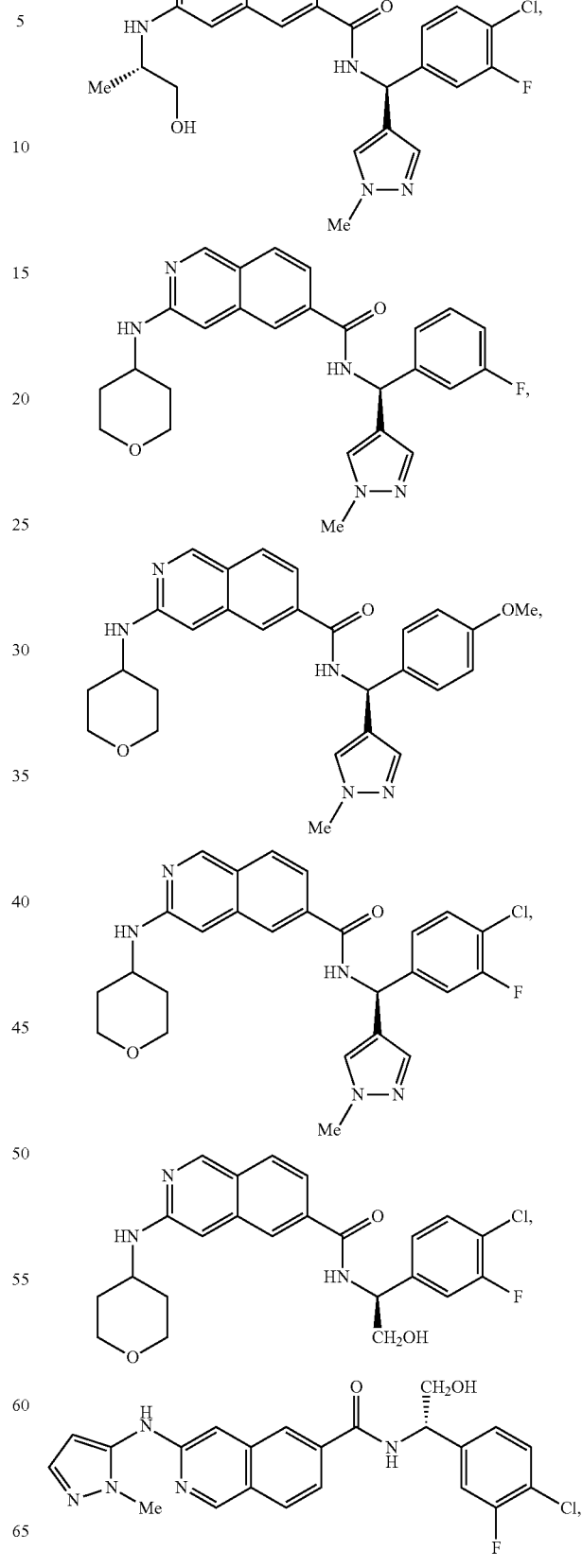

141
-continued
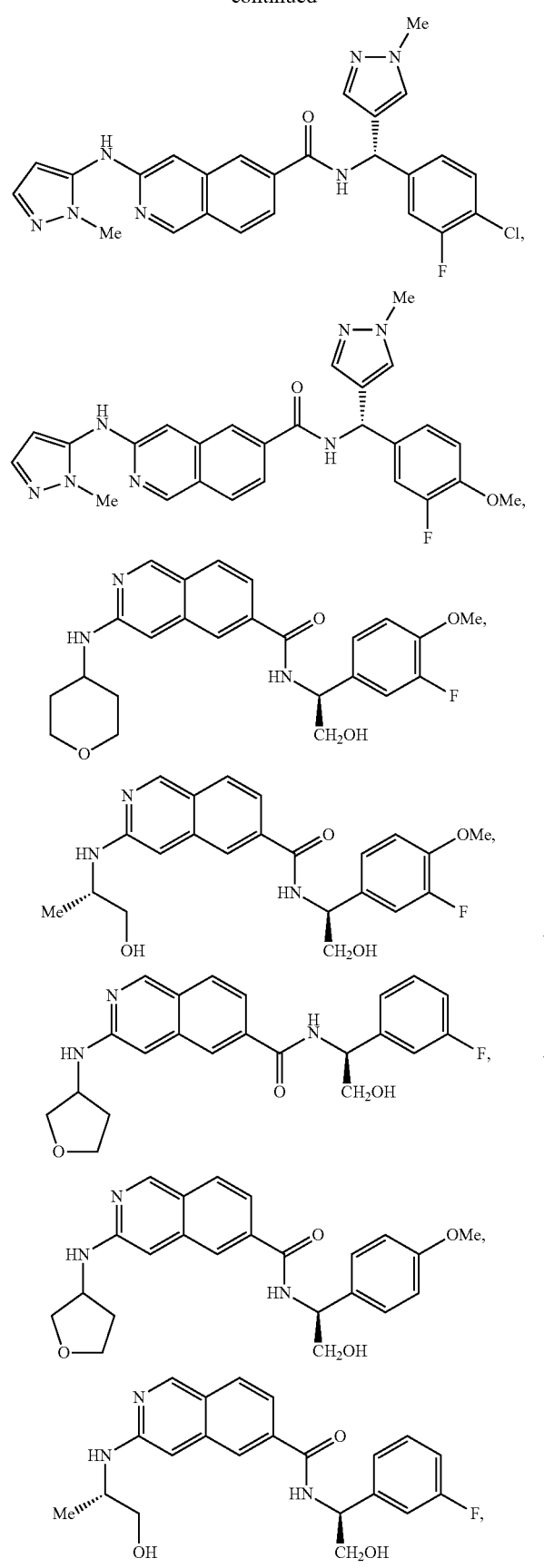
142
-continued
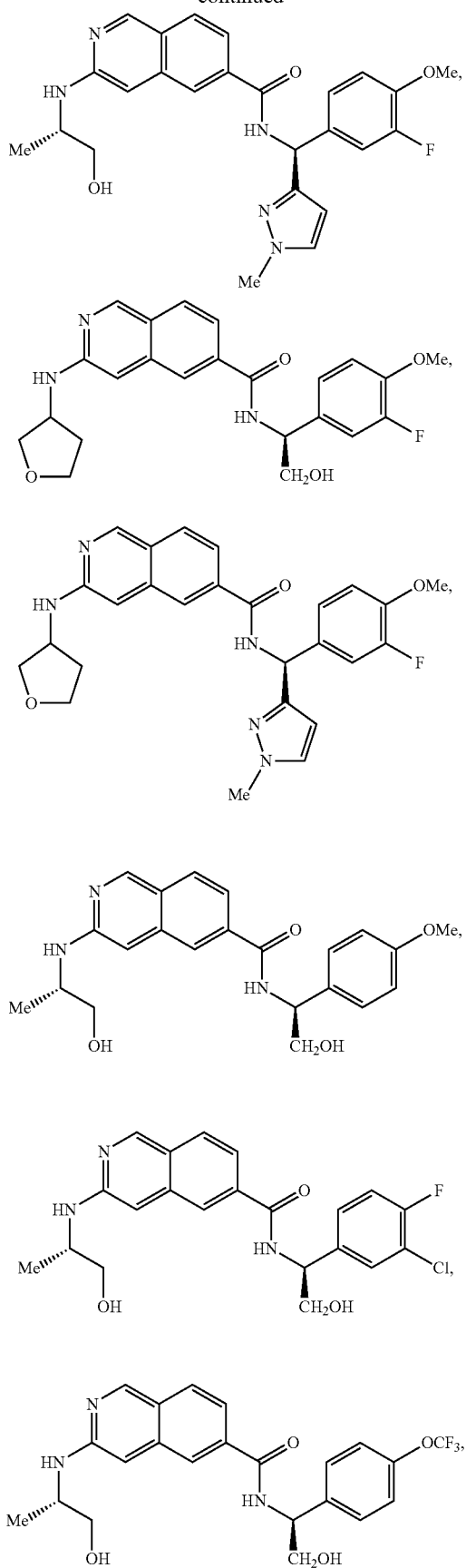

143
-continued
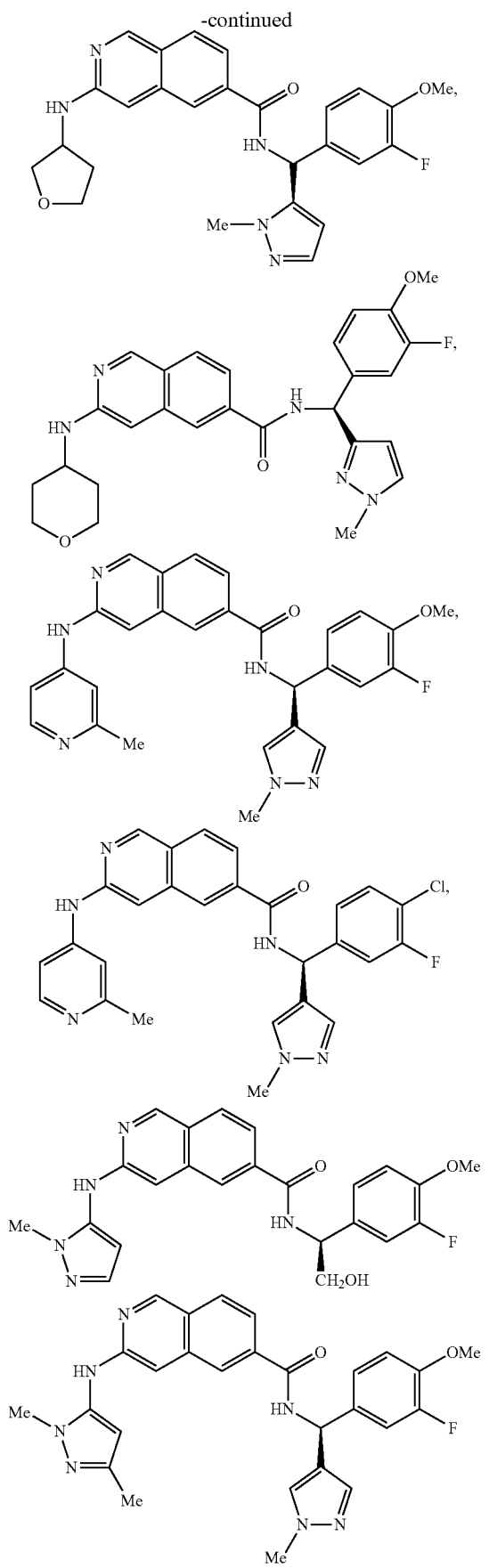
144
-continued
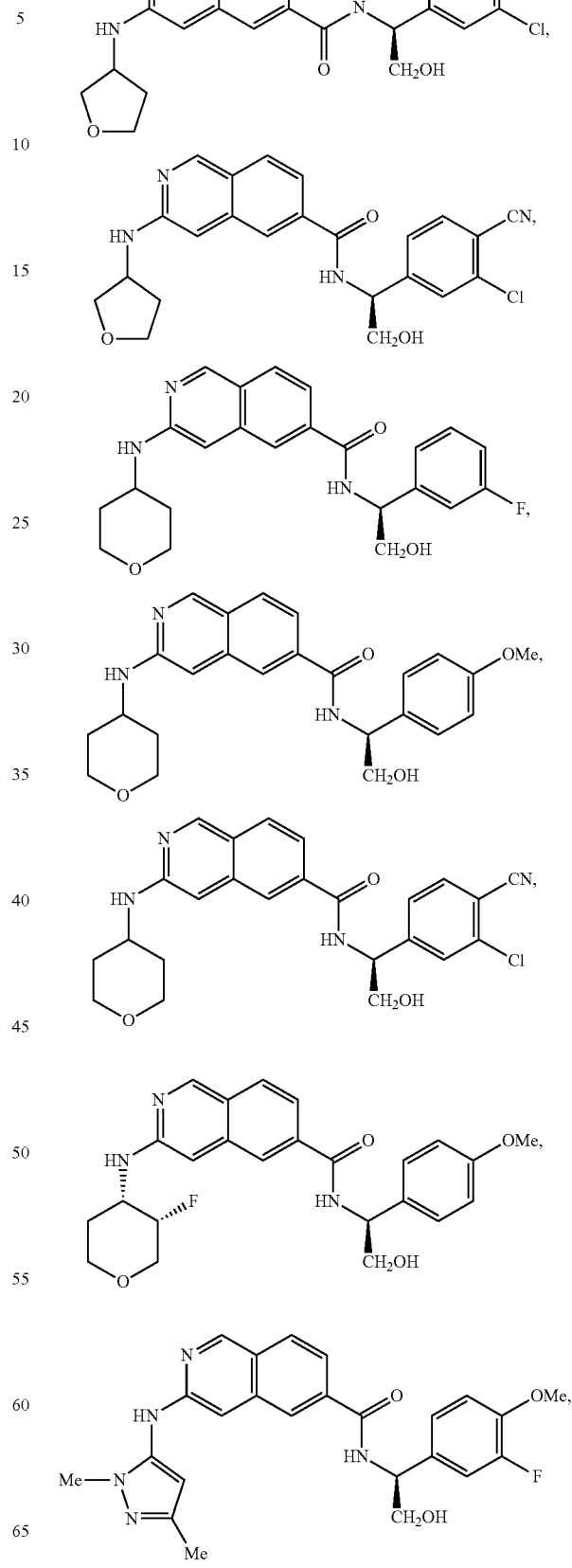

145
-continued
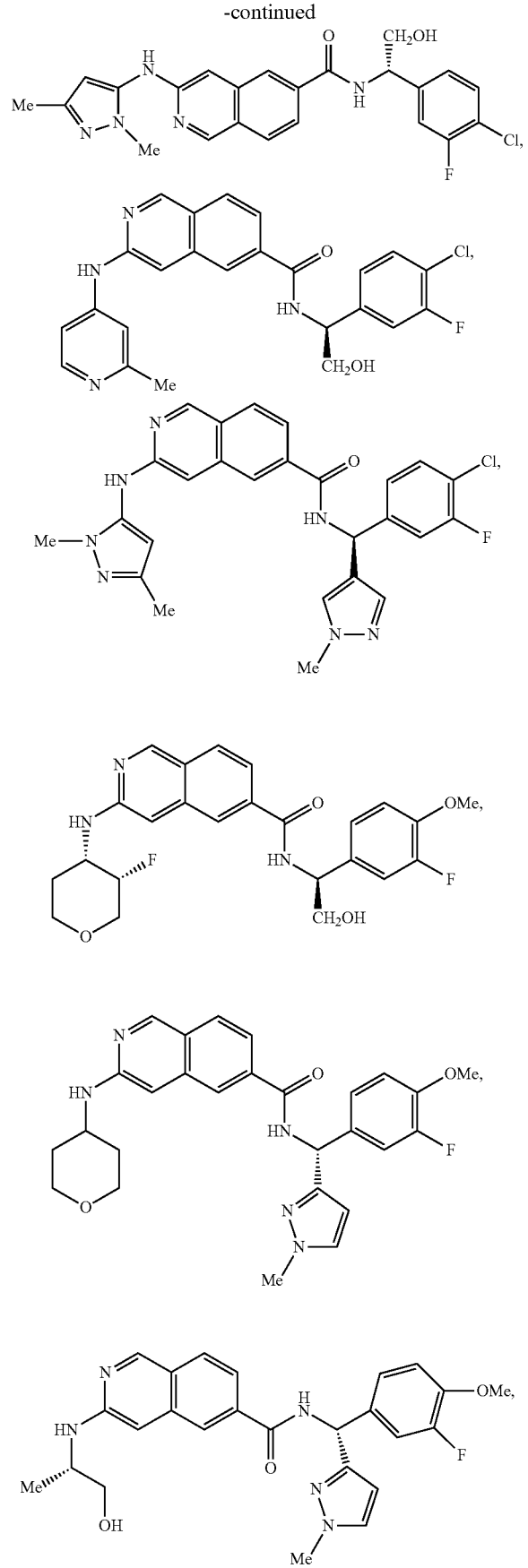
146
-continued
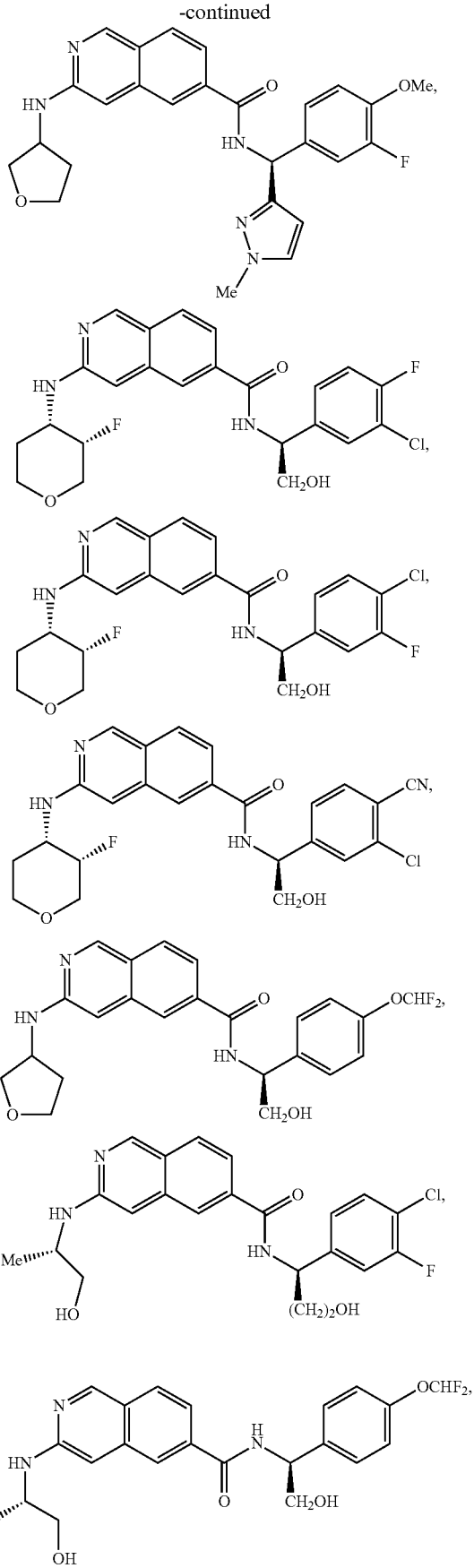

147
-continued
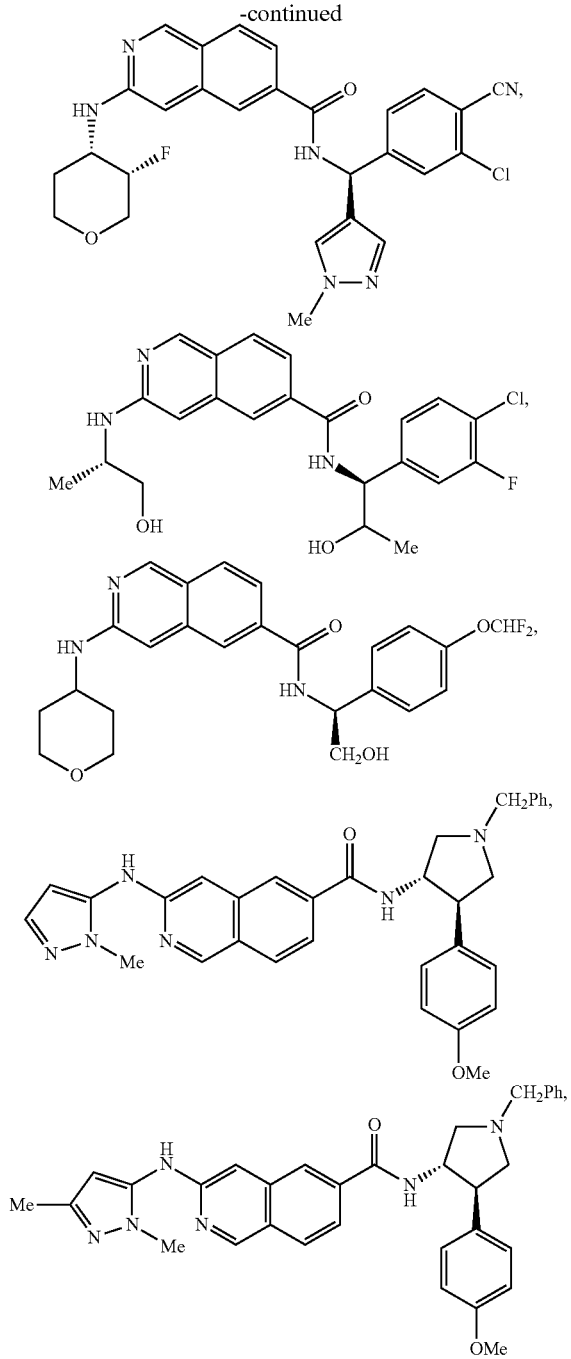
148
-continued
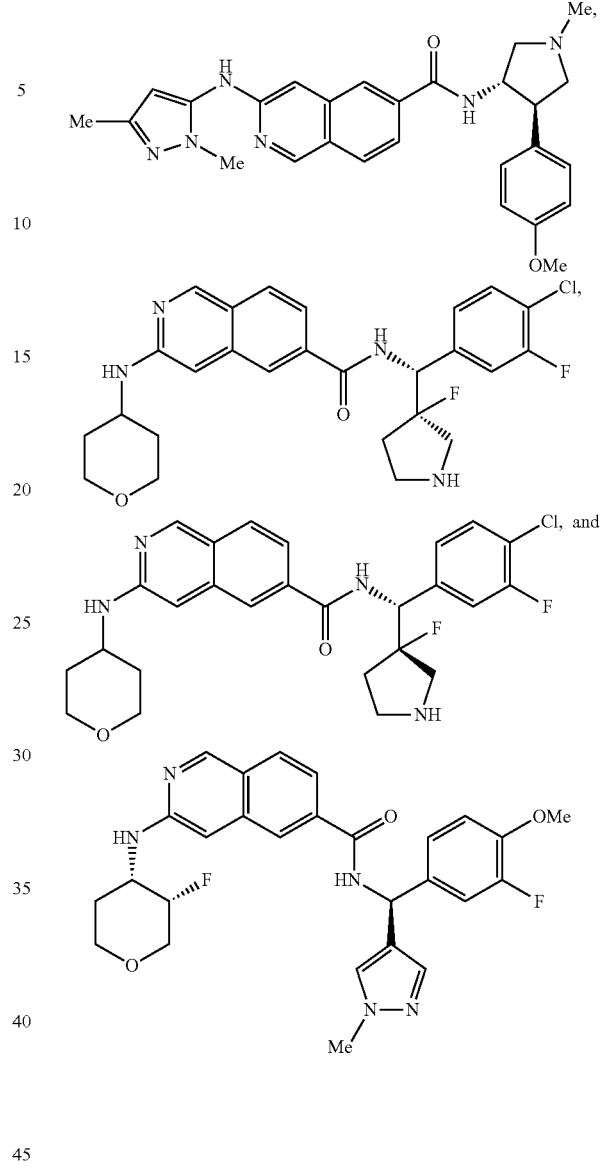
or a pharmaceutically acceptable salt thereof.
2. A pharmaceutical composition comprising a compound according to claim 1 or a pharmaceutically acceptable salt thereof and at least one pharmaceutically acceptable carrier, excipient or diluent.
* * * * *